US012758564B2

(12) United States Patent
Chen et al.

(10) Patent No.: US 12,758,564 B2
(45) Date of Patent: Oct. 13, 2026

(54) METHODS AND MATERIALS FOR INHIBITING CB1 ACTIVITY

(71) Applicant: University of Pittsburgh—Of the Commonwealth System of Higher Education, Pittsburgh, PA (US)

(72) Inventors: Beibei Chen, Pittsburgh, PA (US); Toren Finkel, Pittsburgh, PA (US); Yuan Liu, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 618 days.

(21) Appl. No.: 18/022,654

(22) PCT Filed: Nov. 19, 2021

(86) PCT No.: PCT/US2021/060125
§ 371 (c)(1),
(2) Date: Feb. 22, 2023

(87) PCT Pub. No.: WO2022/109292
PCT Pub. Date: May 27, 2022

(65) Prior Publication Data

US 2024/0000806 A1 Jan. 4, 2024

Related U.S. Application Data

(60) Provisional application No. 63/116,717, filed on Nov. 20, 2020.

(51) Int. Cl.
*A61K 31/635* (2006.01)

(52) U.S. Cl.
CPC .................................. *A61K 31/635* (2013.01)

(58) Field of Classification Search
None
See application file for complete search history.

(56) References Cited

U.S. PATENT DOCUMENTS

| | | | | |
|---|---|---|---|---|
| 4,940,708 | A * | 7/1990 | Sarges ................. | C07D 241/50 514/249 |
| 5,304,121 | A | 4/1994 | Sahatjian | |
| 5,886,026 | A | 3/1999 | Hunter et al. | |
| 6,099,562 | A | 8/2000 | Ding et al. | |
| 6,803,031 | B2 | 10/2004 | Rabinowitz et al. | |
| 7,294,645 | B2 | 11/2007 | Barth et al. | |
| 10,040,816 | B2 | 8/2018 | Piazza et al. | |
| 2006/0172019 | A1 | 8/2006 | Ralston et al. | |
| 2013/0109672 | A1 | 5/2013 | Boxer et al. | |
| 2014/0163016 | A1 | 6/2014 | Ramnauth et al. | |

FOREIGN PATENT DOCUMENTS

WO WO-2011137089 A1 * 11/2011 ........... C07D 223/16

OTHER PUBLICATIONS

Illum et al., "Is nose-to-brain transport of drugs in man a reality?," J. Pharm. Pharmacol., Jan. 2004, 56(1):3-17.
Illum et al., "Transport of drugs from the nasal cavity to the central nervous system," Eur. J. Pharm. Sci., Jul. 2000, 11:1-18.
International Preliminary Report on Patentability in International Appln. No. PCT/US2021/060125, mailed on Jun. 1, 2023, 7 pages.
International Search Report and Written Opinion in International Appln. No. PCT/US2021/060125, mailed on Feb. 8, 2022, 9 pages.

* cited by examiner

*Primary Examiner* — Lauren Wells
(74) *Attorney, Agent, or Firm* — Fish & Richardson P.C.

(57) ABSTRACT

This document provides compounds that can inhibit CB1 activity within a mammal (e.g., a human), as well as the methods of using such compounds for treating diseases, disorders, and conditions such as obesity, fear, metabolic-related disorders, diabetes, dyslipidaemia, and atherosclerosis.

8 Claims, No Drawings

METHODS AND MATERIALS FOR INHIBITING CB1 ACTIVITY

CLAIM OF PRIORITY

This application is a National Stage application under 35 U.S.C. § 371 of International Application No. PCT/US2021/060125, having an International Filing Date of Nov. 19, 2021, which claims priority under 35 USC § 119 (e) to U.S. Patent Application Ser. No. 63/116,717, filed on Nov. 20, 2020, the entire contents of which are hereby incorporated by reference.

FEDERALLY SPONSORED RESEARCH AND DEVELOPMENT

This invention was made with government support under grant number HL139860 awarded by National Institutes of Health (NIH). The government has certain rights in the invention.

TECHNICAL FIELD

This document relates to methods and materials for inhibiting cannabinoid receptor type 1 (CB1) activity. For example, this document provides compounds (e.g., organic compounds) having the ability to inhibit CB1 activity, formulations containing one or more compounds having the ability to inhibit CB1 activity, methods for making one or more compounds having the ability to inhibit CB1 activity, methods for inhibiting CB1 activity, and methods for treating mammals (e.g., humans) having a condition responsive to inhibition of CB1 activity.

BACKGROUND

The CB1 is a G protein-coupled cannabinoid receptor that is expressed in the peripheral nervous system and the central nervous system. Inhibitors of CB1 activity can decrease food intake, regulate body-weight gain, and be used to treat obesity. Inhibitors of CB1 activity also can be used to help people stop smoking.

SUMMARY

This document provides methods and materials for inhibiting CB1 activity. For example, the document provides compounds (e.g., organic compounds) having the ability to inhibit CB1 activity within a mammal, formulations containing one or more compounds having the ability to inhibit CB1 activity within a mammal, methods for making one or more compounds having the ability to inhibit CB1 activity within a mammal, methods for making formulations containing one or more compounds having the ability to inhibit CB1 activity within a mammal, methods for inhibiting CB1 activity within a mammal, and methods for treating mammals (e.g., humans) having a condition responsive to inhibition of CB1 activity within a mammal. Suitable examples of conditions responsive to inhibition of CB1 activity that can be treated as described herein include, without limitation, obesity, fear, metabolic-related disorders, diabetes, dyslipidaemia, and atherosclerosis. In some cases, a CB1 inhibitor described herein can be used to reduce food intake of a mammal (e.g., a human), to reduce the body weight gain of a mammal (e.g., a human), to improve lipid profiles within a mammal (e.g., a human), to improve glycemic profiles within a mammal (e.g., a human), to assist a mammal (e.g., a human) in stopping tobacco use (e.g., cigarette smoking) and/or *cannabis* use, to treat liver disorders (e.g., fatty liver disease, nonalcoholic steatohepatitis (NASH), cirrhosis, and/or liver cancer), to reduce the symptoms or progression of idiopathic pulmonary fibrosis or related fibrotic conditions in the lung, to ameliorate the end-organ damage induced by chronic alcohol usage (e.g., heart failure, pancreatitis, and/or liver disease), and/or to limit or reduce the complications of chronic renal disease characterized by renal fibrosis (e.g., diabetic nephropathy, inherited glomerular diseases, and/or acquired glomerular diseases).

In some cases, a CB1 inhibitor described herein can be used to inhibit CB1 activity within the peripheral nervous system of a mammal (e.g., a human) with little or no inhibition of CB1 activity within the central nervous system of that mammal. For example, a CB1 inhibitor described herein can be used to reduce food intake of a mammal (e.g., a human), to reduce the body weight gain of a mammal (e.g., a human), to improve lipid profiles within a mammal (e.g., a human), to improve glycemic profiles within a mammal (e.g., a human), and/or to assist a mammal (e.g., a human) in stopping tobacco use (e.g., cigarette smoking), with reduced side effects associated with inhibition of CB1 within the central nervous system such as psychiatric disorder side effects.

In general, one aspect of this document features a method of inhibiting CB-1 activity within a mammal. The method comprises (or consists essentially of or consists of) administering, to the mammal, an effective amount of a compound of Formula (I):

(I)

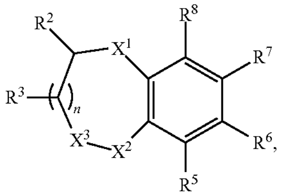

or a pharmaceutically acceptable salt thereof, wherein:

$X^1$ is selected from O and $NR^1$;

$X^2$ is selected from $NR^4$ and C(═O);

$X^3$ is selected from $CHR^3$, $NR^4$ and C(═O), provided that:

(i) $X^2$ is $NR^4$ and $X^3$ is C(═O); or (ii) $X^2$ is C(═O) and $X^3$ is selected from $CHR^3$ and $NR^4$;

n is 0 or 1;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

each $R^3$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with 1, 2, or 3 substituents independently selected from $R^9$;

$R^1$ and $R^4$ are each independently selected from H, $C_{1-6}$ alkyl, $C_{1-6}$ haloalkyl, $C_{2-6}$ alkenyl, $C_{2-6}$ alkynyl, C(O)$R^{b1}$, C(O)$NR^{c1}R^{d1}$, C(O)$OR^{a1}$, $S(O)_2R^{b1}$, and $S(O)_2NR^{c1}R^{d1}$; wherein the $C_{1-6}$ alkyl, $C_{2-6}$ alkenyl, and $C_{2-6}$ alkynyl are each optionally substituted with 1, 2, or 3 substituents independently selected from $R^9$; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^5$, $R^6$, $R^7$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, $S(O)_2NR^{c1}R^{d1}$; and a group of formula (i):

(i)

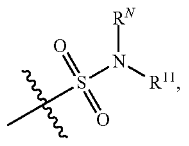

wherein the $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein the $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein the $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, for a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein the $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

At least one of $R^5$, $R^6$, $R^7$ and $R^8$ can be a group of formula (i). At least one of $R^7$ and $R^8$ can be a group of formula (i). The compound of Formula (I) can have formula:

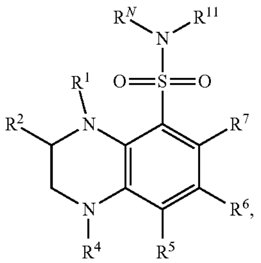

or a pharmaceutically acceptable salt thereof.

The compound of Formula (I) can have formula:

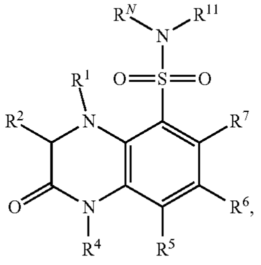

or a pharmaceutically acceptable salt thereof. The compound of Formula (I) can have formula:

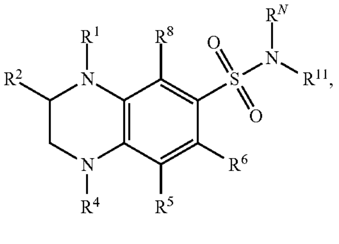

or a pharmaceutically acceptable salt thereof. The compound of Formula (I) can have formula:

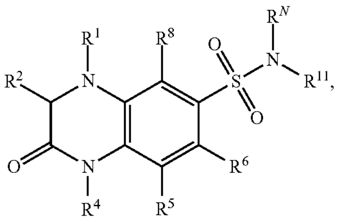

or a pharmaceutically acceptable salt thereof. $R^2$ of any of the above can be selected from H and $C_{1-6}$ alkyl; $R^1$ can be selected from H, $C_{1-6}$ alkyl, $C_{1-6}$ haloalkyl, $C(O)R^{b1}$, and $C(O)NR^{c1}R^{d1}$; and the $C_{1-6}$ alkyl can be optionally substituted with 1, 2, or 3 substituents independently selected from $R^9$. The $R^1$ can be selected from $C_{1-6}$ alkyl, $C(O)R^{b1}$, and $C(O)NR^{c1}R^{d1}$.

The compound of Formula (I) can be selected from:

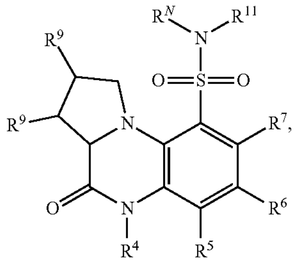

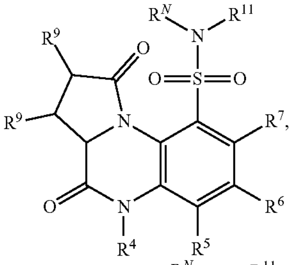

and

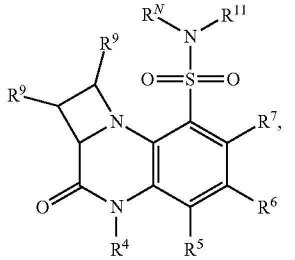

or a pharmaceutically acceptable salt thereof.

The compound of Formula (I) can be selected from:

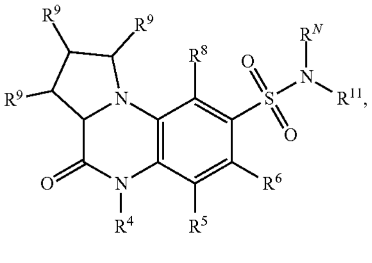

-continued

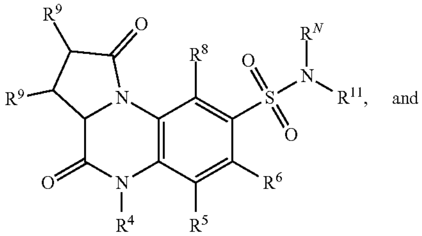

and

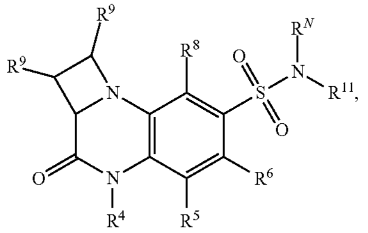

or a pharmaceutically acceptable salt thereof. The compound of Formula (I) can have formula:

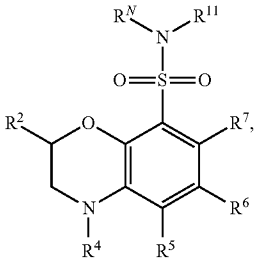

or a pharmaceutically acceptable salt thereof.

The compound of Formula (I) can have formula:

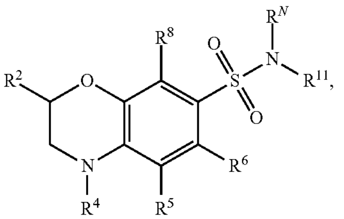

or a pharmaceutically acceptable salt thereof. The compound of Formula (I) can have formula:

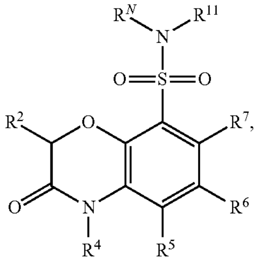

or a pharmaceutically acceptable salt thereof. The compound of Formula (I) can have formula:

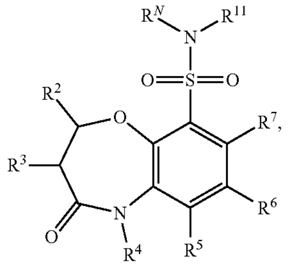

or a pharmaceutically acceptable salt thereof.

The compound of Formula (I) can have formula:

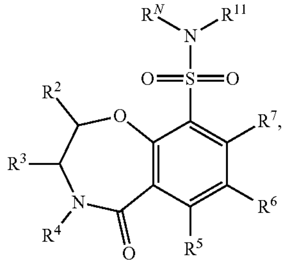

or a pharmaceutically acceptable salt thereof. The compound of Formula (I) can have formula:

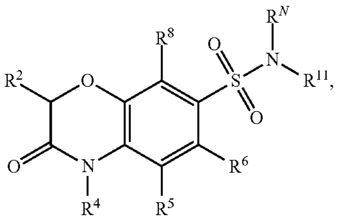

or a pharmaceutically acceptable salt thereof. The compound of Formula (I) can have formula:

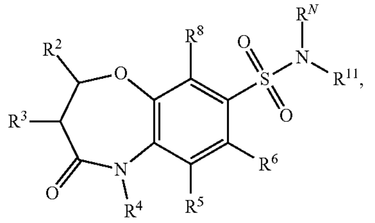

or a pharmaceutically acceptable salt thereof. $R^2$ of any of the above can be selected from H and $C_{1-6}$ alkyl. $R^3$ of any of the above can be selected from H and $C_{1-6}$ alkyl. $R^4$ of any of the above can be selected from H, $C_{1-6}$ alkyl, and $C_{1-6}$ haloalkyl, wherein the $C_{1-6}$ alkyl is optionally substituted with 1, 2, or 3 substituents independently selected from $R^9$. In some cases, $R^4$ can be H. $R^5$ and $R^6$ of any of the above can be each independently selected from H, halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein the $C_{1-6}$ alkyl is optionally substituted with 1, 2, or 3 substituents independently selected from $R^9$. $R^5$ and $R^6$ of any of the above can be each independently selected from H, halo, $C_{1-6}$ alkyl, and $S(O)_2R^{b1}$, wherein the $C_{1-6}$ alkyl is optionally substituted with $R^9$. In some cases, $R^5$ is H, and $R^6$ is $C_{1-6}$ alkyl, optionally substituted with $NR^{c1}R^{d1}$. In some cases, $R^5$ is H, and $R^6$ is halo. In some cases, $R^5$ is H, and $R^6$ is $S(O)_2R^{b1}$. $R^7$ of any of the above can be selected from H and $C_{1-6}$ alkyl. $R^8$ of any of the above can be selected from H and $C_{1-6}$ alkyl. $R^N$ of any of the above can be selected from H and $C_{1-6}$ alkyl. $R^{11}$ of any of the above can be ring A. $R^{11}$ of any of the above can be $C_{1-6}$ alkyl, optionally substituted with ring A. $R^N$ and $R^{11}$, together with the N atom to which they are attached, can form a ring selected from morpholinyl, piperidinyl, and piperazinyl, each of which is optionally substituted with 1, 2, or 3 substituents independently selected from $R^9$. Ring A of any of the above can be selected from any one of the following moieties:

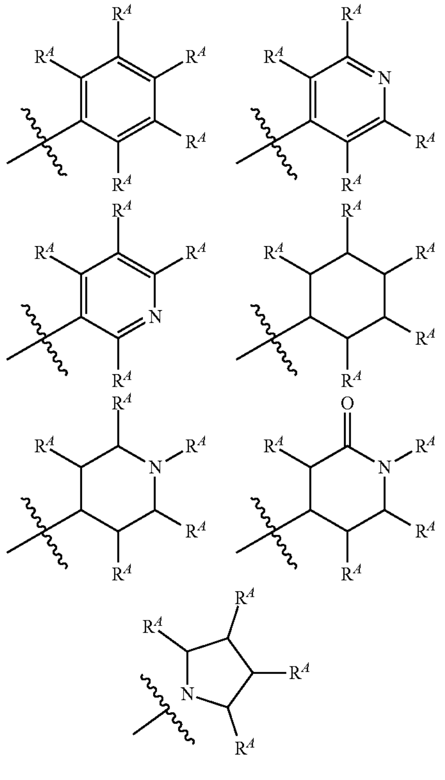

Each $R^A$ of any of the above can be independently selected from H, halo, CN, $C_{1-6}$ alkyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein the $C_{1-6}$ alkyl is optionally substituted with 1, 2, or 3 substituents independently selected from $R^{10}$. Each $R^A$ of any of the above can be independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$ and $NR^{c1}C(O)R^{b1}$, wherein the $C_{1-6}$ alkyl is optionally substituted with 1, 2, or 3 substituents independently selected from $R^{10}$. Each $R^{10}$ of any of the above can be independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$. Each $R^A$ of any of the above can be independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$, and $NR^{c1}C(O)R^{b1}$, wherein the $C_{1-6}$ alkyl is optionally substituted with $C(O)OR^{a1}$. Each $R^{a1}$, $R^{b1}$, $R^{c1}$, and $R^{d1}$ of any of the above can be independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$. Each $R^g$ of any of the above can be independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy. In some cases, $R^2$ can be selected from H and $C_{1-6}$ alkyl; $R^3$ can be selected from H and $C_{1-6}$ alkyl; $R^1$ can be selected from H, $C_{1-6}$ alkyl, $C_{1-6}$ haloalkyl, C(O)$R^{b1}$, and C(O)$NR^{c1}R^{d1}$; wherein the $C_{1-6}$ alkyl is optionally substituted with 1, 2, or 3 substituents independently selected from $R^9$ (or $R^1$ and $R^2$, together with N atom to which $R^1$ is attached and C atom to which $R^2$ is attached, can form a 4-10 membered heterocycloalkyl ring, which is substituted with 1, 2, or 3 substituents independently selected from $R^9$); $R^4$ can be selected from H, $C_{1-6}$ alkyl, and $C_{1-6}$ haloalkyl, wherein the $C_{1-6}$ alkyl is optionally substituted with 1, 2, or 3 substituents independently selected from $R^9$; $R^5$ and $R^6$ can be each independently selected from H, halo, $C_{1-6}$ alkyl, $C_{1-6}$ haloalkyl, $OR^{a1}$, C(O)$NR^{c1}R^{d1}$, C(O)$OR^{a1}$, $NR^{c1}R^{d1}$, $NR^{c1}S(O)_2R^{b1}$, $S(O)_2R^{b1}$, and $S(O)_2NR^{c1}R^{d1}$; wherein the $C_{1-6}$ alkyl is optionally substituted with 1, 2, or 3 substituents independently selected from $R^9$; $R^7$ and $R^8$ can be independently selected from H, $C_{1-6}$ alkyl, and a moiety of formula (i); $R^N$ can be selected from H and $C_{1-6}$ alkyl (or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$); each $R^A$ can be independently selected from H, halo, CN, $C_{1-6}$ alkyl, $C_{1-6}$ haloalkyl, $OR^{a1}$, $SR^{a1}$, C(O)$R^{b1}$, C(O)$NR^{c1}R^{d1}$, C(O)$OR^{a1}$, $NR^{c1}R^{d1}$, $NR^{c1}C(O)R^{d1}$, $NR^{c1}C(O)OR^{a1}$, $NR^{c1}S(O)_2R^{b1}$, $S(O)_2R^{b1}$, and $S(O)_2NR^{c1}R^{d1}$; wherein the $C_{1-6}$ alkyl is optionally substituted with 1, 2, or 3 substituents independently selected from $R^{11}$; $R^{11}$ can be independently selected from $OR^{a1}$, C(O)$NR^{c1}R^{d1}$, C(O)$OR^{a1}$, $NR^{c1}R^{d1}$, $NR^{c1}C(O)R^{b1}$, $NR^{c1}S(O)_2R^{b1}$, and $S(O)_2NR^{c1}R^{d1}$; each $R^{a1}$, $R^{b1}$, $R^{c1}$, and $R^{d1}$ can be independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$; and each $R^g$ can be independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy. In some cases, $R^2$ can be selected from H and $C_{1-6}$ alkyl; $R^3$ can be selected from H and $C_{1-6}$ alkyl; $R^1$ can be selected from $C_{1-6}$ alkyl, C(O)$R^{b1}$, and C(O)$NR^{c1}R^{d1}$ (or $R^1$ and $R^2$, together with N atom to which $R^1$ is attached and C atom to which $R^2$ is attached, can form a 4-10 membered heterocycloalkyl ring, which is substituted with 1, 2, or 3 substituents independently selected from $R^9$); $R^4$ can be H; $R^5$ and $R^6$ can be each independently selected from H, halo, $C_{1-6}$ alkyl, and $S(O)_2R^{b1}$, wherein the $C_{1-6}$ alkyl is optionally substituted with $R^9$; $R^7$ and $R^8$ can be independently selected from H, $C_{1-6}$ alkyl, and a moiety of formula (i); $R^N$ can be selected from H and $C_{1-6}$ alkyl (or $R^N$ and $R^{11}$, together with the N atom to which they are attached, can form a ring selected from morpholinyl, piperidinyl, and piperazinyl, each of which is optionally substituted with 1, 2, or 3 substituents independently selected from $R^9$); each $R^A$ can be independently selected from H, halo, CN, $C_{1-6}$ alkyl, $C_{1-6}$ haloalkyl, $OR^{a1}$, $SR^{a1}$, C(O)$R^{b1}$, C(O)$OR^{a1}$, $NR^{c1}R^{d1}$ and $NR^{c1}C(O)R^{b1}$, wherein the $C_{1-6}$ alkyl is optionally substituted with C(O)$OR^{a1}$; each $R^{a1}$, $R^{b1}$, $R^{c1}$, and $R^{d1}$ can be independently selected from H and $C_{1-6}$ alkyl, wherein the $C_{1-6}$ alkyl is optionally substituted with 1, 2, or 3 substituents independently selected from $R^g$; and each $R^g$ can be independently selected from OH, $NO_2$, CN, halo, $C_{1-6}$ alkyl, $C_{1-6}$ alkoxy, $C_{1-6}$ haloalkoxy, amino, $C_{1-6}$ alkylamino, di($C_{1-6}$ alkyl)amino, and carboxy.

In another embodiment, the compound of Formula (I) can have formula (Ib):

(Ib)

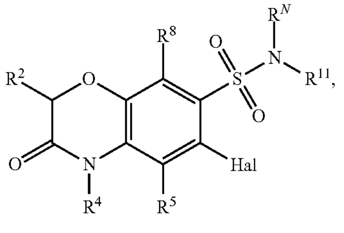

or a pharmaceutically acceptable salt thereof, wherein Hal is halogen. The $R^4$, $R^5$, and $R^8$ can be each H. $R^N$ can be H. Ring A can be selected from $C_{6-10}$ aryl and $C_{3-10}$ cycloalkyl, each of which is optionally substituted with 1-10 substituents independently selected from $R^A$. Each $R^A$ can be independently selected from H, halo, CN, $C_{1-6}$ alkyl, $C_{1-6}$ haloalkyl, $OR^{a1}$, $SR^{a1}$, and C(O)$R^{b1}$, wherein the $C_{1-6}$ alkyl is optionally substituted with 1, 2, or 3 substituents independently selected from $R^{10}$. Each $R^A$ can be independently selected from H, halo, $C_{1-6}$ alkyl, $C_{1-6}$ haloalkyl, $OR^{a1}$, $SR^{a1}$, and C(O)$R^{b1}$, wherein the $C_{1-6}$ alkyl is optionally substituted with 1, 2, or 3 substituents independently selected from $R^{10}$. In some cases, $R^2$ can be selected from H and $C_{1-6}$ alkyl; $R^4$, $R^5$, and $R^8$ can be each H; $R^N$ can be H (or $R^N$ and $R^{11}$, together with the N atom to which they are attached, can form a ring selected from pyrrolidinyl, morpholinyl, and piperazinyl, each of which is optionally substituted with 1, 2, or 3 substituents independently selected from $R^9$); ring A can be selected from $C_{6-10}$ aryl and $C_{3-10}$ cycloalkyl, each of which is optionally substituted with 1-10 substituents independently selected from $R^A$; and each $R^A$ can be independently selected from H, halo, CN, $C_{1-6}$ alkyl, $C_{1-6}$ haloalkyl, $OR^{a1}$, $SR^{a1}$, and C(O)$R^{b1}$, wherein the $C_{1-6}$ alkyl is optionally substituted with 1, 2, or 3 substituents independently selected from $R^{10}$. In some cases, $R^A$ can be independently selected from H, halo, $C_{1-6}$ alkyl, $C_{1-6}$ haloalkyl, $OR^{a1}$, $SR^{a1}$, and C(O)$R^{b1}$, wherein the $C_{1-6}$ alkyl is optionally substituted with 1, 2, or 3 substituents independently selected from $R^{10}$.

In another embodiment, the compound of Formula (I) can have Formula (Ic):

(Ic)

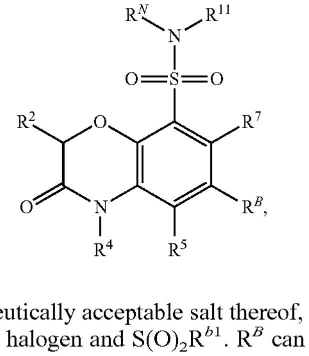

or a pharmaceutically acceptable salt thereof, wherein $R^B$ is selected from halogen and $S(O)_2R^{b1}$. $R^B$ can be a halogen.

$R^B$ can be a $S(O)_2R^{b1}$. $R^2$ can be selected H and $C_{1-6}$ alkyl. $R^4$ can be H. $R^5$ can be H. $R^7$ can be selected H and $C_{1-6}$ alkyl. $R^N$ can be H. $R^N$ and $R^{11}$, together with the N atom to which they are attached, can form a ring selected from morpholinyl and piperazinyl, each of which is optionally substituted with 1, 2, or 3 substituents independently selected from $R^9$. Ring A can be selected from $C_{6-10}$ aryl and $C_{3-10}$ cycloalkyl, optionally substituted with 1-10 substituents independently selected from $R^A$. Each $R^A$ can be independently selected from H, halo, CN, $C_{1-6}$ alkyl, $C_{1-6}$ haloalkyl, and $OR^{a1}$; wherein the $C_{1-6}$ alkyl is optionally substituted with 1, 2, or 3 substituents independently selected from $R^{10}$. In some cases, $R^2$ can be selected H and $C_{1-6}$ alkyl; $R^4$ can be H; $R^5$ can be H; $R^7$ can be selected H and $C_{1-6}$ alkyl; $R^N$ can be H (or $R^N$ and $R^{11}$, together with the N atom to which they are attached, can form a ring selected from morpholinyl and piperazinyl, each of which is optionally substituted with 1, 2, or 3 substituents independently selected from $R^9$); ring A can be selected from $C_{6-10}$ aryl and $C_{3-10}$ cycloalkyl, optionally substituted with 1-10 substituents independently selected from $R^A$; and each $R^A$ can be independently selected from H, halo, CN, $C_{1-6}$ alkyl, $C_{1-6}$ haloalkyl, and $OR^{a1}$; wherein the $C_{1-6}$ alkyl is optionally substituted with 1, 2, or 3 substituents independently selected from $R^{10}$.

In another embodiment, the compound of Formula (I) has Formula (Id):

(Id)

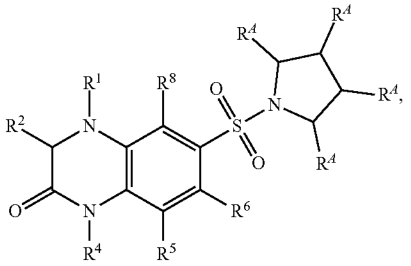

or a pharmaceutically acceptable salt thereof. $R^2$ can be selected from H and $C_{1-6}$ alkyl. $R^4$ can be H. $R^5$, $R^6$, and $R^8$ can be each H. $R^1$ can be selected from H, $C_{1-6}$ alkyl, $C(O)R^{b1}$, and $C(O)NR^{c1}R^{d1}$, wherein the $C_{1-6}$ alkyl is optionally substituted with 1, 2, or 3 substituents independently selected from $R^9$. Each $R^A$ can be H. In some cases, $R^2$ can be selected from H and $C_{1-6}$ alkyl; $R^4$ can be H; $R^5$, $R^6$, and $R^8$ can be each H; $R^1$ can be selected from H, $C_{1-6}$ alkyl, $C(O)R^{b1}$, and $C(O)NR^{c1}R^{d1}$, wherein the $C_{1-6}$ alkyl is optionally substituted with 1, 2, or 3 substituents independently selected from $R^9$; each $R^9$ can be independently selected from OH, $C_{1-6}$ alkoxy, carboxy, $C(O)NH_2$, amino, $C_{1-6}$ alkylamino, and di($C_{1-6}$ alkyl)amino; and each $R^A$ can be H.

In another embodiment, the compound of Formula (I) can have Formula (Ie):

(Ie)

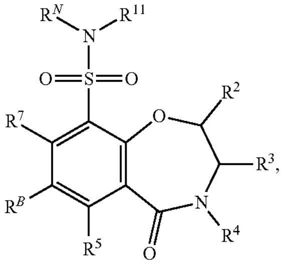

or a pharmaceutically acceptable salt thereof, wherein $R^B$ is selected from halogen and $S(O)_2R^{b1}$.

In another embodiment, the compound of Formula (I) can have Formula (If):

(If)

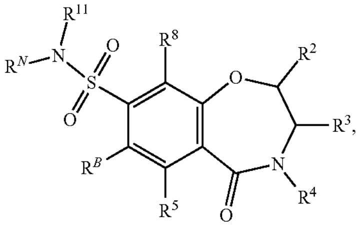

or a pharmaceutically acceptable salt thereof, wherein R is selected from halogen and $S(O)_2R^{b1}$. $R^B$ can be a halogen. $R^B$ can be $S(O)_2R^{b1}$. $R^2$ and $R^3$ can be each independently selected from H and $C_{1-6}$ alkyl. $R^4$ can be H. $R^5$ can be H. $R^8$ can be selected H and $C_{1-6}$ alkyl. $R^N$ can be H. Ring A can be $C_{6-10}$ aryl, optionally substituted with 1-5 substituents independently selected from $R^A$. Each $R^A$ can be independently selected from H, halo, CN, $C_{1-6}$ alkyl, $C_{1-6}$ haloalkyl, and $OR^{a1}$; wherein the $C_{1-6}$ alkyl is optionally substituted with 1, 2, or 3 substituents independently selected from $R^{10}$. In some cases, $R^2$ and $R^3$ can be each independently selected H and $C_{1-6}$ alkyl; $R^4$ can be H; $R^5$ can be H; $R^8$ can be selected H and $C_{1-6}$ alkyl; $R^N$ can be H; $R^{11}$ can be $C_{6-10}$ aryl, optionally substituted with 1-5 substituents independently selected from $R^A$; and each $R^A$ can be independently selected from H, halo, CN, $C_{1-6}$ alkyl, $C_{1-6}$ haloalkyl, $C_{1-6}$ alkoxy, and $C_{1-6}$ haloalkoxy.

In another embodiment, the compound of Formula (I) can have Formula (Ig):

(Ig)

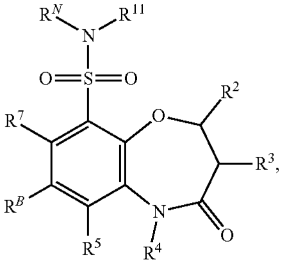

or a pharmaceutically acceptable salt thereof, wherein $R^B$ is selected from halogen and $S(O)_2R^{b1}$. $R^B$ can be a halogen. $R^B$ can be $S(O)_2R^{b1}$. $R^2$ and $R^3$ can be each independently selected from H and $C_{1-6}$ alkyl. $R^4$ can be H. $R^5$ can be H.

$R^7$ can be selected H and $C_{1-6}$ alkyl. $R^N$ can be H. Ring A can be $C_{6-10}$ aryl, optionally substituted with 1-5 substituents independently selected from $R^A$. Each $R^A$ can be independently selected from H, halo, CN, $C_{1-6}$ alkyl, $C_{1-6}$ haloalkyl, and $OR^{a1}$; wherein the $C_{1-6}$ alkyl is optionally substituted with 1, 2, or 3 substituents independently selected from $R^{10}$. In some cases, $R^2$ and $R^3$ can be each independently selected H and $C_{1-6}$ alkyl; $R^4$ can be H; $R^5$ can be H; $R^7$ can be selected H and $C_{1-6}$ alkyl; $R^N$ can be H; $R^{11}$ can be $C_{6-10}$ aryl, optionally substituted with 1-5 substituents independently selected from $R^A$; and each $R^A$ can be independently selected from H, halo, CN, $C_{1-6}$ alkyl, $C_{1-6}$ haloalkyl, $C_{1-6}$ alkoxy, and $C_{1-6}$ haloalkoxy.

In some embodiments, the compound of Formula (I) can be selected from any one of the compounds listed in Table 1, Table 2, Table 3, Table 4, Table 5, Table 6, Table 7, Table 8, Table 9, and Table 10, or a pharmaceutically acceptable salt thereof.

In some cases, the method can comprise identifying the mammal as being in need of inhibited CB1 activity. The method can be a method for treating obesity. The method can be a method for treating fear. The method can be a method for treating a metabolic-related disorder. The method can be a method for treating diabetes. The method can be a method for treating dyslipidaemia. The method can be a method for treating atherosclerosis. The method can be a method for reducing food intake of the mammal. The method can be a method for reducing body weight gain of the mammal. The method can be a method for improving lipid profiles within the mammal. The method can be a method for improving glycemic profiles within the mammal. The method can be a method for assisting the mammal in stopping tobacco use and/or *cannabis* use. The method can be a method for treating a liver disorder. The liver disorder can be fatty liver disease, nonalcoholic steatohepatitis (NASH), cirrhosis, or liver cancer. The method can be a method for reducing a symptom or the progression of idiopathic pulmonary fibrosis or a fibrotic condition in the lung. The method can be a method for reducing the severity of or occurrence of end-organ damage induced by chronic alcohol usage. The end-organ damage can be heart failure, pancreatitis, or liver disease. The method can be a method for reducing a complication of chronic renal disease characterized by renal fibrosis. The chronic renal disease can be diabetic nephropathy or inherited or acquired glomerular diseases. The administering step can reduce CB1 activity within the peripheral nervous system of the mammal. The administering step can reduce little if any CB1 activity within the central nervous system of the mammal. The administering step can be an administering step that does not reduce CB1 activity within the central nervous system of the mammal.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

This document provides methods and materials for inhibiting CB1 activity.

For example, the document provides compounds (e.g., organic compounds) having the ability to inhibit CB1 activity within a mammal (e.g., a human), formulations containing one or more compounds having the ability to inhibit CB1 activity within a mammal (e.g., a human), methods for making one or more compounds having the ability to inhibit CB1 activity within a mammal (e.g., a human), methods for making formulations containing one or more compounds having the ability to inhibit CB1 activity within a mammal (e.g., a human), methods for inhibiting CB1 activity within a mammal (e.g., a human), and methods for treating mammals (e.g., humans) having a condition responsive to inhibition of CB1 activity. Suitable examples of conditions responsive to inhibition of CB1 activity within a mammal include, without limitation, obesity, fear, metabolic-related disorders, diabetes, dyslipidaemia, atherosclerosis, pulmonary fibrosis, renal fibrosis, NASH, and alcohol-induced organ dysfunction.

In some cases, a CB1 inhibitor described herein can be used to reduce food intake of a mammal (e.g., a human), to reduce the body weight gain of a mammal (e.g., a human), to improve lipid profiles within a mammal (e.g., a human), to improve glycemic profiles within a mammal (e.g., a human), and/or to assist a mammal (e.g., a human) in stopping tobacco use (e.g., cigarette smoking).

In some cases, a CB1 inhibitor described herein can be used to inhibit CB1 activity within the peripheral nervous system of a mammal (e.g., a human) with little or no inhibition of CB1 activity within the central nervous system of that mammal. For example, a CB1 inhibitor described herein can be used to reduce food intake of a mammal (e.g., a human), to reduce the body weight gain of a mammal (e.g., a human), to improve lipid profiles within a mammal (e.g., a human), to improve glycemic profiles within a mammal (e.g., a human), and/or to assist a mammal (e.g., a human) in stopping tobacco use (e.g., cigarette smoking), with reduced side effects associated with inhibition of CB1 within the central nervous system such as psychiatric disorder side effects.

Methods of Treatment Using One or More Inhibitors of CB1 Activity

In some cases, this document provides methods for inhibiting CB1 activity within a mammal by contacting a cell with a compound of Formula (I):

(I)

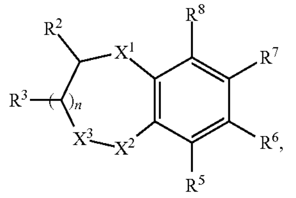

or a pharmaceutically acceptable salt thereof, wherein $X^1$, $X^2$, $X^3$, n, $R^2$, $R^3$, $R^5$, $R^6$, $R^7$, and $R^8$ are as described herein.

In one general aspect, this document provides a pharmaceutical composition comprising a compound of Formula (I), or a pharmaceutically acceptable salt thereof, and a pharmaceutically acceptable a carrier.

In some cases, methods for inhibiting CB1 activity of a cell can be performed in vivo. For example, one or more compounds provided herein (e.g., a compound set forth in Formula (I), or a pharmaceutically acceptable salt thereof) can be administered to a mammal (e.g., a human) to inhibit CB1 activity within that mammal. In some cases, methods for inhibiting CB1 activity of cells can be performed in vitro. For example, one or more compounds provided herein (e.g., a compound set forth in Formula (I), or a pharmaceutically acceptable salt thereof) can be added to a cell culture containing cells (e.g., human cells) to inhibit CB1 activity within those cells. In some cases, such intervention can improve the quality of the cell while in culture or subsequently.

This document also provides methods for treating diseases, disorders, and conditions in a mammal by administering one or more compounds provided herein (e.g., a compound set forth in Formula (I), or a pharmaceutically acceptable salt thereof) to a mammal in need thereof. In some cases, the disease, disorder, or condition being treated can be a disease, disorder, or condition that is responsive to inhibiting CB1 activity within the mammal (e.g., a human). In some cases, the disease, disorder, or condition being treated can be a disease, disorder, or condition that is associated with CB1 activity within the mammal. Examples of diseases, disorders, and conditions that can be treated with one or more compounds provided herein include, without limitation, obesity, fear, metabolic-related disorders, diabetes, dyslipidaemia, atherosclerosis, NASH, idiopathic pulmonary fibrosis, alcohol-induced end-organ damage (e.g., heart failure, pancreatitis, and/or liver disease), and chronic renal disease characterized by renal fibrosis. Examples of metabolic-related disorders that can be treated with one or more compounds provided herein include, without limitation, fatty liver, diabetic nephropathy, and defects of insulin secretion or sensitivity.

In some cases, provided herein are methods for treating obesity in a mammal (e.g., human) by administering one or more compounds provided herein (e.g., a compound set forth in Formula (I), or a pharmaceutically acceptable salt thereof) to a mammal in need thereof.

In some cases, provided herein are methods for treating fear in a mammal (e.g., human) by administering one or more compounds provided herein (e.g., a compound set forth Formula (I), or a pharmaceutically acceptable salt thereof) to a mammal in need thereof.

In some cases, provided herein are methods for treating a metabolic-related disorder (e.g., any one of the metabolic-related disorders described herein) in a mammal (e.g., human) by administering one or more compounds provided herein (e.g., a compound set forth in Formula (I), or a pharmaceutically acceptable salt thereof) to a mammal in need thereof.

In some cases, provided herein are methods for treating diabetes in a mammal (e.g., human) by administering one or more compounds provided herein (e.g., a compound set forth in Formula (I), or a pharmaceutically acceptable salt thereof) to a mammal in need thereof.

In some cases, provided herein are methods for treating dyslipidaemia in a mammal (e.g., human) by administering one or more compounds provided herein (e.g., a compound set forth in Formula (I), or a pharmaceutically acceptable salt thereof) to a mammal in need thereof.

In some cases, provided herein are methods for treating atherosclerosis in a mammal (e.g., human) by administering one or more compounds provided herein (e.g., a compound set forth in Formula (I), or a pharmaceutically acceptable salt thereof) to a mammal in need thereof.

This document also provides methods for reducing food intake of a mammal (e.g., a human), reducing body weight gain of a mammal (e.g., a human), improving lipid profiles within a mammal (e.g., a human), improving glycemic profiles within a mammal (e.g., a human), and/or assisting a mammal (e.g., a human) in stopping tobacco use (e.g., cigarette smoking).

In some cases, provided herein are methods for reducing food intake of a mammal (e.g., a human) by administering one or more compounds provided herein (e.g., a compound set forth in Formula (I), or a pharmaceutically acceptable salt thereof) to a mammal in need thereof.

In some cases, provided herein are methods for reducing body weight gain of a mammal (e.g., a human) by administering one or more compounds provided herein (e.g., a compound set forth in Formula (I), or a pharmaceutically acceptable salt thereof) to a mammal in need thereof.

In some cases, provided herein are methods for improving lipid profiles within a mammal (e.g., a human) by administering one or more compounds provided herein (e.g., a compound set forth in Formula (I), or a pharmaceutically acceptable salt thereof) to a mammal in need thereof.

In some cases, provided herein are methods for improving glycemic profiles within a mammal (e.g., a human) by administering one or more compounds provided herein (e.g., a compound set forth in Formula (I), or a pharmaceutically acceptable salt thereof) to a mammal in need thereof.

In some cases, provided herein are methods for assisting a mammal (e.g., a human) in stopping tobacco use (e.g., cigarette smoking) by administering one or more compounds provided herein (e.g., a compound set forth in Formula (I), or a pharmaceutically acceptable salt thereof) to a mammal in need thereof.

As described herein, one or more compounds provided herein (e.g., a compound set forth in Formula (I), or a pharmaceutically acceptable salt thereof) can be administered to a mammal (e.g., a human) to inhibit CB1 activity within the peripheral nervous system with little or no inhibition within the central nervous system of the mammal. For example, one or more compounds provided herein (e.g., a compound set forth in Formula (I), or a pharmaceutically acceptable salt thereof) can be administered to a mammal (e.g., a human) to treat obesity, fear, metabolic-related disorders, diabetes, dyslipidaemia, and/or atherosclerosis, or to assist in stopping tobacco use (e.g., cigarette smoking), *cannabis* use, or the unwanted use of other addictive agents with reduced side effects associated with inhibition of CB1 within the central nervous system such as psychiatric disorder side effects. As another example, one or more compounds provided herein (e.g., a compound set forth in Formula (I), or a pharmaceutically acceptable salt thereof) can be administered to a mammal (e.g., a human) to reduce food intake of a mammal (e.g., a human), to reduce body weight gain of a mammal (e.g., a human), to improve lipid profiles within a mammal (e.g., a human), to improve glycemic profiles within a mammal (e.g., a human), and/or to assist a mammal (e.g., a human) in stopping tobacco use (e.g., cigarette smoking) with reduced side effects associated with inhibition of CB1 within the central nervous system such as psychiatric disorder side effects.

In some cases, one or more compounds provided herein (e.g., a compound set forth in Formula (I), or a pharmaceutically acceptable salt thereof) can be used as described herein (e.g., to inhibit CB1 activity within a mammal and/or to treat a disease, disorder, or condition as described herein)

as the sole active ingredient(s). For example, a composition containing a compound of Formula (I), or a pharmaceutically acceptable salt thereof, can lack any other active ingredients that inhibit CB1 activity within cells. In some cases, a composition containing a compound set forth in Formula (I), or a pharmaceutically acceptable salt thereof, can lack any other active ingredients that are effective to treat a disease, disorder, or condition as described herein.

Therapeutic Compounds

As described herein, any one or more of the compounds provided herein can be used to inhibit CB1 activity within a mammal and/or can be used to treat (or prevent) a disease, disorder, and condition in a mammal (e.g., a human) as described herein.

Formula (I)

In one general aspect, the present disclosure provides a compound of Formula (I):

(I)

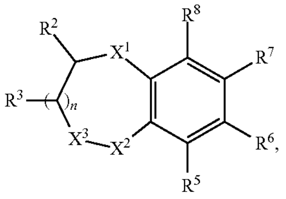

or a pharmaceutically acceptable salt thereof, wherein $X^1$, $X^2$, $X^3$, n, $R^2$, $R^3$, $R^5$, $R^6$, $R^7$, and $R^8$ are as described herein.

In some embodiments:

$X^1$ is selected from O and $NR^1$;

$X^2$ is selected from $NR^4$ and C(═O);

$X^3$ is selected from $CHR^3$, $NR^4$ and C(═O), provided that:

(i) $X^2$ is $NR^4$ and $X^3$ is C(═O); or (ii) $X^2$ is C(═O) and $X^3$ is selected from $CHR^3$ and $NR^4$;

n is 0 or 1;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

each $R^3$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^9$;

each $R^1$ and $R^4$ is independently selected from H, $C_{1-6}$ alkyl, $C_{1-6}$ haloalkyl, $C_{2-6}$ alkenyl, $C_{2-6}$ alkynyl, C(O)$R^{b1}$, C(O)$NR^{c1}R^{d1}$, C(O)$OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^5$, $R^6$, $R^7$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, $S(O)_2NR^{c1}R^{d1}$; and a group of formula (i):

(i)

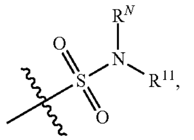

wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, for a -10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is optionally substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is O.

In some embodiments, $X^1$ is $NR^1$.

In some embodiments, $X^2$ is $NR^4$.

In some embodiments, $X^2$ is C(═O).

In some embodiments, $X^2$ is $NR^4$.

In some embodiments, $X^2$ is $CHR^3$.

In some embodiments, $X^2$ is C(═O).

In some embodiments, $X^2$ is $NR^4$ and $X^3$ is C(═O).

In some embodiments, $X^2$ is $NR^4$ and $X^3$ is $CHR^3$.

In some embodiments, $X^2$ is C(═O) and $X^3$ is selected from $CHR^3$ and $NR^4$.

In some embodiments, $X^2$ is C(═O) and $X^3$ is $CHR^3$.

In some embodiments, $X^2$ is C(═O) and $X^3$ is $NR^4$.

In some embodiments, n is 1.

In some embodiments, n is 0 (i.e., there is a bond between $X^3$ and a carbon atom to which $R^2$ is attached).

In some embodiments, at least one of $R^5$, $R^6$, $R^7$, and $R^8$ is a group of formula (i).

In some embodiments, at least one of $R^7$ and $R^8$ is a group of formula (i).

In some embodiments, $R^7$ is a group of formula (i).

In some embodiments, $R^8$ is a group of formula (i).

In some embodiments, the compound of Formula (I) has formula:

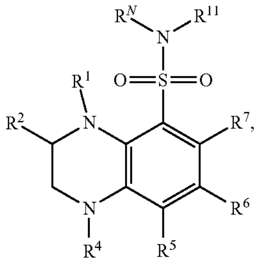

or a pharmaceutically acceptable salt thereof.

In some embodiments, the compound of Formula (I) has formula:

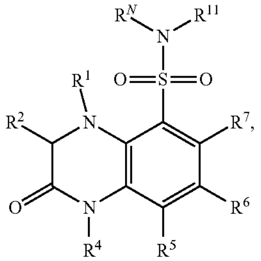

or a pharmaceutically acceptable salt thereof.

In some embodiments, the compound of Formula (I) has formula:

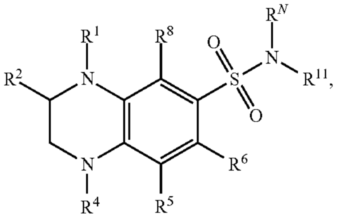

or a pharmaceutically acceptable salt thereof.

In some embodiments, the compound of Formula (I) has formula:

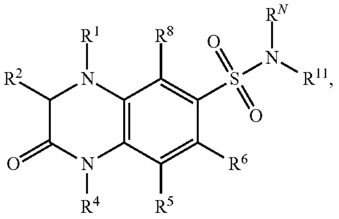

or a pharmaceutically acceptable salt thereof.

In some embodiments:

$R^2$ is selected from H and $C_{1-6}$ alkyl;

$R^1$ is selected from H, $C_{1-6}$ alkyl, $C_{1-6}$ haloalkyl, $C(O)R^{b1}$, and $C(O)NR^{c1}R^{d1}$; wherein said $C_{1-6}$ alkyl is optionally substituted with 1, 2, or 3 substituents independently selected from $R^9$.

In some embodiments:

$R^2$ is selected from H and $C_{1-6}$ alkyl;

$R^1$ is selected from $C_{1-6}$ alkyl, $C(O)R^{b1}$, and $C(O)NR^{c1}R^{d1}$.

In some embodiments, the compound of Formula (I) has formula:

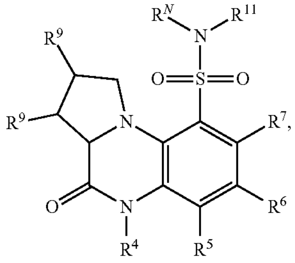

or a pharmaceutically acceptable salt thereof.

In some embodiments, the compound of Formula (I) has formula:

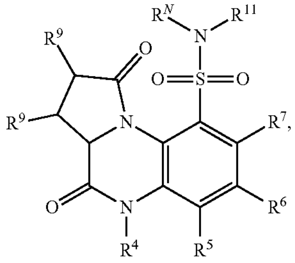

or a pharmaceutically acceptable salt thereof.

In some embodiments, the compound of Formula (I) has formula:

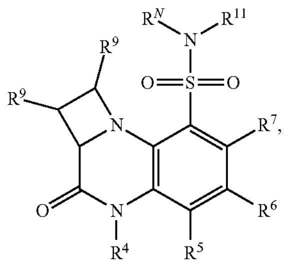

or a pharmaceutically acceptable salt thereof.

In some embodiments, the compound of Formula (I) has formula:

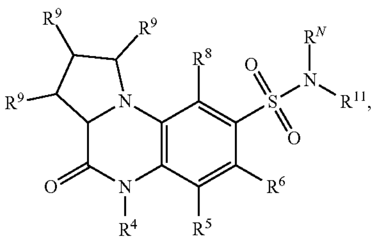

or a pharmaceutically acceptable salt thereof.

In some embodiments, the compound of Formula (I) has formula:

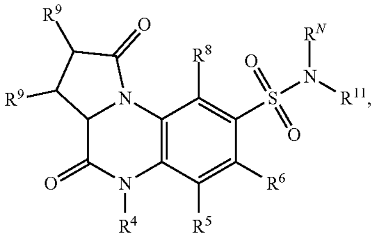

or a pharmaceutically acceptable salt thereof.

In some embodiments, the compound of Formula (I) has formula:

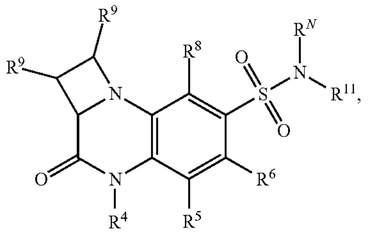

or a pharmaceutically acceptable salt thereof.

In some embodiments, the compound of Formula (I) has formula:

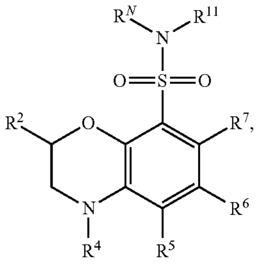

or a pharmaceutically acceptable salt thereof.

In some embodiments, the compound of Formula (I) has formula:

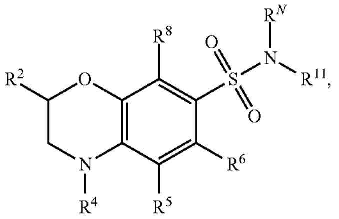

or a pharmaceutically acceptable salt thereof.

In some embodiments, the compound of Formula (I) has formula:

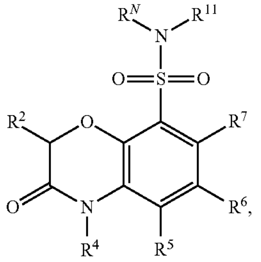

or a pharmaceutically acceptable salt thereof.

In some embodiments, the compound of Formula (I) has formula:

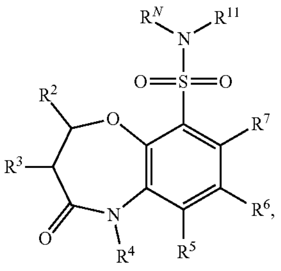

or a pharmaceutically acceptable salt thereof.

In some embodiments, the compound of Formula (I) has formula:

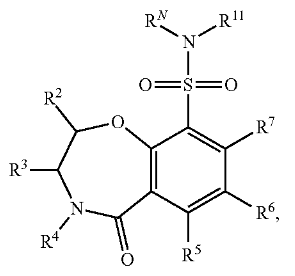

or a pharmaceutically acceptable salt thereof.

In some embodiments, the compound of Formula (I) has formula:

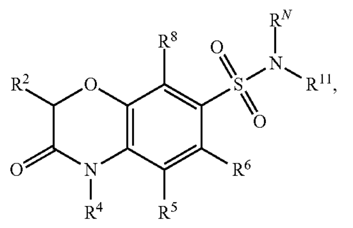

or a pharmaceutically acceptable salt thereof.

In some embodiments, the compound of Formula (I) has formula:

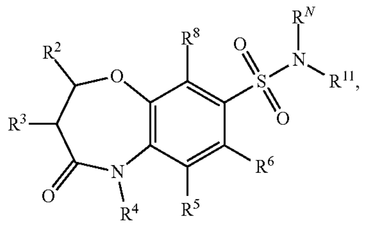

or a pharmaceutically acceptable salt thereof.

In some embodiments, $R^2$ is selected from H and $C_{1-6}$ alkyl. In some embodiments, $R^2$ is H. In some embodiments, $R^2$ is $C_{1-6}$ alkyl.

In some embodiments, $R^3$ is selected from H and $C_{1-6}$ alkyl. In some embodiments, $R^3$ is H. In some embodiments, $R^3$ is $C_{1-6}$ alkyl.

In some embodiments, $R^4$ is selected from H, $C_{1-6}$ alkyl, and $C_{1-6}$ haloalkyl, wherein said $C_{1-6}$ alkyl is optionally substituted with 1, 2, or 3 substituents independently selected from $R^9$. In some embodiments, $R^4$ is H. In some embodiments, $R^4$ is $C_{1-6}$ alkyl.

In some embodiments, $R^5$ and $R^6$ are each independently selected from H, halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$ $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$.

In some embodiments, $R^5$ and $R^6$ are each independently selected from H, halo, $C_{1-6}$ alkyl, and $S(O)_2R^{b1}$, wherein said $C_{1-6}$ alkyl is optionally substituted with $R^9$.

In some embodiments, $R^5$ is H and $R^6$ is $C_{1-6}$ alkyl, optionally substituted with $NR^{c1}R^{d1}$. In some embodiments, $R^5$ is H and $R^6$ is halo. In some embodiments, $R^5$ is H and $R^6$ is $S(O)_2R^{b1}$.

In some embodiments, $R^7$ is selected from H and $C_{1-6}$ alkyl (and $R^8$ is a moiety of formula (i)). In some embodiments, $R^8$ is selected from H and $C_{1-6}$ alkyl (and $R^7$ is a moiety of formula (i)).

In some embodiments, $R^N$ is selected from H and $C_{1-6}$ alkyl. In some embodiments, $R^N$ is H. In some embodiments, $R^N$ is $C_{1-6}$ alkyl.

In some embodiments, $R^{11}$ is ring A.

In some embodiments, $R^{11}$ is $C_{1-6}$ alkyl, optionally substituted with ring A.

In some embodiments, $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$.

In some embodiments, ring A is selected from $C_{6-10}$ aryl and $C_{3-10}$ cycloalkyl, each of which is optionally substituted with 1-10 substituents independently selected from $R^A$.

In some embodiments, ring A is 4-10 membered heterocycloalkyl, optionally substituted with 1-10 substituents independently selected from $R^A$.

In some embodiments, ring A is $C_{6-10}$ aryl, optionally substituted with 1-10 substituents independently selected from $R^A$.

In some embodiments, ring A is $C_{3-10}$ cycloalkyl, optionally substituted with 1-10 substituents independently selected from $R^A$.

In some embodiments, ring A is 5-10 membered heteroaryl, optionally substituted with 1-10 substituents independently selected from $R^A$.

In some embodiments, ring A is selected from any one of the following moieties:

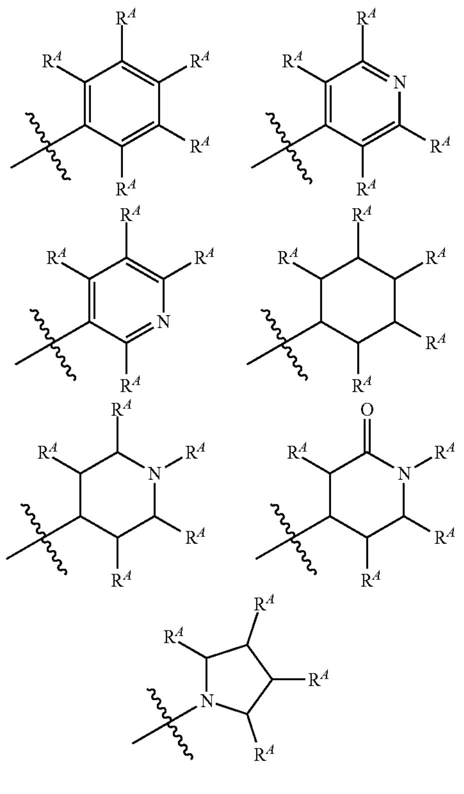

In some embodiments, each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$; $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{11}$.

In some embodiments, each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$ and $NR^{c1}C(O)R^{b1}$, wherein said $C_{1-6}$ alkyl is optionally substituted with 1, 2, or 3 substituents independently selected from $R^{11}$.

In some embodiments, each $R^{11}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$.

In some embodiments, each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$ and $NR^{c1}C(O)R^{b1}$, wherein said $C_{1-6}$ alkyl is optionally substituted with $C(O)OR^{a1}$.

In some embodiments, each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

In some embodiments, each $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

In some embodiments, each $R^9$ is independently selected from H, $C_{1-6}$ alkyl, $C_{1-6}$ haloalkyl, halo, CN, OH, $C_{1-6}$ alkoxy, carboxy, amino, $C(O)NH_2$, $C_{1-6}$ alkylamino, di($C_{1-6}$ alkyl)amino, and $C_{1-6}$ haloalkoxy. In some embodiments, each $R^9$ is independently selected from OH, $C_{1-6}$ alkoxy, carboxy, $C(O)NH_2$, amino, $C_{1-6}$ alkylamino, and di($C_{1-6}$ alkyl)amino.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, $C(O)NH_2$, and carboxy.

In some embodiments, each $R^{a1}$, $R^{b1}$, $R^{c1}$, and $R^{d1}$ is independently selected from H and $C_{1-6}$ alkyl, wherein said $C_{1-6}$ alkyl is optionally substituted with 1, 2, or 3 substituents independently selected from $R^g$; and In some embodiments, each $R^g$ is independently selected from OH, $NO_2$, CN, halo, $C_{1-6}$ alkyl, $C_{1-6}$ alkoxy, $C_{1-6}$ haloalkoxy, amino, $C_{1-6}$ alkylamino, di($C_{1-6}$ alkyl)amino, and carboxy.

In some embodiments:

each $R^3$ is independently selected from H and $C_{1-6}$ alkyl;

$R^1$ is selected from H, $C_{1-6}$ alkyl, $C_{1-6}$ haloalkyl, $C(O)R^{b1}$, and $C(O)NR^{c1}R^{d1}$; wherein said $C_{1-6}$ alkyl is optionally substituted with 1, 2, or 3 substituents independently selected from $R^9$;

$R^2$ is selected from H and $C_{1-6}$ alkyl; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

each $R^4$ is independently selected from H, $C_{1-6}$ alkyl, and $C_{1-6}$ haloalkyl, wherein said $C_{1-6}$ alkyl is optionally substituted with 1, 2, or 3 substituents independently selected from $R^9$;

$R^5$ and $R^6$ are each independently selected from H, halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{10}$;

each $R^{10}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl) amino, and carboxy.

In some embodiments:

each $R^3$ is independently selected from H and $C_{1-6}$ alkyl;

$R^1$ is selected from $C_{1-6}$ alkyl, $C(O)R^{b1}$, and $C(O)NR^{c1}R^{d1}$;

$R^2$ is selected from H and $C_{1-6}$ alkyl; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

each $R^4$ is H;

$R^5$ and $R^6$ are each independently selected from H, halo, $C_{1-6}$ alkyl, and $S(O)_2R^{b1}$, wherein said $C_{1-6}$ alkyl is optionally substituted with $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$ $NR^{c1}R^{d1}$, and $NR^{c1}C(O)R^{b1}$, wherein said $C_{1-6}$ alkyl is optionally substituted with $C(O)OR^{a1}$;

each $R^{a1}$, $R^{b1}$, $R^{c1}$, and $R^{d1}$ is independently selected from H and $C_{1-6}$ alkyl, wherein said $C_{1-6}$ alkyl is optionally substituted with 1, 2, or 3 substituents independently selected from $R^g$; and each $R^g$ is independently selected from OH, $NO_2$, CN, halo, $C_{1-6}$ alkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (I) is selected from any one of the compounds of Table 1, Table 2, Table 3, Table 4, Table 5, Table 6, Table 7, Table 8, Table 9, and Table 10, or a pharmaceutically acceptable salt thereof.

In some embodiments, the compound of Formula (I) is selected from any one of the compounds of Table 1, or a pharmaceutically acceptable salt thereof. In some embodiments, the compound of Formula (I) is selected from any one of the compounds of Table 2, or a pharmaceutically acceptable salt thereof. In some embodiments, the compound of Formula (I) is selected from any one of the compounds of Table 3, or a pharmaceutically acceptable salt thereof. In some embodiments, the compound of Formula (I) is selected from any one of the compounds of Table 4, or a pharmaceutically acceptable salt thereof. In some embodiments, the compound of Formula (I) is selected from any one of the compounds of Table 5, or a pharmaceutically acceptable salt thereof. In some embodiments, the compound of Formula (I) is selected from any one of the compounds of Table 6, or a pharmaceutically acceptable salt thereof. In some embodiments, the compound of Formula (I) is selected from any one of the compounds of Table 7, or a pharmaceutically acceptable salt thereof. In some embodiments, the compound of Formula (I) is selected from any one of the compounds of Table 8, or a pharmaceutically acceptable salt thereof. In some embodiments, the compound of Formula (I) is selected from any one of the compounds of Table 9, or a pharmaceutically acceptable salt thereof. In some embodiments, the compound of Formula (I) is selected from any one of the compounds of Table 10, or a pharmaceutically acceptable salt thereof.

In some embodiments, the compound of Formula (I) has Formula (Ib), or a pharmaceutically acceptable salt thereof. In some embodiments, the compound of Formula (I) has Formula (Ic), or a pharmaceutically acceptable salt thereof. In some embodiments, the compound of Formula (I) has Formula (Id), or a pharmaceutically acceptable salt thereof. In some embodiments, the compound of Formula (I) has Formula (Ie), or a pharmaceutically acceptable salt thereof. In some embodiments, the compound of Formula (I) has Formula (If), or a pharmaceutically acceptable salt thereof. In some embodiments, the compound of Formula (I) has Formula (Ig), or a pharmaceutically acceptable salt thereof.

Formula (Ib)

In one general aspect, the present disclosure provides a compound of Formula (Ib):

(Ib)

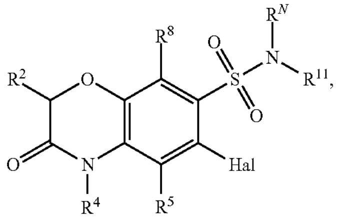

or a pharmaceutically acceptable salt thereof, wherein:

Hal is halogen, and $R^2$, $R^4$, $R^5$, $R^8$, $R^N$, and $R^{11}$ are as described herein for Formula (I).

In some embodiments:

Hal is a halogen;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ is selected from H, $C_{1-6}$ alkyl, $C_{1-6}$ haloalkyl, $C_{2-6}$ alkenyl, $C_{2-6}$ alkynyl, C(O)$R^{b1}$, C(O)N$R^{c1}R^{d1}$, C(O)O$R^{a1}$, S(O)$_2R^{b1}$, and S(O)$_2$N$R^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, O$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, for a -10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, O$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, O$R^{a1}$, S$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, O$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^2$ is H or $C_{1-6}$ alkyl.

In some embodiments, $R^4$ is H or $C_{1-6}$ alkyl.

In some embodiments, $R^5$ is H or $C_{1-6}$ alkyl.

In some embodiments, $R^8$ is H or $C_{1-6}$ alkyl.

In some embodiments, $R^4$, $R^5$, and $R^8$ are each H.

In some embodiments, $R^N$ is H.

In some embodiments, $R^N$ and $R^{11}$, together with the N atom to which they are attached, form a ring selected from pyrrolidinyl, morpholinyl, piperidinyl, and piperazinyl, each of which is optionally substituted with 1, 2, or 3 substituents independently selected from $R^9$.

In some embodiments, $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$.

In some embodiments, $R^{11}$ is ring A. In some embodiments, $R^{11}$ is $C_{1-6}$ alkyl, optionally substituted with ring A.

In some embodiments, ring A is selected from $C_{6-10}$ aryl and $C_{3-10}$ cycloalkyl, each of which is optionally substituted with 1-10 substituents independently selected from $R^A$.

In some embodiments, ring A is $C_{6-10}$ aryl, optionally substituted with 1-10 substituents independently selected from $R^A$.

In some embodiments, ring A is $C_{3-10}$ cycloalkyl, optionally substituted with 1-substituents independently selected from $R^A$.

In some embodiments, each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

In some embodiments, each $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

In some embodiments:

$R^2$ is selected from H and $C_{1-6}$ alkyl;

$R^4$, $R^5$, and $R^8$ are each H;

$R^N$ is H; or $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$;

ring A is selected from $C_{6-10}$ aryl and $C_{3-10}$ cycloalkyl, each of which is optionally substituted with 1-10 substituents independently selected from $R^A$; and each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

In some embodiments, $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Ib) is selected from any one of the compounds of Table 2 or Table 3, or a pharmaceutically acceptable salt thereof.

In some embodiments, the compound of Formula (Ib) is selected from any one of the compounds of Table 2, or a pharmaceutically acceptable salt thereof. In some embodiments, the compound of Formula (Ib) is selected from any one of the compounds of Table 3, or a pharmaceutically acceptable salt thereof.

Formula (Ic)

In one general aspect, the present disclosure provides a compound of Formula (Ic):

(Ic)

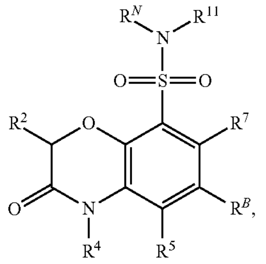

or a pharmaceutically acceptable salt thereof, wherein:

$R^B$ is selected from halogen and $S(O)_2R^{b1}$; and $R^2$, $R^4$, $R^5$, $R^7$, $R^N$, and $R^{11}$ are as described herein for Formula (I).

In some embodiments:

$R^B$ is selected from halogen and $S(O)_2R^{b1}$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is a halogen (e.g., Cl, F, or Br). In some embodiments, $R^B$ is Cl. In some embodiments, $R^B$ is $S(O)_2R^{b1}$ (e.g., $R^{b1}$ is $C_{1-6}$ alkyl).

In some embodiments, $R^B$ is ethylsulfonyl.

In some embodiments, $R^2$ is selected H and $C_{1-6}$ alkyl.

In some embodiments, $R^4$ is H.

In some embodiments, $R^5$ is H.

In some embodiments, $R^7$ is selected H and $C_{1-6}$ alkyl.

In some embodiments, $R^N$ is H.

In some embodiments, $R^N$ and $R^{11}$, together with the N atom to which they are attached, form a ring selected from morpholinyl and piperazinyl, each of which is optionally substituted with 1, 2, or 3 substituents independently selected from $R^9$.

In some embodiments, $R^{11}$ is ring A. In some embodiments, $R^{11}$ is $C_{1-6}$ alkyl, optionally substituted with ring A.

In some embodiments, ring A is selected from $C_{6-10}$ aryl and $C_{3-10}$ cycloalkyl, optionally substituted with 1-10 substituents independently selected from $R^A$.

In some embodiments, ring A is $C_{6-10}$ aryl, optionally substituted with 1-10 substituents independently selected from $R^A$.

In some embodiments, ring A is $C_{3-10}$ cycloalkyl, optionally substituted with 1-10 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

In some embodiments:

$R^2$ is selected H and $C_{1-6}$ alkyl;

$R^4$ is H;

$R^5$ is H;

$R^7$ is selected H and $C_{1-6}$ alkyl;

$R^N$ is H; or $R^N$ and $R^{11}$, together with the N atom to which they are attached, form a ring selected from morpholinyl and piperazinyl, each of which is optionally substituted with 1, 2, or 3 substituents independently selected from $R^9$;

ring A is selected from $C_{6-10}$ aryl and $C_{3-10}$ cycloalkyl, optionally substituted with 1-10 substituents independently selected from $R^A$; and each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^9$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^9$.

In some embodiments, each $R^9$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Ic) is selected from any one of the compounds of Table 4 or Table 5, or a pharmaceutically acceptable salt thereof.

In some embodiments, the compound of Formula (Ic) is selected from any one of the compounds of Table 4, or a pharmaceutically acceptable salt thereof. In some embodiments, the compound of Formula (Ic) is selected from any one of the compounds of Table 5, or a pharmaceutically acceptable salt thereof.

Formula (Id)

In one general aspect, the present disclosure provides a compound of Formula (Id):

(Id)

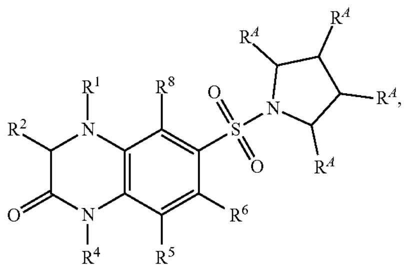

or a pharmaceutically acceptable salt thereof, wherein $R^1$, $R^2$, $R^4$, $R^5$, $R^6$, $R^8$, and $R^A$ are as described herein for Formula (I).

In some embodiments:

$R^1$ and $R^4$ are each independently selected from H, $C_{1-6}$ alkyl, $C_{1-6}$ haloalkyl, $C_{2-6}$ alkenyl, $C_{2-6}$ alkynyl, C(O)$R^{b1}$, C(O)$NR^{c1}R^{d1}$, C(O)$OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^5$, $R^6$, and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, C(O)$R^{b1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, C(O)$R^{b1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}S(O)_2R^{b1}$, $S(O)_2R^{b1}$, and $S(O)_2NR^{c1}R^{d1}$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, C(O)$R^{b1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, C(O)$R^{b1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^2$ is selected from H and $C_{1-6}$ alkyl.

In some embodiments, $R^4$ is H.

In some embodiments, $R^1$ is selected from H, $C_{1-6}$ alkyl, C(O)$R^{b1}$, and C(O)$NR^{c1}R^{d1}$, wherein said $C_{1-6}$ alkyl is optionally substituted with 1, 2, or 3 substituents independently selected from $R^9$.

In some embodiments, each $R^9$ is independently selected from OH, $C_{1-6}$ alkoxy, carboxy, C(O)$NH_2$, amino, $C_{1-6}$ alkylamino, and di($C_{1-6}$ alkyl)amino.

In some embodiments, $R^5$, $R^6$, and $R^8$ are each independently selected from H, halo, $C_{1-6}$ alkyl, $C_{1-6}$ haloalkyl, and $C_{1-6}$ alkoxy. In some embodiments, $R^5$, $R^6$, and $R^8$ are each H.

In some embodiments, each $R^A$ is independently selected from H, halo, CN, $C_{1-6}$ alkyl, $C_{1-6}$ haloalkyl, $OR^{a1}$, $SR^{a1}$, C(O)$R^{b1}$, C(O)$OR^{a1}$, $NR^{c1}R^{d1}$ and $NR^{c1}$C(O)$R^{b1}$, wherein said $C_{1-6}$ alkyl is optionally substituted with 1, 2, or 3 substituents independently selected from $R^{10}$.

In some embodiments, each $R^A$ is independently selected from H, $C_{1-6}$ alkyl, $C_{1-6}$ haloalkyl, halo, CN, OH, $C_{1-6}$ alkoxy, carboxy, amino, C(O)$NH_2$, $C_{1-6}$ alkylamino, di($C_{1-6}$ alkyl)amino, and $C_{1-6}$ haloalkoxy. In some embodiments, each $R^A$ is independently selected from H, $C_{1-6}$ alkyl, $C_{1-6}$ haloalkyl, halo, and $C_{1-6}$ alkoxy. In some embodiments, each $R^A$ is independently selected from H and $C_{1-6}$ alkyl. In some embodiments, each $R^A$ is H.

In some embodiments:

$R^2$ is selected from H and $C_{1-6}$ alkyl;

$R^4$ is H;

$R^5$, $R^6$, and $R^8$ are each H;

$R^1$ is selected from H, $C_{1-6}$ alkyl, $C(O)R^{b1}$, and $C(O)NR^{c1}R^{d1}$, wherein said $C_{1-6}$ alkyl is optionally substituted with 1, 2, or 3 substituents independently selected from $R^9$;

each $R^9$ is independently selected from OH, $C_{1-6}$ alkoxy, carboxy, $C(O)NH_2$, amino, $C_{1-6}$ alkylamino, and di($C_{1-6}$ alkyl)amino; and each $R^A$ is H.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Id) is selected from any one of the compounds of Table 6, or a pharmaceutically acceptable salt thereof.

Formula (Ie)

In one general aspect, the present disclosure provides a compound of Formula (Ie):

(Ie)

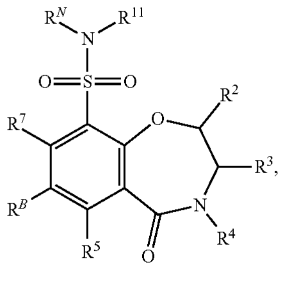

or a pharmaceutically acceptable salt thereof, wherein:

$R^B$ is selected from halogen and $S(O)_2R^{b1}$; and $R^2$, $R^3$, $R^4$, $R^5$, $R^7$, $R^N$, and $R^{11}$ are as described herein for Formula (I).

In some embodiments:

$R^2$ and $R^3$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is a halogen.

In some embodiments, $R^B$ is $S(O)_2R^{b1}$.

In some embodiments, $R^2$ and $R^3$ are each independently selected from H and $C_{1-6}$ alkyl.

In some embodiments, $R^4$ is H.

In some embodiments, $R^5$ is H.

In some embodiments, $R^7$ is selected H and $C_{1-6}$ alkyl.

In some embodiments, $R^N$ is H.

In some embodiments, ring A is $C_{6-10}$ aryl, optionally substituted with 1-5 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

In some embodiments:

$R^2$ and $R^3$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

In some embodiments, the compound of Formula (Ie) is selected from any one of the compounds of Table 8, or a pharmaceutically acceptable salt thereof.

Formula (If)

In one general aspect, the present disclosure provides a compound of Formula (If):

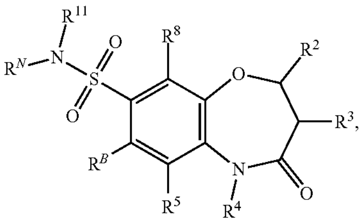

(If)

or a pharmaceutically acceptable salt thereof, wherein:

$R^B$ is selected from halogen and $S(O)_2R^{b1}$;

and $R^2$, $R^3$, $R^4$, $R^5$, $R^8$, $R^N$, and $R^{11}$ are as described herein for Formula (I).

In some embodiments:

$R^2$ and $R^3$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$; $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is a halogen.

In some embodiments, $R^B$ is $S(O)_2R^{b1}$.

In some embodiments, $R^2$ and $R^3$ are each independently selected from H and $C_{1-6}$ alkyl.

In some embodiments, $R^4$ is H.

In some embodiments, $R^5$ is H.

In some embodiments, $R^8$ is selected H and $C_{1-6}$ alkyl.

In some embodiments, $R^N$ is H.

In some embodiments, ring A is $C_{6-10}$ aryl, optionally substituted with 1-5 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

In some embodiments:

$R^2$ and $R^3$ are each independently selected H and $C_{1-6}$ alkyl;

$R^4$ is H;

$R^5$ is H;

$R^8$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

In some embodiments, the compound of Formula (If) is selected from any one of the compounds of Table 9, or a pharmaceutically acceptable salt thereof.

Formula (Ig)

In one general aspect, the present disclosure provides a compound of Formula (Ig):

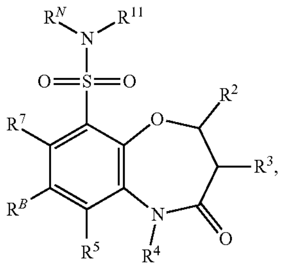

(Ig)

or a pharmaceutically acceptable salt thereof, wherein:

$R^B$ is selected from halogen and $S(O)_2R^{b1}$; and $R^2$, $R^3$, $R^4$, $R^5$, $R^7$, $R^N$, and $R^{11}$ are as described herein.

In some embodiments:

$R^2$ and $R^3$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$; $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is a halogen.

In some embodiments, $R^B$ is $S(O)_2R^{b1}$.

In some embodiments, $R^2$ and $R^3$ are each independently selected from H and $C_{1-6}$ alkyl.

In some embodiments, $R^4$ is H.

In some embodiments, $R^5$ is H.

In some embodiments, $R^7$ is selected H and $C_{1-6}$ alkyl.

In some embodiments, $R^N$ is H.

In some embodiments, ring A is $C_{6-10}$ aryl, optionally substituted with 1-5 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

In some embodiments:

$R^2$ and $R^3$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

In some embodiments, the compound of Formula (Ig) is selected from any one of the compounds of Table 10, or a pharmaceutically acceptable salt thereof.

In some embodiments, a salt of any one of the compounds disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and those formed with organic acids such as maleic acid.

In some embodiments, bases commonly employed to form pharmaceutically acceptable salts of the compounds disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, any one of the compounds disclosed herein, or a pharmaceutically acceptable salt thereof, is substantially isolated.

Methods of Making Therapeutic Compounds

Compounds as set forth in any one of the Formulae disclosed herein, including salts thereof, can be prepared using organic synthesis techniques and can be synthesized according to any of numerous possible synthetic routes. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates, and products can be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*J. Heterocyclic Chemistry,* 1964-2012); Carreira et al., (Ed.) *Science of Synthesis*, Vols. 1-48 (2001-2010) and Knowledge Updates KU2010/1-4; 2011/1-4; 2012/1-2 (Thieme, 2001-2012); Katritzky et al., (Ed.) *Comprehensive Organic Functional Group Transformations*, (Pergamon Press, 1996); Katritzky et al., (Ed.) *Comprehensive Organic Functional Group Transformations II* (Elsevier, 2$^{nd}$ Edition, 2004); Katritzky et al., (Ed.) *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry*: Reactions, *Mechanisms, and Structure,* 6$^{th}$ Ed. (Wiley, 2007); Trost et al. (Ed.) *Comprehensive Organic Synthesis* (Pergamon Press, 1991).

The reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis,* 4$^{th}$ Ed., Wiley & Sons, Inc., New York (2006).

Pharmaceutical Compositions and Formulations

This document also provides pharmaceutical compositions comprising an effective amount of a compound disclosed herein, or a pharmaceutically acceptable salt thereof, and a pharmaceutically acceptable carrier. The pharmaceutical composition also can comprise any one of the additional therapeutic agents and/or therapeutic molecules described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants, and vehicles that can be used in the pharmaceutical compositions provided herein include, without limitation, ion exchangers, alumina, aluminum stearate, lecithin, serum proteins (e.g., human serum albumin), buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one or more of the compounds or therapeutic agents described herein in the range of 0.005 percent to 100 percent with the balance made up from the suitable pharmaceutically acceptable carriers or excipients. The contemplated compositions can contain from about 0.001 percent to about 100 percent (e.g., from about 0.1 percent to about 95 percent, from about 75 percent to about 85 percent, or from about 20 percent to about 80 percent) of any one or more of the compounds or therapeutic agents provided herein, wherein the balance can be made up of any pharmaceutically acceptable carrier or excipient described herein, or any combination of these carriers or excipients.

Routes of Administration and Dosage Forms

The therapeutic compounds and/or pharmaceutical compositions provided herein (e.g., a composition containing one or more compounds disclosed herein, or a pharmaceutically acceptable salt thereof) can include those suitable for any acceptable route of administration. Acceptable routes of administration include, without limitation, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral, vaginal, intravitreal, subretinal or other intraocular routes of administrations.

Compositions and formulations described herein can conveniently be presented in a unit dosage form, e.g., tablets, sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include, without limitation, the step of bringing into association with the molecule to be administered ingredients such as a carrier that constitutes one or more accessory ingredients. In general, the compositions can be prepared by uniformly and intimately bringing into association the active ingredients with liquid carriers, liposomes, or finely divided solid carriers, or both, and then, if necessary, shaping the product.

In some embodiments, any one or more of the compounds or therapeutic agents described herein can be administered orally. Compositions described herein that are suitable for oral administration can be presented as discrete units such as capsules, sachets, granules, or tablets each containing a predetermined amount (e.g., effective amount) of the active ingredient(s); a powder or granules; a solution or a suspension in an aqueous liquid or a non-aqueous liquid; an oil-in-water liquid emulsion; a water-in-oil liquid emulsion; packed in liposomes; or as a bolus. Soft gelatin capsules can be useful for containing such suspensions, which can beneficially increase the rate of compound absorption. In the case of tablets for oral use, carriers that are commonly used include, without limitation, lactose, sucrose, glucose, mannitol, silicic acid, and starches. Other acceptable excipients can include, without limitation, (a) fillers or extenders such as starches, lactose, sucrose, glucose, mannitol, and silicic acid, (b) binders such as carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. For oral administration in a capsule form, useful diluents include, without limitation, lactose and dried cornstarch. When aqueous suspensions are administered orally, the active ingredient(s) can be combined with emulsifying and suspending agents. If desired, certain sweetening and/or flavoring and/or coloring agents can be added. Compositions suitable for oral administration include, without limitation, lozenges comprising ingredients in a flavored basis, usually sucrose and acacia or tragacanth; and pastilles comprising the active ingredient(s) in an inert basis such as gelatin and glycerin, or sucrose and acacia.

Compositions suitable for parenteral administration include, without limitation, aqueous and non-aqueous sterile injection solutions or infusion solutions that may contain antioxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water, for injections, saline (e.g., 0.9% saline solution), or 5% dextrose solution, immediately prior to use. Extemporaneous injection solutions and suspensions can be prepared from sterile powders, granules, and tablets. The injection solutions can be in the form of, for example, a sterile injectable aqueous or oleaginous suspension. This suspension can be formulated according to techniques known in the art using suitable dispersing or wetting agents and suspending agents. A sterile injectable preparation also can be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution, and isotonic sodium chloride solution. In addition, sterile, fixed oils can be used as a solvent or suspending medium. For this purpose, any bland fixed oil can be used including, without limitation, synthetic mono- or diglycerides. Fatty acids such as oleic acid and its glyceride derivatives can be used to prepare injectables. In some cases, natural pharmaceutically acceptable oils such as olive oil or castor oil, especially in their polyoxyethylated versions, can be used to prepare injectables. These oil solutions or suspensions also can contain a long-chain alcohol diluent or dispersant.

In some cases, a therapeutic compound and/or pharmaceutical composition provided herein can be administered in the form of suppository for rectal administration. These compositions can be prepared by mixing a compound described herein (e.g., any one of the compounds disclosed herein, or a pharmaceutically acceptable salt thereof) with a suitable non-irritating excipient that is solid at room temperature but liquid at the rectal temperature and therefore will melt in the rectum to release the active component(s). Such materials include, without limitation, cocoa butter, beeswax, and polyethylene glycols.

In some cases, a therapeutic compounds and/or pharmaceutical composition provided herein can be administered by nasal aerosol or inhalation. Such compositions can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J. Pharm. Pharmacol.*, 56:3-17 (2004); and Ilium, L., *Eur. J. Pharm. Sci.*, 11:1-18 (2000).

In some cases, a therapeutic compounds and/or pharmaceutical composition provided herein can be prepared as a topical composition and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of a therapeutic compounds and/or pharmaceutical composition provided herein can be useful when the desired treatment involves areas or organs readily accessible by topical application. In some cases, a topical composition can include a combination of any one or more of the compounds or therapeutic agents described herein (e.g., a compound set forth in any one of Formulae herein, or a pharmaceutically acceptable salt thereof), and one or more additional ingredients, carriers, excipients, or diluents including, without limitation, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

In some cases, one or more compounds or therapeutic agent described herein (e.g., any one of the compounds disclosed herein, or a pharmaceutically acceptable salt thereof) can be incorporated into a composition for coating an implantable medical device such as a prosthesis, artificial valve, vascular graft, stent, or catheter. Suitable coatings and the general preparation of coated implantable devices are known in the art and are exemplified in U.S. Pat. Nos. 6,099,562; 5,886,026; and 5,304,121. The coatings can be biocompatible polymeric materials such as a hydrogel polymer, polymethyldisiloxane, polycaprolactone, polyethylene glycol, polylactic acid, ethylene vinyl acetate, or mixture thereof. In some cases, the coating can optionally be further covered by a suitable topcoat of fluorosilicone, polysaccharides, polyethylene glycol, phospholipids or combinations thereof to impart controlled release characteristics in the composition.

In some cases, this document provides an implantable drug release device impregnated with or containing one or more compounds or therapeutic agents described herein (e.g., any one of the compounds disclosed herein, or a pharmaceutically acceptable salt thereof) such that the compound(s) or therapeutic agent(s) are released from the device and are therapeutically active.

Dosages and Regimens

A composition (e.g., pharmaceutical compositions provided herein) containing a compound provided herein, or a pharmaceutically acceptable salt thereof, can include that compound in an effective amount (e.g., a therapeutically effective amount).

Effective doses can vary, depending on the diseases being treated, the severity of the disease, the route of administration, the sex, age and general health condition of the subject, excipient usage, the possibility of co-usage with other therapeutic treatments such as use of other agents, and the judgment of the treating physician.

In some embodiments, an effective amount of a compound as disclosed herein, or a pharmaceutically acceptable salt thereof, can range, for example, from about 0.1 mg to about 1000 mg. In some cases, the effective amount can be from about 0.5 mg to about 500 mg of a compound disclosed herein, or any amount in between these two values, for example, one of about 0.5 mg, about 1 mg, about 2 mg, about 5 mg, about 10 mg, about 20 mg, about 50 mg, about 100 mg, about 200 mg, about 250 mg, about 300 mg, about 400 mg, or about 500 mg. The effective amount can be an amount sufficient to alleviate or reduce one or more of the symptoms associated with a disease, disorder, or condition being treated as described herein.

In some cases, an effective amount of a compound as disclosed herein, or a pharmaceutically acceptable salt thereof, can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; from about 0.1 mg/kg to about 0.5 mg/kg, or from about 0.5 mg/kg to about 500 mg/kg).

In some cases, an effective amount of a compound as disclosed herein, or a pharmaceutically acceptable salt thereof, can be about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or on a non-daily basis (e.g., every other day, every two days, every three days, once weekly, twice weekly, once every two weeks, or once a month). In some cases, the dosages can be administered every 4 hours, 6 hours, 8 hours, 12 hours, or 24 hours.

Kits

This document also provides pharmaceutical kits useful, for example, to inhibit CB1 within a mammal (e.g., a human). In some cases, this document provides pharmaceutical kits useful, for example, to treat diseases, disorders, and conditions referred to herein. Such pharmaceutical kits can include one or more containers containing a pharmaceutical composition that includes a therapeutically effective amount of a compound provided herein, or a pharmaceutically acceptable salt thereof. In some cases, such kits can further include, if desired, one or more of various conventional pharmaceutical kit components such as containers with one or more pharmaceutically acceptable carriers. Instructions, either as inserts or as labels, indicating quantities of the components to be administered, guidelines for administration, and/or guidelines for mixing the components also can be included in a kit provided herein.

Combination Therapies

In some cases, one or more compounds provided herein, or a pharmaceutically acceptable salt thereof, can be combined with one or more therapeutic molecules. Examples of therapeutic molecules that can be used in combination with one or more compounds provided herein, or a pharmaceutically acceptable salt thereof, include, without limitation, nicotine-replacement therapy, varenicline or bupropion, anti-fibrotic agents (e.g., nintedanib or pirfenidone), and anti-inflammatory agents (e.g., hydrocortisone or mycophenolic acid).

One or more compounds provided herein, or a pharmaceutically acceptable salt thereof, and the one or more therapeutic molecules can be administered in any order or simultaneously. If simultaneously administered, they can be provided in a single, unified, form or in multiple forms (e.g., either as a single pill or as two separate pills). One of the items can be given in multiple doses, or both can be given as multiple doses. If not simultaneous, the timing between the multiple doses can vary from more than zero weeks to less than four weeks.

Definitions

As used herein, the term "about" means "approximately" (e.g., plus or minus approximately 10% of the indicated value).

At various places in this document, substituents of compounds provided herein are disclosed in groups or in ranges. It is specifically intended that these groups and ranges include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in this document various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features described herein, which are, for clarity, described in the context of separate embodiments, can also be provided in combination in a single embodiment. Conversely, various features described herein which are, for brevity, described in the context of a single embodiment, also can be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution can be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, without limitation, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms that may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, without limitation, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, without limitation, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl-linking group having n to m carbons. Examples of alkylene groups include, without limitation, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, without limitation, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, without limitation, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di($C_{n-m}$-alkyl)amino" refers to a group of formula —N$(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, without limitation, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, without limitation, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS$(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S$(O)_2NH_2$.

As used herein, the term "$C_{n-m}$ alkylaminosulfonyl" refers to a group of formula —S$(O)_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S$(O)_2$N$(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS$(O)_2NH_2$.

As used herein, the term "$C_{n-m}$ alkylaminosulfonylamino" refers to a group of formula —NHS$(O)_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS$(O)_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)$NH_2$.

As used herein, the term "$C_{n-m}$ alkylaminocarbonylamino" refers to a group of formula —NHC(O)NH (alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N$(alkyl)_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —C(O)$NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N$(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S$(O)_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(═O)— group, which may also be written as C(O).

As used herein, the term "carboxy" refers to a —C(O)OH group. In some embodiments, the "carboxy" group also refers to a bioisostere replacement group selected from the group consisting of:

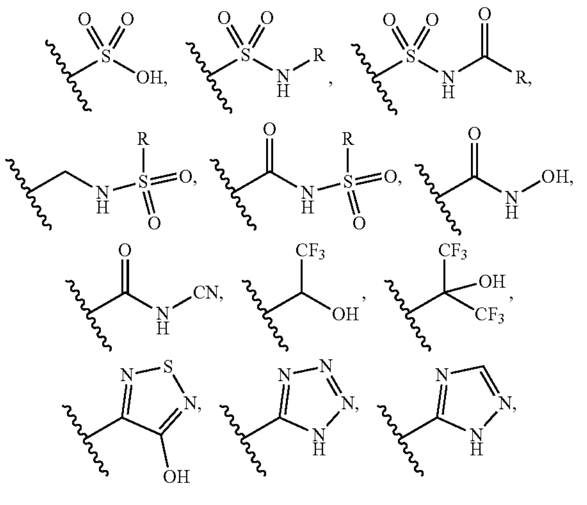

-continued

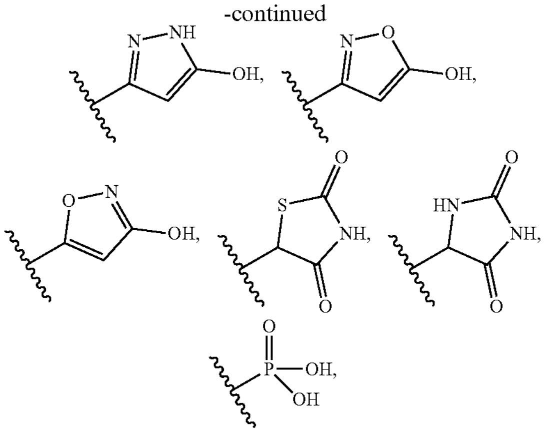

and the like, where R refers to a hydrogen, ($C_1$-$C_8$) alkyl, or $C_6$ aryl.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which can be monocyclic or polycyclic (e.g., having 2, 3, or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups can have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3, or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include, without limitation, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur, and oxygen. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from nitrogen, sulfur, and oxygen. In some embodiments, the heteroaryl is a 5-6 monocyclic heteroaryl having 1 or 2 heteroatom ring members independently selected from nitrogen, sulfur, and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls include, without limitation, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls include, without limitation, pyridyl, pyrazinyl, pyrimidinyl, triazinyl, and pyridazinyl. Ring-forming carbon atoms of a heteroaryl group can be optionally substituted by 1 or 2 independently selected oxo or sulfide groups (e.g., C(O) or C(S)).

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9-, or 10-membered heterocycloalkyl groups. Heterocycloalkyl groups can also include spirocycles. Example heterocycloalkyl groups include, without limitation, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring can be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C═O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Any appropriate method can be used to prepare optically active forms from, for example, optically inactive starting materials. For example, techniques such as resolution of racemic mixtures or stereoselective synthesis can be used to prepare optically active forms of a compound provided herein. Many geometric isomers of olefins, C═N double bonds, N═N double bonds, and the like also can be present in a compound described herein, and all such stable isomers are contemplated herein. Cis and trans geometric isomers of the compounds provided herein are described and can be isolated as a mixture of isomers or as separated isomeric forms. In some embodiments, a compound provided herein has the (R)-configuration. In some embodiments, a compound provided herein has the (S)-configuration.

Compounds provided herein also include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include, without limitation, ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H-, and 4H-1,2,4-triazole, 1H- and 2H-isoindole, and 1H- and 2H-pyrazole. Tautomeric forms can be in equilibrium or sterically locked into one form by appropriate substitution. For example, in aqueous solution, pyrazoles can exhibit the following isomeric forms, which are referred to as tautomers of each other:

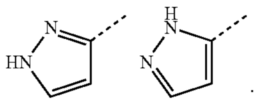

As readily understood by one skilled in the art, a wide variety of functional groups and other structures can exhibit tautomerism, and all tautomers of compounds as described herein are within the scope provided herein.

As used herein, the term "cell" is meant to refer to a cell that is in vitro, ex vivo, or in vivo. In some embodiments, an ex vivo cell can be part of a tissue sample excised from an organism such as a mammal (e.g., a human). In some embodiments, an in vitro cell can be a cell in cell culture. In some embodiments, an in vivo cell is a cell living in an organism such as a mammal (e.g., a human).

As used herein, the term "contacting" refers to the bringing together of indicated moieties or items in an in vitro system, an ex vivo system, or an in vivo system. For example, "contacting" a cell with a compound provided herein includes the act of administering that compound to a mammal (e.g., a human) containing that cell as well as, for example, introducing that compound into a cell culture containing that cell.

As used herein, the term "mammal" includes, without limitation, mice, rats, other rodents, rabbits, dogs, cats, swine, cattle, sheep, horses, elephants, deer, non-human primates (e.g., monkeys and apes), house pets, and humans.

As used herein, the phrase "effective amount" or "therapeutically effective amount" refers to the amount of active compound or pharmaceutical agent that elicits the biological or medicinal response in a tissue, system, mammal, or human that is being sought by a researcher, veterinarian, medical doctor, or other clinician.

As used herein, the term "treating" or "treatment" refers to (a) inhibiting a disease, disorder, or condition, for example, inhibiting a disease, disorder, or condition in a mammal (e.g., human) that is experiencing or displaying the pathology or symptomatology of the disease, disorder, or condition (e.g., arresting further development of the pathology and/or symptomatology), or (b) ameliorating the disease, disorder, or condition, for example, ameliorating a disease, disorder, or condition in a mammal (e.g., a human) that is experiencing or displaying the pathology or symptomatology of the disease, disorder, or condition (e.g., reversing the pathology and/or symptomatology).

As used herein, the term "preventing" or "prevention" of a disease, disorder, or condition refers to decreasing the risk of occurrence of the disease, disorder, or condition in a mammal or group of mammals (e.g., a mammal or group of mammals predisposed to or susceptible to the disease, disorder, or condition). In some embodiments, preventing a disease, disorder, or condition refers to decreasing the possibility of acquiring the disease, disorder, or condition and/or its associated symptoms. In some embodiments, preventing a disease, disorder, or condition refers to completely or almost completely stopping the disease, disorder, or condition from occurring.

EXAMPLES

Methods cAMP CNR1 Hunter cell line (Eurofins DiscoveryX) were expanded from freezer stocks and seeded in a total volume of 20 μL into white walled, 384-well microplates and incubated at 37° C. for the appropriate time prior to testing. For antagonist determination, cell media was aspirated from cells and replaced with 10 μL 1:1 HBSS/Hepes: cAMP XS+Ab reagent. 5 μL of 4× compound was added to the cells and incubated at 37° C. for 30 minutes. 5 μL of 4× EC80 agonist was added to cells and incubated at 37° C. for 30 minutes. After appropriate compound incubation, assay signal was generated through incubation with 20 μL cAMP XS+ED/CL lysis cocktail for one hour followed by incubation with 20 μL cAMP XS+EA reagent for three hours at room temperature. Microplates were read following signal generation with a PerkinElmer Envision™ instrument for chemiluminescent signal detection. Compound activity ($IC_{50}$) was analyzed using CBIS data analysis suite (ChemInnovation, CA).

Efficacy ($IC_{50}$): "+"≥25 μM, "++"≥1 μM and <25 μM, and "+++"<1 μM.

Bioassay Results for Tested Compounds

TABLE 1

| BC No. | Compound | CB1 assay |
|---|---|---|
| BC19132 | 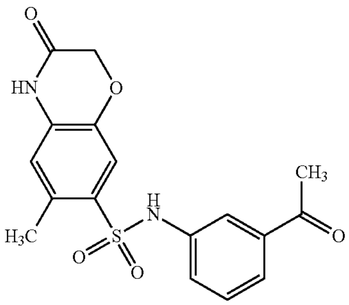 [SMILES: CC(=O)c1cccc(NS(=O)(=O)c2cc3c(cc2C)NC(=O)CO3)c1] | + |

TABLE 1-continued

| BC No. | Compound | CB1 assay |
|---|---|---|
| BC19131 | 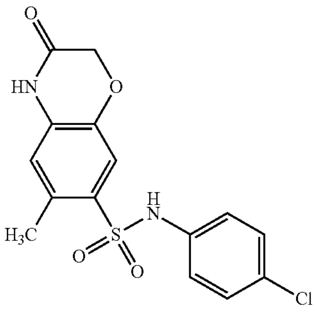 [SMILES: Cc1cc2c(cc1S(=O)(=O)Nc1ccc(Cl)cc1)OCC(=O)N2] | +++ |
| BC19134 | 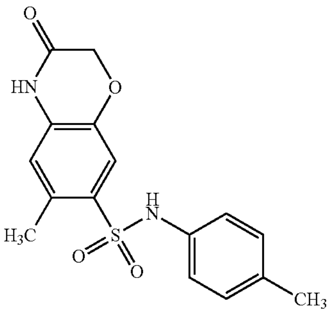 [SMILES: Cc1ccc(NS(=O)(=O)c2cc3c(cc2C)NC(=O)CO3)cc1] | +++ |

TABLE 2

| BC No. | Structure | CB1 assay |
|---|---|---|
| BC19133 | 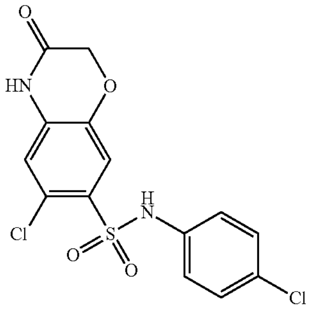 [SMILES: O=C1COc2cc(S(=O)(=O)Nc3ccc(Cl)cc3)c(Cl)cc2N1] | +++ |
| BC19135 | 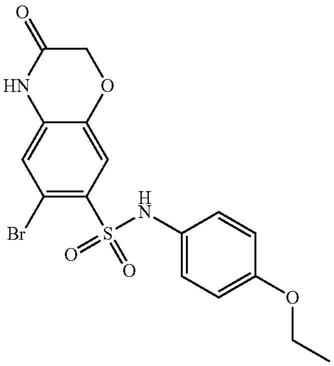 [SMILES: CCOc1ccc(NS(=O)(=O)c2cc3c(cc2Br)NC(=O)CO3)cc1] | ++ |

TABLE 2-continued
| BC No. | Structure | CB1 assay |
|---|---|---|
| BC19136 | 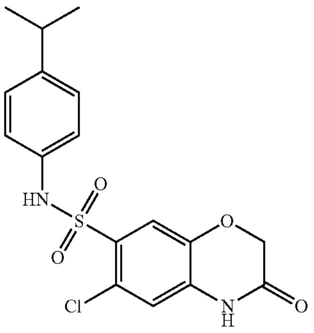 [SMILES: CC(C)c1ccc(NS(=O)(=O)c2cc3c(cc2Cl)NC(=O)CO3)cc1] | +++ |
| BC19137 | 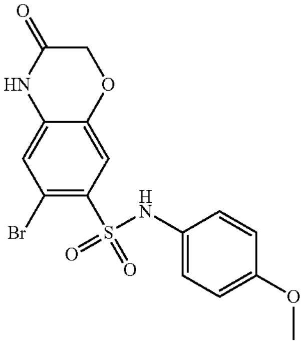 [SMILES: COc1ccc(NS(=O)(=O)c2cc3c(cc2Br)NC(=O)CO3)cc1] | +++ |
| BC19138 | 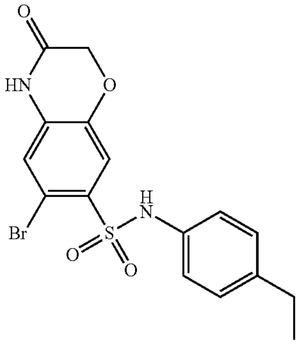 [SMILES: CCc1ccc(NS(=O)(=O)c2cc3c(cc2Br)NC(=O)CO3)cc1] | +++ |
| BC19161 | 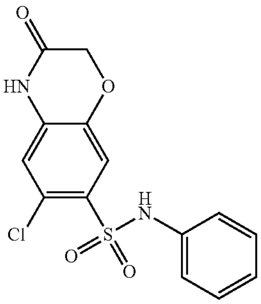 [SMILES: O=C1COc2cc(S(=O)(=O)Nc3ccccc3)c(Cl)cc2N1] | +++ |

TABLE 2-continued
| BC No. | Structure | CB1 assay |
| --- | --- | --- |
| BC19162 | 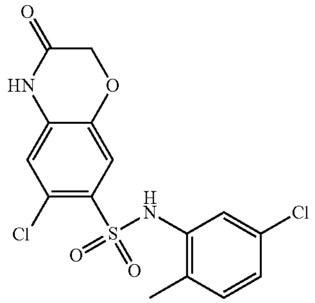 [SMILES: Cc1ccc(Cl)cc1NS(=O)(=O)c1cc2c(cc1Cl)NC(=O)CO2] | +++ |
| BC19163 | 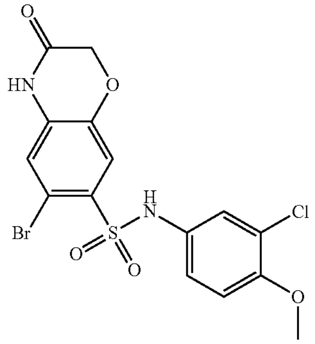 [SMILES: COc1ccc(NS(=O)(=O)c2cc3c(cc2Br)NC(=O)CO3)cc1Cl] | +++ |
| BC19164 | 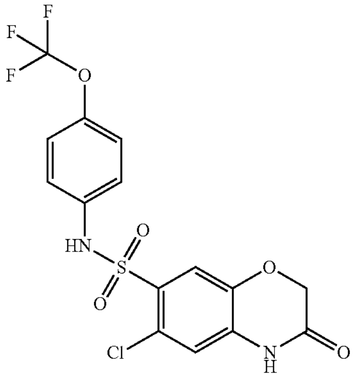 [SMILES: O=C1COc2cc(S(=O)(=O)Nc3ccc(OC(F)(F)F)cc3)c(Cl)cc2N1] | +++ |
| BC19165 | 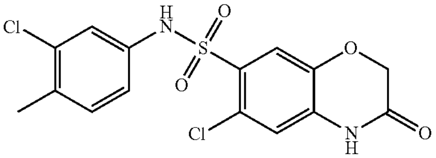 [SMILES: Cc1ccc(NS(=O)(=O)c2cc3c(cc2Cl)NC(=O)CO3)cc1Cl] | ++ |
| BC19166 | 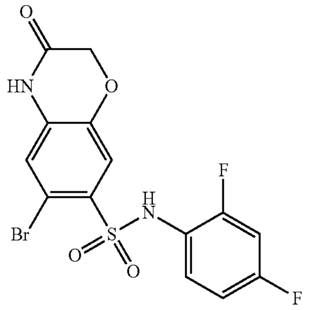 [SMILES: O=C1COc2cc(S(=O)(=O)Nc3ccc(F)cc3F)c(Br)cc2N1] | +++ |

TABLE 2-continued
| BC No. | Structure | CB1 assay |
|---|---|---|
| BC19167 | 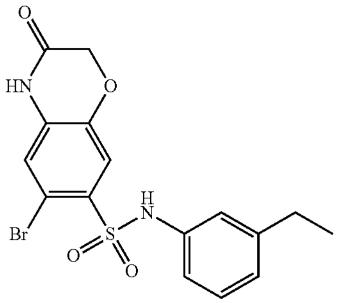 [SMILES: CCc1cccc(NS(=O)(=O)c2cc3c(cc2Br)NC(=O)CO3)c1] | +++ |
| BC19206 | 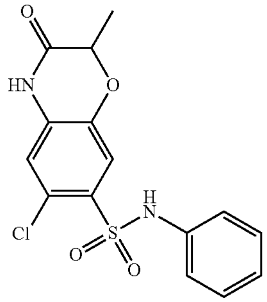 [SMILES: CC1Oc2cc(S(=O)(=O)Nc3ccccc3)c(Cl)cc2NC1=O] | + |
| BC19207 | 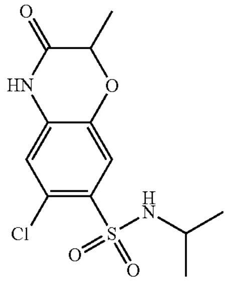 [SMILES: CC(C)NS(=O)(=O)c1cc2c(cc1Cl)NC(=O)C(C)O2] | + |
| BC19208 | 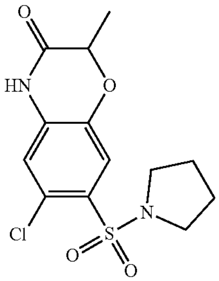 [SMILES: CC1Oc2cc(S(=O)(=O)N3CCCC3)c(Cl)cc2NC1=O] | + |
| BC19209 | 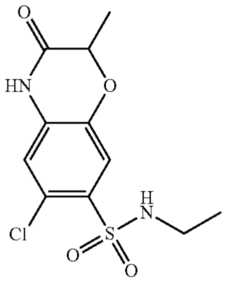 [SMILES: CCNS(=O)(=O)c1cc2c(cc1Cl)NC(=O)C(C)O2] | + |

TABLE 2-continued
| BC No. | Structure | CB1 assay |
|---|---|---|
| BC19210 | 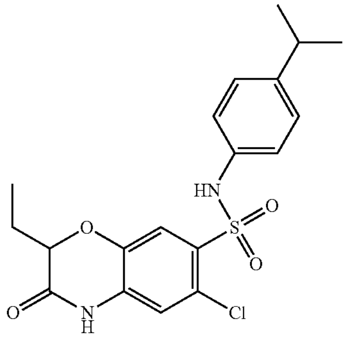 | +++ |
| BC19211 | 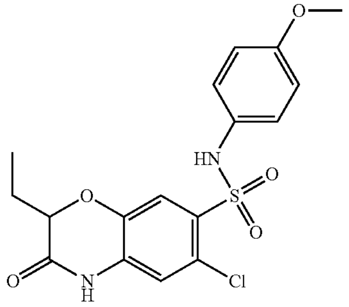 [SMILES: CCC1Oc2cc(S(=O)(=O)Nc3ccc(OC)cc3)c(Cl)cc2NC1=O] | ++ |
| BC19212 | 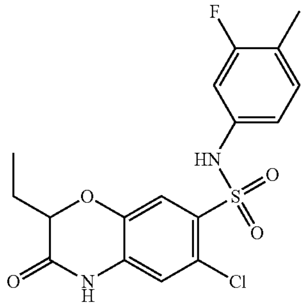 [SMILES: CCC1Oc2cc(S(=O)(=O)Nc3ccc(C)c(F)c3)c(Cl)cc2NC1=O] | ++ |
| BC19213 | 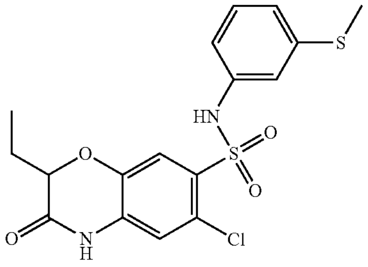 [SMILES: CCC1Oc2cc(S(=O)(=O)Nc3cccc(SC)c3)c(Cl)cc2NC1=O] | + |
| BC19214 | 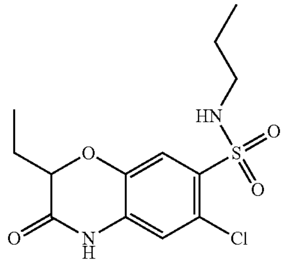 [SMILES: CCCNS(=O)(=O)c1cc2c(cc1Cl)NC(=O)C(CC)O2] | + |

TABLE 2-continued
| BC No. | Structure | CB1 assay |
| --- | --- | --- |
| BC19215 | 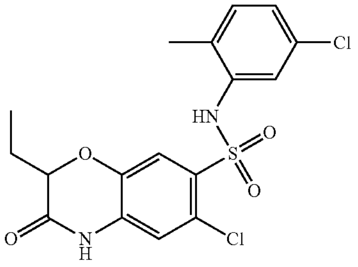 [SMILES: CCC1Oc2cc(S(=O)(=O)Nc3cc(Cl)ccc3C)c(Cl)cc2NC1=O] | + |
| BC19216 | 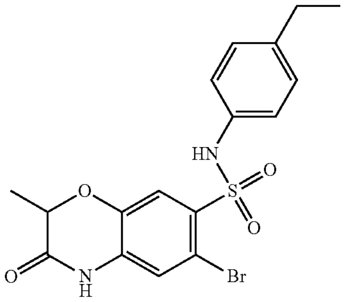 [SMILES: CCc1ccc(NS(=O)(=O)c2cc3c(cc2Br)NC(=O)C(C)O3)cc1] | +++ |
| BC19217 | 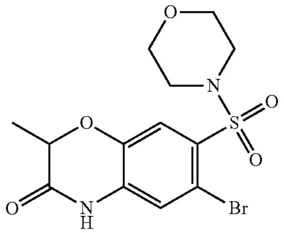 [SMILES: CC1Oc2cc(S(=O)(=O)N3CCOCC3)c(Br)cc2NC1=O] | + |
| BC19218 | 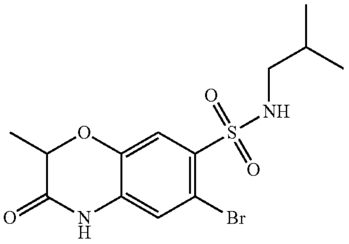 [SMILES: CC(C)CNS(=O)(=O)c1cc2c(cc1Br)NC(=O)C(C)O2] | ++ |
| BC19219 | 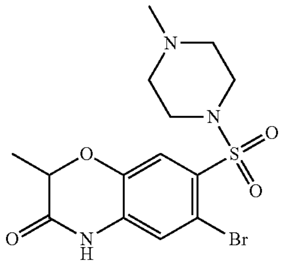 [SMILES: CC1Oc2cc(S(=O)(=O)N3CCN(C)CC3)c(Br)cc2NC1=O] | + |

TABLE 2-continued
| BC No. | Structure | CB1 assay |
|---|---|---|
| BC19220 | 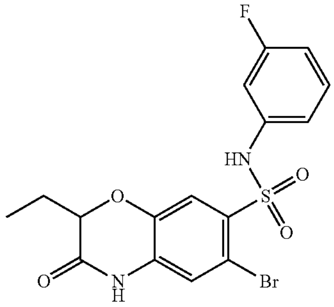 [SMILES: CCC1Oc2cc(S(=O)(=O)Nc3cccc(F)c3)c(Br)cc2NC1=O] | + |
| BC19221 | 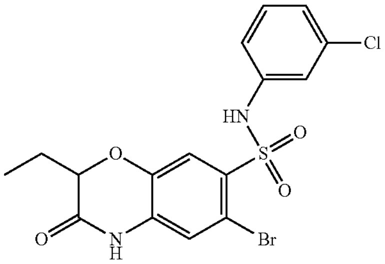 [SMILES: CCC1Oc2cc(S(=O)(=O)Nc3cccc(Cl)c3)c(Br)cc2NC1=O] | ++ |
| BC19222 | 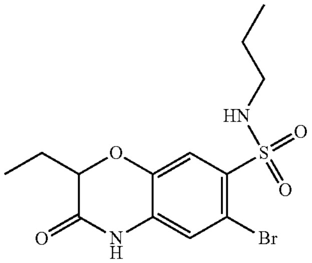 [SMILES: CCCNS(=O)(=O)c1cc2c(cc1Br)NC(=O)C(CC)O2] | ++ |
| BC19223 | 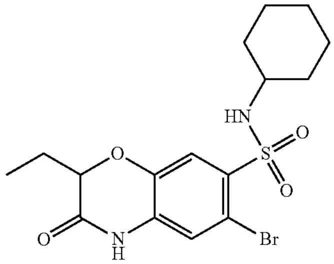 [SMILES: CCC1Oc2cc(S(=O)(=O)NC3CCCCC3)c(Br)cc2NC1=O] | ++ |
| BC19224 | 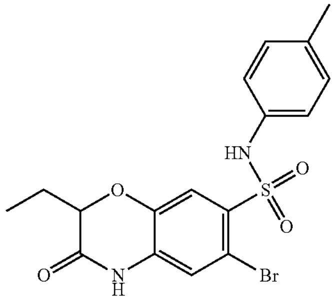 [SMILES: CCC1Oc2cc(S(=O)(=O)Nc3ccc(C)cc3)c(Br)cc2NC1=O] | + |

TABLE 2-continued
| BC No. | Structure | CB1 assay |
|---|---|---|
| BC19280 | 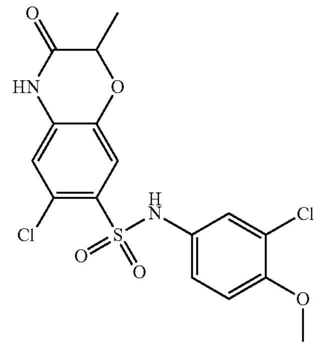 [SMILES: COc1ccc(NS(=O)(=O)c2cc3c(cc2Cl)NC(=O)C(C)O3)cc1Cl] | ++ |
| BC19281 | 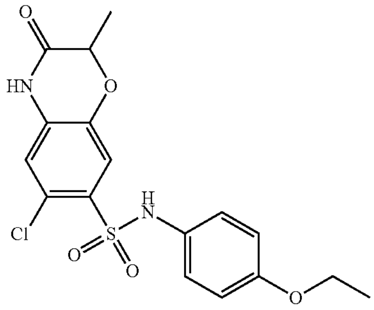 [SMILES: CCOc1ccc(NS(=O)(=O)c2cc3c(cc2Cl)NC(=O)C(C)O3)cc1] | + |
| BC19282 | 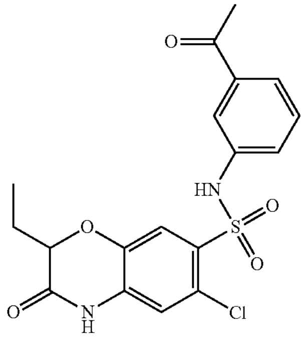 [SMILES: CCC1Oc2cc(S(=O)(=O)Nc3cccc(C(C)=O)c3)c(Cl)cc2NC1=O] | ++ |
| BC19283 | 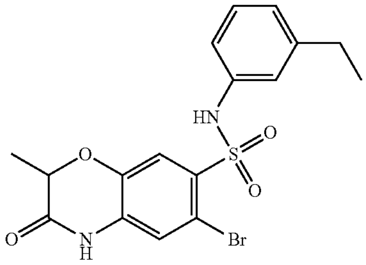 [SMILES: CCc1cccc(NS(=O)(=O)c2cc3c(cc2Br)NC(=O)C(C)O3)c1] | ++ |
| BC19284 | 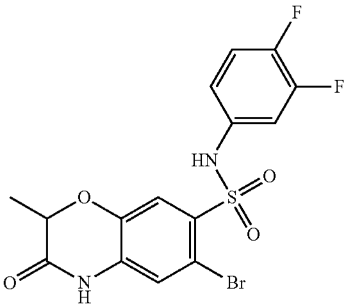 [SMILES: CC1Oc2cc(S(=O)(=O)Nc3ccc(F)c(F)c3)c(Br)cc2NC1=O] | + |

TABLE 2-continued
| BC No. | Structure | CB1 assay |
|---|---|---|
| BC19285 | 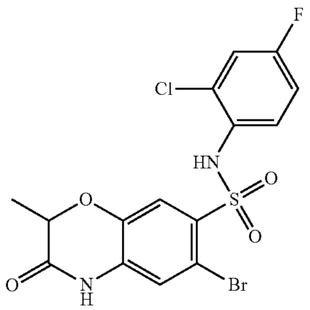 [SMILES: CC1Oc2cc(S(=O)(=O)Nc3ccc(F)cc3Cl)c(Br)cc2NC1=O] | ++ |
| BC19286 | 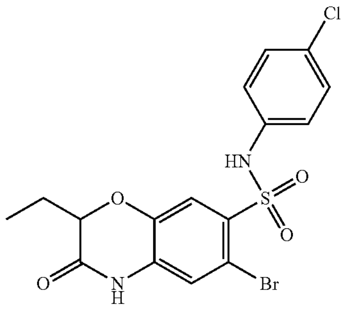 [SMILES: CCC1Oc2cc(S(=O)(=O)Nc3ccc(Cl)cc3)c(Br)cc2NC1=O] | + |
| BC19287 | 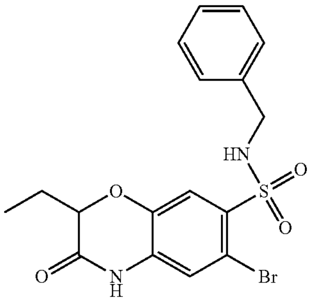 [SMILES: CCC1Oc2cc(S(=O)(=O)NCc3ccccc3)c(Br)cc2NC1=O] | ++ |
| BC19354 | 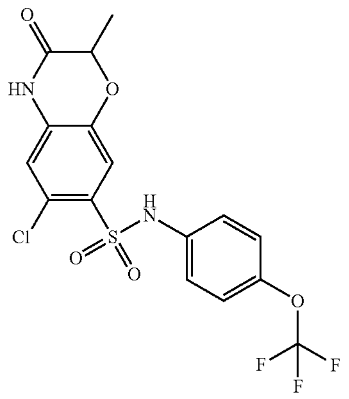 [SMILES: CC1Oc2cc(S(=O)(=O)Nc3ccc(OC(F)(F)F)cc3)c(Cl)cc2NC1=O] | + |
| BC19356 | 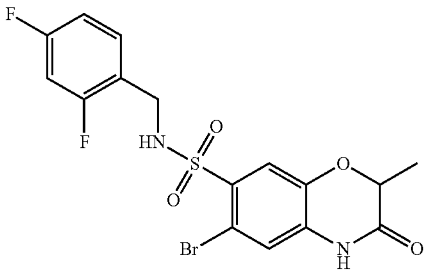 [SMILES: CC1Oc2cc(S(=O)(=O)NCc3ccc(F)cc3F)c(Br)cc2NC1=O] | + |

TABLE 2-continued
| BC No. | Structure | CB1 assay |
|---|---|---|
| BC19357 | 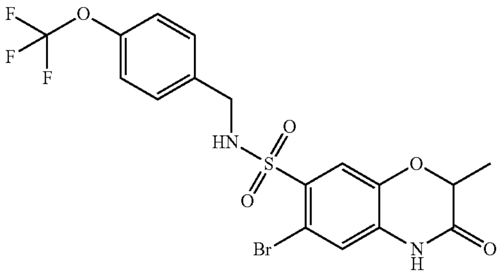 [SMILES: CC1Oc2cc(S(=O)(=O)NCc3ccc(OC(F)(F)F)cc3)c(Br)cc2NC1=O] | ++ |
| BC19358 | 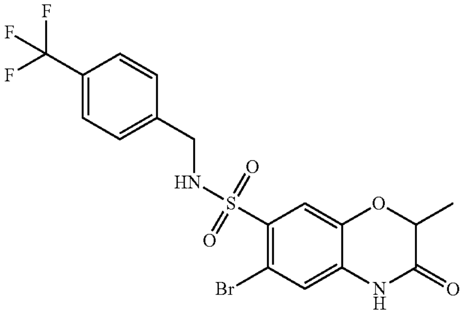 [SMILES: CC1Oc2cc(S(=O)(=O)NCc3ccc(C(F)(F)F)cc3)c(Br)cc2NC1=O] | ++ |
| BC19359 | 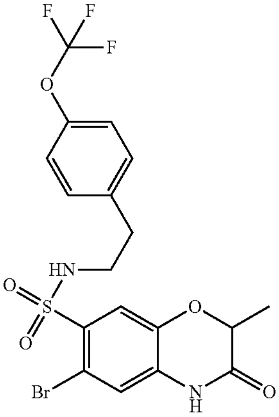 [SMILES: CC1Oc2cc(S(=O)(=O)NCCc3ccc(OC(F)(F)F)cc3)c(Br)cc2NC1=O] | ++ |
| BC19360 | 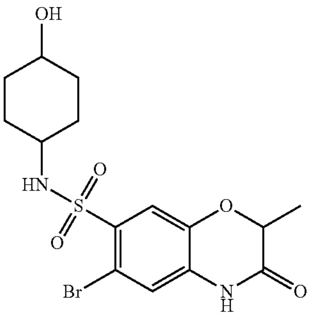 [SMILES: CC1Oc2cc(S(=O)(=O)NC3CCC(O)CC3)c(Br)cc2NC1=O] | + |
| BC19361 | 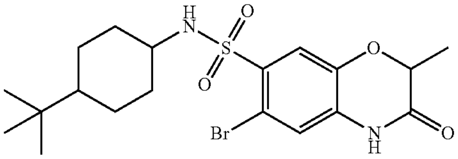 [SMILES: CC1Oc2cc(S(=O)(=O)NC3CCC(C(C)(C)C)CC3)c(Br)cc2NC1=O] | ++ |

TABLE 2-continued
| BC No. | Structure | CB1 assay |
|---|---|---|
| BC19368 | 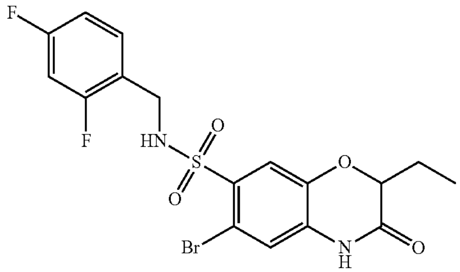 [SMILES: CCC1Oc2cc(S(=O)(=O)NCc3ccc(F)cc3F)c(Br)cc2NC1=O] | + |
| BC19369 | 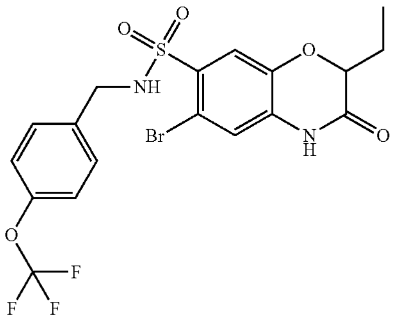 [SMILES: CCC1Oc2cc(S(=O)(=O)NCc3ccc(OC(F)(F)F)cc3)c(Br)cc2NC1=O] | + |
| BC19370 | 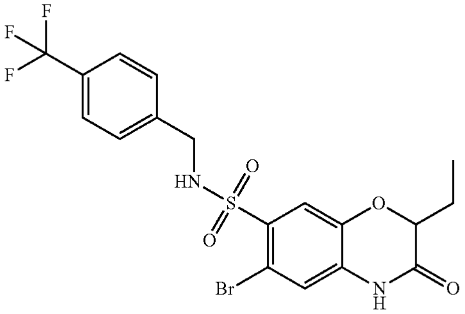 [SMILES: CCC1Oc2cc(S(=O)(=O)NCc3ccc(C(F)(F)F)cc3)c(Br)cc2NC1=O] | + |
| BC19371 | 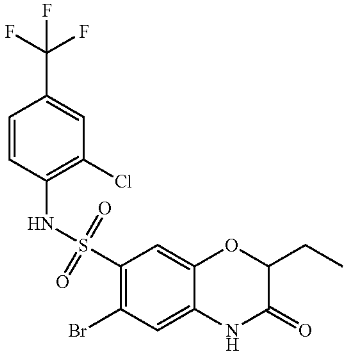 [SMILES: CCC1Oc2cc(S(=O)(=O)Nc3ccc(C(F)(F)F)cc3Cl)c(Br)cc2NC1=O] | + |
| BC19372 | 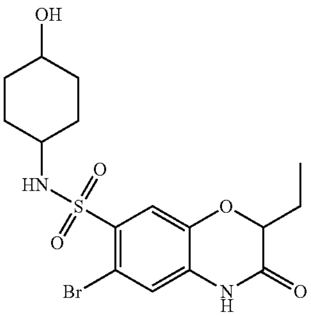 [SMILES: CCC1Oc2cc(S(=O)(=O)NC3CCC(O)CC3)c(Br)cc2NC1=O] | + |

TABLE 2-continued
| BC No. | Structure | CB1 assay |
|---|---|---|
| BC19373 | 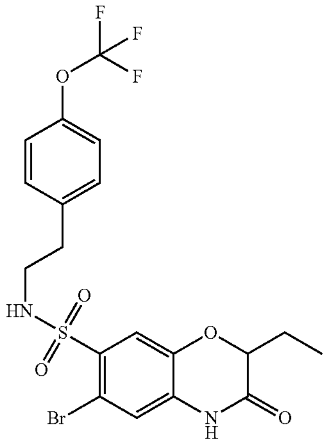 [SMILES: CCC1Oc2cc(S(=O)(=O)NCCc3ccc(OC(F)(F)F)cc3)c(Br)cc2NC1=O] | + |
| BC19387 | 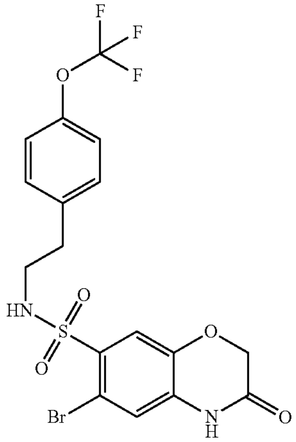 [SMILES: O=C1COc2cc(S(=O)(=O)NCCc3ccc(OC(F)(F)F)cc3)c(Br)cc2N1] | + |
| BC19388 | 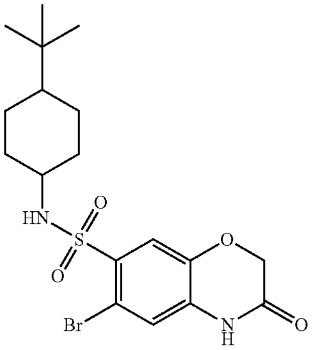 [SMILES: CC(C)(C)C1CCC(NS(=O)(=O)c2cc3c(cc2Br)NC(=O)CO3)CC1] | + |
| BC19389 | 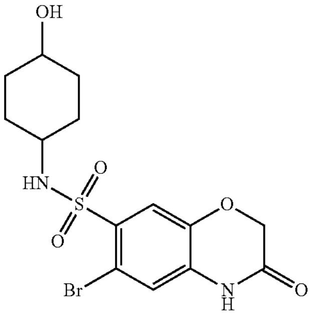 [SMILES: O=C1COc2cc(S(=O)(=O)NC3CCC(O)CC3)c(Br)cc2N1] | + |

TABLE 2-continued
| BC No. | Structure | CB1 assay |
|---|---|---|
| BC19390 | 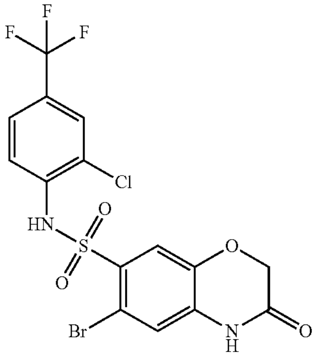 [SMILES: O=C1COc2cc(S(=O)(=O)Nc3ccc(C(F)(F)F)cc3Cl)c(Br)cc2N1] | + |
| BC19391 | 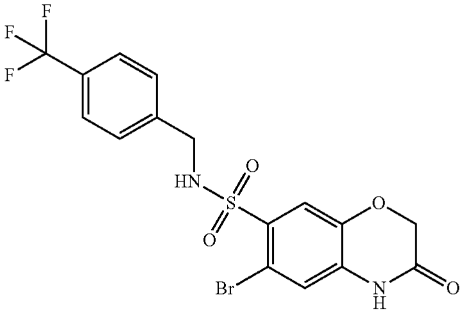 [SMILES: O=C1COc2cc(S(=O)(=O)NCc3ccc(C(F)(F)F)cc3)c(Br)cc2N1] | + |
| BC19392 | 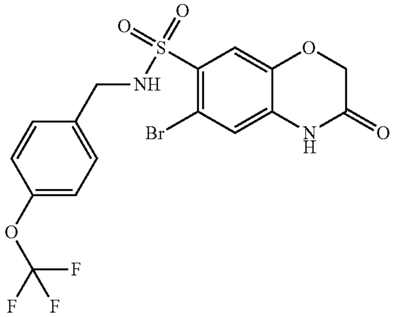 [SMILES: O=C1COc2cc(S(=O)(=O)NCc3ccc(OC(F)(F)F)cc3)c(Br)cc2N1] | + |
| BC19393 | 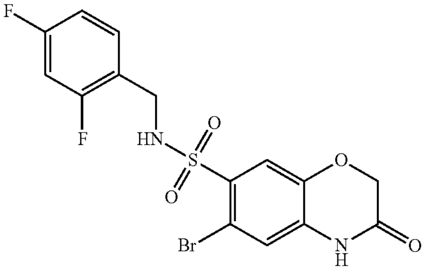 | + |
TABLE 3
| BC No. | Structure | CB1 assay |
|---|---|---|
| BC19696 | 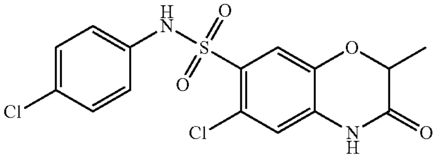 [SMILES: CC1Oc2cc(S(=O)(=O)Nc3ccc(Cl)cc3)c(Cl)cc2NC1=O] | ++ |

TABLE 3-continued
| BC No. | Structure | CB1 assay |
| --- | --- | --- |
| BC19698 | 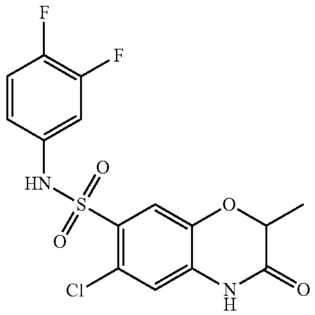 [SMILES: CC1Oc2cc(S(=O)(=O)Nc3ccc(F)c(F)c3)c(Cl)cc2NC1=O] | + |
| BC19700 | 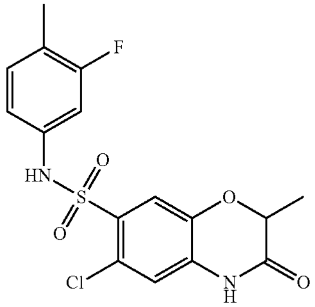 [SMILES: Cc1ccc(NS(=O)(=O)c2cc3c(cc2Cl)NC(=O)C(C)O3)cc1F] | ++ |
| BC19702 | 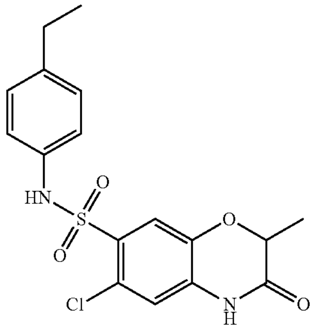 [SMILES: CCc1ccc(NS(=O)(=O)c2cc3c(cc2Cl)NC(=O)C(C)O3)cc1] | + |
| BC19704 | 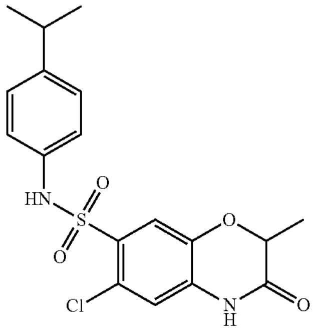 [SMILES: CC1Oc2cc(S(=O)(=O)Nc3ccc(C(C)C)cc3)c(Cl)cc2NC1=O] | + |

TABLE 3-continued
| BC No. | Structure | CB1 assay |
|---|---|---|
| BC19706 | 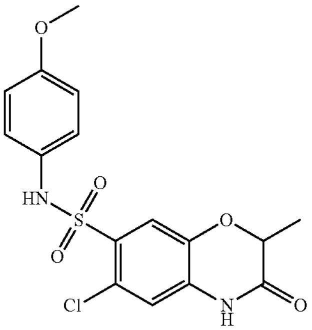 [SMILES: COc1ccc(NS(=O)(=O)c2cc3c(cc2Cl)NC(=O)C(C)O3)cc1] | + |
| BC19708 | 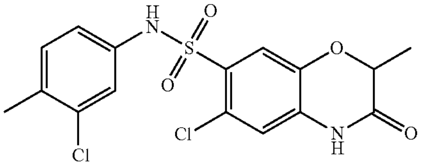 | + |
| BC19709 | 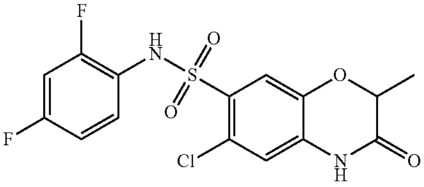 [SMILES: CC1Oc2cc(S(=O)(=O)Nc3ccc(F)cc3F)c(Cl)cc2NC1=O] | ++ |
| BC19711 | 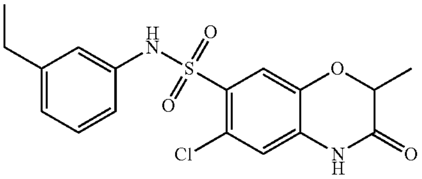 [SMILES: CCc1cccc(NS(=O)(=O)c2cc3c(cc2Cl)NC(=O)C(C)O3)c1] | + |
| BC19713 | 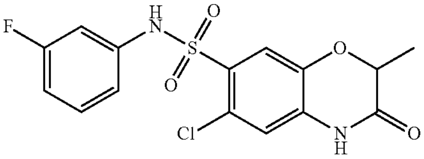 [SMILES: CC1Oc2cc(S(=O)(=O)Nc3cccc(F)c3)c(Cl)cc2NC1=O] | ++ |
| BC19715 | 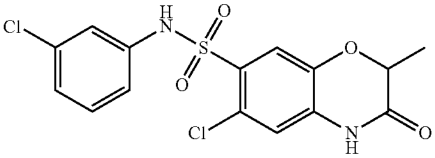 [SMILES: CC1Oc2cc(S(=O)(=O)Nc3cccc(Cl)c3)c(Cl)cc2NC1=O] | +++ |
| BC19717 | 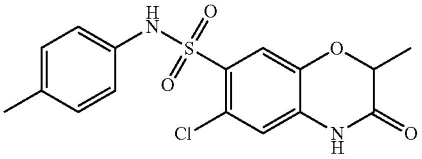 | + |
| BC19719 | 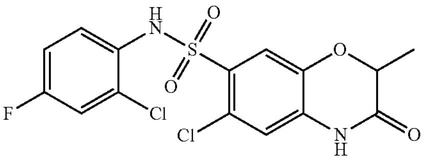 [SMILES: CC1Oc2cc(S(=O)(=O)Nc3ccc(F)cc3Cl)c(Cl)cc2NC1=O] | ++ |

TABLE 3-continued
| BC No. | Structure | CB1 assay |
|---|---|---|
| BC19721 | 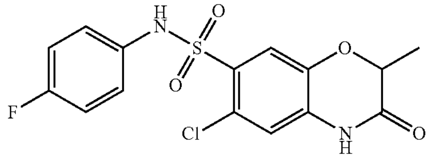 [SMILES: CC1Oc2cc(S(=O)(=O)Nc3ccc(F)cc3)c(Cl)cc2NC1=O] | +++ |
| BC19729 | 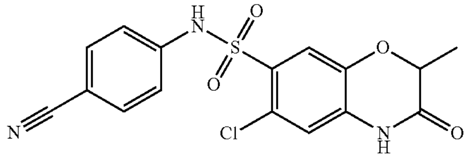 [SMILES: CC1Oc2cc(S(=O)(=O)Nc3ccc(C#N)cc3)c(Cl)cc2NC1=O] | +++ |
| BC19731 | 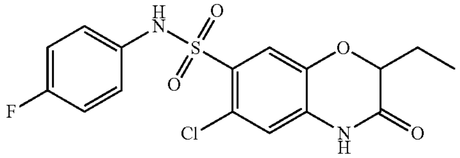 [SMILES: CCC1Oc2cc(S(=O)(=O)Nc3ccc(F)cc3)c(Cl)cc2NC1=O] | ++ |
| BC19733 | 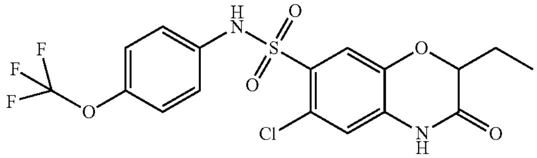 [SMILES: CCC1Oc2cc(S(=O)(=O)Nc3ccc(OC(F)(F)F)cc3)c(Cl)cc2NC1=O] | ++ |
| BC19735 | 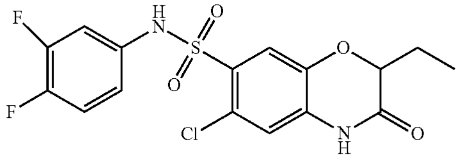 [SMILES: CCC1Oc2cc(S(=O)(=O)Nc3ccc(F)c(F)c3)c(Cl)cc2NC1=O] | + |
| BC19737 | 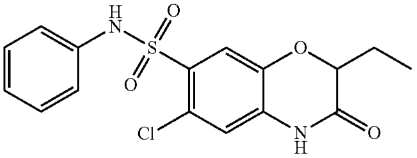 [SMILES: CCC1Oc2cc(S(=O)(=O)Nc3ccccc3)c(Cl)cc2NC1=O] | ++ |
| BC19739 | 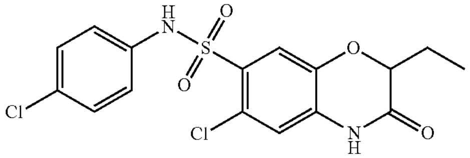 [SMILES: CCC1Oc2cc(S(=O)(=O)Nc3ccc(Cl)cc3)c(Cl)cc2NC1=O] | ++ |
| BC19741 | 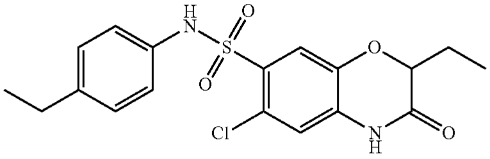 [SMILES: CCc1ccc(NS(=O)(=O)c2cc3c(cc2Cl)NC(=O)C(CC)O3)cc1] | ++ |
| BC19743 | 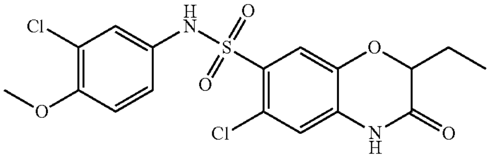 [SMILES: CCC1Oc2cc(S(=O)(=O)Nc3ccc(OC)c(Cl)c3)c(Cl)cc2NC1=O] | + |

TABLE 3-continued
| BC No. | Structure | CB1 assay |
|---|---|---|
| BC19745 | 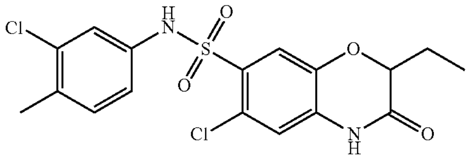 [SMILES: CCC1Oc2cc(S(=O)(=O)Nc3ccc(C)c(Cl)c3)c(Cl)cc2NC1=O] | ++ |
| BC19747 | 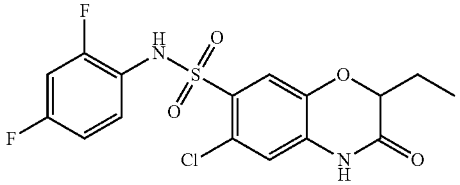 [SMILES: CCC1Oc2cc(S(=O)(=O)Nc3ccc(F)cc3F)c(Cl)cc2NC1=O] | ++ |
| BC19749 | 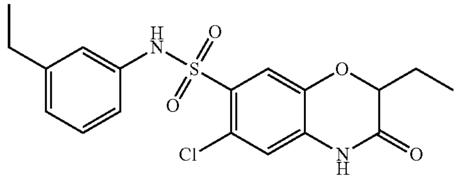 [SMILES: CCc1cccc(NS(=O)(=O)c2cc3c(cc2Cl)NC(=O)C(CC)O3)c1] | ++ |
| BC19751 | 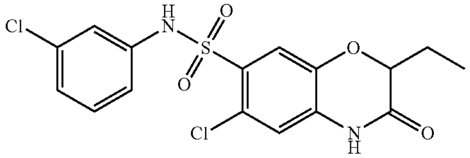 [SMILES: CCC1Oc2cc(S(=O)(=O)Nc3cccc(Cl)c3)c(Cl)cc2NC1=O] | +++ |
| BC19753 | 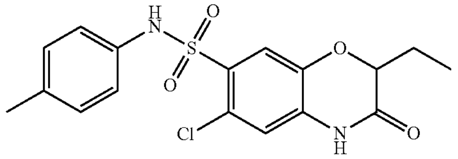 [SMILES: CCC1Oc2cc(S(=O)(=O)Nc3ccc(C)cc3)c(Cl)cc2NC1=O] | ++ |
| BC19755 | 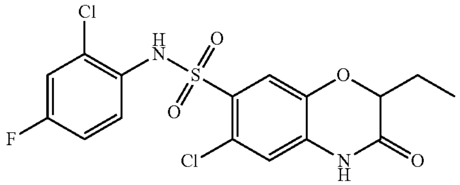 [SMILES: CCC1Oc2cc(S(=O)(=O)Nc3ccc(F)cc3Cl)c(Cl)cc2NC1=O] | ++ |
| BC19758 | 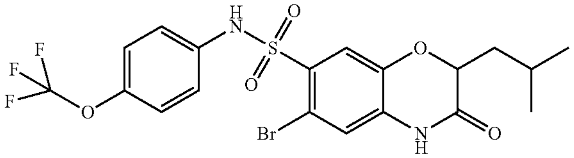 [SMILES: CC(C)CC1Oc2cc(S(=O)(=O)Nc3ccc(OC(F)(F)F)cc3)c(Br)cc2NC1=O] | + |
| BC19760 | 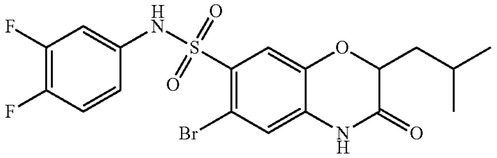 [SMILES: CC(C)CC1Oc2cc(S(=O)(=O)Nc3ccc(F)c(F)c3)c(Br)cc2NC1=O] | ++ |
| BC19762 | 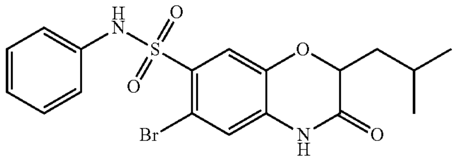 [SMILES: CC(C)CC1Oc2cc(S(=O)(=O)Nc3ccccc3)c(Br)cc2NC1=O] | + |

TABLE 3-continued
| BC No. | Structure | CB1 assay |
| --- | --- | --- |
| BC19764 | 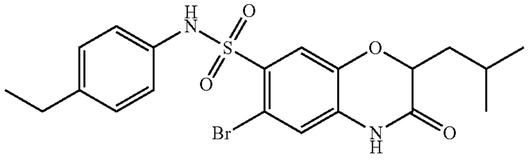 [SMILES: CCc1ccc(NS(=O)(=O)c2cc3c(cc2Br)NC(=O)C(CC(C)C)O3)cc1] | ++ |
| BC19766 | 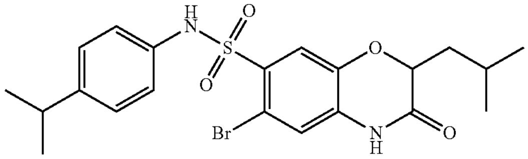 [SMILES: CC(C)CC1Oc2cc(S(=O)(=O)Nc3ccc(C(C)C)cc3)c(Br)cc2NC1=O] | + |
| BC19768 | 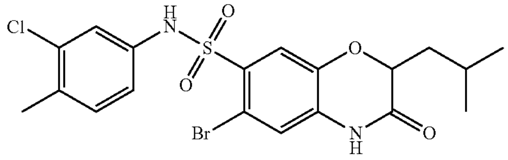 [SMILES: Cc1ccc(NS(=O)(=O)c2cc3c(cc2Br)NC(=O)C(CC(C)C)O3)cc1Cl] | ++ |
| BC19770 | 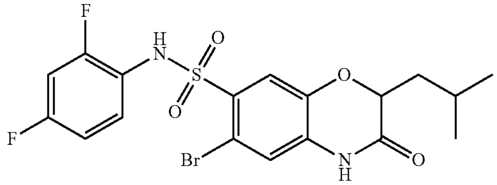 | + |
| BC19772 | 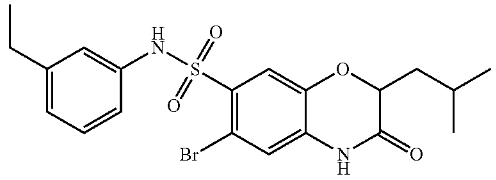 [SMILES: CCc1cccc(NS(=O)(=O)c2cc3c(cc2Br)NC(=O)C(CC(C)C)O3)c1] | ++ |
| BC19774 | 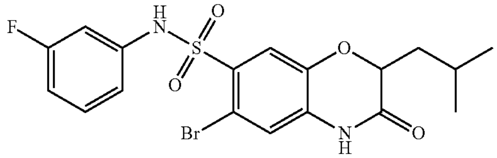 [SMILES: CC(C)CC1Oc2cc(S(=O)(=O)Nc3cccc(F)c3)c(Br)cc2NC1=O] | + |
| BC19776 | 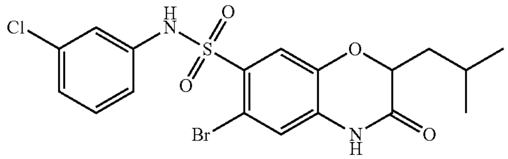 [SMILES: CC(C)CC1Oc2cc(S(=O)(=O)Nc3cccc(Cl)c3)c(Br)cc2NC1=O] | + |
| BC19778 | 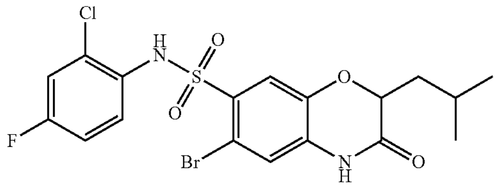 [SMILES: CC(C)CC1Oc2cc(S(=O)(=O)Nc3ccc(F)cc3Cl)c(Br)cc2NC1=O] | + |

TABLE 3-continued
| BC No. | Structure | CB1 assay |
|---|---|---|
| BC19780 | 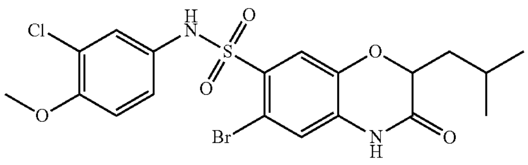 [SMILES: COc1ccc(NS(=O)(=O)c2cc3c(cc2Br)NC(=O)C(CC(C)C)O3)cc1Cl] | ++ |
| BC19782 | 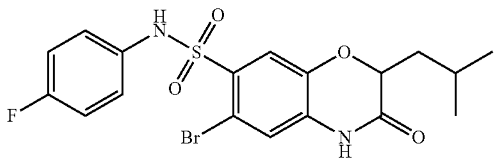 [SMILES: CC(C)CC1Oc2cc(S(=O)(=O)Nc3ccc(F)cc3)c(Br)cc2NC1=O] | + |
| BC19784 | 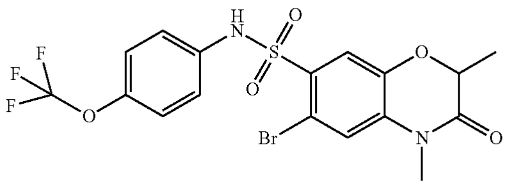 [SMILES: CC1Oc2cc(S(=O)(=O)Nc3ccc(OC(F)(F)F)cc3)c(Br)cc2N(C)C1=O] | + |
| BC19786 | 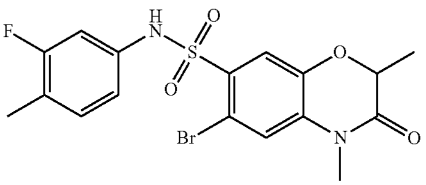 | + |
| BC19788 | 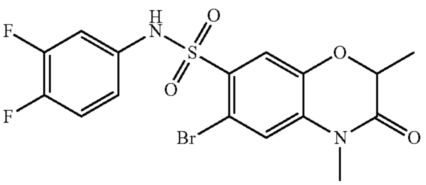 [SMILES: CC1Oc2cc(S(=O)(=O)Nc3ccc(F)c(F)c3)c(Br)cc2N(C)C1=O] | ++ |
| BC19790 | 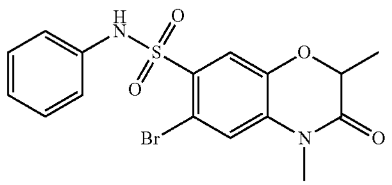 [SMILES: CC1Oc2cc(S(=O)(=O)Nc3ccccc3)c(Br)cc2N(C)C1=O] | ++ |
| BC19792 | 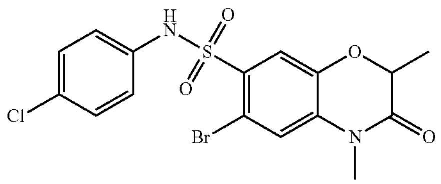 [SMILES: CC1Oc2cc(S(=O)(=O)Nc3ccc(Cl)cc3)c(Br)cc2N(C)C1=O] | + |
| BC19794 | 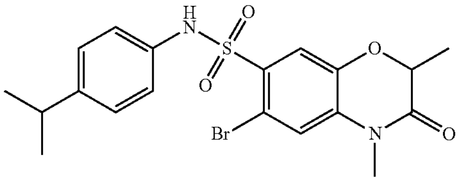 [SMILES: CC1Oc2cc(S(=O)(=O)Nc3ccc(C(C)C)cc3)c(Br)cc2N(C)C1=O] | + |

TABLE 3-continued
| BC No. | Structure | CB1 assay |
|---|---|---|
| BC19795 | 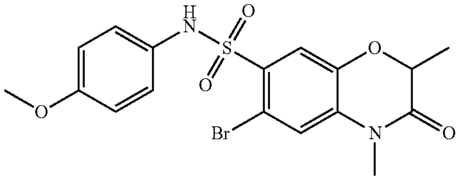 | + |
| BC19797 | 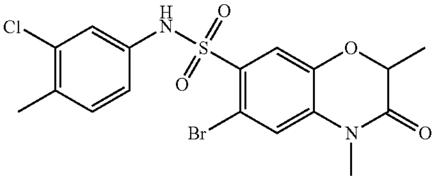 | + |
| BC19799 | 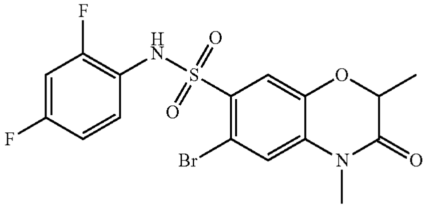 [SMILES: CC1Oc2cc(S(=O)(=O)Nc3ccc(F)cc3F)c(Br)cc2N(C)C1=O] | + |
| BC19901 | 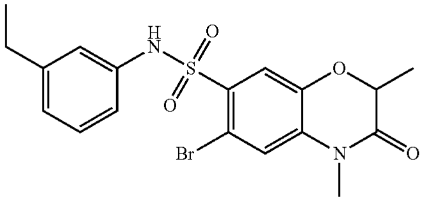 [SMILES: CCc1cccc(NS(=O)(=O)c2cc3c(cc2Br)N(C)C(=O)C(C)O3)c1] | + |
| BC19903 | 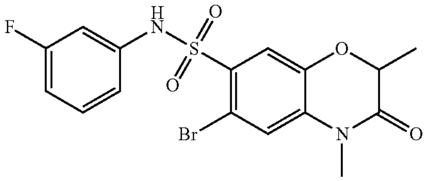 [SMILES: CC1Oc2cc(S(=O)(=O)Nc3cccc(F)c3)c(Br)cc2N(C)C1=O] | ++ |
| BC19905 | 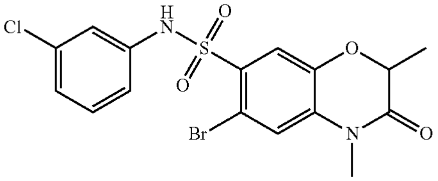 [SMILES: CC1Oc2cc(S(=O)(=O)Nc3cccc(Cl)c3)c(Br)cc2N(C)C1=O] | + |
| BC19907 | 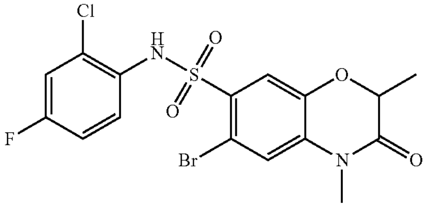 | + |
| BC19910 | 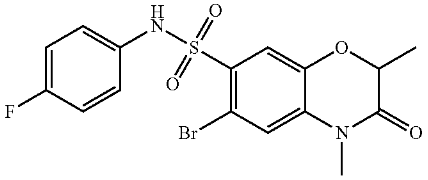 [SMILES: CC1Oc2cc(S(=O)(=O)Nc3ccc(F)cc3)c(Br)cc2N(C)C1=O] | + |

TABLE 3-continued
| BC No. | Structure | CB1 assay |
|---|---|---|
| BC19912 | 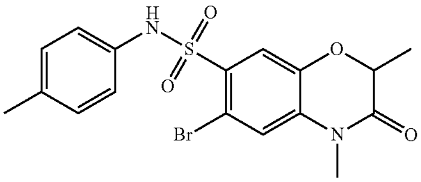 | + |
| BC19914 | 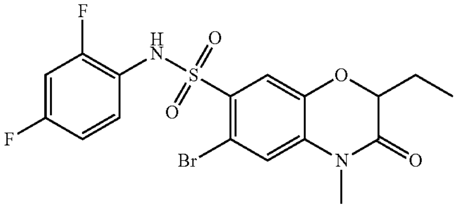 [SMILES: CCC1Oc2cc(S(=O)(=O)Nc3ccc(F)cc3F)c(Br)cc2N(C)C1=O] | ++ |
| BC19916 | 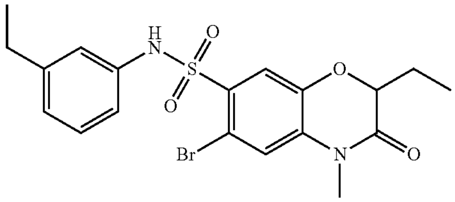 [SMILES: CCc1cccc(NS(=O)(=O)c2cc3c(cc2Br)N(C)C(=O)C(CC)O3)c1] | ++ |
| BC19919 | 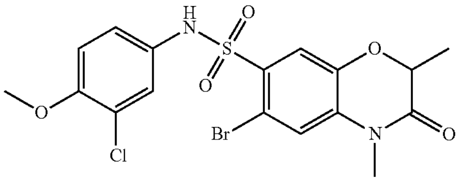 | + |
| BC19920 | 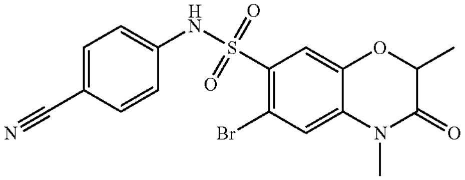 [SMILES: CC1Oc2cc(S(=O)(=O)Nc3ccc(C#N)cc3)c(Br)cc2N(C)C1=O] | ++ |
| BC19922 | 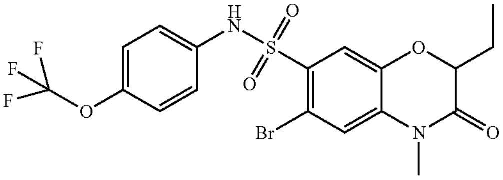 [SMILES: CCC1Oc2cc(S(=O)(=O)Nc3ccc(OC(F)(F)F)cc3)c(Br)cc2N(C)C1=O] | + |
| BC19924 | 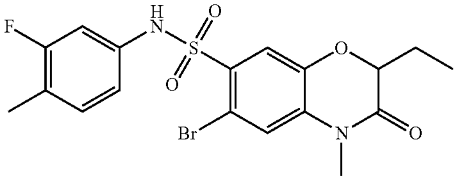 [SMILES: CCC1Oc2cc(S(=O)(=O)Nc3ccc(C)c(F)c3)c(Br)cc2N(C)C1=O] | ++ |
| BC19926 | 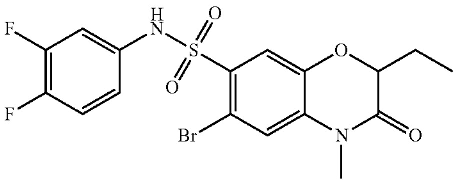 [SMILES: CCC1Oc2cc(S(=O)(=O)Nc3ccc(F)c(F)c3)c(Br)cc2N(C)C1=O] | + |

TABLE 3-continued
| BC No. | Structure | CB1 assay |
| --- | --- | --- |
| BC19928 | 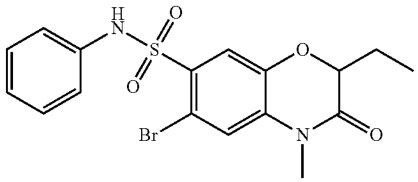 [SMILES: CCC1Oc2cc(S(=O)(=O)Nc3ccccc3)c(Br)cc2N(C)C1=O] | + |
| BC19930 | 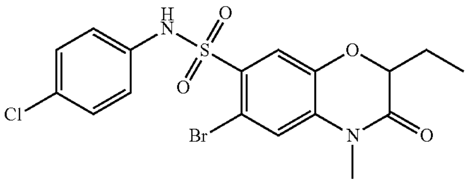 [SMILES: CCC1Oc2cc(S(=O)(=O)Nc3ccc(Cl)cc3)c(Br)cc2N(C)C1=O] | + |
| BC19932 | 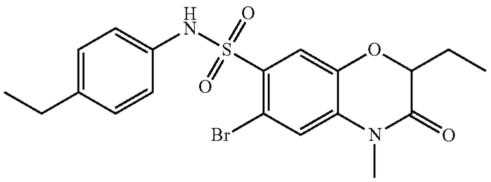 [SMILES: CCc1ccc(NS(=O)(=O)c2cc3c(cc2Br)N(C)C(=O)C(CC)O3)cc1] | + |
| BC19934 | 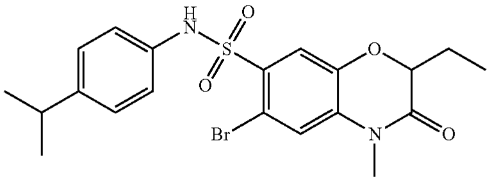 [SMILES: CCC1Oc2cc(S(=O)(=O)Nc3ccc(C(C)C)cc3)c(Br)cc2N(C)C1=O] | + |
| BC19936 | 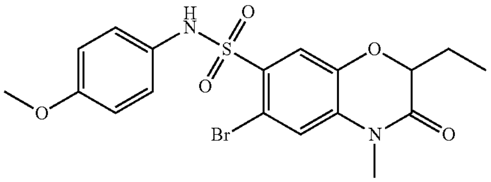 [SMILES: CCC1Oc2cc(S(=O)(=O)Nc3ccc(OC)cc3)c(Br)cc2N(C)C1=O] | + |
| BC19938 | 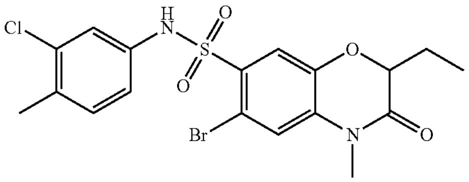 [SMILES: CCC1Oc2cc(S(=O)(=O)Nc3ccc(C)c(Cl)c3)c(Br)cc2N(C)C1=O] | + |

TABLE 4
| BC No. | Structure | CB1 assay |
|---|---|---|
| BC19168 | 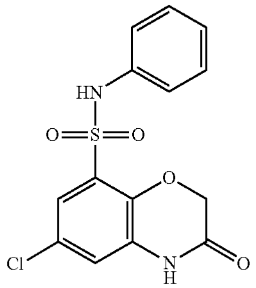 [SMILES: O=C1COc2c(cc(Cl)cc2S(=O)(=O)Nc2ccccc2)N1] | ++ |
| BC19169 | 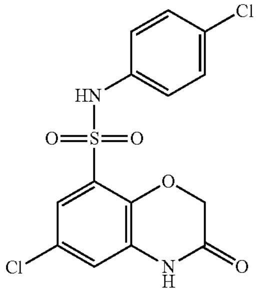 [SMILES: O=C1COc2c(cc(Cl)cc2S(=O)(=O)Nc2ccc(Cl)cc2)N1] | +++ |
| BC19170 | 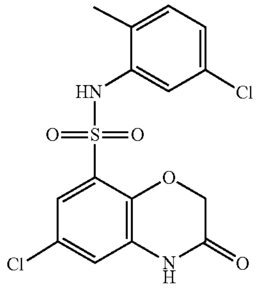 [SMILES: Cc1ccc(Cl)cc1NS(=O)(=O)c1cc(Cl)cc2c1OCC(=O)N2] | ++ |
| BC19171 | 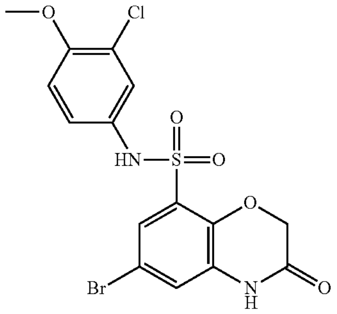 [SMILES: COc1ccc(NS(=O)(=O)c2cc(Br)cc3c2OCC(=O)N3)cc1Cl] | ++ |
| BC19172 | 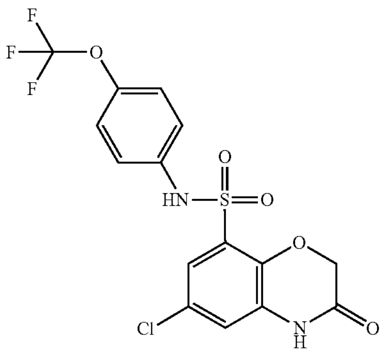 [SMILES: O=C1COc2c(cc(Cl)cc2S(=O)(=O)Nc2ccc(OC(F)(F)F)cc2)N1] | + |
TABLE 4-continued
| BC No. | Structure | CB1 assay |
|---|---|---|
| BC19173 | 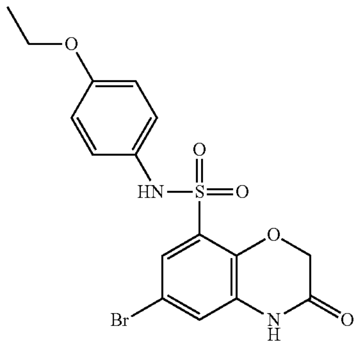 [SMILES: CCOc1ccc(NS(=O)(=O)c2cc(Br)cc3c2OCC(=O)N3)cc1] | + |
| BC19174 | 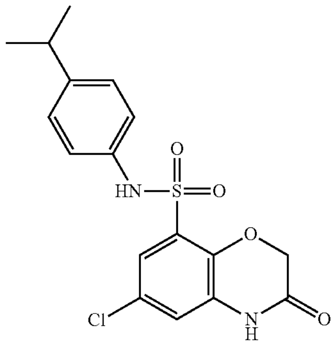 [SMILES: CC(C)c1ccc(NS(=O)(=O)c2cc(Cl)cc3c2OCC(=O)N3)cc1] | + |
| BC19175 | 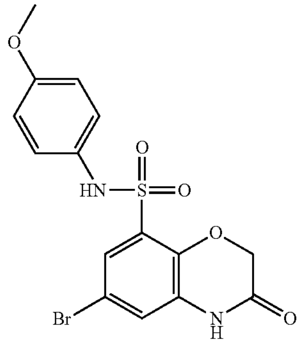 [SMILES: COc1ccc(NS(=O)(=O)c2cc(Br)cc3c2OCC(=O)N3)cc1] | + |
| BC19176 | 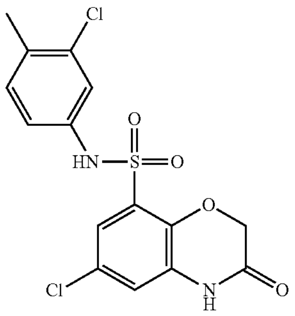 [SMILES: Cc1ccc(NS(=O)(=O)c2cc(Cl)cc3c2OCC(=O)N3)cc1Cl] | +++ |

TABLE 4-continued
| BC No. | Structure | CB1 assay |
|---|---|---|
| BC19177 | 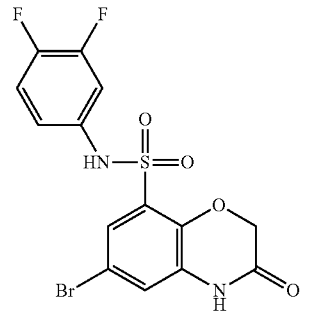 [SMILES: O=C1COc2c(cc(Br)cc2S(=O)(=O)Nc2ccc(F)c(F)c2)N1] | ++ |
| BC19178 | 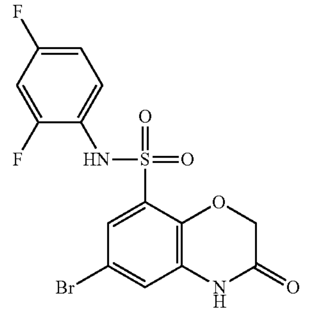 [SMILES: O=C1COc2c(cc(Br)cc2S(=O)(=O)Nc2ccc(F)cc2F)N1] | +++ |
| BC19179 | 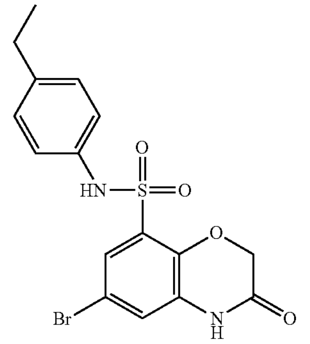 [SMILES: CCc1ccc(NS(=O)(=O)c2cc(Br)cc3c2OCC(=O)N3)cc1] | ++ |
| BC19180 | 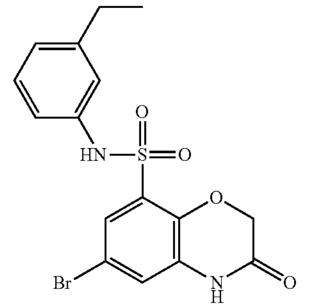 [SMILES: CCc1cccc(NS(=O)(=O)c2cc(Br)cc3c2OCC(=O)N3)c1] | + |
| BC19225 | 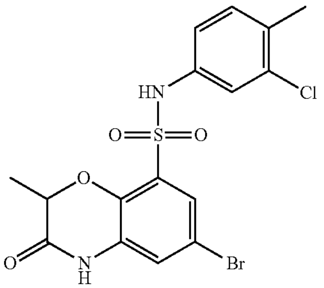 [SMILES: Cc1ccc(NS(=O)(=O)c2cc(Br)cc3c2OC(C)C(=O)N3)cc1Cl] | + |
TABLE 4-continued
| BC No. | Structure | CB1 assay |
|---|---|---|
| BC19226 | 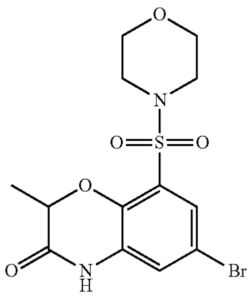 [SMILES: CC1Oc2c(cc(Br)cc2S(=O)(=O)N2CCOCC2)NC1=O] | + |
| BC19227 | 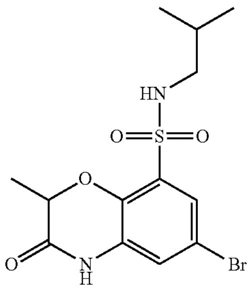 [SMILES: CC(C)CNS(=O)(=O)c1cc(Br)cc2c1OC(C)C(=O)N2] | + |
| BC19228 | 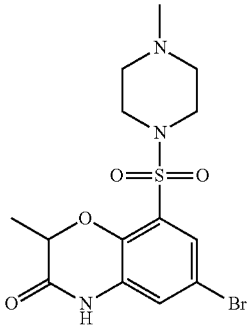 [SMILES: CC1Oc2c(cc(Br)cc2S(=O)(=O)N2CCN(C)CC2)NC1=O] | ++ |
| BC19229 | 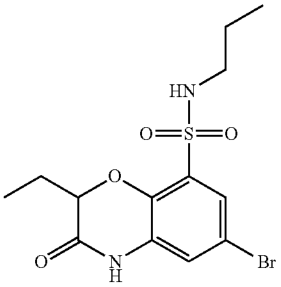 [SMILES: CCCNS(=O)(=O)c1cc(Br)cc2c1OC(CC)C(=O)N2] | + |

TABLE 4-continued
| BC No. | Structure | CB1 assay |
|---|---|---|
| BC19230 | 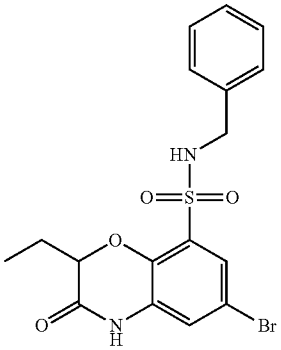 [SMILES: CCC1Oc2c(cc(Br)cc2S(=O)(=O)NCc2ccccc2)NC1=O] | + |
| BC19231 | 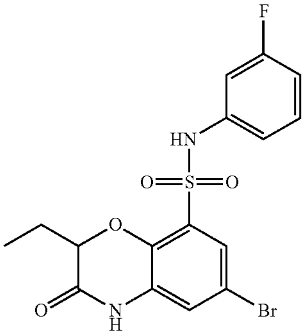 [SMILES: CCC1Oc2c(cc(Br)cc2S(=O)(=O)Nc2cccc(F)c2)NC1=O] | + |
| BC19232 | 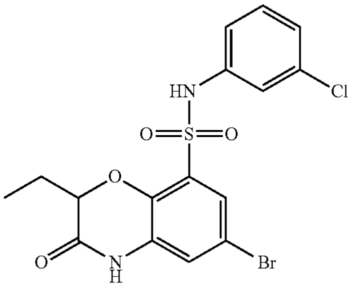 [SMILES: CCC1Oc2c(cc(Br)cc2S(=O)(=O)Nc2cccc(Cl)c2)NC1=O] | + |
| BC19233 | 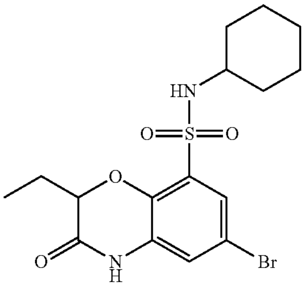 [SMILES: CCC1Oc2c(cc(Br)cc2S(=O)(=O)NC2CCCCC2)NC1=O] | + |
| BC19234 | 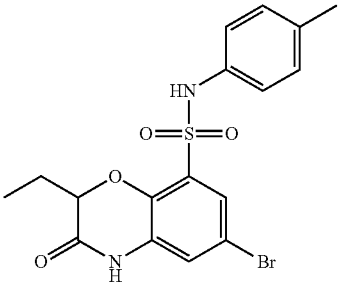 [SMILES: CCC1Oc2c(cc(Br)cc2S(=O)(=O)Nc2ccc(C)cc2)NC1=O] | + |
TABLE 4-continued
| BC No. | Structure | CB1 assay |
|---|---|---|
| BC19288 | 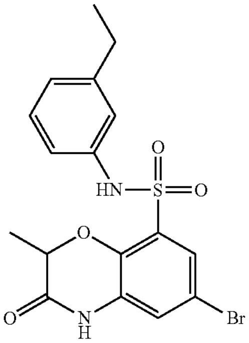 [SMILES: CCc1cccc(NS(=O)(=O)c2cc(Br)cc3c2OC(C)C(=O)N3)c1] | ++ |
| BC19289 | 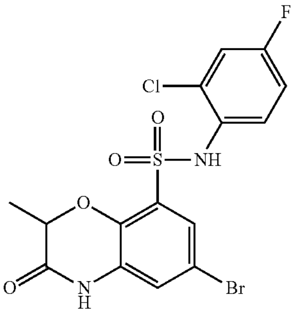 [SMILES: CC1Oc2c(cc(Br)cc2S(=O)(=O)Nc2ccc(F)cc2Cl)NC1=O] | + |
| BC19290 | 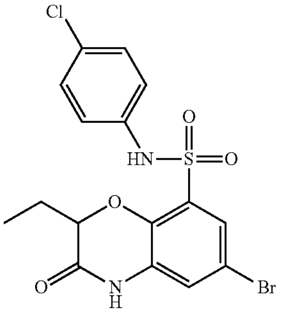 [SMILES: CCC1Oc2c(cc(Br)cc2S(=O)(=O)Nc2ccc(Cl)cc2)NC1=O] | + |
| BC19291 | 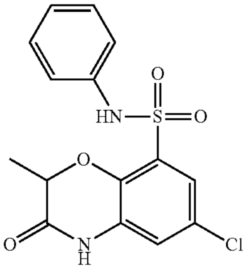 [SMILES: CC1Oc2c(cc(Cl)cc2S(=O)(=O)Nc2ccccc2)NC1=O] | + |

TABLE 4-continued
| BC No. | Structure | CB1 assay |
|---|---|---|
| BC19292 | 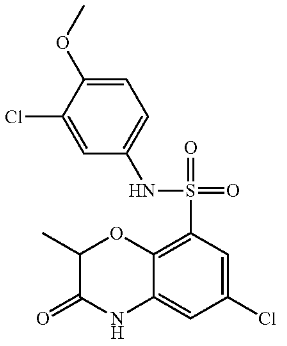 [SMILES: COc1ccc(NS(=O)(=O)c2cc(Cl)cc3c2OC(C)C(=O)N3)cc1Cl] | ++ |
| BC19293 | 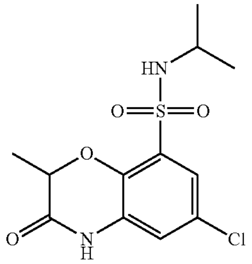 [SMILES: CC(C)NS(=O)(=O)c1cc(Cl)cc2c1OC(C)C(=O)N2] | + |
| BC19294 | 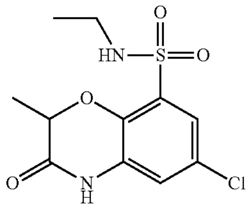 [SMILES: CCNS(=O)(=O)c1cc(Cl)cc2c1OC(C)C(=O)N2] | ++ |
| BC19355 | 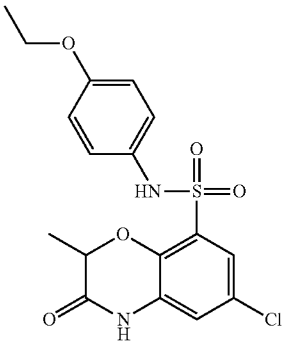 [SMILES: CCOc1ccc(NS(=O)(=O)c2cc(Cl)cc3c2OC(C)C(=O)N3)cc1] | ++ |
| BC19362 | 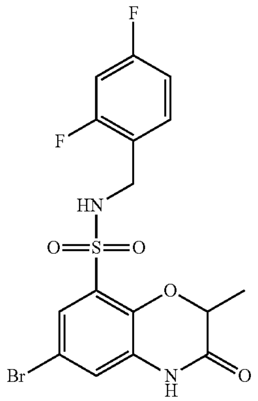 [SMILES: CC1Oc2c(cc(Br)cc2S(=O)(=O)NCc2ccc(F)cc2F)NC1=O] | + |
TABLE 4-continued
| BC No. | Structure | CB1 assay |
|---|---|---|
| BC19363 | 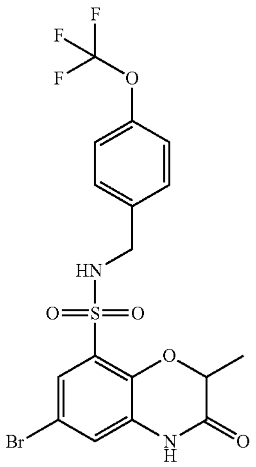 [SMILES: CC1Oc2c(cc(Br)cc2S(=O)(=O)NCc2ccc(OC(F)(F)F)cc2)NC1=O] | ++ |
| BC19364 | 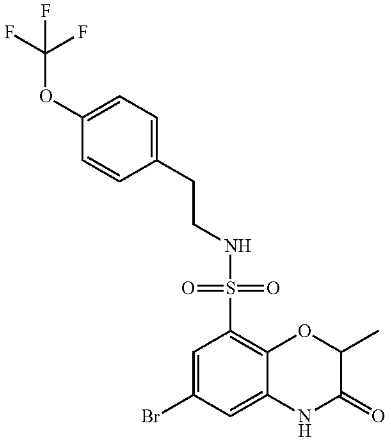 [SMILES: CC1Oc2c(cc(Br)cc2S(=O)(=O)NCCc2ccc(OC(F)(F)F)cc2)NC1=O] | ++ |
| BC19365 | 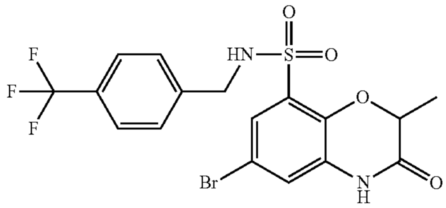 [SMILES: CC1Oc2c(cc(Br)cc2S(=O)(=O)NCc2ccc(C(F)(F)F)cc2)NC1=O] | ++ |
| BC19366 | 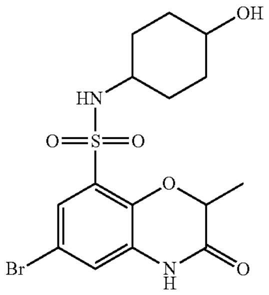 [SMILES: CC1Oc2c(cc(Br)cc2S(=O)(=O)NC2CCC(O)CC2)NC1=O] | + |

TABLE 4-continued
| BC No. | Structure | CB1 assay |
|---|---|---|
| BC19367 | 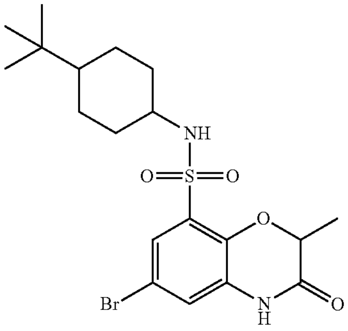 [SMILES: CC1Oc2c(cc(Br)cc2S(=O)(=O)NC2CCC(C(C)(C)C)CC2)NC1=O] | + |
| BC19374 | 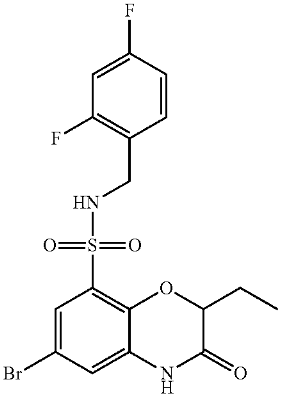 [SMILES: CCC1Oc2c(cc(Br)cc2S(=O)(=O)NCc2ccc(F)cc2F)NC1=O] | + |
| BC19375 | 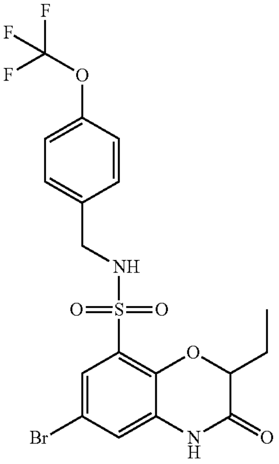 [SMILES: CCC1Oc2c(cc(Br)cc2S(=O)(=O)NCc2ccc(OC(F)(F)F)cc2)NC1=O] | ++ |
TABLE 4-continued
| BC No. | Structure | CB1 assay |
|---|---|---|
| BC19376 | 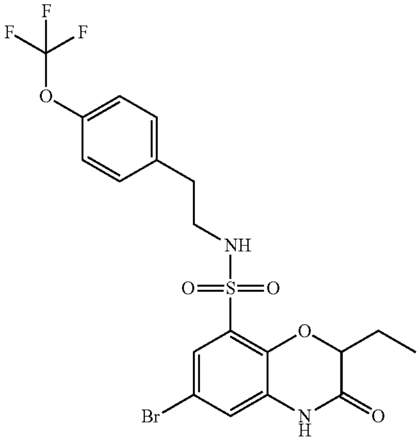 [SMILES: CCC1Oc2c(cc(Br)cc2S(=O)(=O)NCCc2ccc(OC(F)(F)F)cc2)NC1=O] | ++ |
| BC19377 | 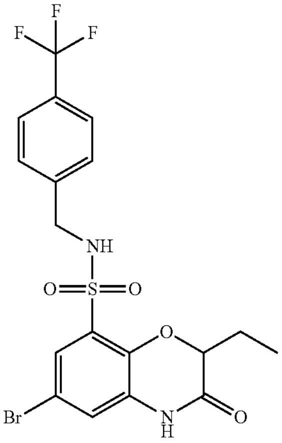 [SMILES: CCC1Oc2c(cc(Br)cc2S(=O)(=O)NCc2ccc(C(F)(F)F)cc2)NC1=O] | + |
| BC19378 | 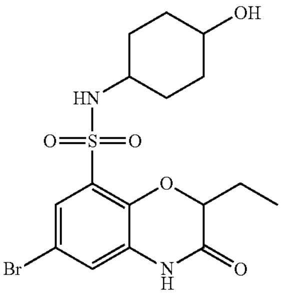 [SMILES: CCC1Oc2c(cc(Br)cc2S(=O)(=O)NC2CCC(O)CC2)NC1=O] | ++ |
| BC19379 | 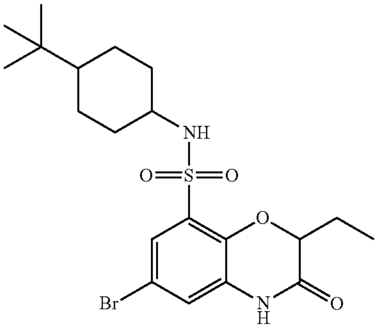 [SMILES: CCC1Oc2c(cc(Br)cc2S(=O)(=O)NC2CCC(C(C)(C)C)CC2)NC1=O] | ++ |

TABLE 4-continued
| BC No. | Structure | CB1 assay |
|---|---|---|
| BC19380 | 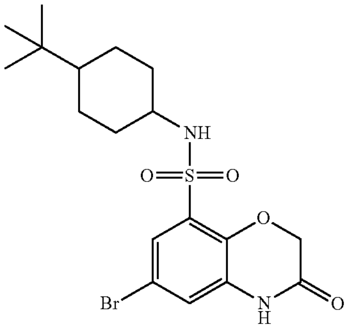 [SMILES: CC(C)(C)C1CCC(NS(=O)(=O)c2cc(Br)cc3c2OCC(=O)N3)CC1] | + |
| BC19381 | 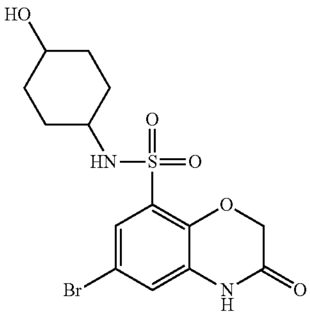 [SMILES: O=C1COc2c(cc(Br)cc2S(=O)(=O)NC2CCC(O)CC2)N1] | + |
| BC19382 | 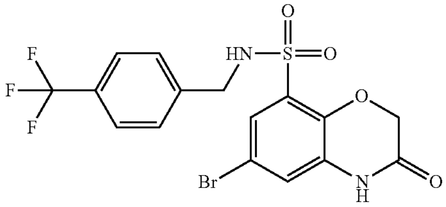 [SMILES: O=C1COc2c(cc(Br)cc2S(=O)(=O)NCc2ccc(C(F)(F)F)cc2)N1] | ++ |
| BC19383 | 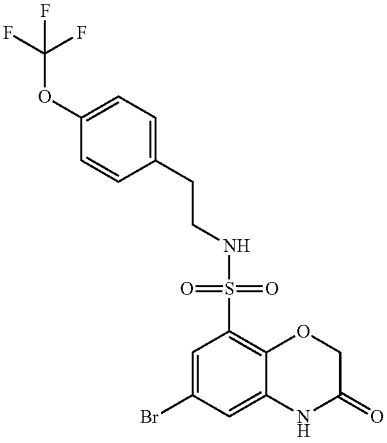 [SMILES: O=C1COc2c(cc(Br)cc2S(=O)(=O)NCCc2ccc(OC(F)(F)F)cc2)N1] | + |
TABLE 4-continued
| BC No. | Structure | CB1 assay |
|---|---|---|
| BC19384 | 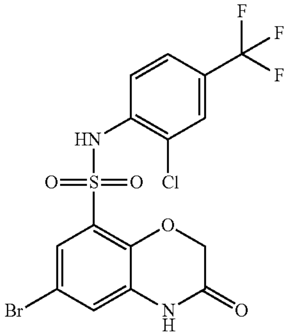 [SMILES: O=C1COc2c(cc(Br)cc2S(=O)(=O)Nc2ccc(C(F)(F)F)cc2Cl)N1] | + |
| BC19385 | 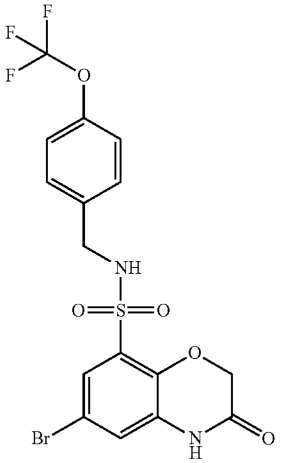 [SMILES: O=C1COc2c(cc(Br)cc2S(=O)(=O)NCc2ccc(OC(F)(F)F)cc2)N1] | + |
| BC19386 | 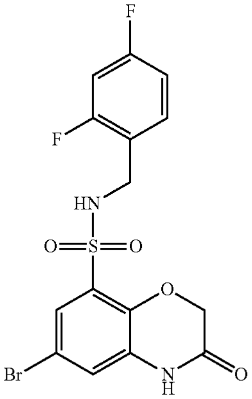 [SMILES: O=C1COc2c(cc(Br)cc2S(=O)(=O)NCc2ccc(F)cc2F)N1] | + |
| BC19394 | 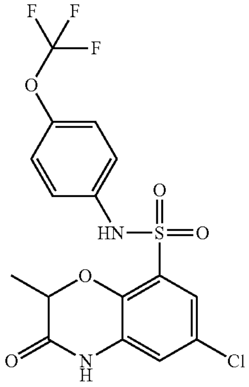 [SMILES: CC1Oc2c(cc(Cl)cc2S(=O)(=O)Nc2ccc(OC(F)(F)F)cc2)NC1=O] | + |

TABLE 4-continued
| BC No. | Structure | CB1 assay |
|---|---|---|
| BC19421 | 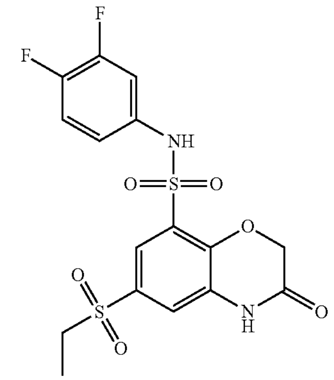 [SMILES: CCS(=O)(=O)c1cc2c(c(S(=O)(=O)Nc3ccc(F)c(F)c3)c1)OCC(=O)N2] | + |
| BC19422 | 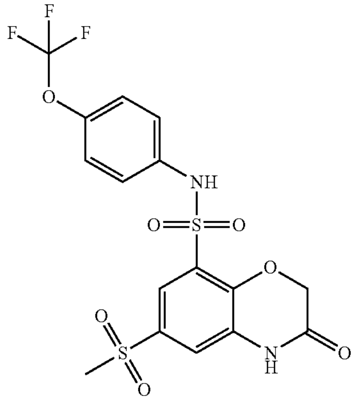 [SMILES: CS(=O)(=O)c1cc2c(c(S(=O)(=O)Nc3ccc(OC(F)(F)F)cc3)c1)OCC(=O)N2] | + |
| BC19423 | 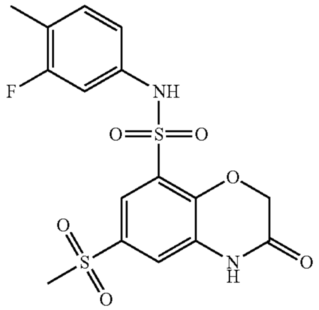 [SMILES: Cc1ccc(NS(=O)(=O)c2cc(S(C)(=O)=O)cc3c2OCC(=O)N3)cc1F] | + |
| BC19424 | 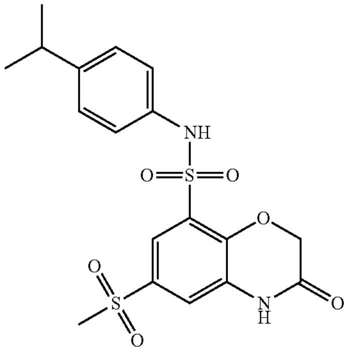 [SMILES: CC(C)c1ccc(NS(=O)(=O)c2cc(S(C)(=O)=O)cc3c2OCC(=O)N3)cc1] | + |
TABLE 4-continued
| BC No. | Structure | CB1 assay |
|---|---|---|
| BC19425 | 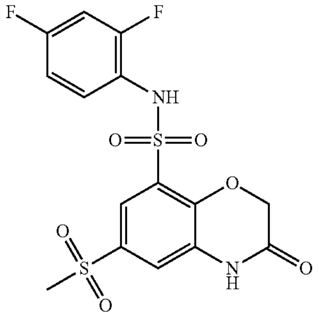 | + |
| BC19426 | 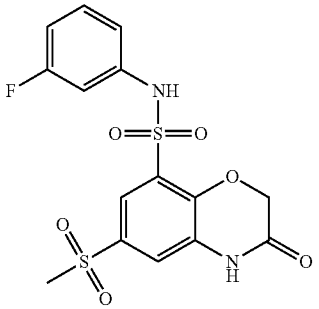 [SMILES: CS(=O)(=O)c1cc2c(c(S(=O)(=O)Nc3cccc(F)c3)c1)OCC(=O)N2] | + |
| BC19427 | 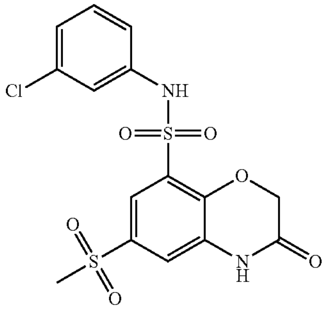 [SMILES: CS(=O)(=O)c1cc2c(c(S(=O)(=O)Nc3cccc(Cl)c3)c1)OCC(=O)N2] | + |
| BC19428 | 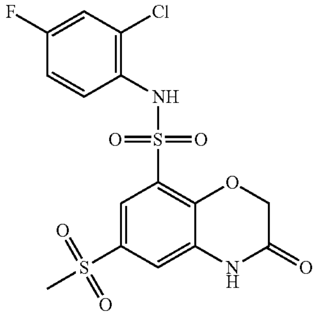 | + |

TABLE 4-continued
| BC No. | Structure | CB1 assay |
|---|---|---|
| BC19429 | 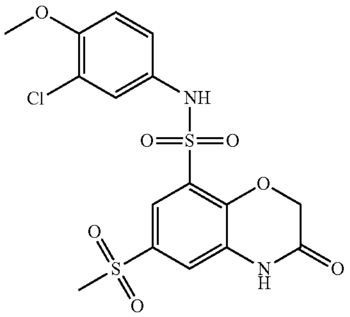 [SMILES: COc1ccc(NS(=O)(=O)c2cc(S(C)(=O)=O)cc3c2OCC(=O)N3)cc1Cl] | + |
| BC19430 | 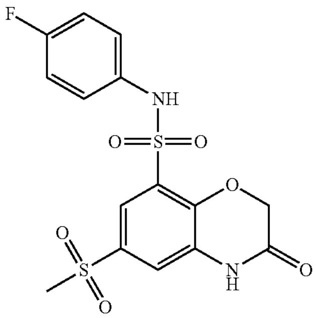 [SMILES: CS(=O)(=O)c1cc2c(c(S(=O)(=O)Nc3ccc(F)cc3)c1)OCC(=O)N2] | + |
| BC19431 | 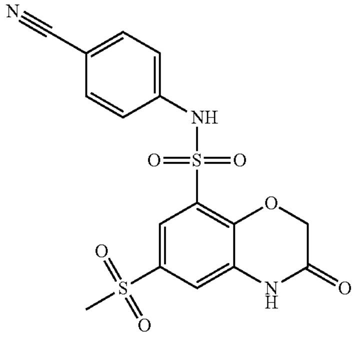 [SMILES: CS(=O)(=O)c1cc2c(c(S(=O)(=O)Nc3ccc(C#N)cc3)c1)OCC(=O)N2] | + |
| BC19432 | 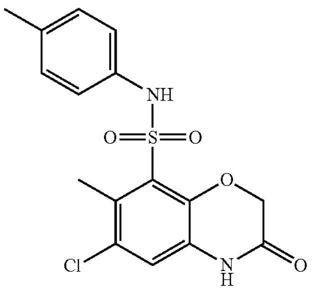 [SMILES: Cc1ccc(NS(=O)(=O)c2c(C)c(Cl)cc3c2OCC(=O)N3)cc1] | + |
| BC19433 | 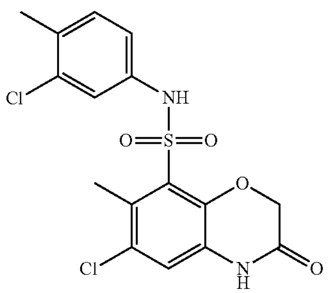 [SMILES: Cc1ccc(NS(=O)(=O)c2c(C)c(Cl)cc3c2OCC(=O)N3)cc1Cl] | + |
| BC19434 | 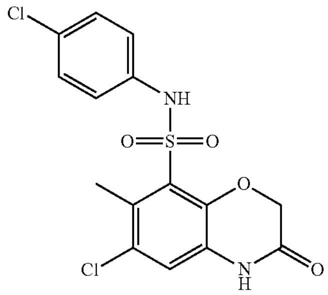 [SMILES: Cc1c(Cl)cc2c(c1S(=O)(=O)Nc1ccc(Cl)cc1)OCC(=O)N2] | + |
| BC19435 | 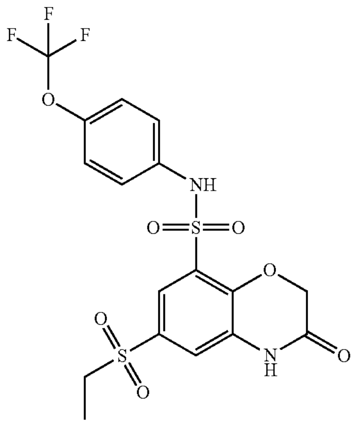 [SMILES: CCS(=O)(=O)c1cc2c(c(S(=O)(=O)Nc3ccc(OC(F)(F)F)cc3)c1)OCC(=O)N2] | + |
| BC19436 | 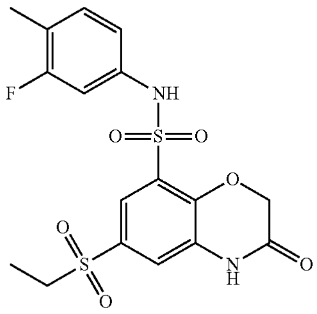 [SMILES: CCS(=O)(=O)c1cc2c(c(S(=O)(=O)Nc3ccc(C)c(F)c3)c1)OCC(=O)N2] | + |
| BC19437 | 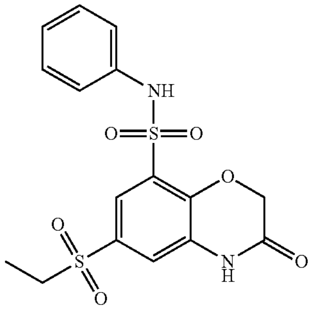 [SMILES: CCS(=O)(=O)c1cc2c(c(S(=O)(=O)Nc3ccccc3)c1)OCC(=O)N2] | + |

TABLE 4-continued
| BC No. | Structure | CB1 assay |
|---|---|---|
| BC19438 | 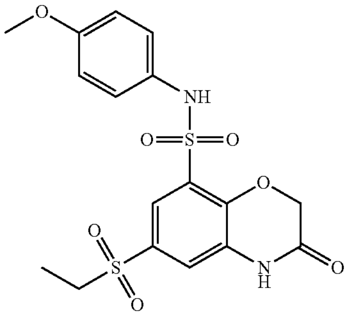 [SMILES: CCS(=O)(=O)c1cc2c(c(S(=O)(=O)Nc3ccc(OC)cc3)c1)OCC(=O)N2] | + |
| BC19439 | 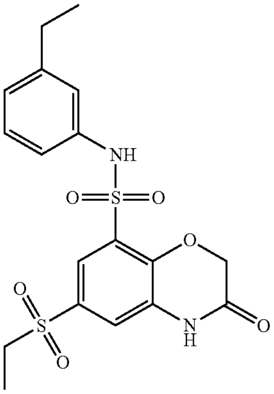 [SMILES: CCc1cccc(NS(=O)(=O)c2cc(S(=O)(=O)CC)cc3c2OCC(=O)N3)c1] | + |
| BC19440 | 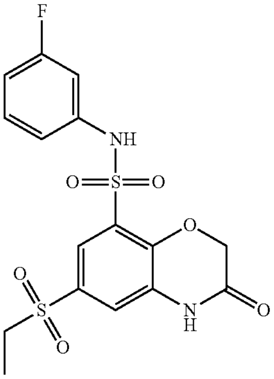 [SMILES: CCS(=O)(=O)c1cc2c(c(S(=O)(=O)Nc3cccc(F)c3)c1)OCC(=O)N2] | + |
| BC19441 | 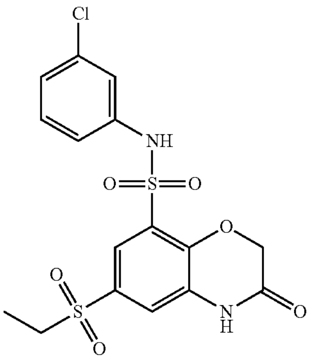 [SMILES: CCS(=O)(=O)c1cc2c(c(S(=O)(=O)Nc3cccc(Cl)c3)c1)OCC(=O)N2] | + |
TABLE 4-continued
| BC No. | Structure | CB1 assay |
|---|---|---|
| BC19442 | 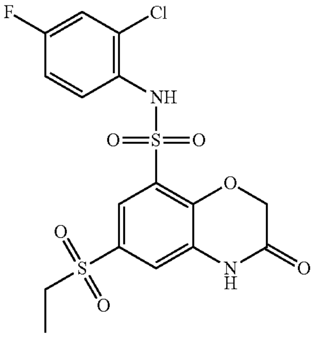 [SMILES: CCS(=O)(=O)c1cc2c(c(S(=O)(=O)Nc3ccc(F)cc3Cl)c1)OCC(=O)N2] | + |
| BC19443 | 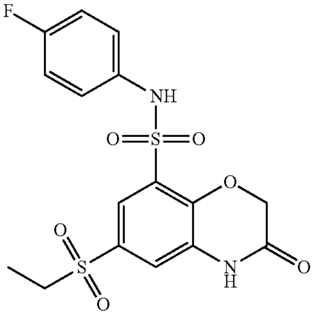 [SMILES: CCS(=O)(=O)c1cc2c(c(S(=O)(=O)Nc3ccc(F)cc3)c1)OCC(=O)N2] | + |
TABLE 5
| BC No. | Structure | CB1 assay |
|---|---|---|
| BC19481 | 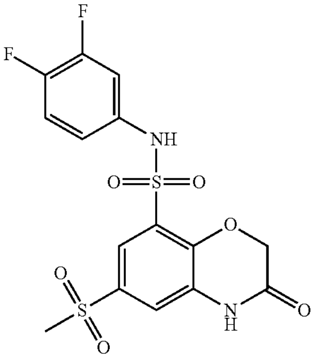 [SMILES: CS(=O)(=O)c1cc2c(c(S(=O)(=O)Nc3ccc(F)c(F)c3)c1)OCC(=O)N2] | + |
| BC19482 | 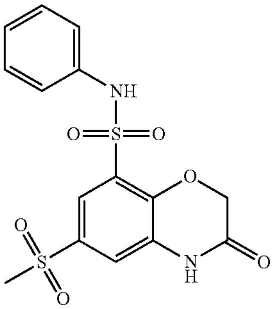 [SMILES: CS(=O)(=O)c1cc2c(c(S(=O)(=O)Nc3ccccc3)c1)OCC(=O)N2] | + |

TABLE 5-continued
| BC No. | Structure | CB1 assay |
|---|---|---|
| BC19483 | 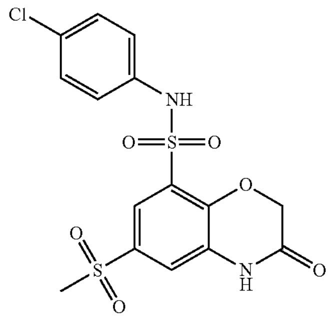 [SMILES: CS(=O)(=O)c1cc2c(c(S(=O)(=O)Nc3ccc(Cl)cc3)c1)OCC(=O)N2] | + |
| BC19484 | 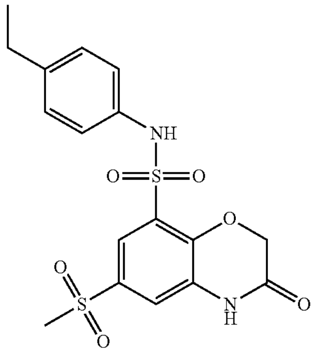 [SMILES: CCc1ccc(NS(=O)(=O)c2cc(S(C)(=O)=O)cc3c2OCC(=O)N3)cc1] | + |
| BC19485 | 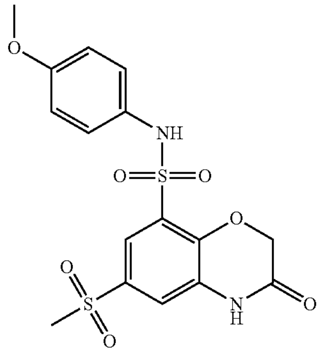 [SMILES: COc1ccc(NS(=O)(=O)c2cc(S(C)(=O)=O)cc3c2OCC(=O)N3)cc1] | + |
| BC19486 | 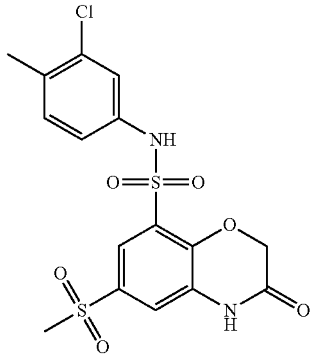 [SMILES: Cc1ccc(NS(=O)(=O)c2cc(S(C)(=O)=O)cc3c2OCC(=O)N3)cc1Cl] | + |
TABLE 5-continued
| BC No. | Structure | CB1 assay |
|---|---|---|
| BC19487 | 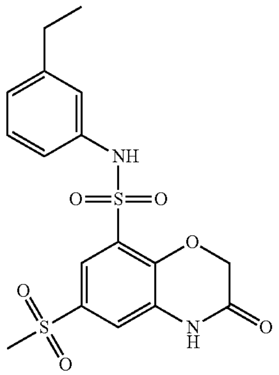 [SMILES: CCc1cccc(NS(=O)(=O)c2cc(S(C)(=O)=O)cc3c2OCC(=O)N3)c1] | + |
| BC19488 | 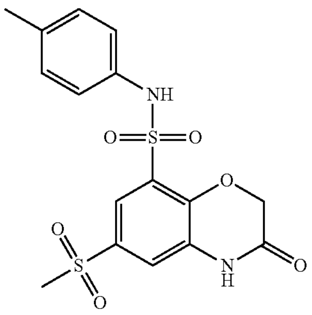 [SMILES: Cc1ccc(NS(=O)(=O)c2cc(S(C)(=O)=O)cc3c2OCC(=O)N3)cc1] | + |
| BC19489 | 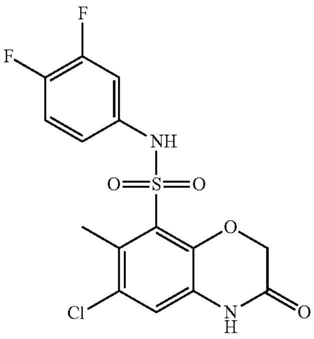 [SMILES: Cc1c(Cl)cc2c(c1S(=O)(=O)Nc1ccc(F)c(F)c1)OCC(=O)N2] | + |
| BC19490 | 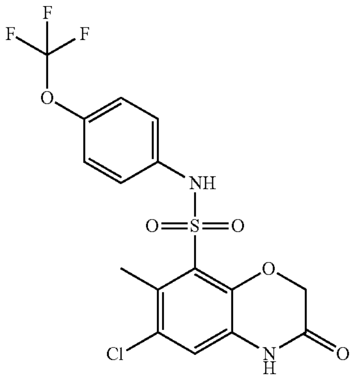 [SMILES: Cc1c(Cl)cc2c(c1S(=O)(=O)Nc1ccc(OC(F)(F)F)cc1)OCC(=O)N2] | + |

TABLE 5-continued
| BC No. | Structure | CB1 assay |
| --- | --- | --- |
| BC19491 | 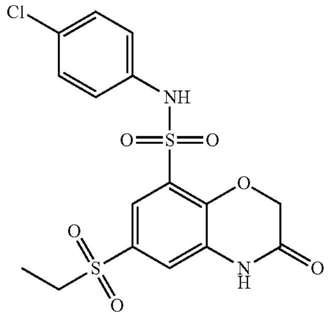 [SMILES: CCS(=O)(=O)c1cc2c(c(S(=O)(=O)Nc3ccc(Cl)cc3)c1)OCC(=O)N2] | + |
| BC19492 | 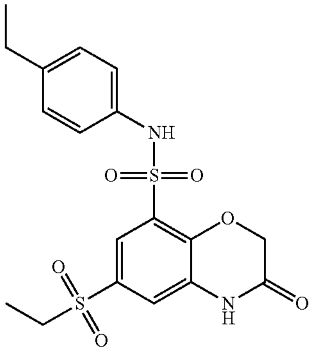 [SMILES: CCc1ccc(NS(=O)(=O)c2cc(S(=O)(=O)CC)cc3c2OCC(=O)N3)cc1] | + |
| BC19493 | 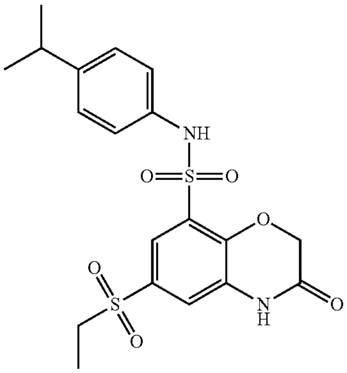 [SMILES: CCS(=O)(=O)c1cc2c(c(S(=O)(=O)Nc3ccc(C(C)C)cc3)c1)OCC(=O)N2] | + |
| BC19544 | 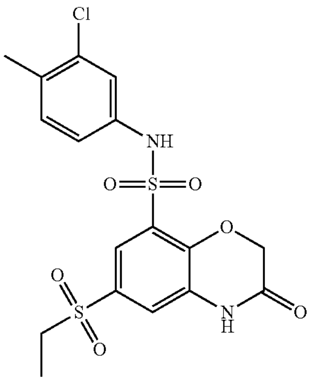 [SMILES: CCS(=O)(=O)c1cc2c(c(S(=O)(=O)Nc3ccc(C)c(Cl)c3)c1)OCC(=O)N2] | + |
| BC19545 | 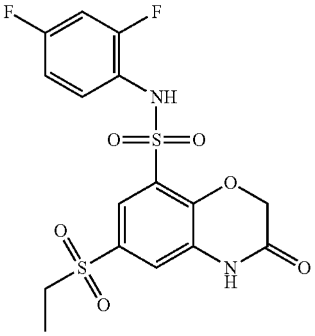 | + |
| BC19546 | 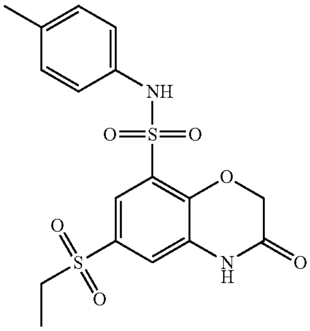 [SMILES: CCS(=O)(=O)c1cc2c(c(S(=O)(=O)Nc3ccc(C)cc3)c1)OCC(=O)N2] | + |
| BC19547 | 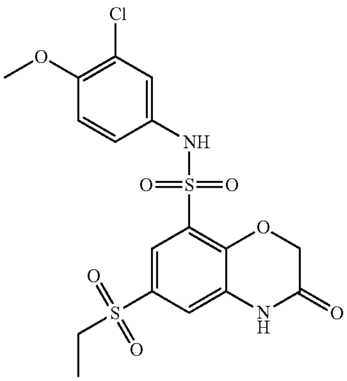 [SMILES: CCS(=O)(=O)c1cc2c(c(S(=O)(=O)Nc3ccc(OC)c(Cl)c3)c1)OCC(=O)N2] | + |
| BC19548 | 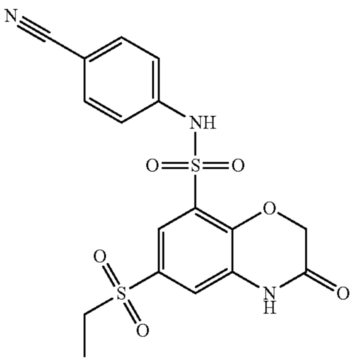 [SMILES: CCS(=O)(=O)c1cc2c(c(S(=O)(=O)Nc3ccc(C#N)cc3)c1)OCC(=O)N2] | + |

TABLE 5-continued
| BC No. | Structure | CB1 assay |
| --- | --- | --- |
| BC19697 | 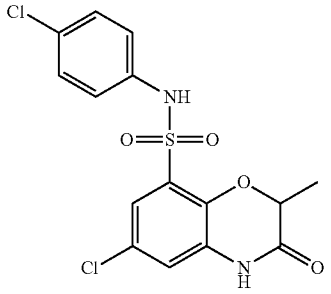 [SMILES: CC1Oc2c(cc(Cl)cc2S(=O)(=O)Nc2ccc(Cl)cc2)NC1=O] | + |
| BC19699 | 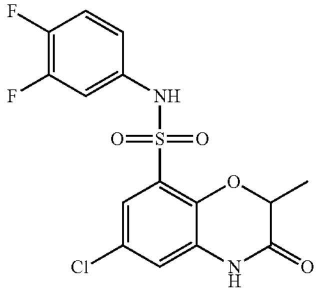 [SMILES: CC1Oc2c(cc(Cl)cc2S(=O)(=O)Nc2ccc(F)c(F)c2)NC1=O] | ++ |
| BC19701 | 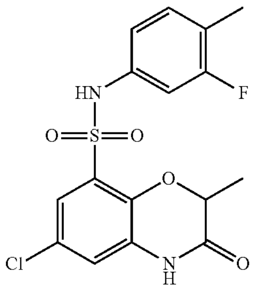 [SMILES: Cc1ccc(NS(=O)(=O)c2cc(Cl)cc3c2OC(C)C(=O)N3)cc1F] | ++ |
| BC19703 | 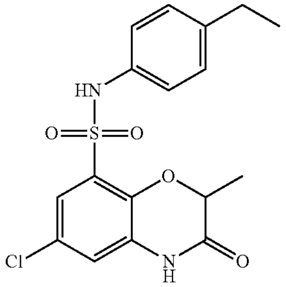 [SMILES: CCc1ccc(NS(=O)(=O)c2cc(Cl)cc3c2OC(C)C(=O)N3)cc1] | ++ |
| BC19705 | 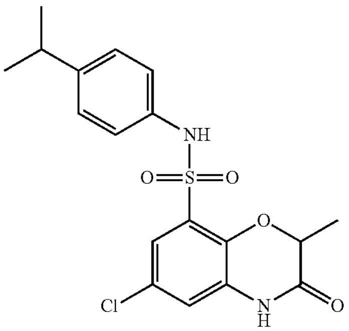 [SMILES: CC1Oc2c(cc(Cl)cc2S(=O)(=O)Nc2ccc(C(C)C)cc2)NC1=O] | ++ |
TABLE 5-continued
| BC No. | Structure | CB1 assay |
| --- | --- | --- |
| BC19707 | 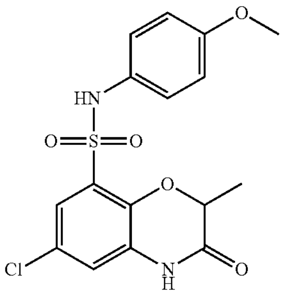 [SMILES: COc1ccc(NS(=O)(=O)c2cc(Cl)cc3c2OC(C)C(=O)N3)cc1] | + |
| BC19710 | 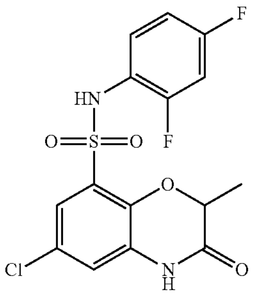 [SMILES: CC1Oc2c(cc(Cl)cc2S(=O)(=O)Nc2ccc(F)cc2F)NC1=O] | + |
| BC19712 | 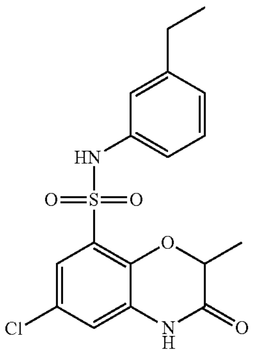 [SMILES: CCc1cccc(NS(=O)(=O)c2cc(Cl)cc3c2OC(C)C(=O)N3)c1] | + |
| BC19714 | 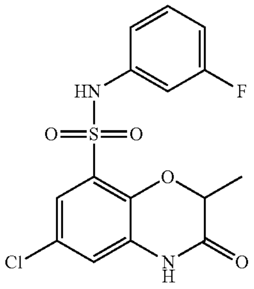 [SMILES: CC1Oc2c(cc(Cl)cc2S(=O)(=O)Nc2cccc(F)c2)NC1=O] | + |
| BC19716 | 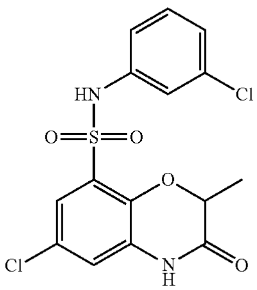 [SMILES: CC1Oc2c(cc(Cl)cc2S(=O)(=O)Nc2cccc(Cl)c2)NC1=O] | ++ |

TABLE 5-continued
| BC No. | Structure | CB1 assay |
|---|---|---|
| BC19718 | 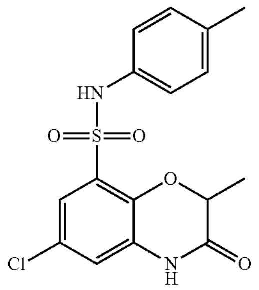 [SMILES: Cc1ccc(NS(=O)(=O)c2cc(Cl)cc3c2OC(C)C(=O)N3)cc1] | + |
| BC19720 | 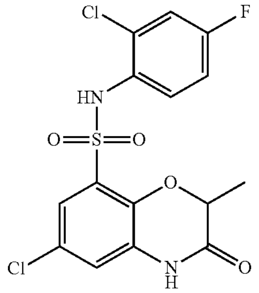 [SMILES: CC1Oc2c(cc(Cl)cc2S(=O)(=O)Nc2ccc(F)cc2Cl)NC1=O] | + |
| BC19722 | 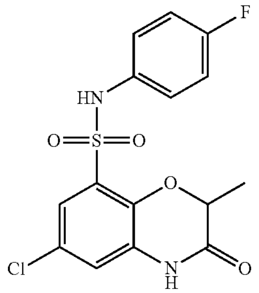 [SMILES: CC1Oc2c(cc(Cl)cc2S(=O)(=O)Nc2ccc(F)cc2)NC1=O] | ++ |
| BC19730 | 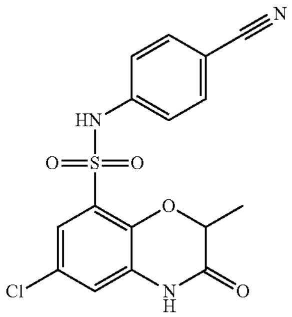 [SMILES: CC1Oc2c(cc(Cl)cc2S(=O)(=O)Nc2ccc(C#N)cc2)NC1=O] | ++ |
| BC19732 | 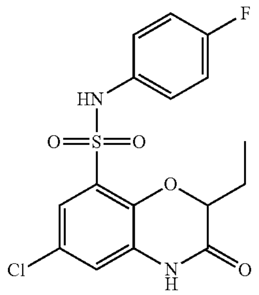 [SMILES: CCC1Oc2c(cc(Cl)cc2S(=O)(=O)Nc2ccc(F)cc2)NC1=O] | ++ |
TABLE 5-continued
| BC No. | Structure | CB1 assay |
|---|---|---|
| BC19734 | 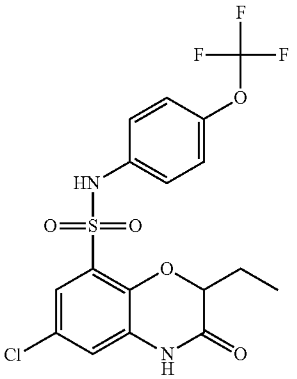 [SMILES: CCC1Oc2c(cc(Cl)cc2S(=O)(=O)Nc2ccc(OC(F)(F)F)cc2)NC1=O] | ++ |
| BC19736 | 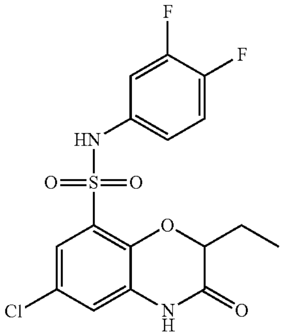 [SMILES: CCC1Oc2c(cc(Cl)cc2S(=O)(=O)Nc2ccc(F)c(F)c2)NC1=O] | + |
| BC19738 | 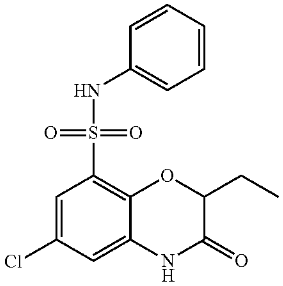 [SMILES: CCC1Oc2c(cc(Cl)cc2S(=O)(=O)Nc2ccccc2)NC1=O] | +++ |
| BC19740 | 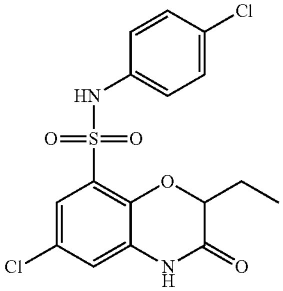 [SMILES: CCC1Oc2c(cc(Cl)cc2S(=O)(=O)Nc2ccc(Cl)cc2)NC1=O] | ++ |
| BC19742 | 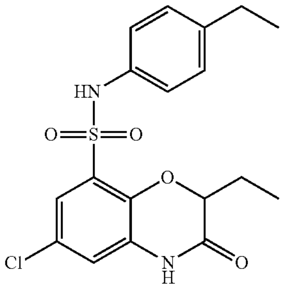 [SMILES: CCc1ccc(NS(=O)(=O)c2cc(Cl)cc3c2OC(CC)C(=O)N3)cc1] | ++ |

TABLE 5-continued
| BC No. | Structure | CB1 assay |
|---|---|---|
| BC19744 | 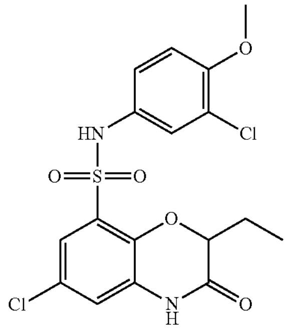 [SMILES: CCC1Oc2c(cc(Cl)cc2S(=O)(=O)Nc2ccc(OC)c(Cl)c2)NC1=O] | + |
| BC19746 | 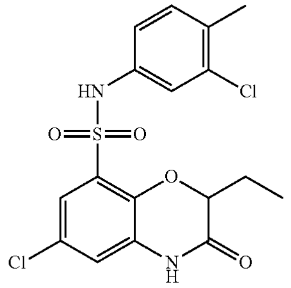 [SMILES: CCC1Oc2c(cc(Cl)cc2S(=O)(=O)Nc2ccc(C)c(Cl)c2)NC1=O] | ++ |
| BC19748 | 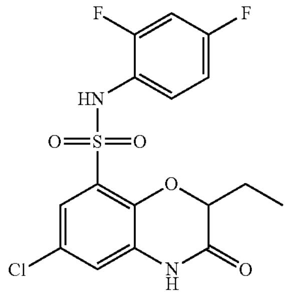 [SMILES: CCC1Oc2c(cc(Cl)cc2S(=O)(=O)Nc2ccc(F)cc2F)NC1=O] | + |
| BC19750 | 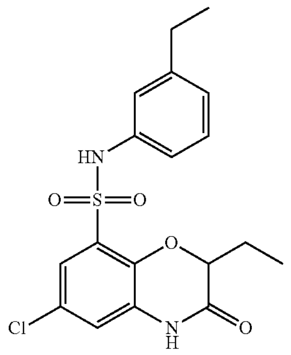 [SMILES: CCc1cccc(NS(=O)(=O)c2cc(Cl)cc3c2OC(CC)C(=O)N3)c1] | + |
TABLE 5-continued
| BC No. | Structure | CB1 assay |
|---|---|---|
| BC19752 | 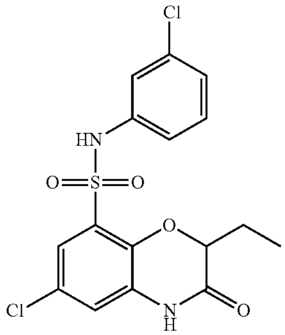 [SMILES: CCC1Oc2c(cc(Cl)cc2S(=O)(=O)Nc2cccc(Cl)c2)NC1=O] | ++ |
| BC19754 | 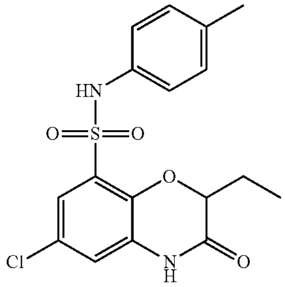 [SMILES: CCC1Oc2c(cc(Cl)cc2S(=O)(=O)Nc2ccc(C)cc2)NC1=O] | ++ |
| BC19756 | 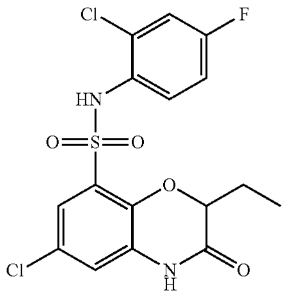 [SMILES: CCC1Oc2c(cc(Cl)cc2S(=O)(=O)Nc2ccc(F)cc2Cl)NC1=O] | ++ |
| BC19757 | 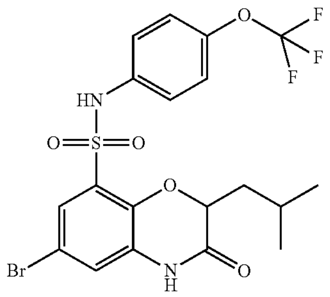 [SMILES: CC(C)CC1Oc2c(cc(Br)cc2S(=O)(=O)Nc2ccc(OC(F)(F)F)cc2)NC1=O] | + |
| BC19759 | 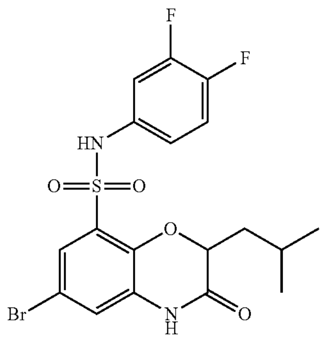 [SMILES: CC(C)CC1Oc2c(cc(Br)cc2S(=O)(=O)Nc2ccc(F)c(F)c2)NC1=O] | ++ |

TABLE 5-continued
| BC No. | Structure | CB1 assay |
|---|---|---|
| BC19761 | 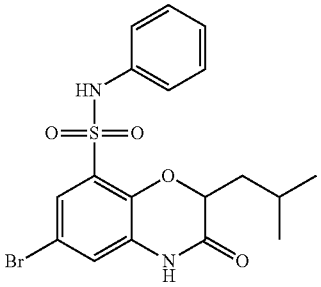 [SMILES: CC(C)CC1Oc2c(cc(Br)cc2S(=O)(=O)Nc2ccccc2)NC1=O] | ++ |
| BC19763 | 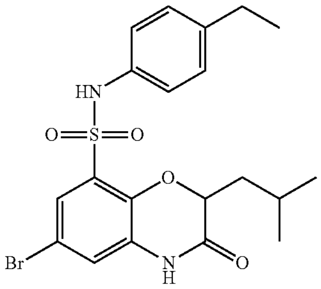 [SMILES: CCc1ccc(NS(=O)(=O)c2cc(Br)cc3c2OC(CC(C)C)C(=O)N3)cc1] | ++ |
| BC19765 | 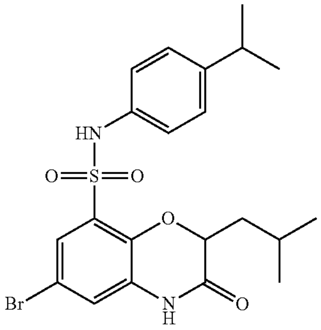 [SMILES: CC(C)CC1Oc2c(cc(Br)cc2S(=O)(=O)Nc2ccc(C(C)C)cc2)NC1=O] | + |
| BC19767 | 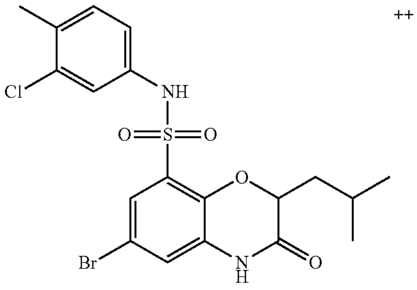 | ++ |
| BC19769 | 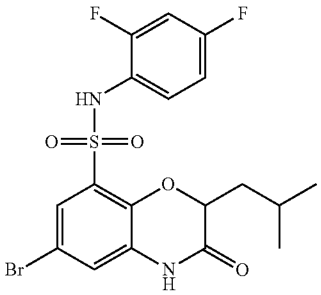 | ++ |
TABLE 5-continued
| BC No. | Structure | CB1 assay |
|---|---|---|
| BC19771 | 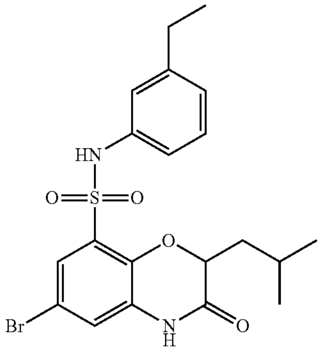 [SMILES: CCc1cccc(NS(=O)(=O)c2cc(Br)cc3c2OC(CC(C)C)C(=O)N3)c1] | ++ |
| BC19773 | 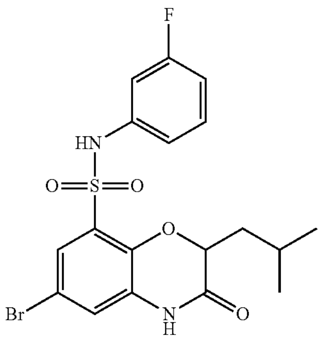 [SMILES: CC(C)CC1Oc2c(cc(Br)cc2S(=O)(=O)Nc2cccc(F)c2)NC1=O] | ++ |
| BC19775 | 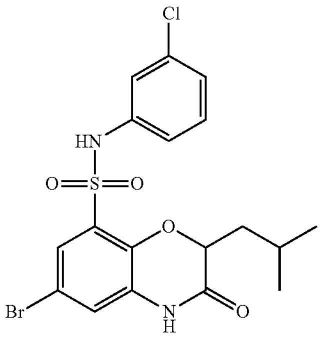 | + |
| BC19777 | 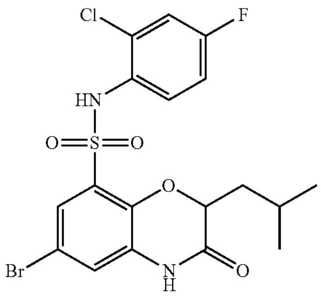 [SMILES: CC(C)CC1Oc2c(cc(Br)cc2S(=O)(=O)Nc2ccc(F)cc2Cl)NC1=O] | + |

TABLE 5-continued
| BC No. | Structure | CB1 assay |
|---|---|---|
| BC19779 | 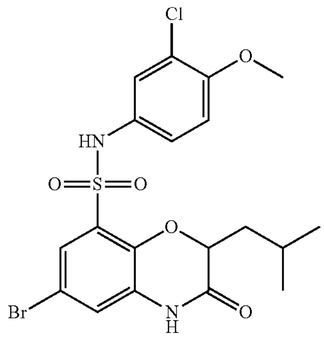 [SMILES: COc1ccc(NS(=O)(=O)c2cc(Br)cc3c2OC(CC(C)C)C(=O)N3)cc1Cl] | + |
| BC19781 | 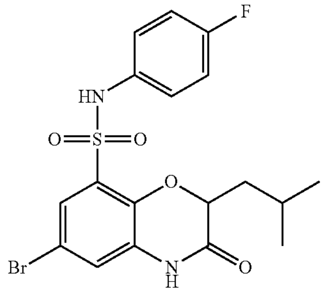 [SMILES: CC(C)CC1Oc2c(cc(Br)cc2S(=O)(=O)Nc2ccc(F)cc2)NC1=O] | ++ |
| BC19783 | 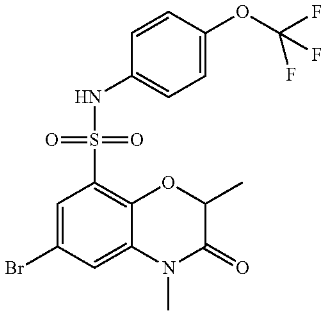 [SMILES: CC1Oc2c(cc(Br)cc2S(=O)(=O)Nc2ccc(OC(F)(F)F)cc2)N(C)C1=O] | ++ |
| BC19785 | 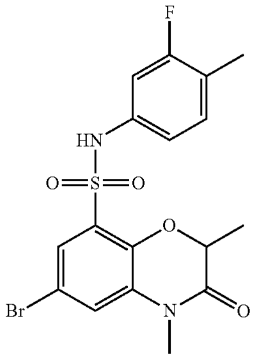 [SMILES: Cc1ccc(NS(=O)(=O)c2cc(Br)cc3c2OC(C)C(=O)N3C)cc1F] | + |
| BC19787 | 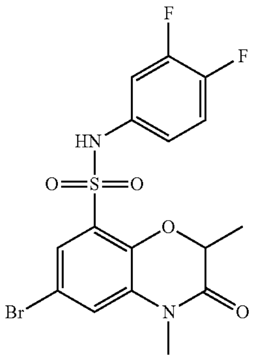 [SMILES: CC1Oc2c(cc(Br)cc2S(=O)(=O)Nc2ccc(F)c(F)c2)N(C)C1=O] | + |
| BC19789 | 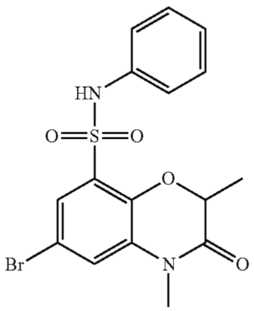 [SMILES: CC1Oc2c(cc(Br)cc2S(=O)(=O)Nc2ccccc2)N(C)C1=O] | + |
| BC19791 | 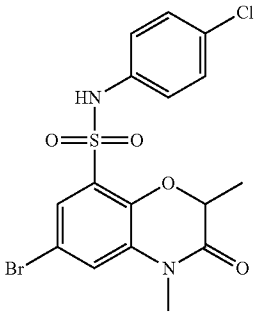 [SMILES: CC1Oc2c(cc(Br)cc2S(=O)(=O)Nc2ccc(Cl)cc2)N(C)C1=O] | + |
| BC19793 | 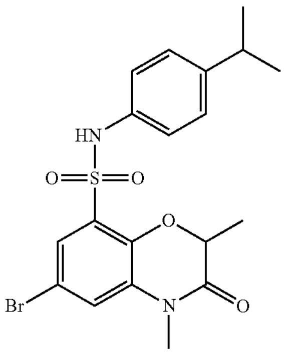 [SMILES: CC1Oc2c(cc(Br)cc2S(=O)(=O)Nc2ccc(C(C)C)cc2)N(C)C1=O] | + |

TABLE 5-continued
| BC No. | Structure | CB1 assay |
|---|---|---|
| BC19796 | 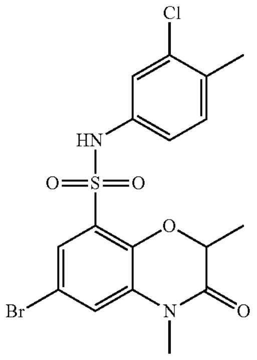 | ++ |
| BC19798 | 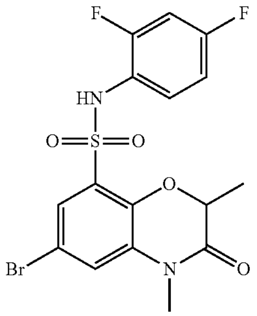 [SMILES: CC1Oc2c(cc(Br)cc2S(=O)(=O)Nc2ccc(F)cc2F)N(C)C1=O] | + |
| BC19900 | 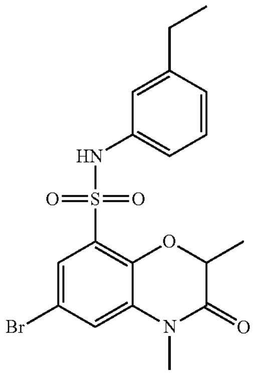 [SMILES: CCc1cccc(NS(=O)(=O)c2cc(Br)cc3c2OC(C)C(=O)N3C)c1] | + |
| BC19902 | 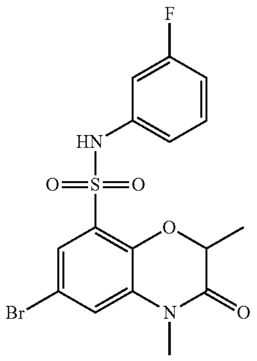 [SMILES: CC1Oc2c(cc(Br)cc2S(=O)(=O)Nc2cccc(F)c2)N(C)C1=O] | + |
| BC19904 | 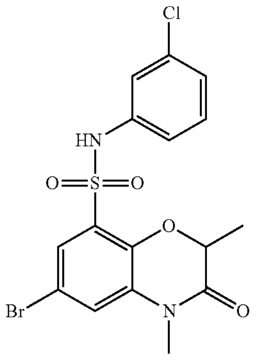 [SMILES: CC1Oc2c(cc(Br)cc2S(=O)(=O)Nc2cccc(Cl)c2)N(C)C1=O] | ++ |
| BC19906 | 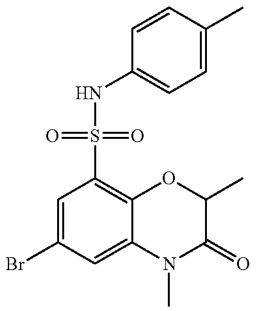 [SMILES: Cc1ccc(NS(=O)(=O)c2cc(Br)cc3c2OC(C)C(=O)N3C)cc1] | + |
| BC19908 | 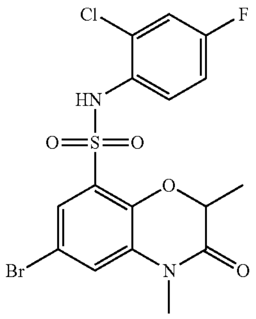 [SMILES: CC1Oc2c(cc(Br)cc2S(=O)(=O)Nc2ccc(F)cc2Cl)N(C)C1=O] | + |
| BC19909 | 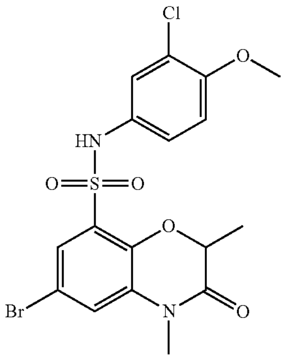 [SMILES: COc1ccc(NS(=O)(=O)c2cc(Br)cc3c2OC(C)C(=O)N3C)cc1Cl] | + |

TABLE 5-continued
| BC No. | Structure | CB1 assay |
|---|---|---|
| BC19911 | 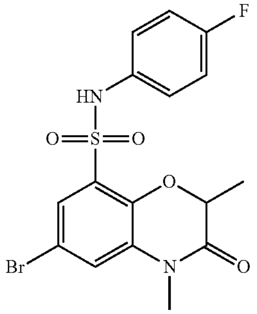 [SMILES: CC1Oc2c(cc(Br)cc2S(=O)(=O)Nc2ccc(F)cc2)N(C)C1=O] | + |
| BC19913 | 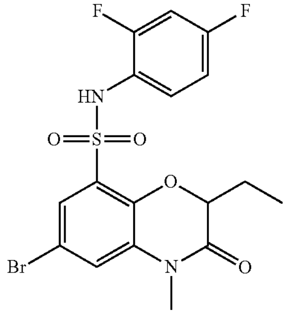 [SMILES: CCC1Oc2c(cc(Br)cc2S(=O)(=O)Nc2ccc(F)cc2F)N(C)C1=O] | ++ |
| BC19915 | 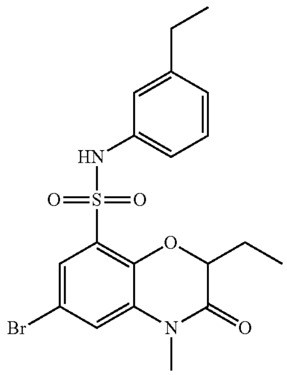 [SMILES: CCc1cccc(NS(=O)(=O)c2cc(Br)cc3c2OC(CC)C(=O)N3C)c1] | ++ |
| BC19921 | 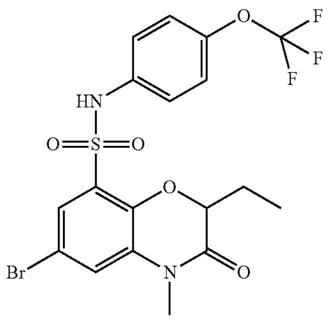 [SMILES: CCC1Oc2c(cc(Br)cc2S(=O)(=O)Nc2ccc(OC(F)(F)F)cc2)N(C)C1=O] | ++ |
TABLE 5-continued
| BC No. | Structure | CB1 assay |
|---|---|---|
| BC19923 | 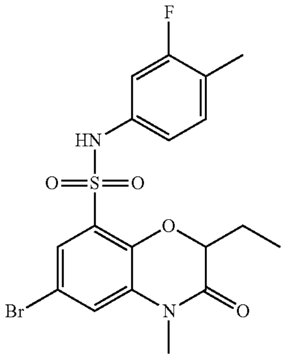 [SMILES: CCC1Oc2c(cc(Br)cc2S(=O)(=O)Nc2ccc(C)c(F)c2)N(C)C1=O] | + |
| BC19925 | 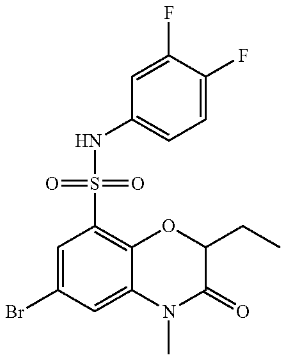 [SMILES: CCC1Oc2c(cc(Br)cc2S(=O)(=O)Nc2ccc(F)c(F)c2)N(C)C1=O] | ++ |
| BC19927 | 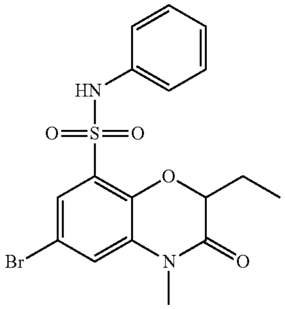 [SMILES: CCC1Oc2c(cc(Br)cc2S(=O)(=O)Nc2ccccc2)N(C)C1=O] | + |
| BC19929 | 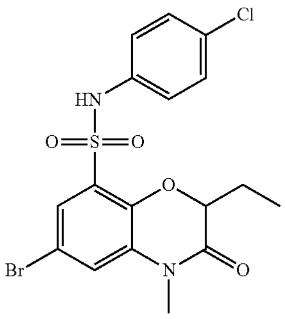 [SMILES: CCC1Oc2c(cc(Br)cc2S(=O)(=O)Nc2ccc(Cl)cc2)N(C)C1=O] | + |

TABLE 5-continued
| BC No. | Structure | CB1 assay |
|---|---|---|
| BC19931 | 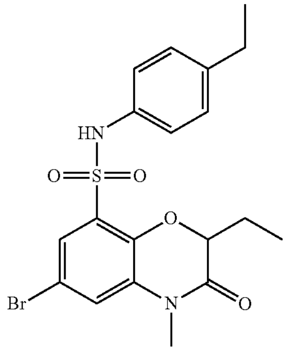 [SMILES: CCc1ccc(NS(=O)(=O)c2cc(Br)cc3c2OC(CC)C(=O)N3C)cc1] | + |
| BC19933 | 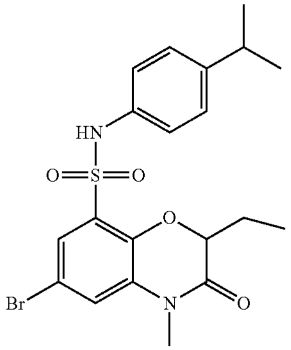 [SMILES: CCC1Oc2c(cc(Br)cc2S(=O)(=O)Nc2ccc(C(C)C)cc2)N(C)C1=O] | + |
| BC19935 | 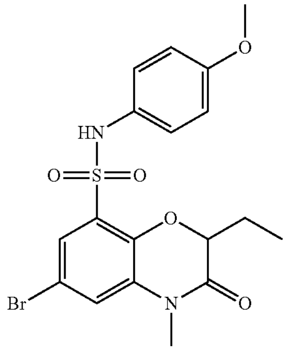 [SMILES: CCC1Oc2c(cc(Br)cc2S(=O)(=O)Nc2ccc(OC)cc2)N(C)C1=O] | + |
| BC19937 | 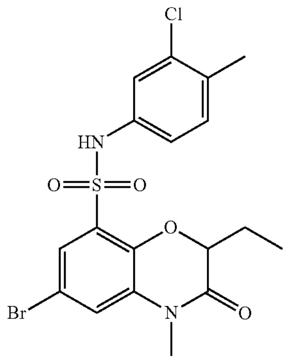 [SMILES: CCC1Oc2c(cc(Br)cc2S(=O)(=O)Nc2ccc(C)c(Cl)c2)N(C)C1=O] | + |
TABLE 6
| BC No. | Structure | CB1 assay |
|---|---|---|
| BC19181 | 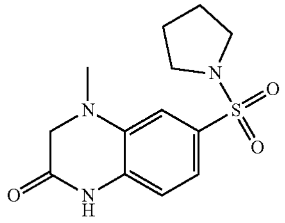 [SMILES: CN1CC(=O)Nc2ccc(S(=O)(=O)N3CCCC3)cc21] | + |
| BC19182 | 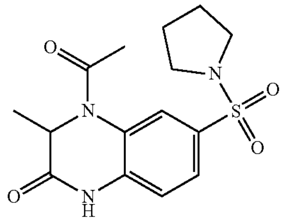 [SMILES: CC(=O)N1c2cc(S(=O)(=O)N3CCCC3)ccc2NC(=O)C1C] | +++ |
| BC19183 | 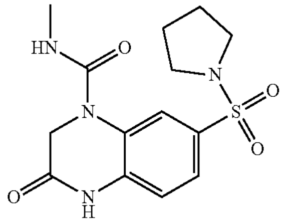 [SMILES: CNC(=O)N1CC(=O)Nc2ccc(S(=O)(=O)N3CCCC3)cc21] | ++ |
| BC19184 | 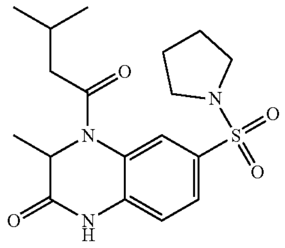 [SMILES: CC(C)CC(=O)N1c2cc(S(=O)(=O)N3CCCC3)ccc2NC(=O)C1C] | ++ |
| BC19235 | 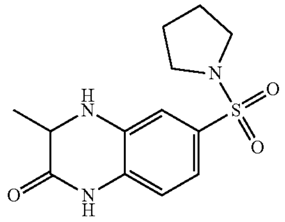 [SMILES: CC1Nc2cc(S(=O)(=O)N3CCCC3)ccc2NC1=O] | + |
| BC19236 | 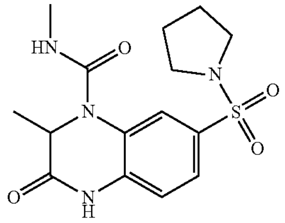 [SMILES: CNC(=O)N1c2cc(S(=O)(=O)N3CCCC3)ccc2NC(=O)C1C] | + |

TABLE 6-continued
| BC No. | Structure | CB1 assay |
|---|---|---|
| BC19295 | 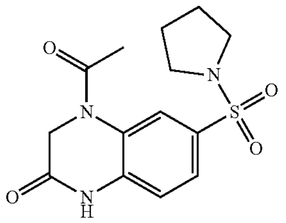 [SMILES: CC(=O)N1CC(=O)Nc2ccc(S(=O)(=O)N3CCCC3)cc21] | + |
| BC19296 | 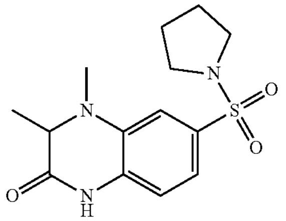 [SMILES: CC1C(=O)Nc2ccc(S(=O)(=O)N3CCCC3)cc2N1C] | ++ |
| BC19297 | 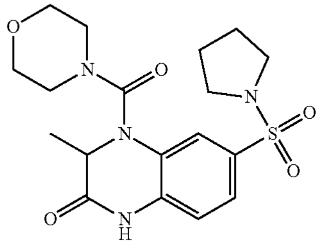 [SMILES: CC1C(=O)Nc2ccc(S(=O)(=O)N3CCCC3)cc2N1C(=O)N1CCOCC1] | + |
| BC19298 | 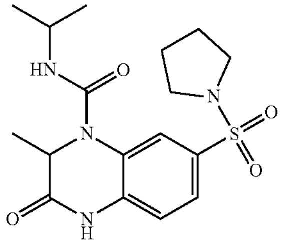 [SMILES: CC(C)NC(=O)N1c2cc(S(=O)(=O)N3CCCC3)ccc2NC(=O)C1C] | + |
| BC19299 | 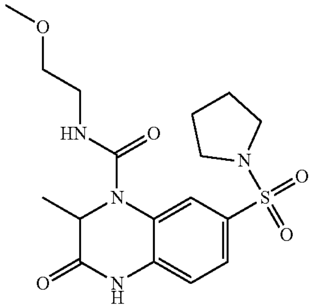 [SMILES: COCCNC(=O)N1c2cc(S(=O)(=O)N3CCCC3)ccc2NC(=O)C1C] | ++ |
| BC19300 | 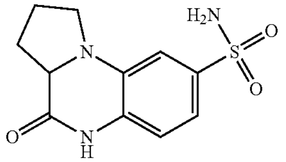 [SMILES: NS(=O)(=O)c1ccc2c(c1)N1CCCC1C(=O)N2] | + |
TABLE 7
| BC No. | Structure | CB1 assay |
|---|---|---|
| BC19917 | 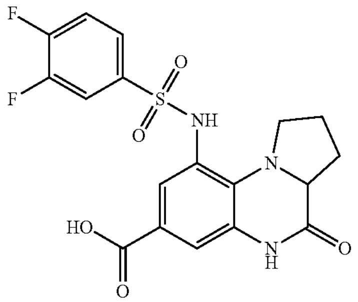 [SMILES: O=C(O)c1cc2c(c(NS(=O)(=O)c3ccc(F)c(F)c3)c1)N1CCCC1C(=O)N2] | ++ |
TABLE 8
| BC No. | Structure | CB1 assay |
|---|---|---|
| BC19549 | 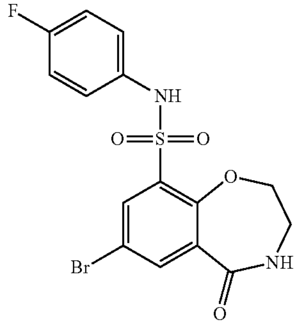 [SMILES: O=C1NCCOc2c1cc(Br)cc2S(=O)(=O)Nc1ccc(F)cc1] | + |
| BC19550 | 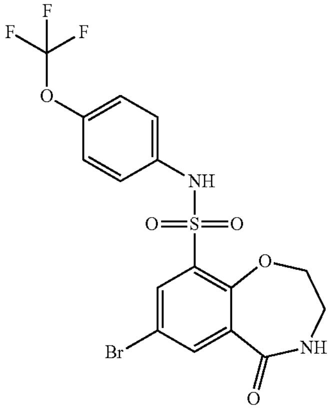 [SMILES: O=C1NCCOc2c1cc(Br)cc2S(=O)(=O)Nc1ccc(OC(F)(F)F)cc1] | + |
| BC19551 | 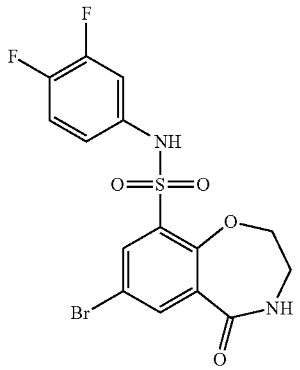 [SMILES: O=C1NCCOc2c1cc(Br)cc2S(=O)(=O)Nc1ccc(F)c(F)c1] | + |

TABLE 8-continued
| BC No. | Structure | CB1 assay |
| --- | --- | --- |
| BC19552 | 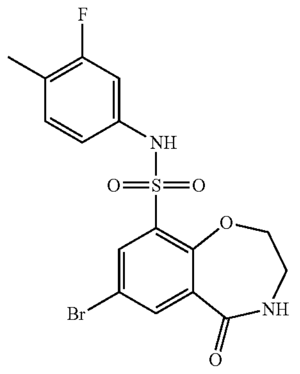 [SMILES: Cc1ccc(NS(=O)(=O)c2cc(Br)cc3c2OCCNC3=O)cc1F] | + |
| BC19553 | 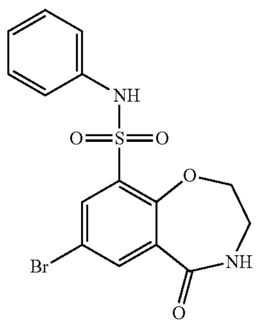 [SMILES: O=C1NCCOc2c1cc(Br)cc2S(=O)(=O)Nc1ccccc1] | + |
| BC19603 | 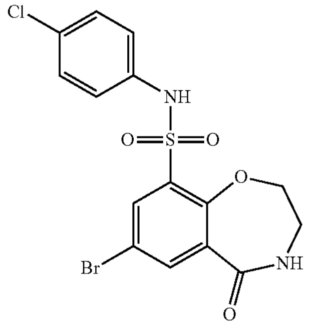 [SMILES: O=C1NCCOc2c1cc(Br)cc2S(=O)(=O)Nc1ccc(Cl)cc1] | + |
| BC19604 | 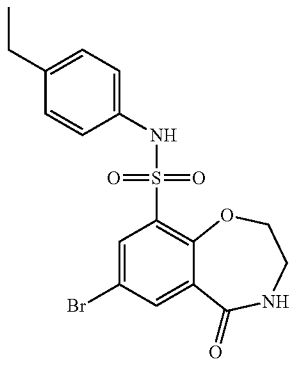 [SMILES: CCc1ccc(NS(=O)(=O)c2cc(Br)cc3c2OCCNC3=O)cc1] | ++ |
| BC19605 | 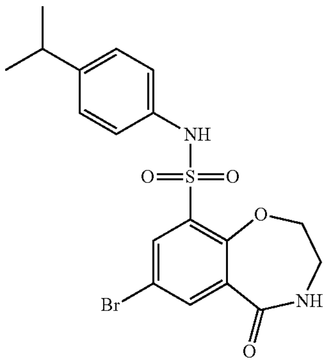 [SMILES: CC(C)c1ccc(NS(=O)(=O)c2cc(Br)cc3c2OCCNC3=O)cc1] | + |
| BC19606 | 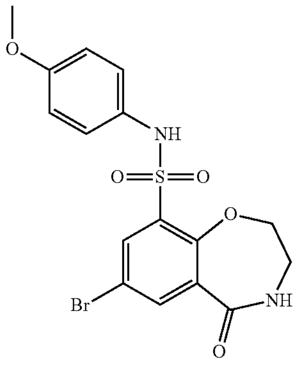 [SMILES: COc1ccc(NS(=O)(=O)c2cc(Br)cc3c2OCCNC3=O)cc1] | + |
| BC19607 | 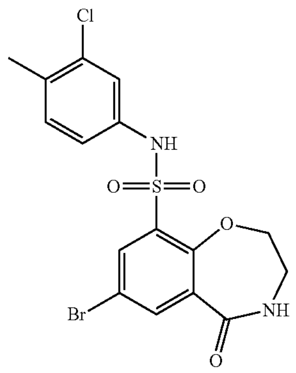 [SMILES: Cc1ccc(NS(=O)(=O)c2cc(Br)cc3c2OCCNC3=O)cc1Cl] | ++ |
| BC19608 | 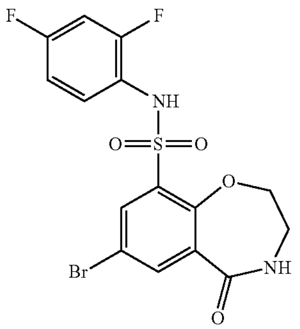 [SMILES: O=C1NCCOc2c1cc(Br)cc2S(=O)(=O)Nc1ccc(F)cc1F] | + |

TABLE 8-continued
| BC No. | Structure | CB1 assay |
|---|---|---|
| BC19609 | 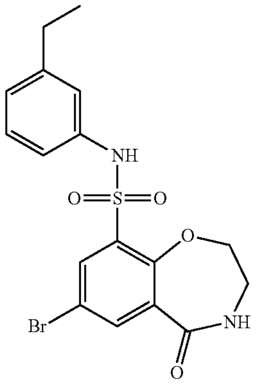 [SMILES: CCc1cccc(NS(=O)(=O)c2cc(Br)cc3c2OCCNC3=O)c1] | ++ |
| BC19610 | 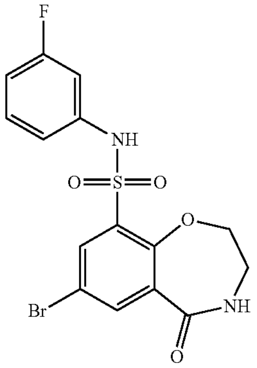 [SMILES: O=C1NCCOc2c1cc(Br)cc2S(=O)(=O)Nc1cccc(F)c1] | ++ |
| BC19611 | 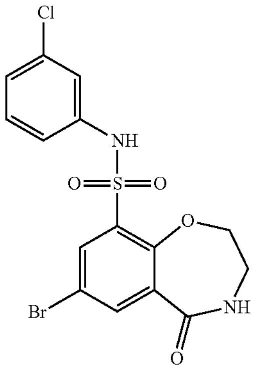 [SMILES: O=C1NCCOc2c1cc(Br)cc2S(=O)(=O)Nc1cccc(Cl)c1] | + |
| BC19612 | 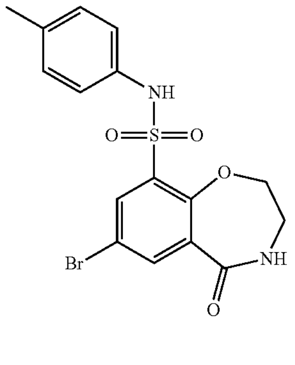 [SMILES: Cc1ccc(NS(=O)(=O)c2cc(Br)cc3c2OCCNC3=O)cc1] | + |
| BC19613 | 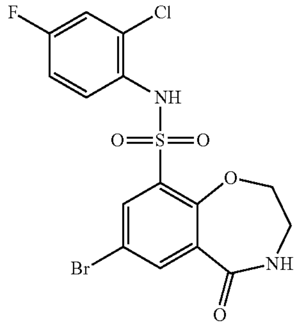 | + |
| BC19614 | 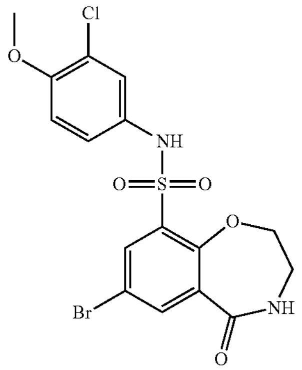 [SMILES: COc1ccc(NS(=O)(=O)c2cc(Br)cc3c2OCCNC3=O)cc1Cl] | + |
| BC19615 | 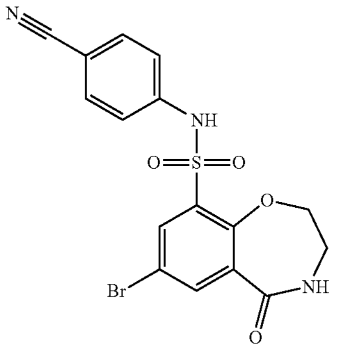 [SMILES: N#Cc1ccc(NS(=O)(=O)c2cc(Br)cc3c2OCCNC3=O)cc1] | + |
TABLE 9
| BC No. | Structure | CB1 assay |
|---|---|---|
| BC19652 | 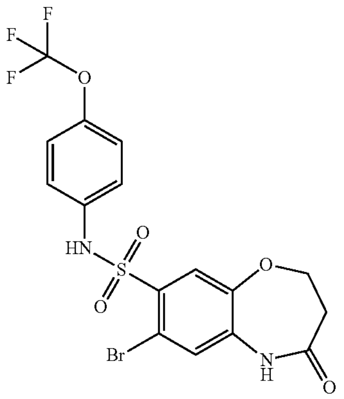 [SMILES: O=C1CCOc2cc(S(=O)(=O)Nc3ccc(OC(F)(F)F)cc3)c(Br)cc2N1] | + |

TABLE 9-continued
| BC No. | Structure | CB1 assay |
|---|---|---|
| BC19653 | 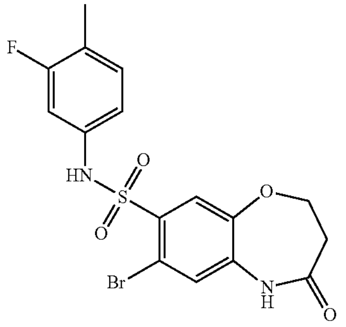 [SMILES: Cc1ccc(NS(=O)(=O)c2cc3c(cc2Br)NC(=O)CCO3)cc1F] | + |
| BC19654 | 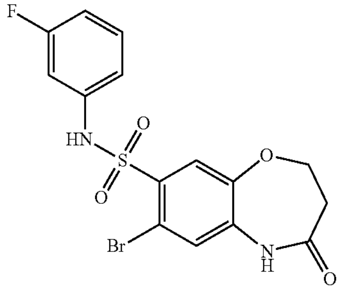 [SMILES: O=C1CCOc2cc(S(=O)(=O)Nc3cccc(F)c3)c(Br)cc2N1] | + |
| BC19655 | 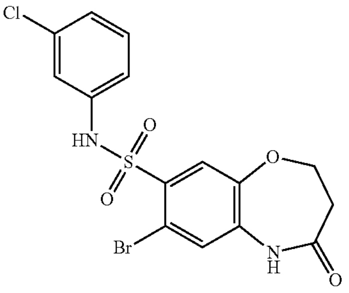 [SMILES: O=C1CCOc2cc(S(=O)(=O)Nc3cccc(Cl)c3)c(Br)cc2N1] | + |
| BC19656 | 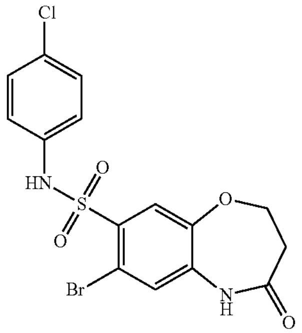 | + |
| BC19657 | 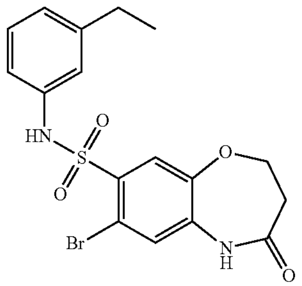 [SMILES: CCc1cccc(NS(=O)(=O)c2cc3c(cc2Br)NC(=O)CCO3)c1] | + |
| BC19658 | 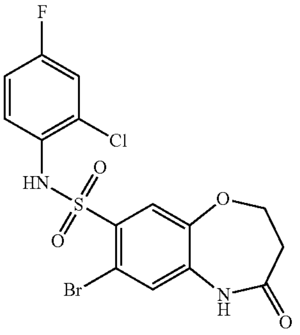 [SMILES: O=C1CCOc2cc(S(=O)(=O)Nc3ccc(F)cc3Cl)c(Br)cc2N1] | + |
| BC19659 | 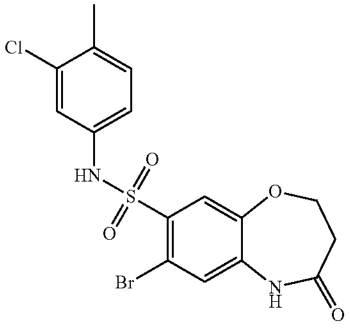 [SMILES: Cc1ccc(NS(=O)(=O)c2cc3c(cc2Br)NC(=O)CCO3)cc1Cl] | + |
| BC19660 | 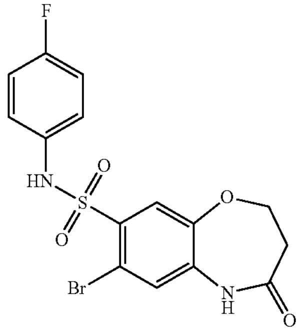 [SMILES: O=C1CCOc2cc(S(=O)(=O)Nc3ccc(F)cc3)c(Br)cc2N1] | + |
| BC19661 | 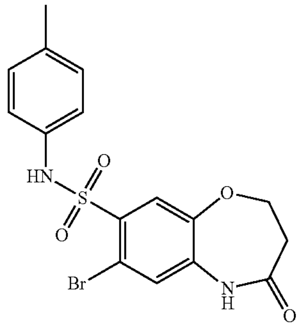 [SMILES: Cc1ccc(NS(=O)(=O)c2cc3c(cc2Br)NC(=O)CCO3)cc1] | +++ |
| BC19689 | 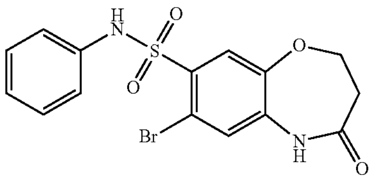 [SMILES: O=C1CCOc2cc(S(=O)(=O)Nc3ccccc3)c(Br)cc2N1] | + |

TABLE 9-continued
| BC No. | Structure | CB1 assay |
|---|---|---|
| BC19690 | 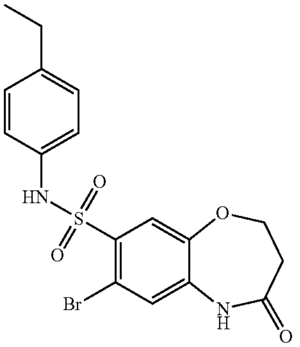 [SMILES: CCc1ccc(NS(=O)(=O)c2cc3c(cc2Br)NC(=O)CCO3)cc1] | +++ |
| BC19691 | 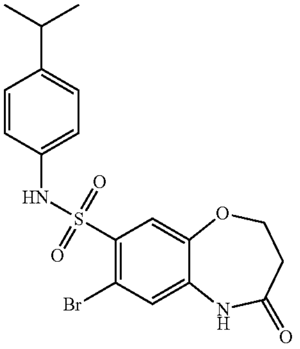 [SMILES: CC(C)c1ccc(NS(=O)(=O)c2cc3c(cc2Br)NC(=O)CCO3)cc1] | ++ |
| BC19692 | 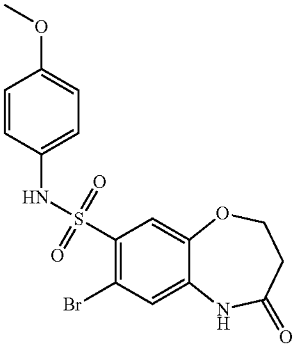 [SMILES: COc1ccc(NS(=O)(=O)c2cc3c(cc2Br)NC(=O)CCO3)cc1] | +++ |
| BC19693 | 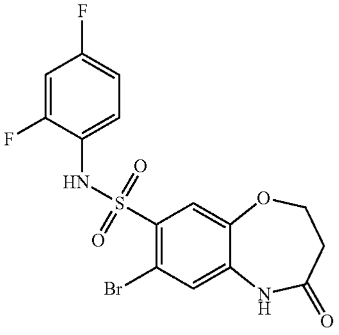 [SMILES: O=C1CCOc2cc(S(=O)(=O)Nc3ccc(F)cc3F)c(Br)cc2N1] | ++ |
| BC19694 | 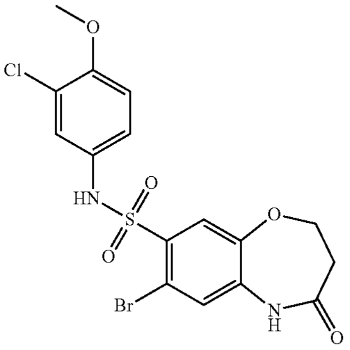 [SMILES: COc1ccc(NS(=O)(=O)c2cc3c(cc2Br)NC(=O)CCO3)cc1Cl] | ++ |
| BC19695 | 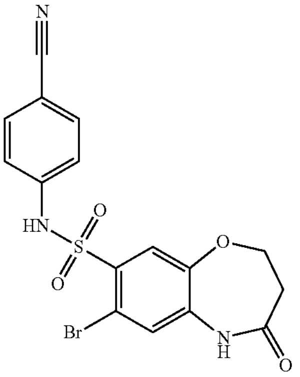 [SMILES: N#Cc1ccc(NS(=O)(=O)c2cc3c(cc2Br)NC(=O)CCO3)cc1] | + |
TABLE 10
| BC No. | Structure | CB1 assay |
|---|---|---|
| BC19648 | 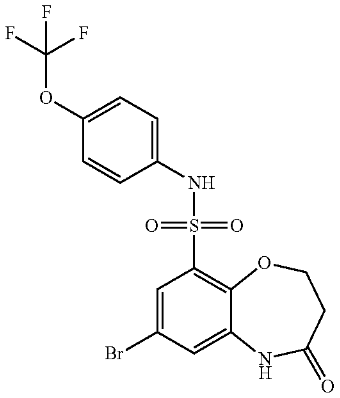 [SMILES: O=C1CCOc2c(cc(Br)cc2S(=O)(=O)Nc2ccc(OC(F)(F)F)cc2)N1] | + |
| BC19649 | 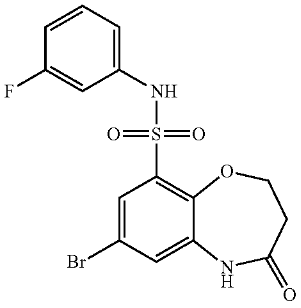 [SMILES: O=C1CCOc2c(cc(Br)cc2S(=O)(=O)Nc2cccc(F)c2)N1] | + |

TABLE 10-continued

| BC No. | Structure | CB1 assay |
|---|---|---|
| BC19650 | 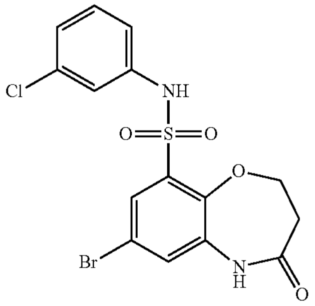 [SMILES: O=C1CCOc2c(cc(Br)cc2S(=O)(=O)Nc2cccc(Cl)c2)N1] | + |
| BC19651 | 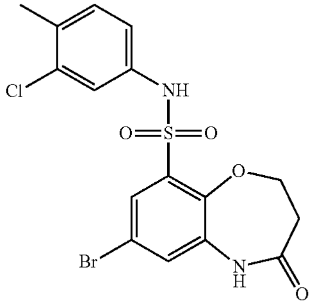 [SMILES: Cc1ccc(NS(=O)(=O)c2cc(Br)cc3c2OCCC(=O)N3)cc1Cl] | + |
| BC19685 | 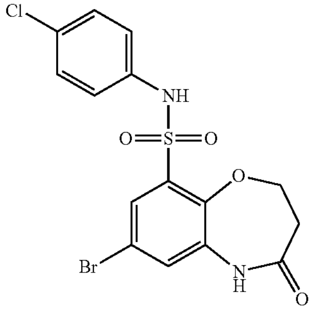 [SMILES: O=C1CCOc2c(cc(Br)cc2S(=O)(=O)Nc2ccc(Cl)cc2)N1] | + |
| BC19686 | 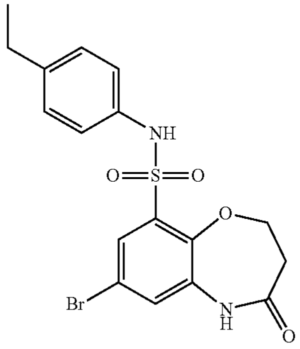 [SMILES: CCc1ccc(NS(=O)(=O)c2cc(Br)cc3c2OCCC(=O)N3)cc1] | ++ |
| BC19687 | 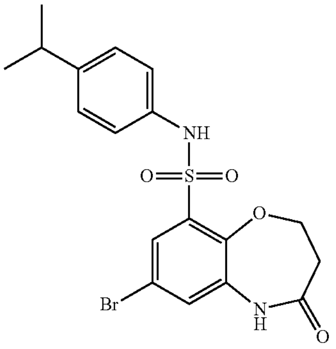 [SMILES: CC(C)c1ccc(NS(=O)(=O)c2cc(Br)cc3c2OCCC(=O)N3)cc1] | + |
| BC19688 | 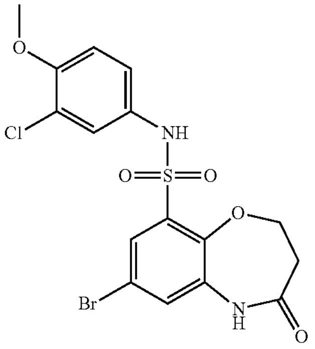 [SMILES: COc1ccc(NS(=O)(=O)c2cc(Br)cc3c2OCCC(=O)N3)cc1Cl] | ++ |

Numbered Paragraphs

1. A method of inhibiting CB-1 activity within a mammal, wherein said method comprises administering, to said mammal, an effective amount of a compound of Formula (I):

(I)

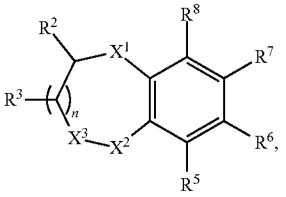

or a pharmaceutically acceptable salt thereof, wherein:

$X^1$ is selected from 0 and $NR^1$;

$X^2$ is selected from $NR^4$ and C(═O);

$X^3$ is selected from $CHR^3$, $NR^4$ and C(═O), provided that:

(i) $X^2$ is $NR^4$ and $X^3$ is C(═O); or (ii) $X^2$ is C(═O) and $X^3$ is selected from $CHR^3$ and $NR^4$;

n is 0 or 1;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

each $R^3$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^9$;

each $R^1$ and $R^4$ is each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^5$, $R^6$, $R^7$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, $S(O)_2NR^{c1}R^{d1}$; and a group of formula (i):

(i)

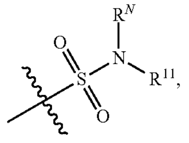

wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, for a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$ $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$.

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The method of paragraph 1, wherein at least one of $R^5$, $R^6$, $R^7$ and $R^8$ is a group of formula (i).

3. The method of paragraph 2, wherein at least one of $R^7$ and $R^8$ is a group of formula (i).

4. The method of paragraph 1, wherein the compound of Formula (I) has formula:

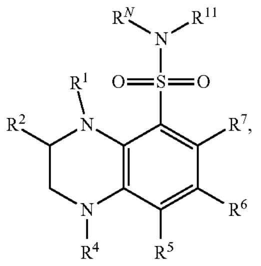

or a pharmaceutically acceptable salt thereof.

5. The method of paragraph 1, wherein the compound of Formula (I) has formula:

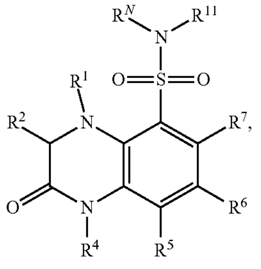

or a pharmaceutically acceptable salt thereof.

6. The method of paragraph 1, wherein the compound of Formula (I) has formula:

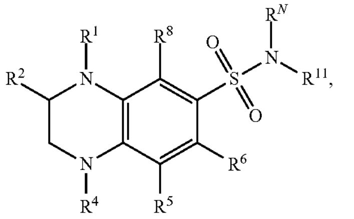

or a pharmaceutically acceptable salt thereof.

7. The method of paragraph 1, wherein the compound of Formula (I) has formula:

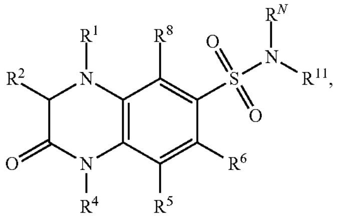

or a pharmaceutically acceptable salt thereof.

8. The method of any one of paragraphs 4-7, wherein:

$R^2$ is selected from H and $C_{1-6}$ alkyl;

$R^1$ is selected from H, $C_{1-6}$ alkyl, $C_{1-6}$ haloalkyl, C(O)$R^{b1}$, and C(O)N$R^{c1}R^{d1}$; wherein said $C_{1-6}$ alkyl is optionally substituted with 1, 2, or 3 substituents independently selected from $R^9$.

9. The method of paragraph 8, wherein $R^1$ is selected from $C_{1-6}$ alkyl, C(O)$R^{b1}$, and C(O)N$R^{c1}R^{d1}$.

10. The method of paragraph 1, wherein the compound of Formula (I) is selected from:

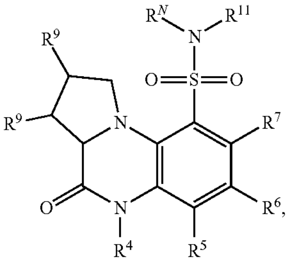

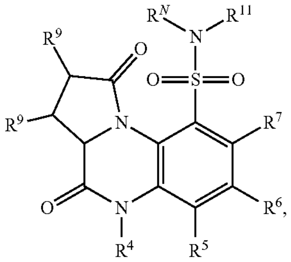

and

-continued

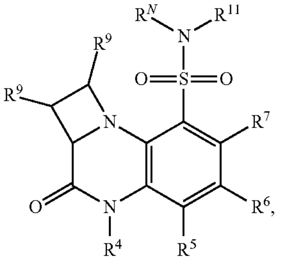

or a pharmaceutically acceptable salt thereof.

11. The method of paragraph 1, wherein the compound of Formula (I) is selected from:

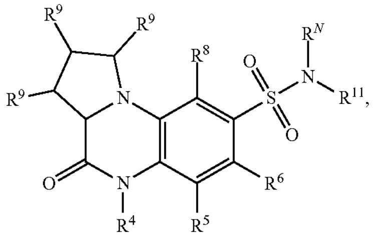

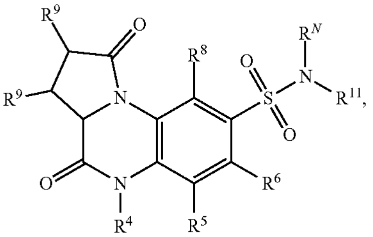

and

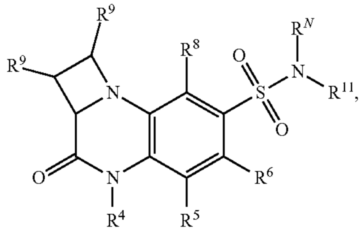

or a pharmaceutically acceptable salt thereof.

12. The method of paragraph 1, wherein the compound of Formula (I) has formula:

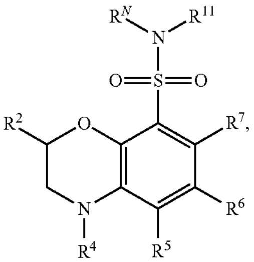

or a pharmaceutically acceptable salt thereof.

13. The method of paragraph 1, wherein the compound of Formula (I) has formula:

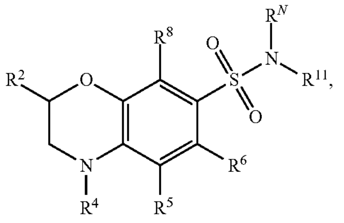

or a pharmaceutically acceptable salt thereof.

14. The method of paragraph 1, wherein the compound of Formula (I) has formula:

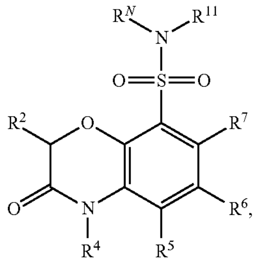

or a pharmaceutically acceptable salt thereof.

15. The method of paragraph 1, wherein the compound of Formula (I) has formula:

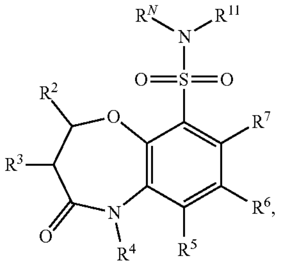

or a pharmaceutically acceptable salt thereof.

16. The method of paragraph 1, wherein the compound of Formula (I) has formula:

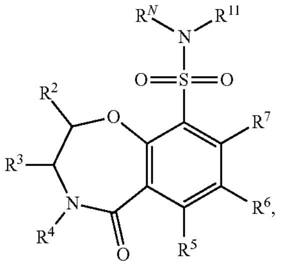

or a pharmaceutically acceptable salt thereof.

17. The method of paragraph 1, wherein the compound of Formula (I) has formula:

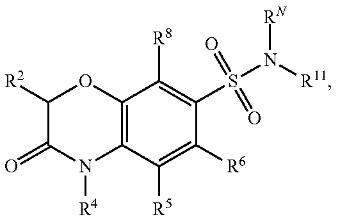

or a pharmaceutically acceptable salt thereof.

18. The method of paragraph 1, wherein the compound of Formula (I) has formula:

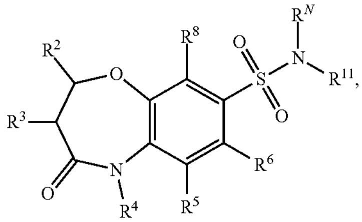

or a pharmaceutically acceptable salt thereof.

19. The method of any one of paragraphs 1-18, wherein $R^2$ is selected from H and $C_{1-6}$ alkyl.

20. The method of any one of paragraphs 1-19, wherein $R^3$ is selected from H and $C_{1-6}$ alkyl.

21. The method of any one of paragraphs 1-20, wherein $R^4$ is selected from H, $C_{1-6}$ alkyl, and $C_{1-6}$ haloalkyl, wherein said $C_{1-6}$ alkyl is optionally substituted with 1, 2, or 3 substituents independently selected from $R^9$.

22. The method of paragraph 21, wherein $R^4$ is H.

23. The method of any one of paragraphs 1-22, wherein $R^5$ and $R^6$ are each independently selected from H, halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$.

24. The method of any one of paragraphs 1-22, wherein $R^5$ and $R^6$ are each independently selected from H, halo, $C_{1-6}$ alkyl, and $S(O)_2R^{b1}$, wherein said $C_{1-6}$ alkyl is optionally substituted with $R^9$.

25. The method of paragraph 24, wherein $R^5$ is H and $R^6$ is $C_{1-6}$ alkyl, optionally substituted with $NR^{c1}R^{d1}$.

26. The method of paragraph 24, wherein $R^5$ is H and $R^6$ is halo.

27. The method of paragraph 24, wherein $R^5$ is H and $R^6$ is $S(O)_2R^{b1}$.

28. The method of any one of paragraphs 1-27, wherein $R^7$ is selected from H and $C_{1-6}$ alkyl.

29. The method of any one of paragraphs 1-27, wherein $R^8$ is selected from H and $C_{1-6}$ alkyl.

30. The method of any one of paragraphs 1-29, wherein $R^N$ is selected from H and $C_{1-6}$ alkyl.

31. The method of any one of paragraphs 1-30, wherein $R^{11}$ is ring A.

32. The method of any one of paragraphs 1-30, wherein $R^{11}$ is $C_{1-6}$ alkyl, optionally substituted with ring A.

33. The method of any one of paragraphs 1-32, wherein $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$.

34. The method of any one of paragraphs 1-33, wherein ring A is selected from any one of the following moieties:

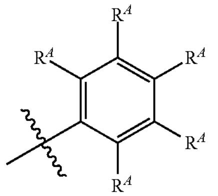
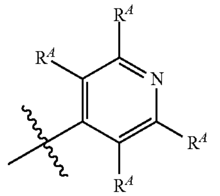
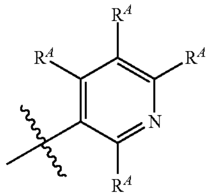
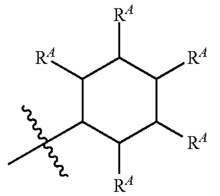
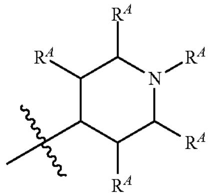
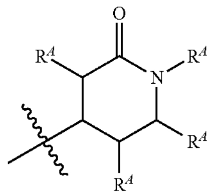
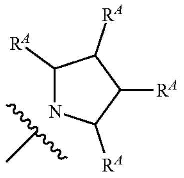

35. The method of any one of paragraphs 1-34, wherein each R is independently selected from H, halo, CN, $C_{1-6}$ alkyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{10}$.

36. The method of any one of paragraphs 1-34, wherein each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$ and $NR^{c1}C(O)R^{b1}$, wherein said $C_{1-6}$ alkyl is optionally substituted with 1, 2, or 3 substituents independently selected from $R^{10}$.

37. The method of any one of paragraphs 1-36, wherein each $R^{10}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$.

38. The method of any one of paragraphs 1-34, wherein each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$ and $NR^{c1}C(O)R^{b1}$, wherein said $C_{1-6}$ alkyl is optionally substituted with $C(O)OR^{a1}$.

39. The method of any one of paragraphs 1-38, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$.

40. The method of any one of paragraph 1-39, wherein each $R^9$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

41. The method of paragraph 1, wherein:

each $R^3$ is independently selected from H and $C_{1-6}$ alkyl;

$R^1$ is selected from H, $C_{1-6}$ alkyl, $C_{1-6}$ haloalkyl, $C(O)R^{b1}$, and $C(O)NR^{c1}R^{d1}$; wherein said $C_{1-6}$ alkyl is optionally substituted with 1, 2, or 3 substituents independently selected from $R^9$;

$R^2$ is selected from H and $C_{1-6}$ alkyl; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

each $R^4$ is independently selected from H, $C_{1-6}$ alkyl, and $C_{1-6}$ haloalkyl, wherein said $C_{1-6}$ alkyl is optionally substituted with 1, 2, or 3 substituents independently selected from $R^9$;

$R^5$ and $R^6$ are each independently selected from H, halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{10}$;

each $R^{10}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

42. The method of paragraph 1, wherein:

each $R^3$ is independently selected from H and $C_{1-6}$ alkyl;

$R^1$ is selected from $C_{1-6}$ alkyl, $C(O)R^{b1}$, and $C(O)NR^{c1}R^{d1}$;

$R^2$ is selected from H and $C_{1-6}$ alkyl; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

each $R^4$ is H;

$R^5$ and $R^6$ are each independently selected from H, halo, $C_{1-6}$ alkyl, and $S(O)_2R^{b1}$, wherein said $C_{1-6}$ alkyl is optionally substituted with $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$, and $NR^{c1}C(O)R^{b1}$, wherein said $C_{1-6}$ alkyl is optionally substituted with $C(O)OR^{a1}$;

each $R^{a1}$, $R^{b1}$, $R^{c1}$, and $R^{d1}$ is independently selected from H and $C_{1-6}$ alkyl, wherein said $C_{1-6}$ alkyl is optionally substituted with 1, 2, or 3 substituents independently selected from $R^g$; and each $R^g$ is independently selected from OH, $NO_2$, CN, halo, $C_{1-6}$ alkyl, $C_{1-6}$ alkoxy, $C_{1-6}$ haloalkoxy, amino, $C_{1-6}$ alkylamino, di($C_{1-6}$ alkyl)amino, and carboxy.

43. The method of paragraph 1, wherein the compound of Formula (I) has formula (Ib):

(Ib)

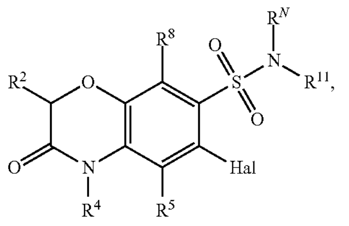

or a pharmaceutically acceptable salt thereof, wherein Hal is halogen.

44. The method of paragraph 43, wherein $R^4$, $R^5$, and $R^8$ are each H.

45. The method of paragraph 43, wherein $R^N$ is H.

46. The method of any one of paragraphs 43-45, wherein ring A is selected from $C_{6-10}$ aryl and $C_{3-10}$ cycloalkyl, each of which is optionally substituted with 1-10 substituents independently selected from $R^A$.

47. The method of any one of paragraphs 43-46, wherein each $R^A$ is independently selected from H, halo, CN, $C_{1-6}$ alkyl, $C_{1-6}$ haloalkyl, $OR^{a1}$, $SR^{a1}$, and $C(O)R^{b1}$ wherein said $C_{1-6}$ alkyl is optionally substituted with 1, 2, or 3 substituents independently selected from $R^{10}$.

48. The method of any one of paragraphs 43-46, wherein each $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

49. The method of paragraph 43:

$R^2$ is selected from H and $C_{1-6}$ alkyl;

$R^4$, $R^5$, and $R^8$ are each H;

$R^N$ is H; or $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$;

ring A is selected from $C_{6-10}$ aryl and $C_{3-10}$ cycloalkyl, each of which is optionally substituted with 1-10 substituents independently selected from $R^A$; and each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

50. The method of paragraph 49, wherein $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

51. The method of paragraph 43, wherein the compound of Formula (I) has Formula (Ic):

(Ic)

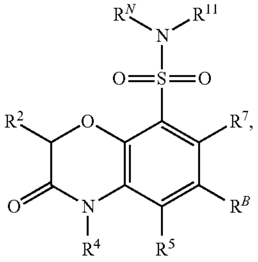

or a pharmaceutically acceptable salt thereof, wherein $R^B$ is selected from halogen and $S(O)_2R^{b1}$.

52. The method of paragraph 51, wherein $R^B$ is a halogen.

53. The method of paragraph 51, wherein $R^B$ is a $S(O)_2R^{b1}$.

54. The method of any one of paragraphs 51-53, wherein $R^2$ is selected H and $C_{1-6}$ alkyl.

55. The method of any one of paragraphs 51-54, wherein $R^4$ is H.

56. The method of any one of paragraphs 51-55, wherein $R^5$ is H.

57. The method of any one of paragraphs 51-56, wherein $R^7$ is selected H and $C_{1-6}$ alkyl.

58. The method of any one of paragraphs 51-57, wherein $R^N$ is H.

59. The method of any one of paragraphs 51-58, wherein $R^N$ and $R^{11}$, together with the N atom to which they are attached, form a ring selected from morpholinyl and piperazinyl, each of which is optionally substituted with 1, 2, or 3 substituents independently selected from $R^9$.

60. The method of any one of paragraphs 51-59, wherein ring A is selected from $C_{6-10}$ aryl and $C_{3-10}$ cycloalkyl, optionally substituted with 1-10 substituents independently selected from $R^A$.

61. The method of any one of paragraphs 51-60, wherein each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

62. The method of paragraph 51, wherein:

$R^2$ is selected H and $C_{1-6}$ alkyl;

$R^4$ is H;

$R^5$ is H;

$R^7$ is selected H and $C_{1-6}$ alkyl;

$R^N$ is H; or $R^N$ and $R^{11}$, together with the N atom to which they are attached, form a ring selected from morpholinyl and piperazinyl, each of which is optionally substituted with 1, 2, or 3 substituents independently selected from $R^9$;

ring A is selected from $C_{6-10}$ aryl and $C_{3-10}$ cycloalkyl, optionally substituted with 1-10 substituents independently selected from $R^A$; and each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

63. The method of paragraph 1, wherein the compound of Formula (I) has Formula (Id):

(Id)

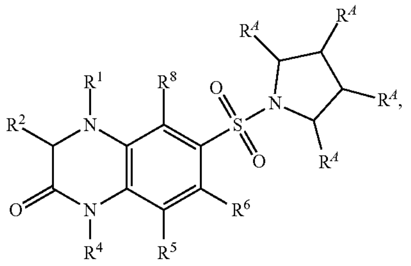

or a pharmaceutically acceptable salt thereof.

64. The method of paragraph 63, wherein $R^2$ is selected from H and $C_{1-6}$ alkyl.

65. The method of paragraph 63, wherein $R^4$ is H.

66. The method of paragraph 63, wherein $R^5$, $R^6$, and $R^8$ are each H.

67. The method of any one of paragraphs 63-66, wherein $R^1$ is selected from H, $C_{1-6}$ alkyl, $C(O)R^{b1}$, and $C(O)NR^{c1}R^{d1}$, wherein said $C_{1-6}$ alkyl is optionally substituted with 1, 2, or 3 substituents independently selected from $R^9$.

68. The method of any one of paragraphs 63-67, wherein each $R^A$ is H.

69. The method of paragraph 63, wherein:

$R^2$ is selected from H and $C_{1-6}$ alkyl;

$R^4$ is H;

$R^5$, $R^6$, and $R^8$ are each H;

$R^1$ is selected from H, $C_{1-6}$ alkyl, $C(O)R^{b1}$, and $C(O)NR^{c1}R^{d1}$, wherein said $C_{1-6}$ alkyl is optionally substituted with 1, 2, or 3 substituents independently selected from $R^9$;

each $R^9$ is independently selected from OH, $C_{1-6}$ alkoxy, carboxy, $C(O)NH_2$, amino, $C_{1-6}$ alkylamino, and di($C_{1-6}$ alkyl)amino; and each $R^A$ is H.

70. The method of paragraph 1, wherein the compound of Formula (I) has Formula (Ie):

(Ie)

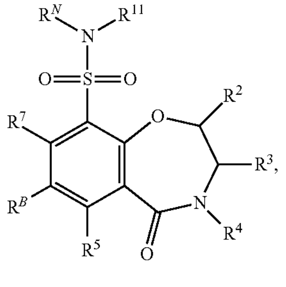

or a pharmaceutically acceptable salt thereof, wherein $R^B$ is selected from halogen and $S(O)_2R^{b1}$.

71. The method of paragraph 1, wherein the compound of Formula (I) has Formula (Ig):

(Ig)

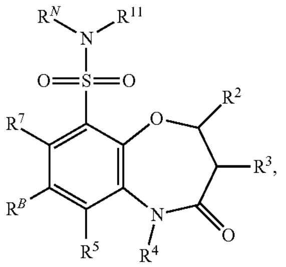

or a pharmaceutically acceptable salt thereof, wherein $R^B$ is selected from halogen and $S(O)_2R^{b1}$.

72. The method of paragraph 70 or 71, wherein $R^B$ is a halogen.

73. The method of paragraph 70 or 71, wherein $R^B$ is $S(O)_2R^{b1}$.

74. The method of any one of paragraphs 70-73, wherein $R^2$ and $R^3$ are each independently selected from H and $C_{1-6}$ alkyl.

75. The method of any one of paragraphs 70-74, wherein $R^4$ is H.

76. The method of any one of paragraphs 70-75, wherein $R^5$ is H.

77. The method of any one of paragraphs 70-76, wherein $R^7$ is selected H and $C_{1-6}$ alkyl.

78. The method of any one of paragraphs 70-77, wherein $R^N$ is H.

79. The method of any one of paragraphs 70-78, wherein ring A is $C_{6-10}$ aryl, optionally substituted with 1-5 substituents independently selected from $R^A$.

80. The method of any one of paragraphs 70-79, wherein each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

81. The method of paragraph 70 or 71, wherein:

$R^2$ and $R^3$ are each independently selected H and $C_{1-6}$ alkyl;

$R^4$ is H;

$R^8$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

82. The method of paragraph 1, wherein the compound of Formula (I) has Formula (If):

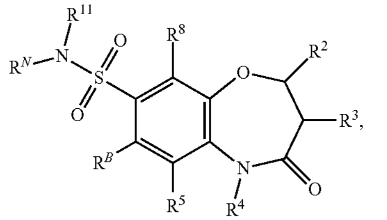

(If)

or a pharmaceutically acceptable salt thereof, wherein $R^B$ is selected from halogen and $S(O)_2R^{b1}$.

83. The method of paragraph 82, wherein $R^B$ is a halogen.

84. The method of paragraph 82, wherein $R^B$ is $S(O)_2R^{b1}$.

85. The method of any one of paragraphs 82-84, wherein $R^2$ and $R^3$ are each independently selected from H and $C_{1-6}$ alkyl.

86. The method of any one of paragraphs 82-85, wherein $R^4$ is H.

87. The method of any one of paragraphs 82-86, wherein $R^5$ is H.

88. The method of any one of paragraphs 82-87, wherein $R^8$ is selected H and $C_{1-6}$ alkyl.

89. The method of any one of paragraphs 82-88, wherein $R^N$ is H.

90. The method of any one of paragraphs 82-89, wherein ring A is $C_{6-10}$ aryl, optionally substituted with 1-5 substituents independently selected from $R^A$.

91. The method of any one of paragraphs 82-90, wherein each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

92. The method of paragraph 82, wherein:

$R^2$ and $R^3$ are each independently selected H and $C_{1-6}$ alkyl;

$R^4$ is H;

$R^5$ is H;

$R^8$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

93. The method of paragraph 1, wherein the compound of Formula (I) is selected from any one of the compounds listed in Table 1, Table 2, Table 3, Table 4, Table 5, Table 6, Table 7, Table 8, Table 9, and Table 10, or a pharmaceutically acceptable salt thereof.

94. The method of any one of paragraphs 1-93, wherein said method comprises identifying said mammal as being in need of inhibited CB1 activity.

95. The method of any one of paragraphs 1-94, wherein said method is a method for treating obesity.

96. The method of any one of paragraphs 1-94, wherein said method is a method for treating fear.

97. The method of any one of paragraphs 1-94, wherein said method is a method for treating a metabolic-related disorder.

98. The method of any one of paragraphs 1-94, wherein said method is a method for treating diabetes.

99. The method of any one of paragraphs 1-94, wherein said method is a method for treating dyslipidaemia.

100. The method of any one of paragraphs 1-94, wherein said method is a method for treating atherosclerosis.

101. The method of any one of paragraphs 1-94, wherein said method is a method for reducing food intake of said mammal.

102. The method of any one of paragraphs 1-94, wherein said method is a method for reducing body weight gain of said mammal.

103. The method of any one of paragraphs 1-94, wherein said method is a method for improving lipid profiles within said mammal.

104. The method of any one of paragraphs 1-94, wherein said method is a method for improving glycemic profiles within said mammal.

105. The method of any one of paragraphs 1-94, wherein said method is a method for assisting said mammal in stopping tobacco use and/or *cannabis* use.

106. The method of any one of paragraphs 1-94, wherein said method is a method for treating a liver disorder.

107. The method of paragraph 106, wherein said liver disorder is fatty liver disease, nonalcoholic steatohepatitis (NASH), cirrhosis, or liver cancer.

108. The method of any one of paragraphs 1-94, wherein said method is a method for reducing a symptom or the progression of idiopathic pulmonary fibrosis or a fibrotic condition in the lung.

109. The method of any one of paragraphs 1-94, wherein said method is a method for reducing the severity of or occurrence of end-organ damage induced by chronic alcohol usage.

110. The method of paragraph 106, wherein said end-organ damage is heart failure, pancreatitis, or liver disease.

111. The method of any one of paragraphs 1-94, wherein said method is a method for reducing a complication of chronic renal disease characterized by renal fibrosis.

112. The method of paragraph 111, wherein said chronic renal disease is diabetic nephropathy or inherited or acquired glomerular diseases.

113. The method of any one of paragraphs 1-112, wherein said administering step reduces CB1 activity within the peripheral nervous system of said mammal.

114. The method of paragraph 113, wherein said administering step reduces little if any CB1 activity within the central nervous system of said mammal.

115. The method of paragraph 113, wherein said administering step does not reduce CB1 activity within the central nervous system of said mammal.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of inhibiting CB-1 activity within a mammal, wherein said method comprises administering, to said mammal, an effective amount of a compound of Formula (I):

(I)

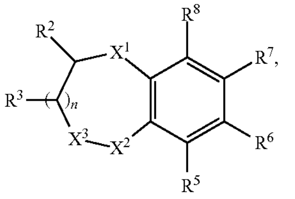

or a pharmaceutically acceptable salt thereof, wherein:

$X^1$ is selected from O;

$X^2$ is $NR^4$;

$X^3$ is C(=O), n is 0 or 1;

$R^2$ is selected from H, $C_{1-6}$ alkyl, $C_{1-6}$ haloalkyl, $C_{2-6}$ alkenyl, and $C_{2-6}$ alkynyl, wherein each of $C_{1-6}$ alkyl, $C_{1-6}$ haloalkyl, $C_{2-6}$ alkenyl, and $C_{2-6}$ alkynyl is optionally substituted with 1, 2, or 3 substituents independently selected from $R^9$;

each $R^3$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^9$;

each $R^4$ is each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ is H or halo, $R^6$ is halo or $C_1$-$C_6$ alkyl, $R^7$ a group of formula (i):

(i)

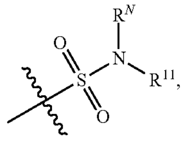

and $R^8$ is H;

or $R^8$ is a group of formula (i):

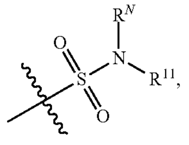

and $R^7$ is H;

$R^{11}$ is selected from $C_{1-3}$ alkyl and ring A, wherein $C_{1-3}$ alkyl is optionally substituted with $C_6$ aryl;

$R^N$ is selected from H, or $R^{11}$ and $R^N$, together with the N atom to which they are attached, for a 5-6 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, ring A is selected from $C_{6-10}$ aryl, $C_{3-10}$ cycloalkyl, each of which is substituted with 1-10 substituents independently selected from $R^A$;

each $R^A$ is independently selected from halo, CN, $OR^{a1}$, and $C(O)R^{b1}$, each $R^{a1}$, $R^{b1}$, $R^{c1}$, and $R^{d1}$ is independently selected from H, $C_{1-6}$ alkyl, $C_{1-4}$ haloalkyl.

2. The method of claim 1, wherein:

each $R^3$ is independently selected from H and $C_{1-6}$ alkyl;

$R^2$ is selected from H and $C_{1-6}$ alkyl; or each $R^4$ is independently selected from H, $C_{1-6}$ alkyl, and $C_{1-6}$ haloalkyl, wherein said $C_{1-6}$ alkyl is optionally substituted with 1, 2, or 3 substituents independently selected from $R^9$;

$R^5$ is H or halo;

$R^6$ is halo;

$R^N$ is selected from H; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from halo, CN, and each $R^{a1}$, $R^{b1}$, $R^{c1}$, and $R^{d1}$ is independently selected from H, $C_{1-6}$ alkyl, and $C_{1-4}$ haloalkyl.

3. The method of claim 1, wherein the compound of Formula (I) has formula (Ib):

(Ib)

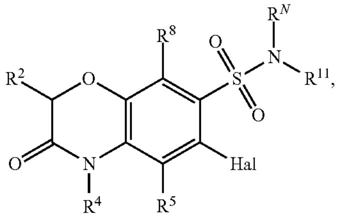

or a pharmaceutically acceptable salt thereof, wherein Hal is halogen.

4. The method of claim 3:

$R^2$ is selected from H and $C_{1-6}$ alkyl;

$R^4$, $R^5$, and $R^8$ are each H;

$R^N$ is H; or $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$;

ring A is selected from $C_{6-10}$ aryl and $C_{3-10}$ cycloalkyl, each of which is optionally substituted with 1-10 substituents independently selected from $R^A$, and each $R^A$ is independently selected from halo, CN, $OR^{a1}$, and $C(O)R^{b1}$.

5. The method of claim 1, wherein said inhibiting CB-1 activity comprises treating a disease or condition selected from obesity, fear, metabolic-related disorder, diabetes, dyslipidaemia, atherosclerosis, and liver disorder.

6. The method of claim 5, wherein said liver disorder is fatty liver disease, nonalcoholic steatohepatitis (NASH), cirrhosis, or liver cancer.

7. A method of inhibiting CB-1 activity within a mammal, wherein said method comprises administering, to said mammal, an effective amount of a compound selected from:

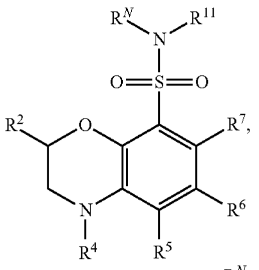

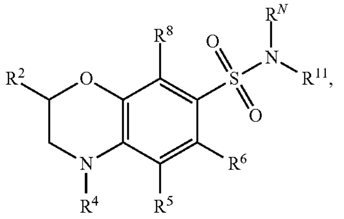

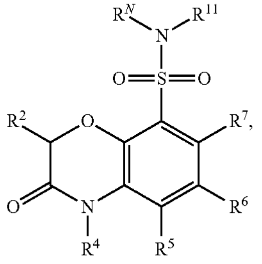

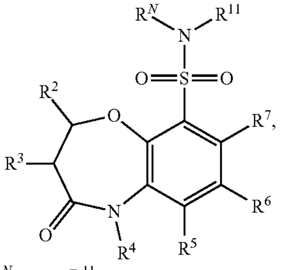

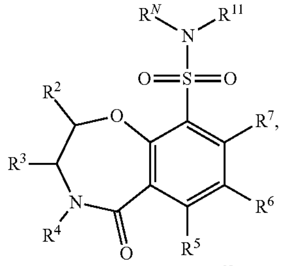

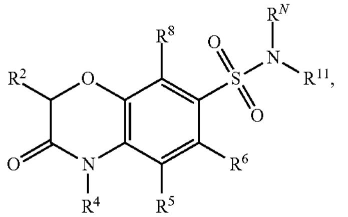

and

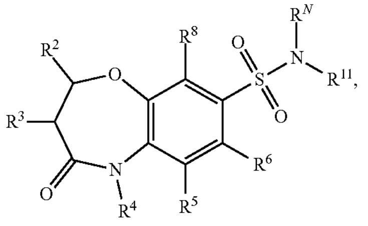

or a pharmaceutically acceptable salt thereof, wherein $R^2$ is selected from H, $C_{1-6}$ alkyl, $C_{1-6}$ haloalkyl, $C_{2-6}$ alkenyl, and $C_{2-6}$ alkynyl, wherein each of $C_{1-6}$ alkyl, $C_{1-6}$ haloalkyl, $C_{2-6}$ alkenyl, and $C_{2-6}$ alkynyl is optionally substituted with 1, 2, or 3 substituents independently selected from $R^9$:

each $R^3$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^9$;

each $R^4$ is each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ is H or halo, $R^6$ is halo or $C_1$-$C_6$ alkyl $R^7$ is a group of formula (i):

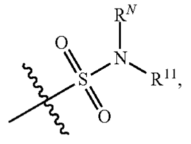

and $R^8$ is H;

or $R^8$ is a group of formula (i):

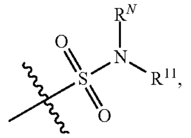

and $R^7$ is H;

$R^{11}$ is selected from $C_{1-3}$ alkyl and ring A, wherein $C_{1-3}$ alkyl is optionally substituted with $C_6$ aryl;

$R^N$ is selected from H, or $R^{11}$ and $R^N$, together with the N atom to which they are attached, for a 5-6 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)^2R^{b1}$, $S(O)_2R^{b1}$, and $S(O)_2NR^{c1}R^{d1}$;

ring A is selected from $C_{6-10}$ aryl, $C_{3-10}$ cycloalkyl, each of which is substituted with 1-10 substituents independently selected from $R^A$;

each $R^A$ is independently selected from halo, CN, $OR^{a1}$, $C(O)R^{b1}$ and each $R^{a1}$ and $R^{b1}$, $R^{c1}$, and $R^{d1}$ is independently selected from H, $C_{1-6}$ alkyl, $C_{1-4}$ haloalkyl.

8. A method of inhibiting CB-1 activity within a mammal, wherein said method comprises administering, to said mammal, an effective amount of a compound selected from any one of the following compounds:

BC19132

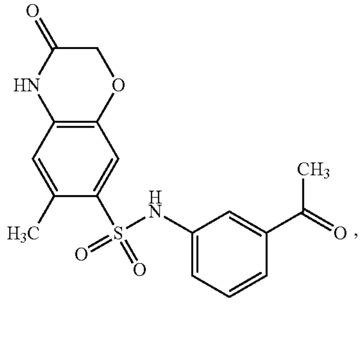

-continued
BC19131
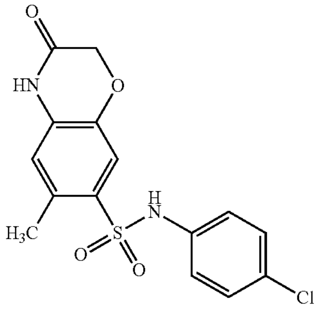
,
BC19134
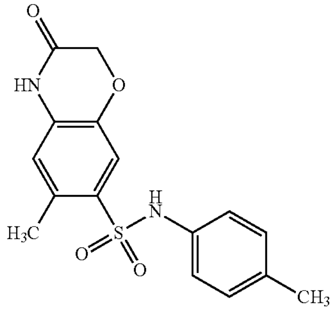
,
BC19133
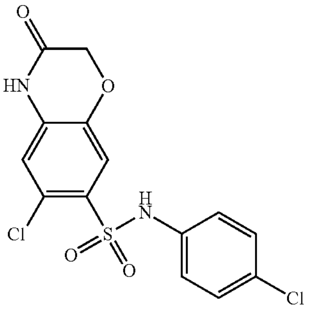
,
BC19135
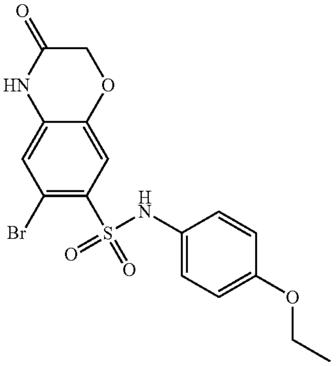
,
-continued
BC19136
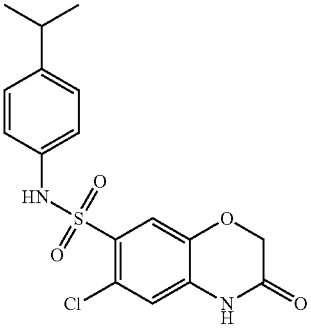
,
BC19137
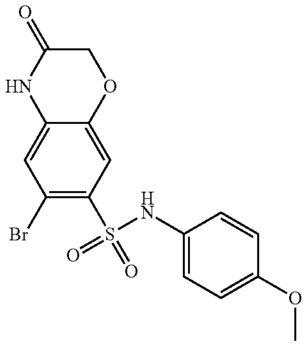
,
BC19138
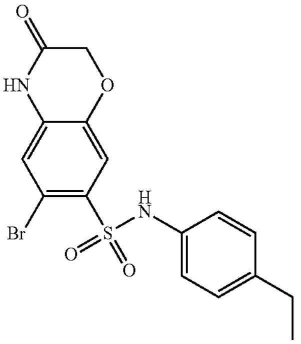
,
BC19161
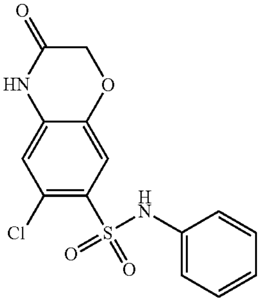
,
BC19162
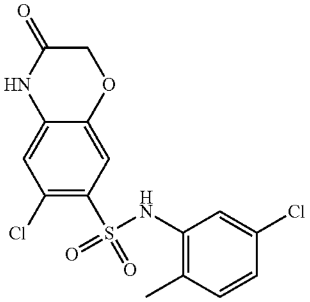
, -continued
BC19163
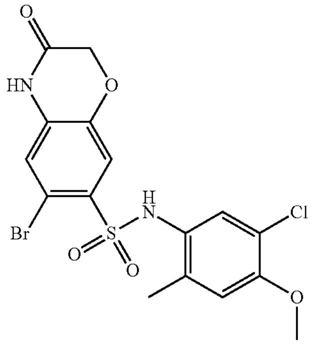
,
BC19164
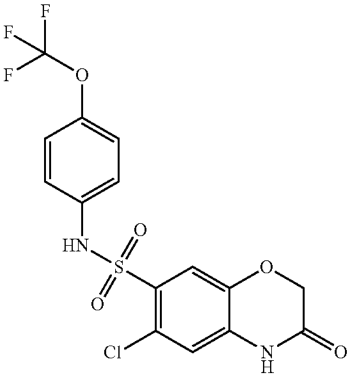
,
BC19165
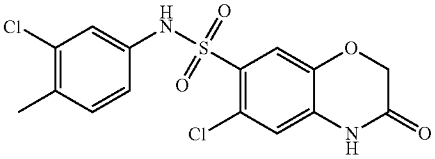
,
BC19166
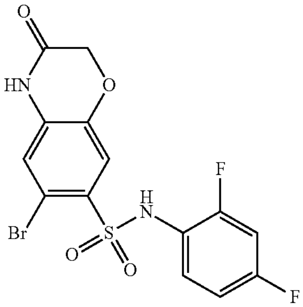
,
BC19167
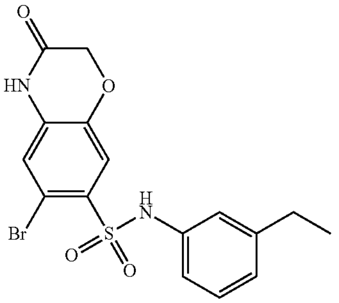
,
-continued
BC19206
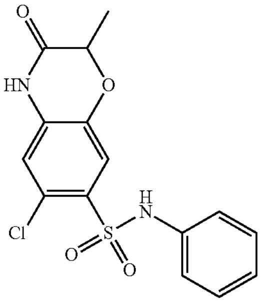
,
BC19207
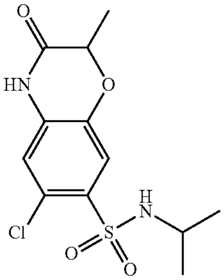
,
BC19208
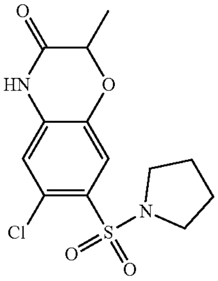
,
BC19209
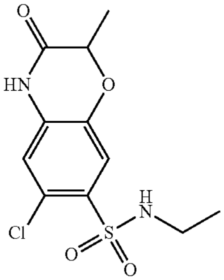
,
BC19210
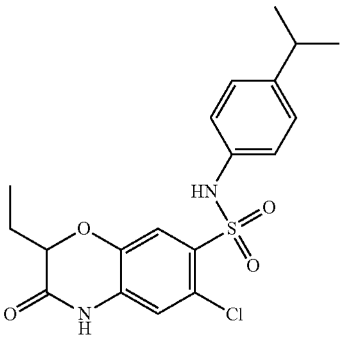
, -continued
BC19211
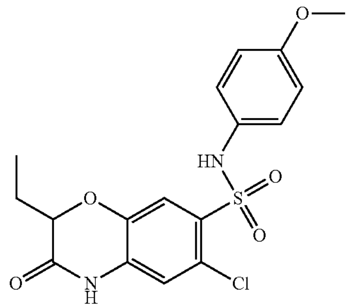
,
BC19212
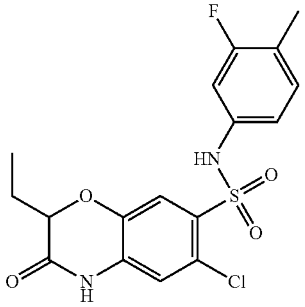
,
BC19213
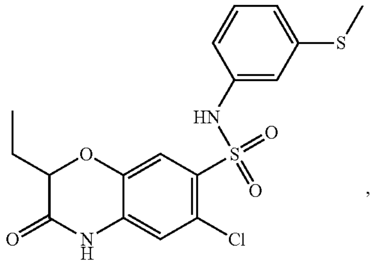
,
BC19214
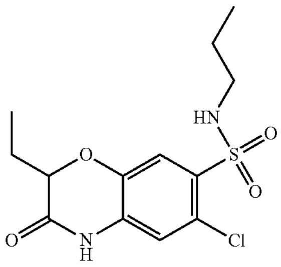
,
BC19215
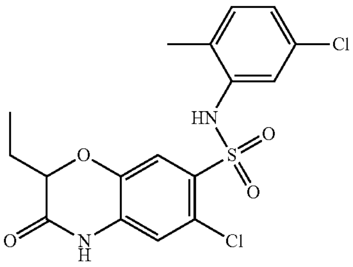
,
-continued
BC19216
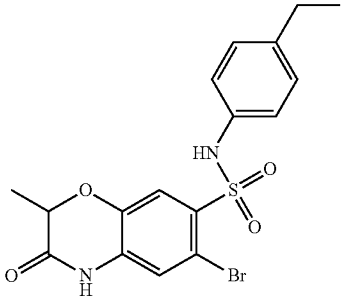
,
BC19217
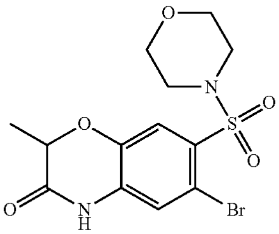
,
BC19218
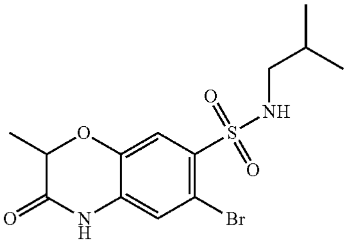
,
BC19219
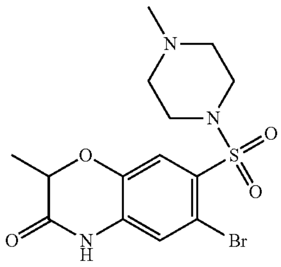
,
BC19220
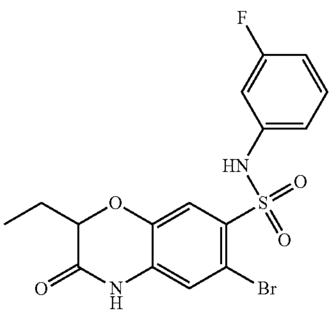
, -continued
BC19221
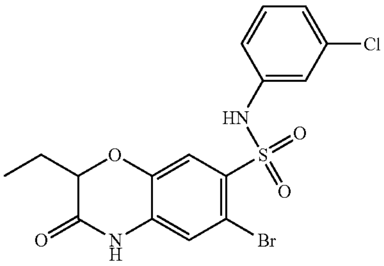
,
BC19222
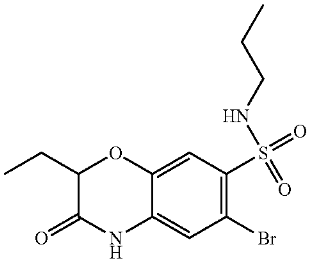
,
BC19223
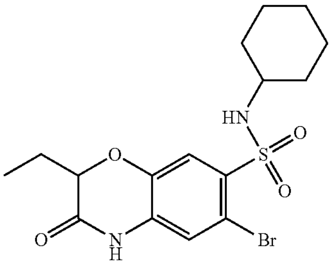
,
BC19224
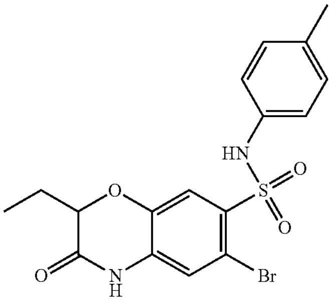
,
BC19280
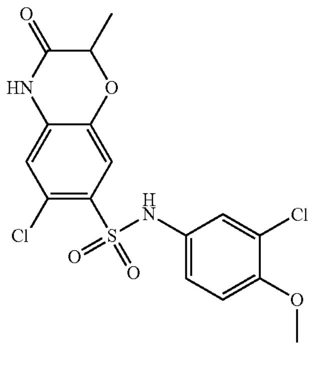
,
-continued
BC19281
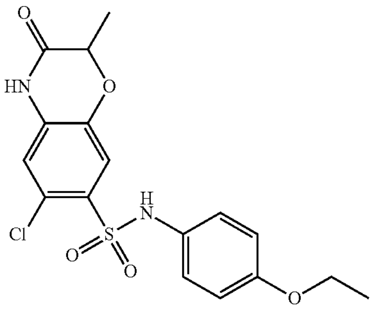
,
BC19282
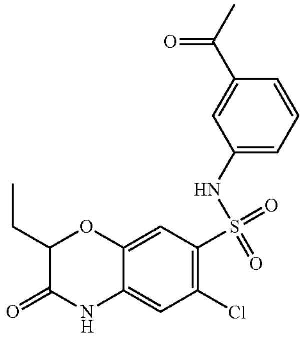
,
BC19283
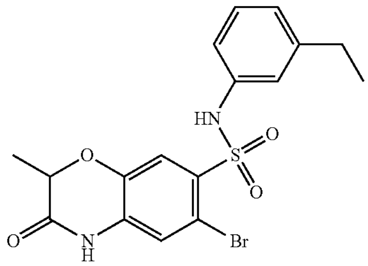
,
BC19284
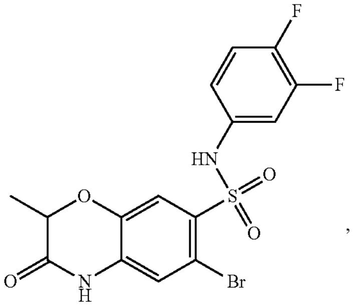
,
BC19285
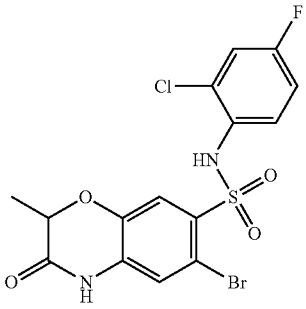
, -continued
BC19286
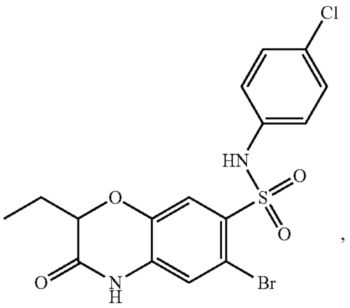
BC19287
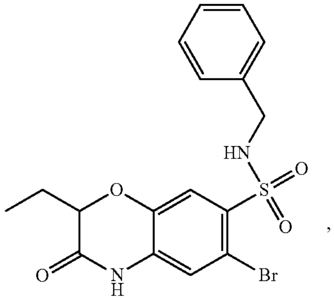
BC19354
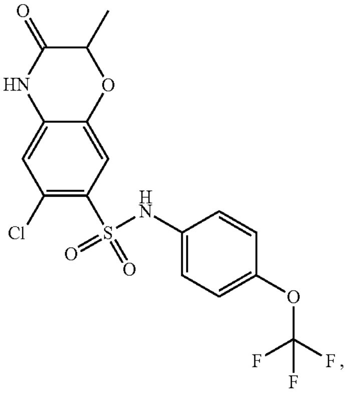
BC19356
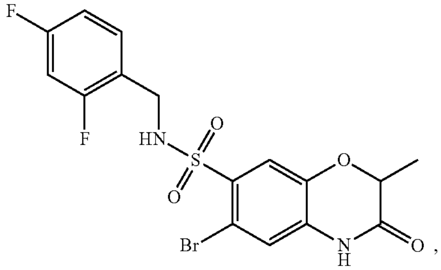
BC19357
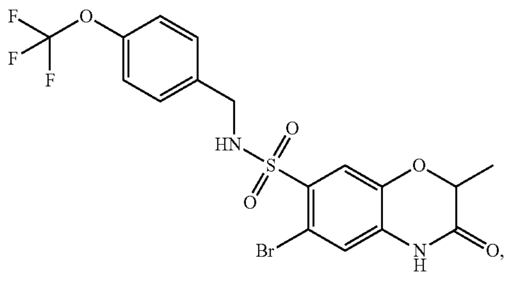
-continued
BC19358
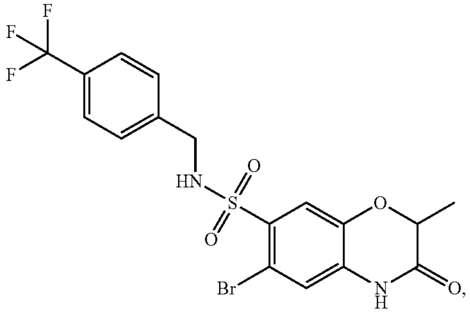
BC19359
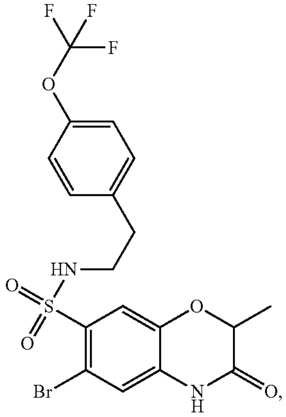
BC19360
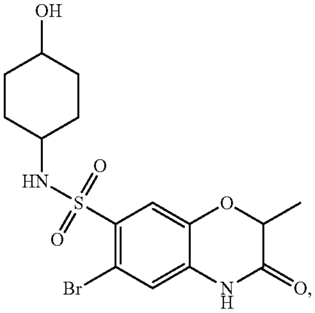
BC19361
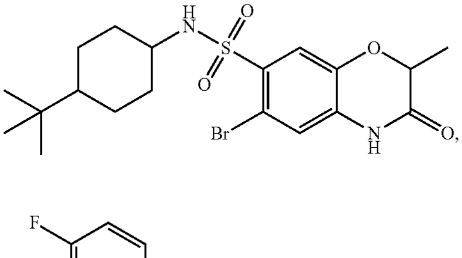
BC19368
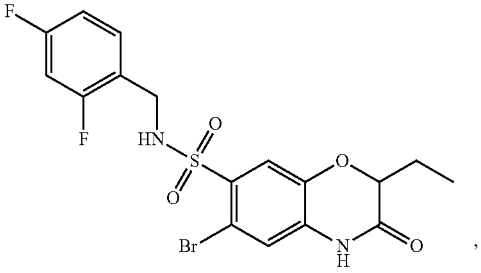

-continued
BC19369
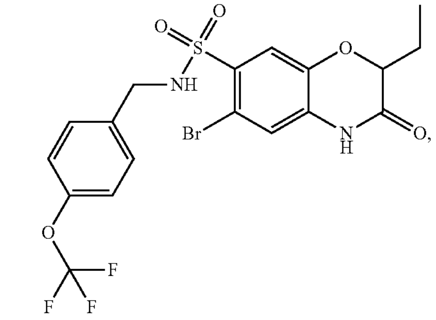
BC19370
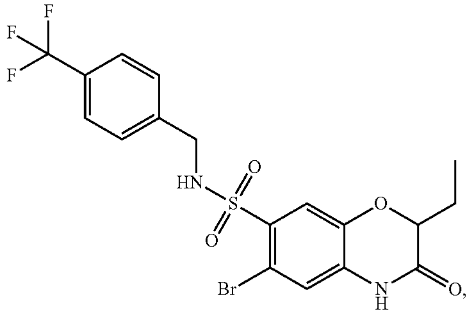
BC19371
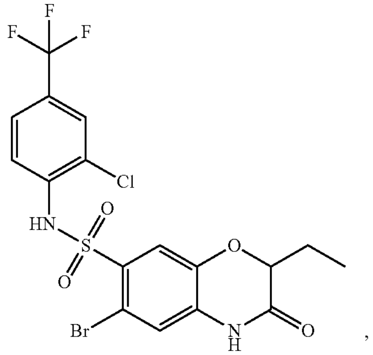
BC19732
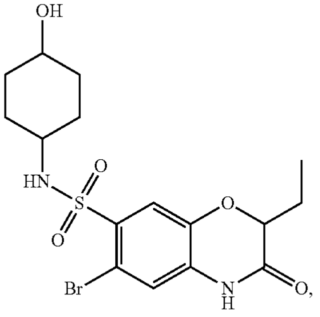
-continued
BC19373
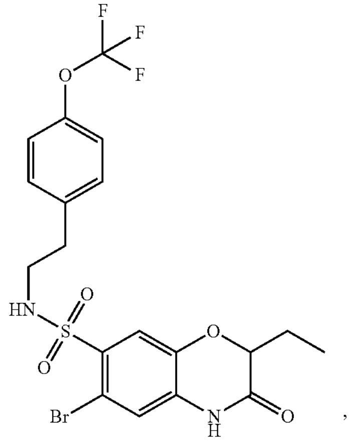
BC19387
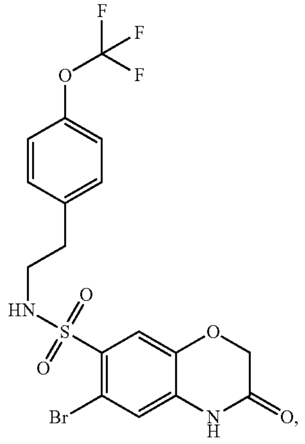
BC19388
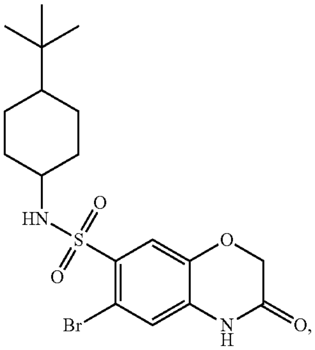
BC19389
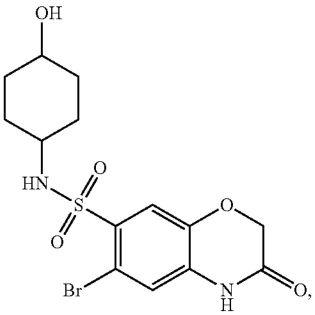

-continued
BC19390
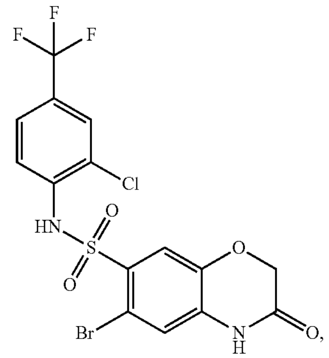
BC19391
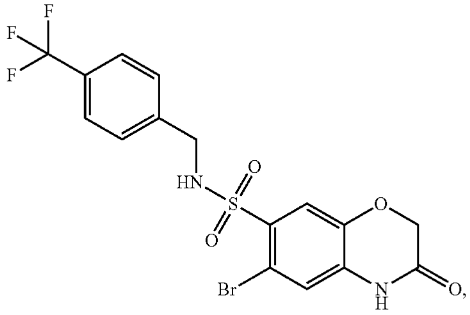
BC19392
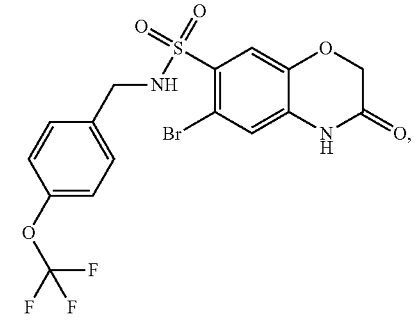
BC19393
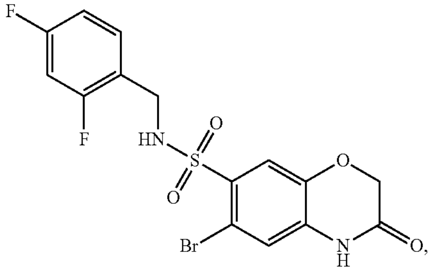
BC19696
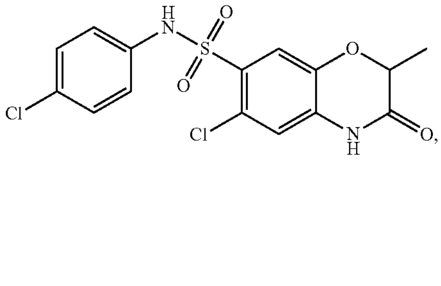
-continued
BC19698
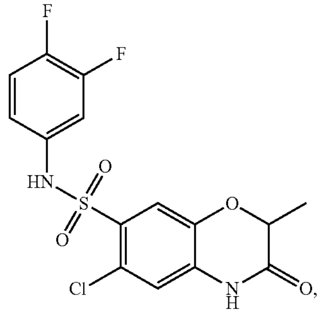
BC19700
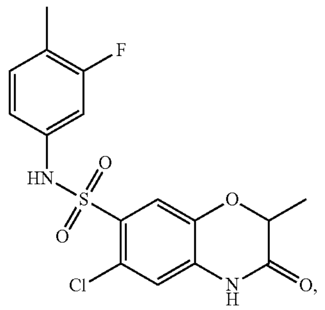
BC19702
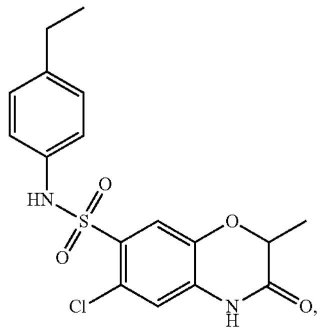
BC19704
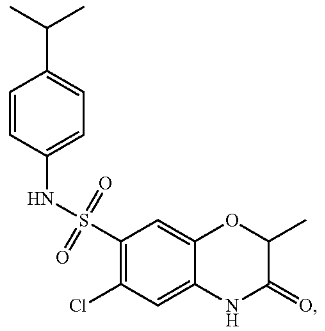
BC19706
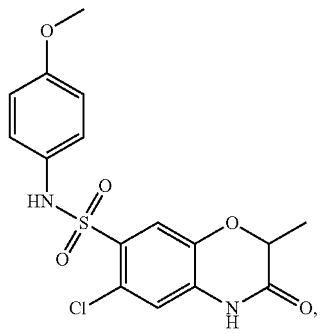

-continued
BC19708
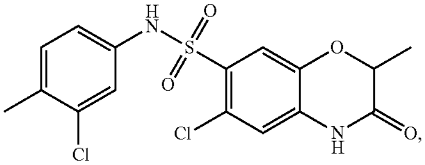
,
BC19709
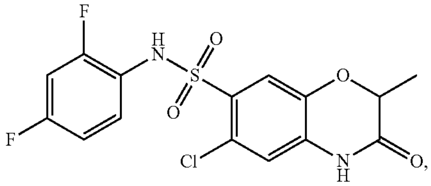
,
BC19711
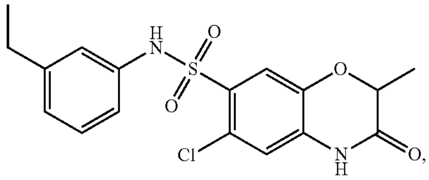
,
BC19713
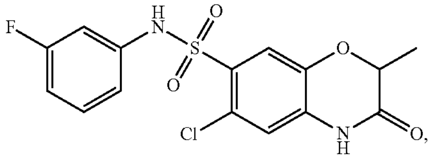
,
BC19715
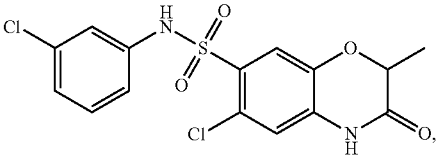
,
BC19717
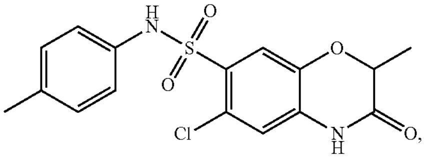
,
BC19719
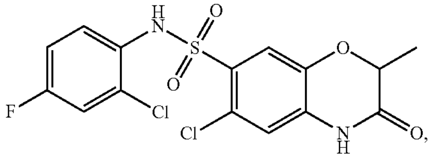
,
BC19721
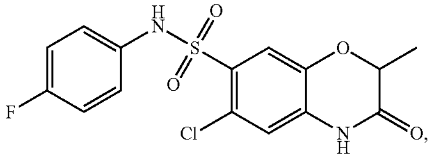
,
BC19729
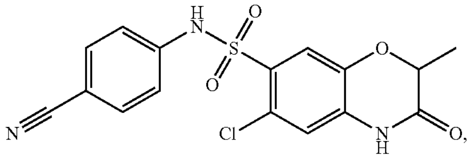
,
-continued
BC19731
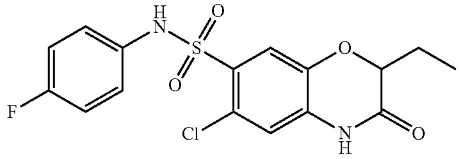
,
BC19733
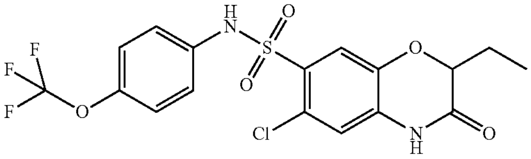
,
BC19735
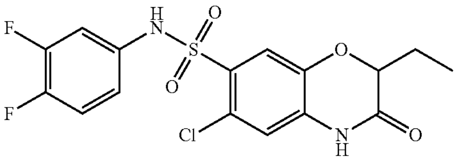
,
BC19737
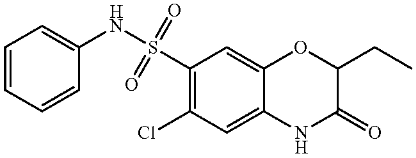
,
BC19739
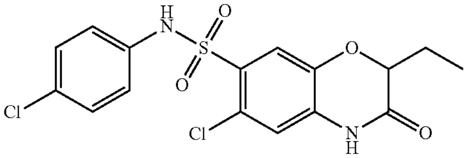
,
BC19741
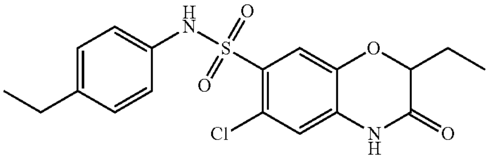
,
BC19743
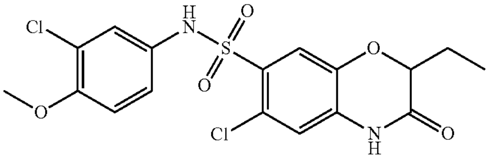
,
BC19745
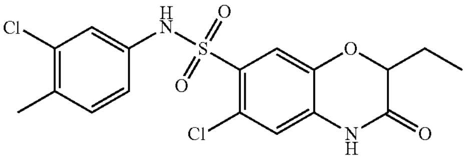
, -continued
BC19747
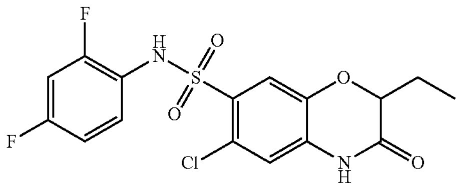
,
BC19749
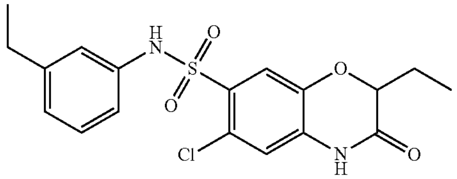
,
BC19751
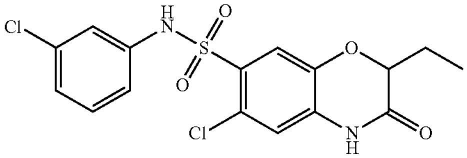
,
BC19753
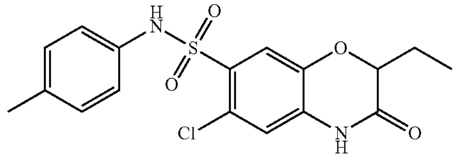
,
BC19755
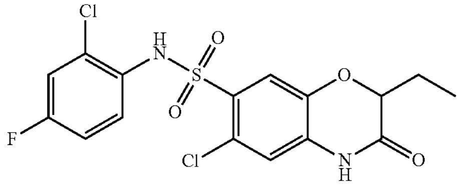
,
BC19758
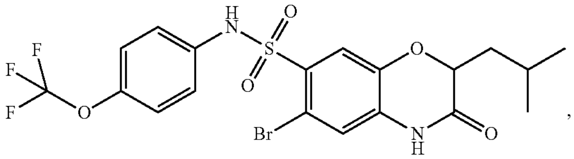
,
BC19760
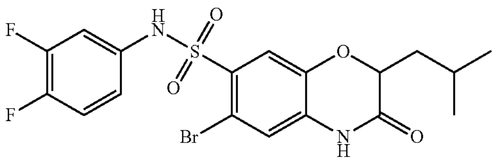
,
BC19762
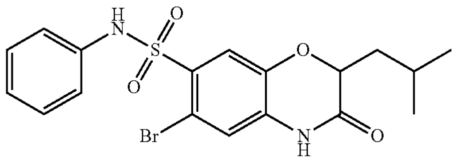
,
-continued
BC19764
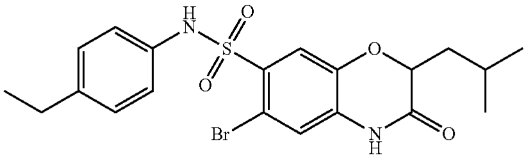
,
BC19766
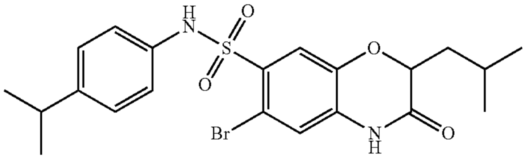
,
BC19768
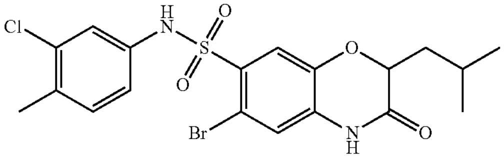
,
BC19770
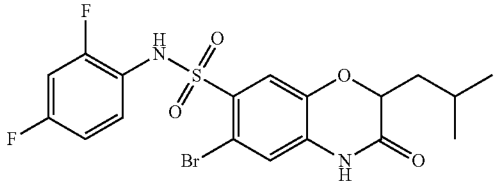
,
BC19772
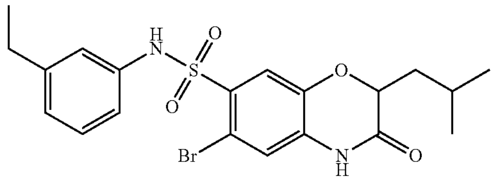
,
BC19774
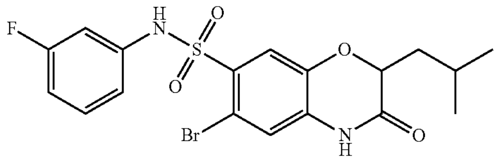
,
BC19776
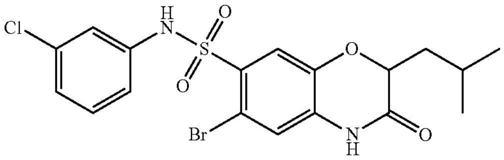
,
BC19778
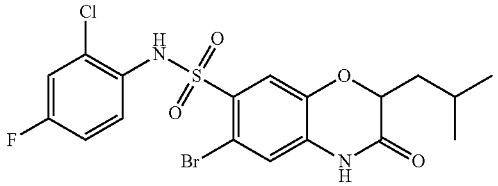
, -continued
BC19780
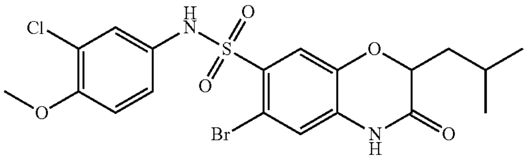
,
BC19782
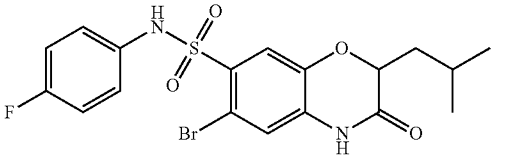
,
BC19784
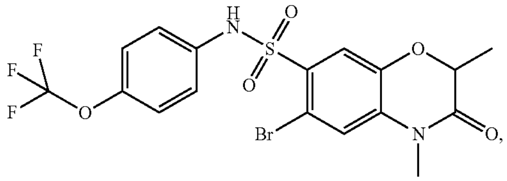
BC19786
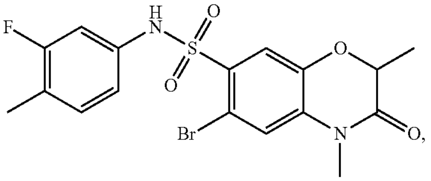
BC19788
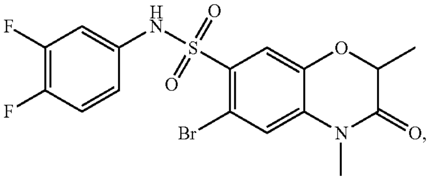
BC19790
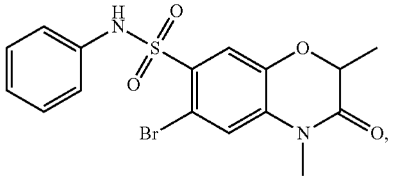
BC19792
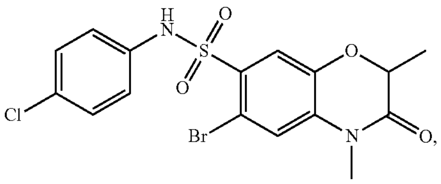
BC19794
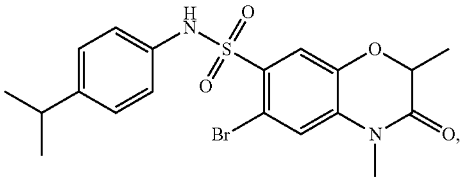
-continued
BC19795
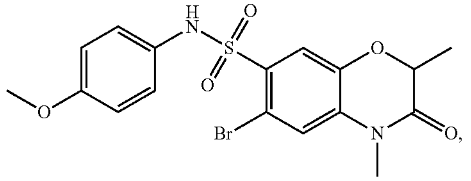
BC19797
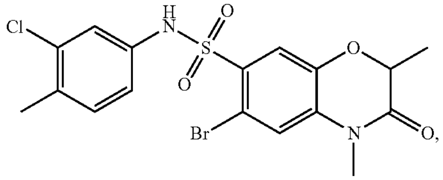
BC19799
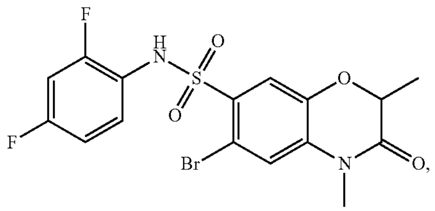
BC19901
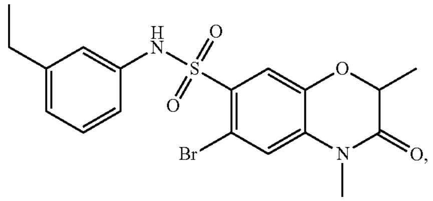
BC19903
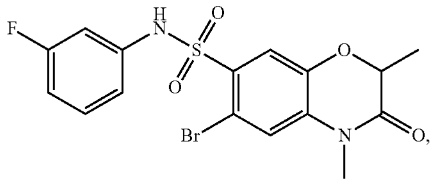
BC19905
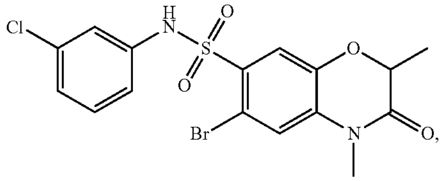
BC19907
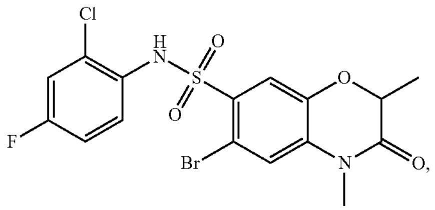
BC19910
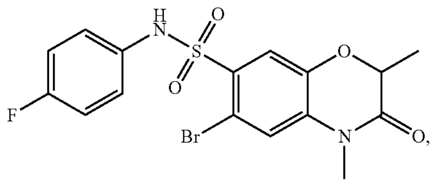

-continued
BC19912
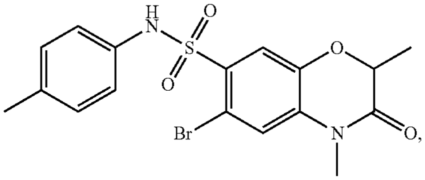
BC19914
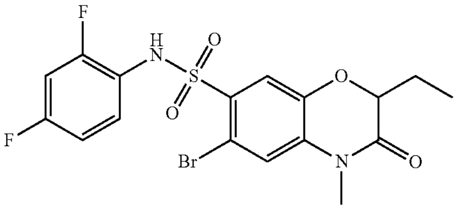
,
BC19916
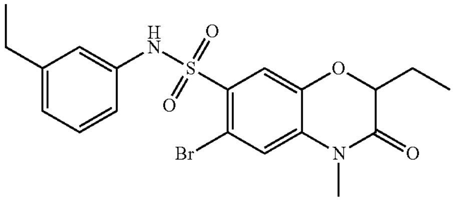
,
BC19919
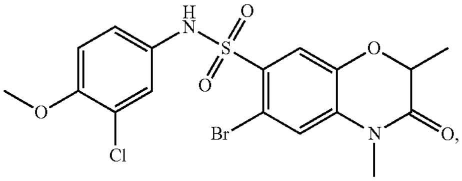
BC19920
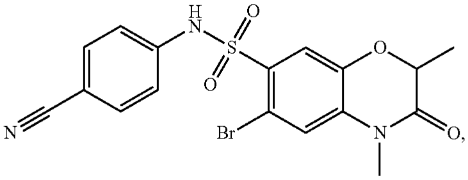
BC19922
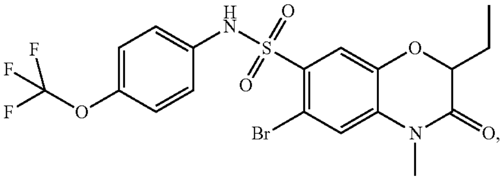
BC19924
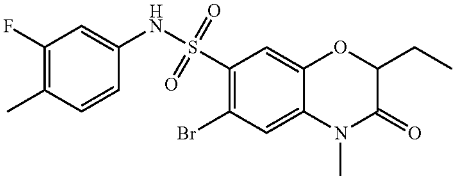
,
-continued
BC19926
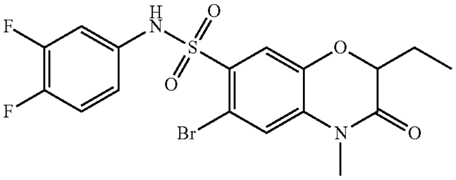
,
BC19928
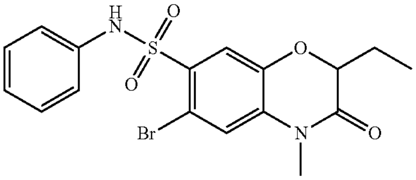
,
BC19930
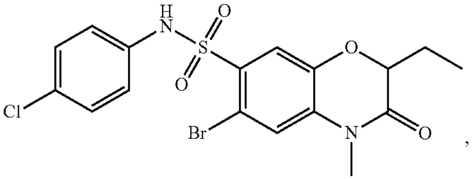
,
BC19932
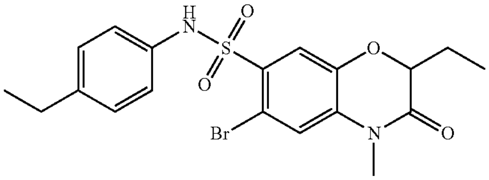
,
BC19934
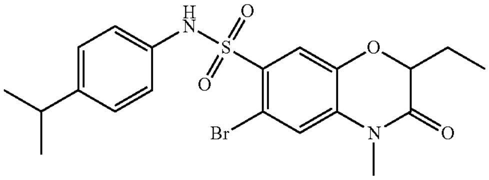
,
BC19936
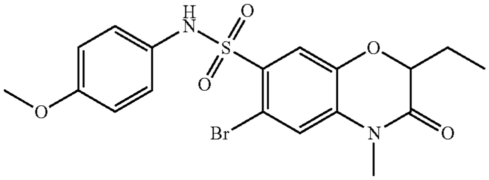
,
BC19938
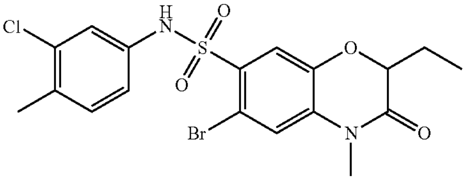
, -continued
BC19168
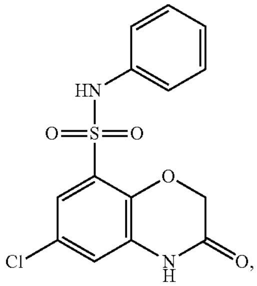
BC19169
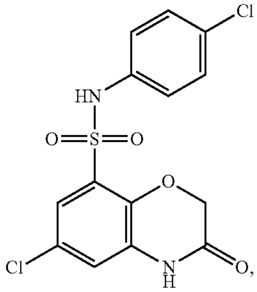
BC19170
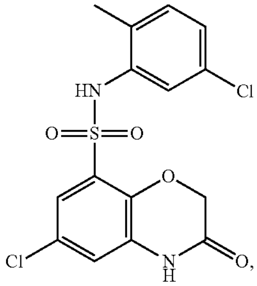
BC19171
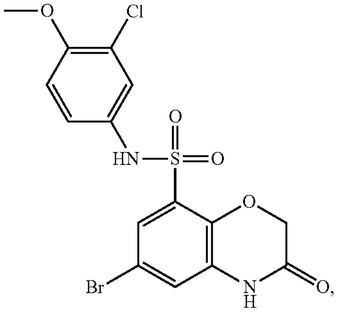
BC19172
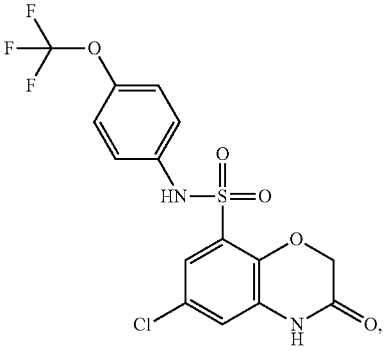
-continued
BC19173
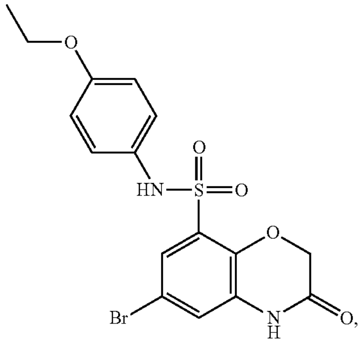
BC19174
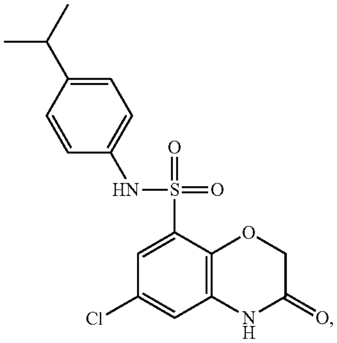
BC19175
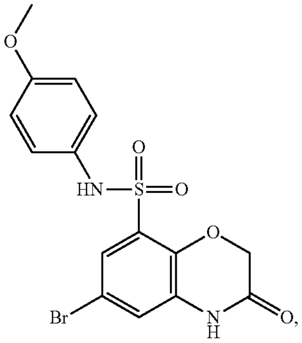
BC19176
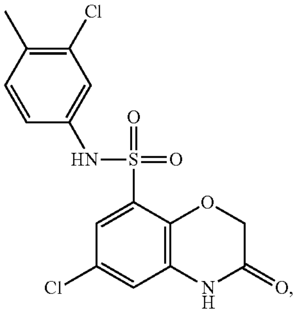

-continued
BC19177
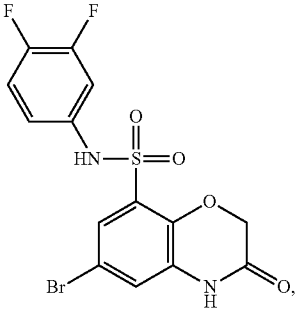
BC19178
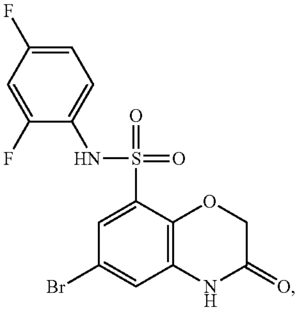
BC19179
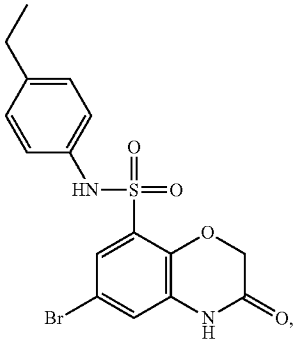
BC19180
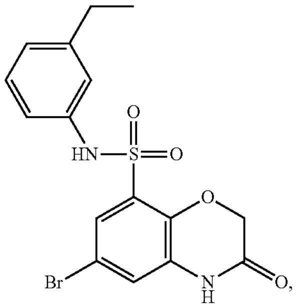
-continued
BC19225
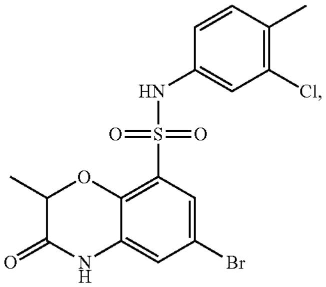
BC19226
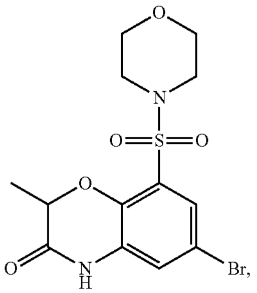
BC19227
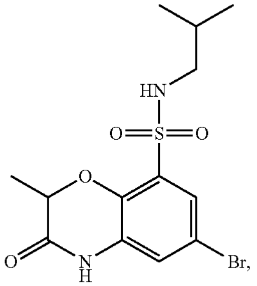
BC19228
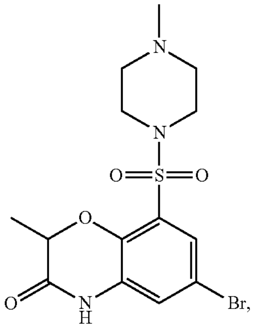
BC19229
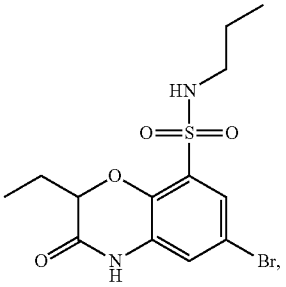

-continued
BC19230
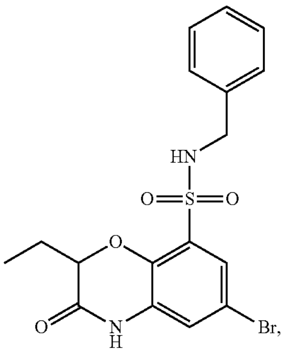
BC19231
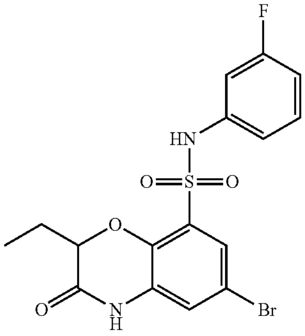
,
BC19232
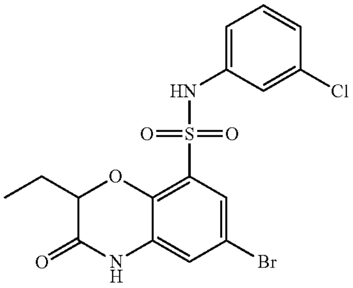
,
BC19233
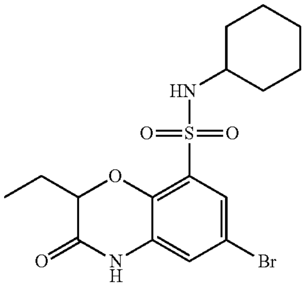
,
-continued
BC19234
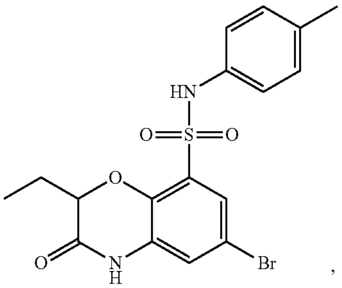
,
BC19288
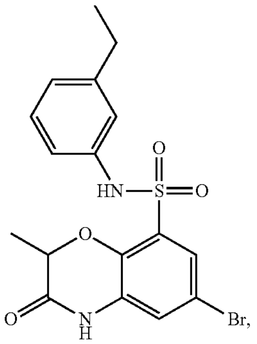
BC19289
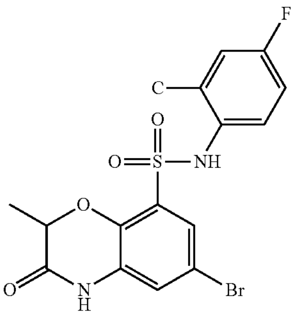
,
BC19290
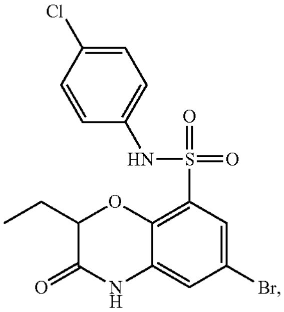
BC19291
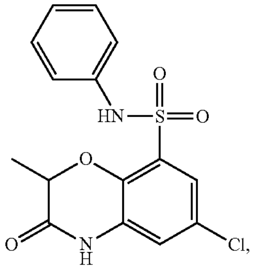

-continued
BC19292
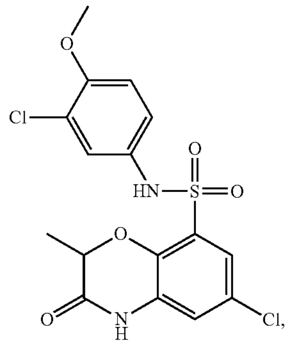
BC19293
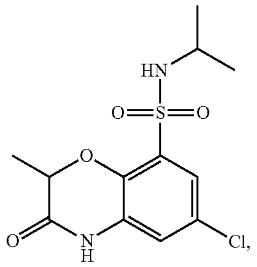
BC19294
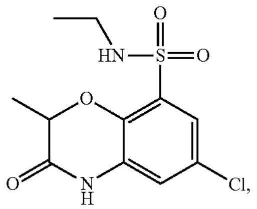
BC19355
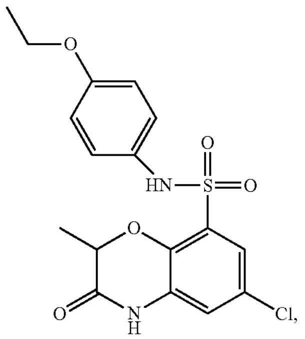
-continued
BC19362
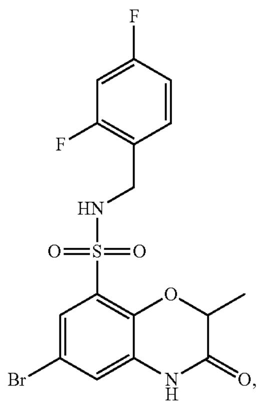
BC19363
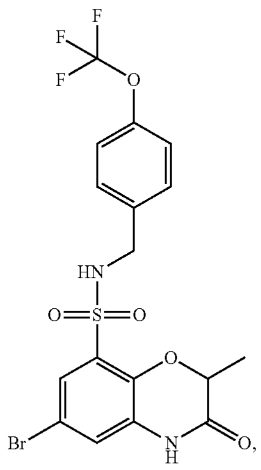
BC19364
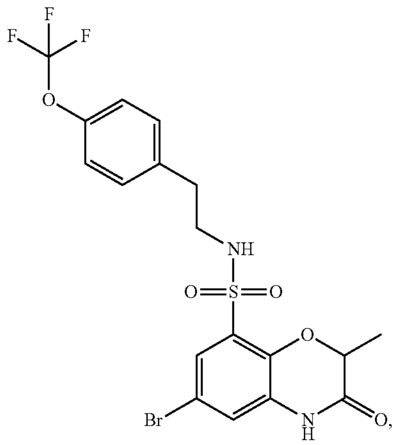
BC19365
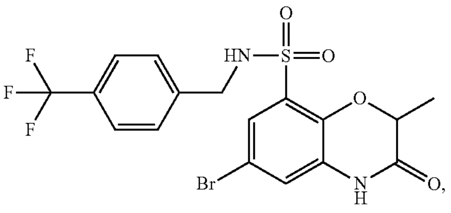

-continued
BC19366
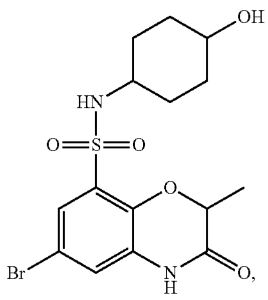
BC19367
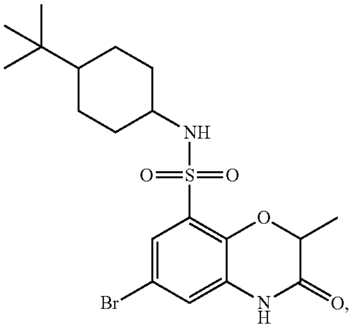
BC19374
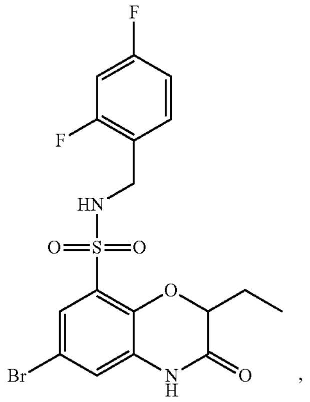
BC19375
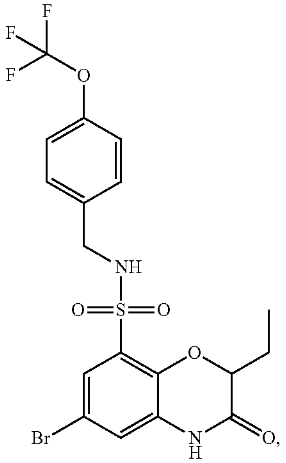
-continued
BC19376
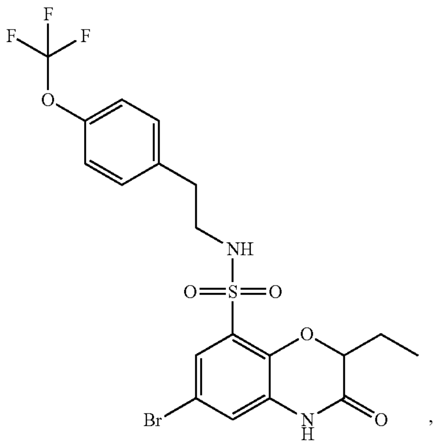
BC19377
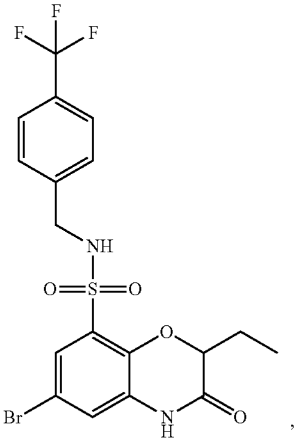
BC19378
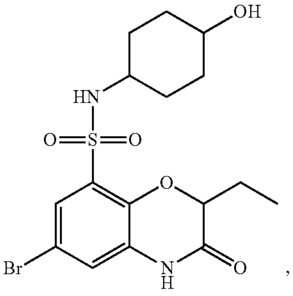
BC19379
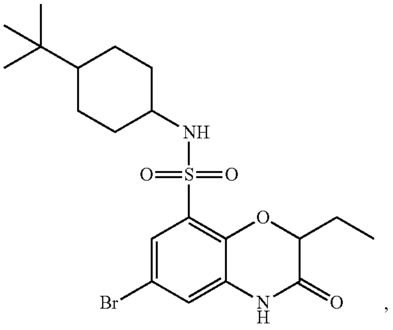

-continued
BC19380
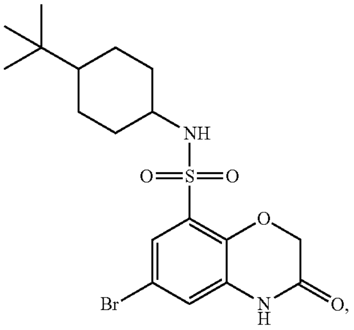
BC19381
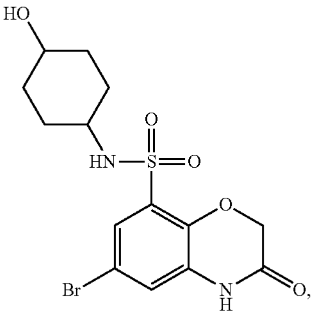
BC19382
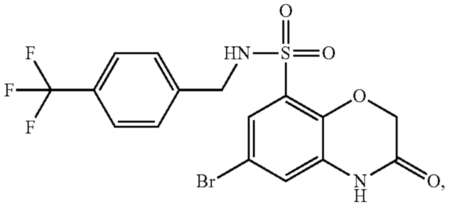
BC19383
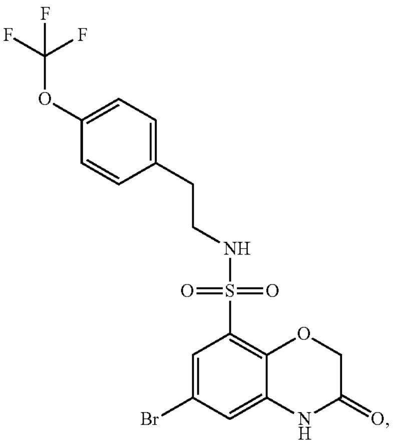
-continued
BC19384
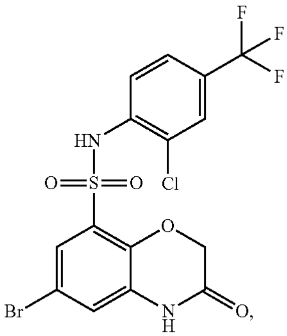
BC19385
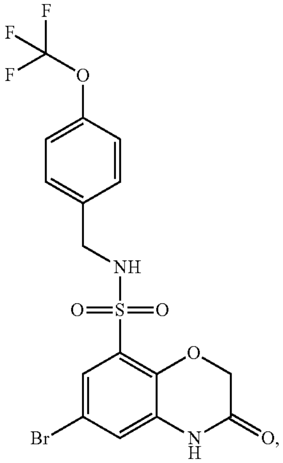
BC19386
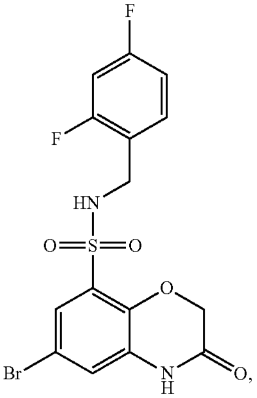

BC19394
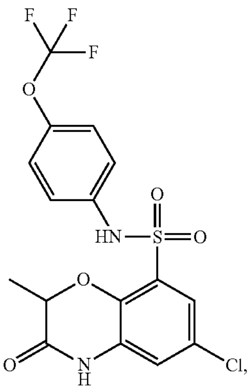
BC19421
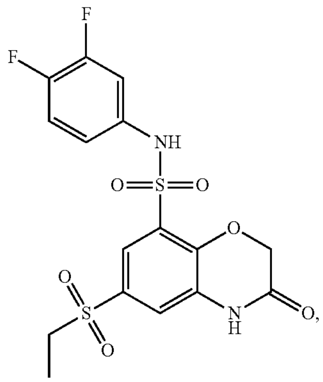
BC19422
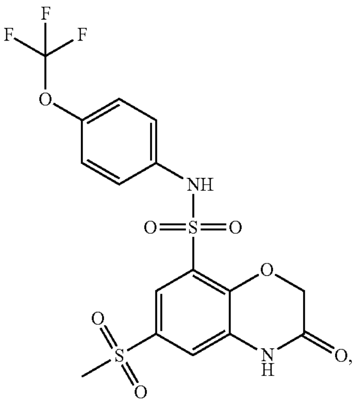
BC19423
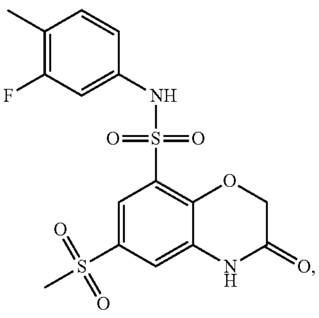
BC19424
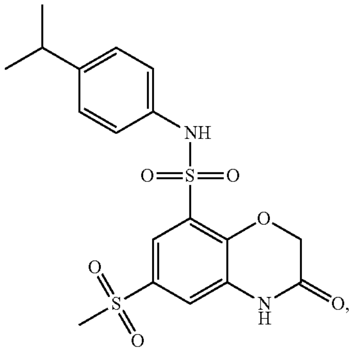
BC19425
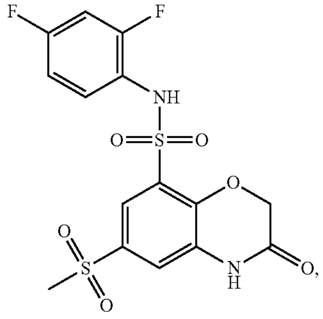
BC19426
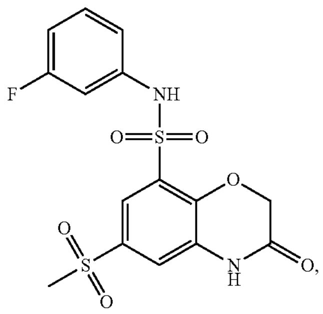
BC19427
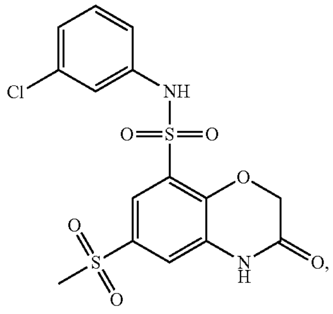

BC19428
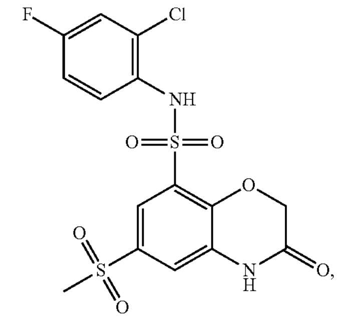
BC19429
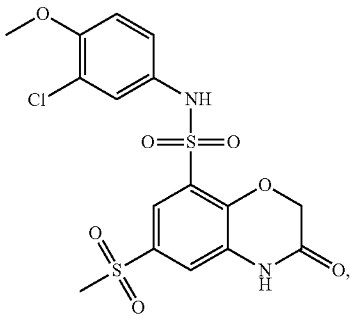
BC19430
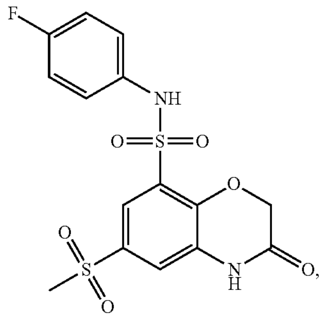
BC19431
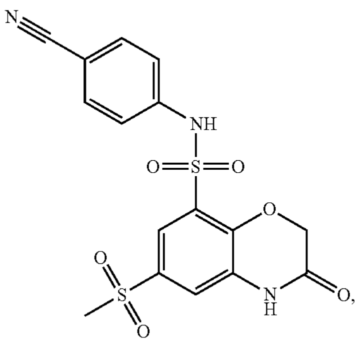
BC19432
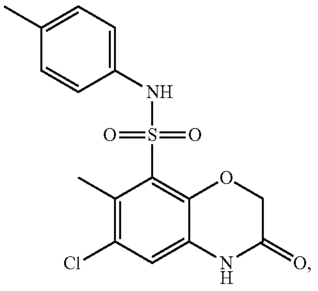
BC14933
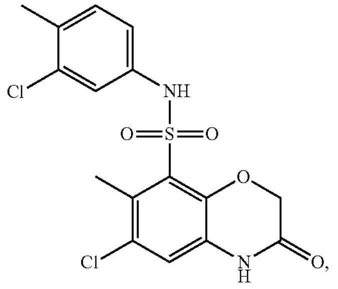
BC14934
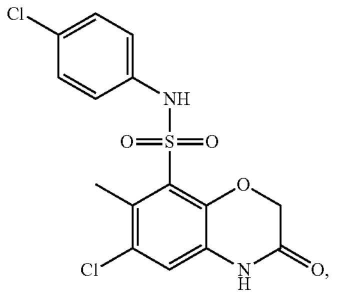
BC14935
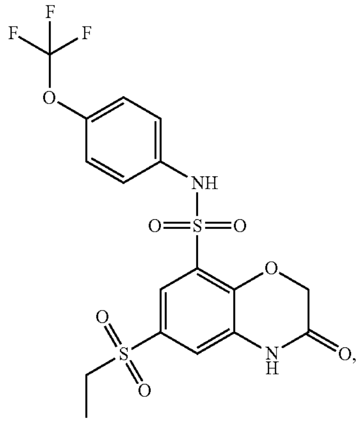

-continued
BC14936
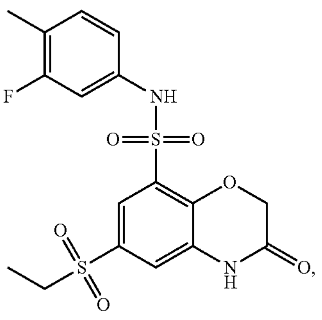
BC14937
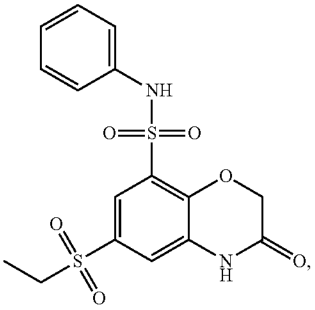
BC19438
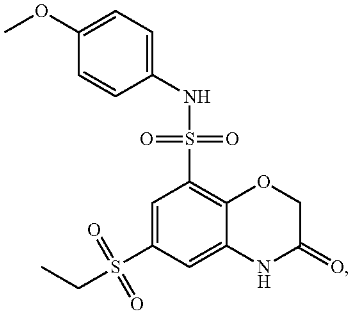
BC19439
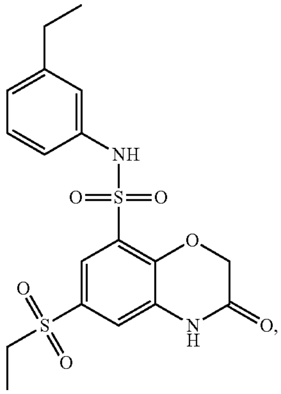
-continued
BC19440
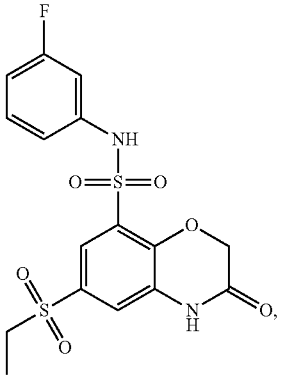
BC19441
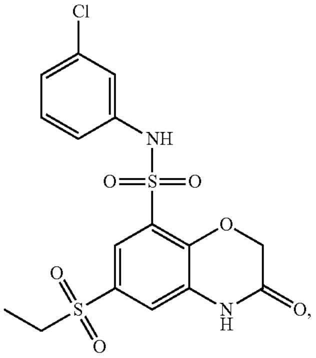
BC19442
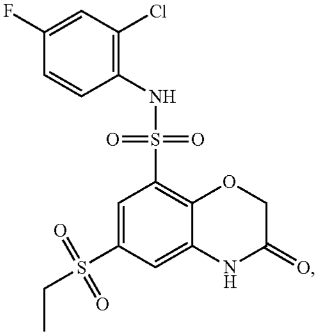
BC19443
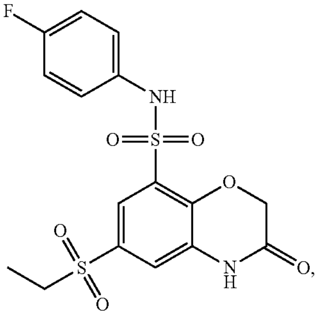

BC19481
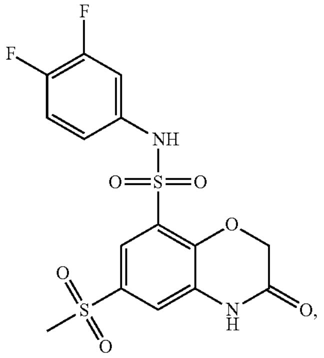
BC19482
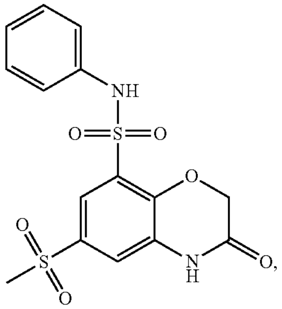
BC19483
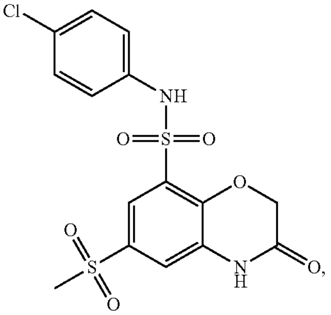
BC19484
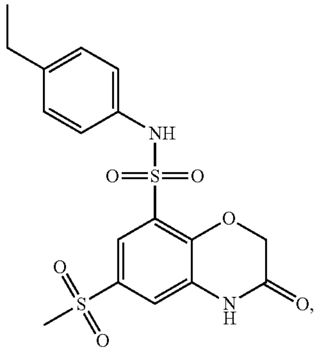
BC19485
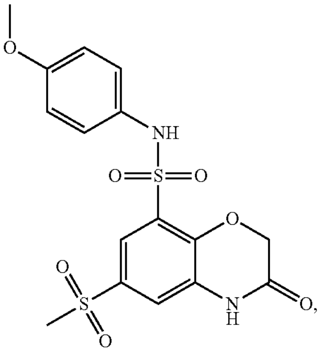
BC19486
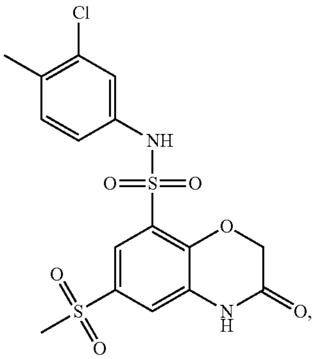
BC19487
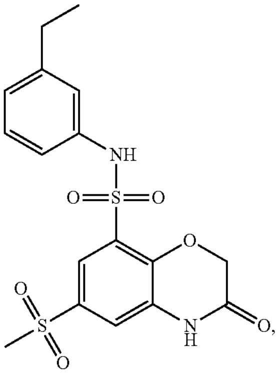
BC19488
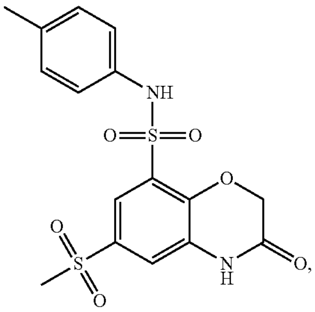

BC19489
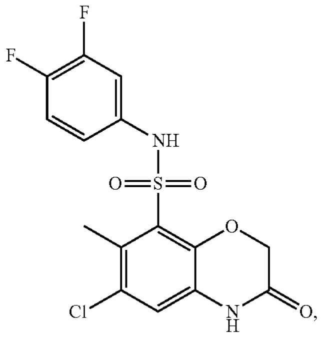
BC19490
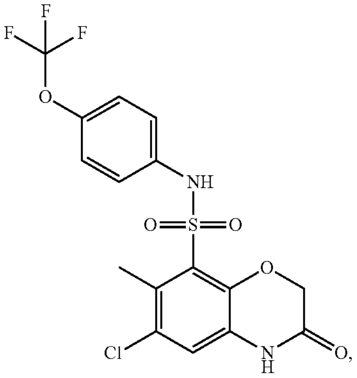
BC19491
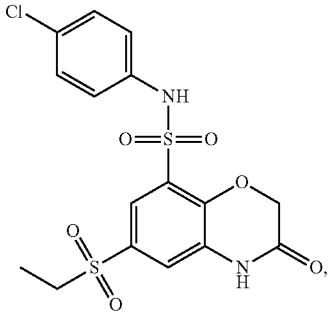
BC19492
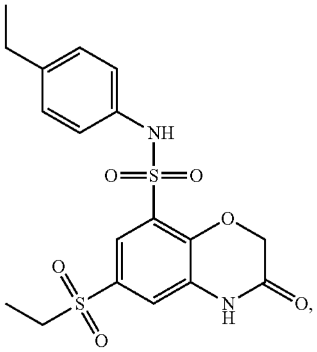
BC19493
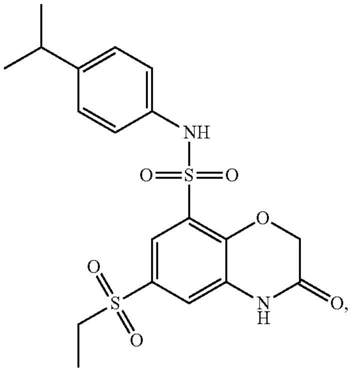
BC19544
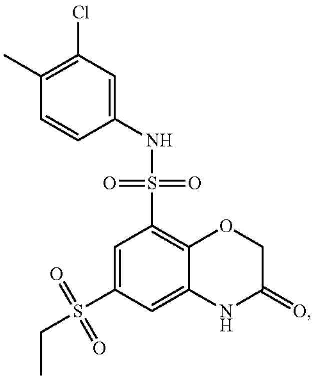
BC19545
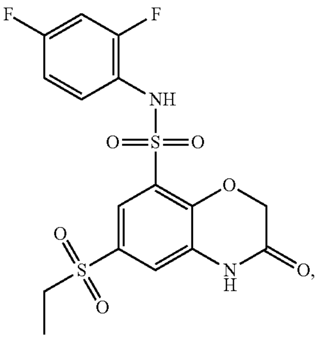
BC19546
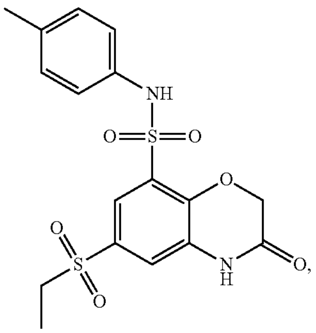

-continued
BC19547
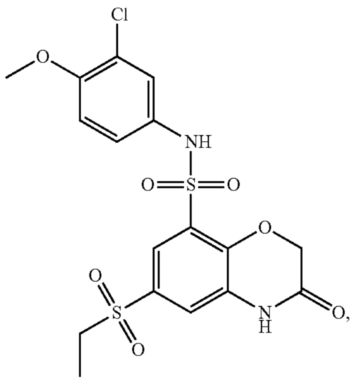
BC19548
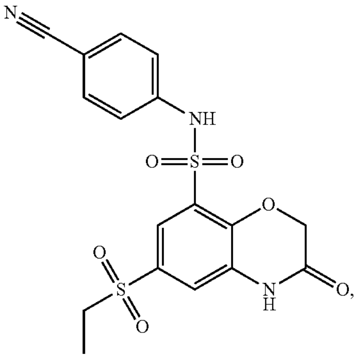
BC19697
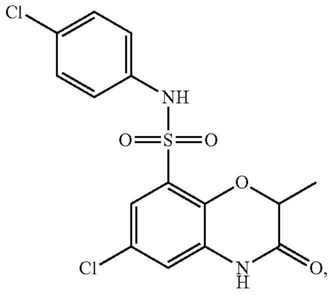
BC19699
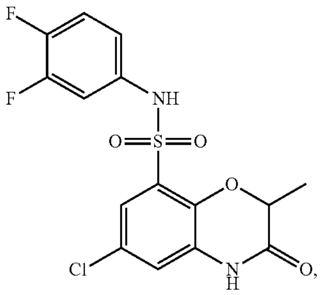
-continued
BC19701
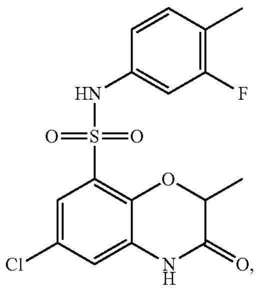
BC19703
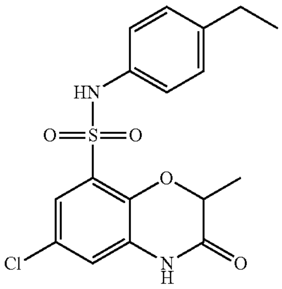
,
BC19705
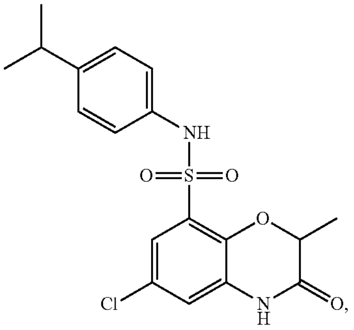
BC19707
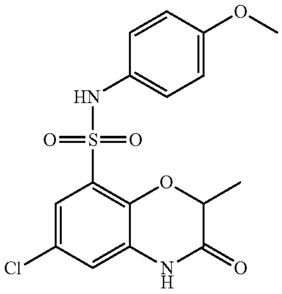
,
BC19710
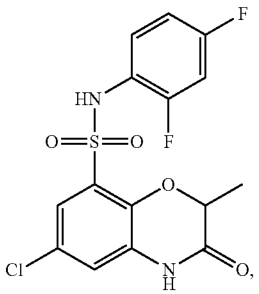

-continued
BC19712
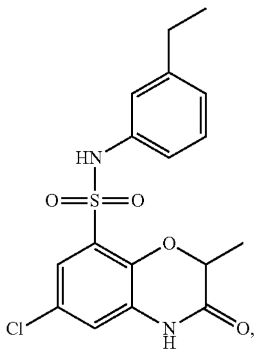
BC19714
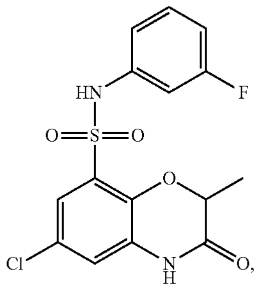
BC19716
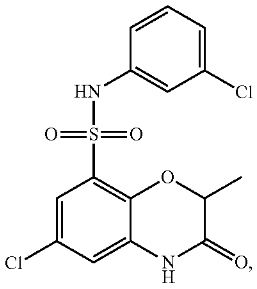
BC19718
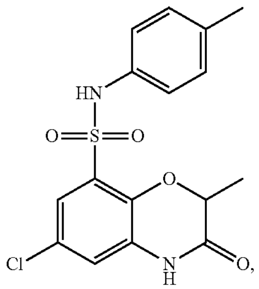
BC19720
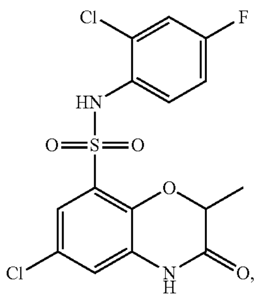
-continued
BC19722
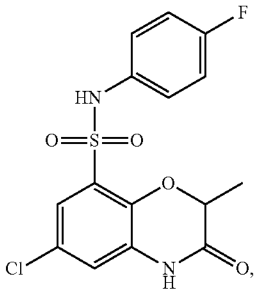
BC19730
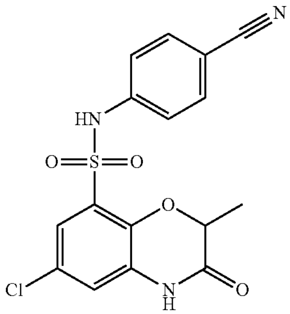
,
BC19732
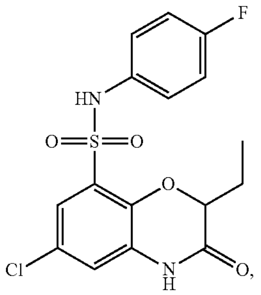
BC19734
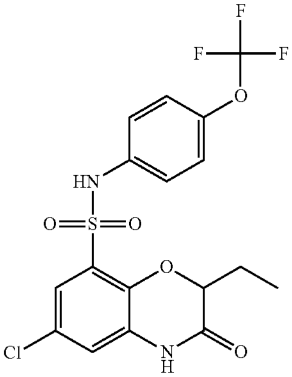
, BC19736
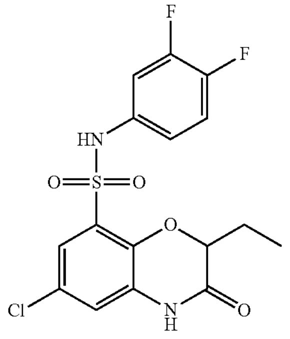
,
BC19738
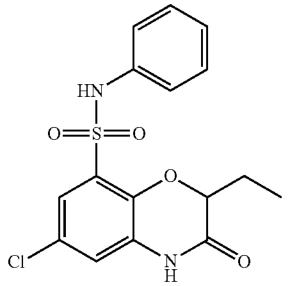
,
BC19740
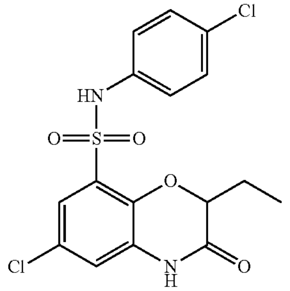
,
BC19742
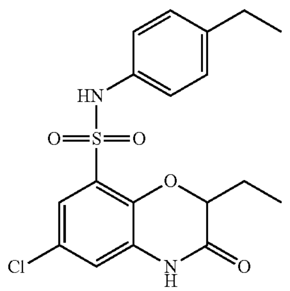
,
BC19744
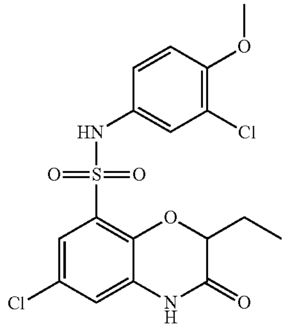
,
BC19746
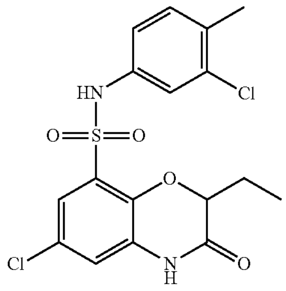
,
BC19748
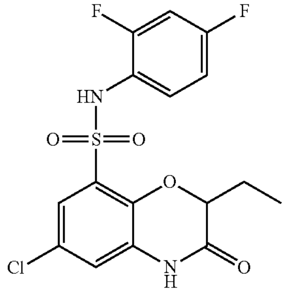
,
BC19750
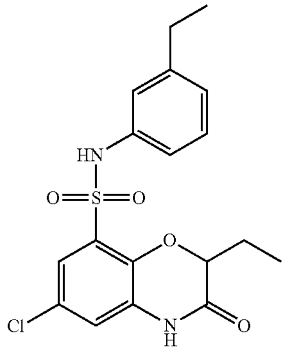
,
BC19752
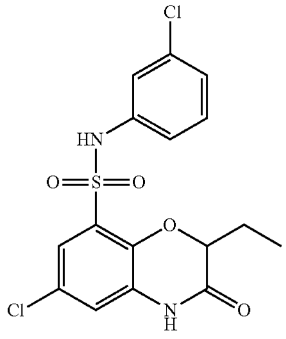
, -continued
BC19754
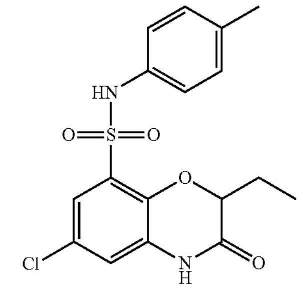
,
BC19756
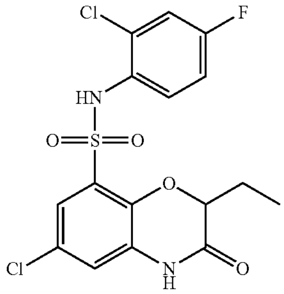
,
BC19757
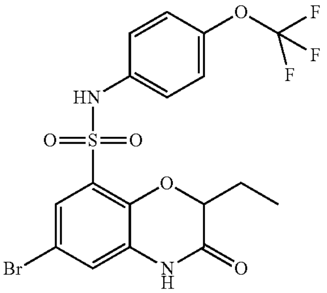
,
BC19759
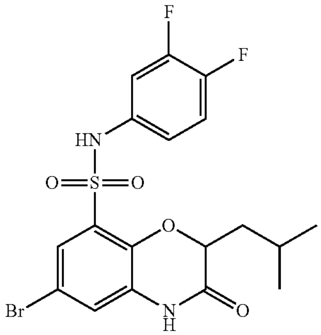
,
BC19761
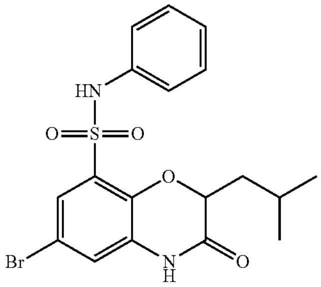
,
-continued
BC19763
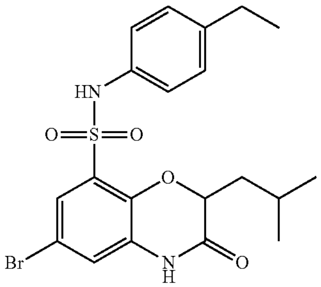
,
BC19765
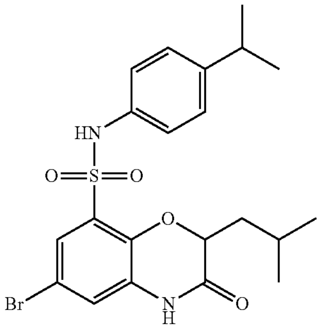
,
BC19767
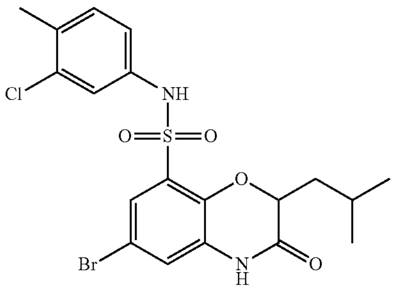
,
BC19769
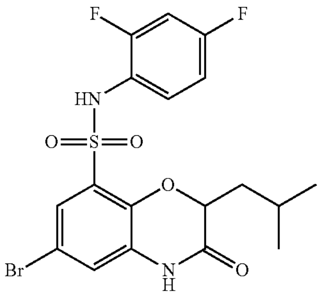
, -continued
BC19771
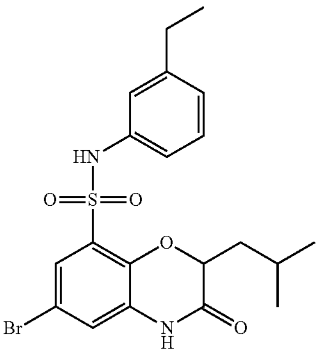
,
BC19773
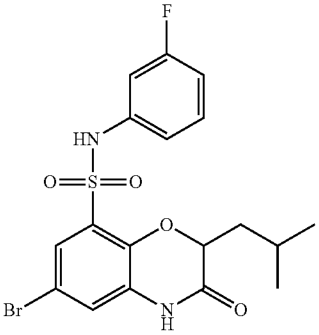
,
BC19775
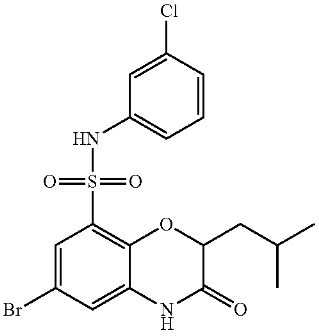
,
BC19777
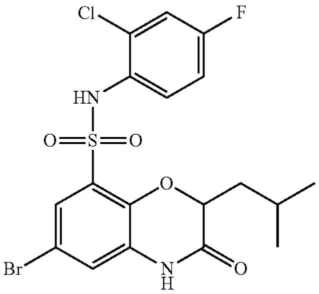
,
-continued
BC19779
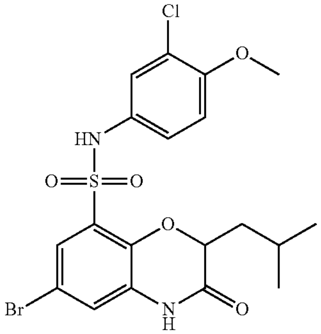
,
BC19781
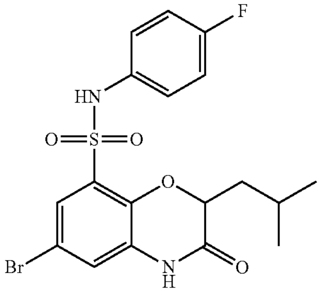
,
BC19783
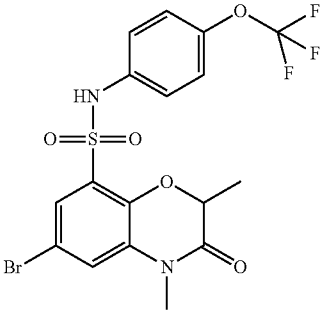
,
BC19785
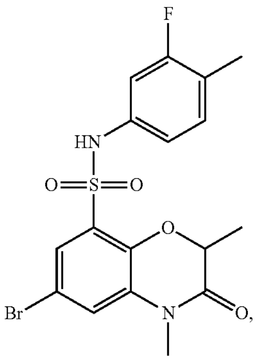
, -continued
BC19787
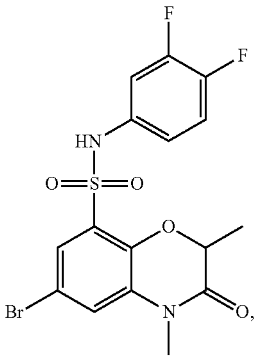
BC19789
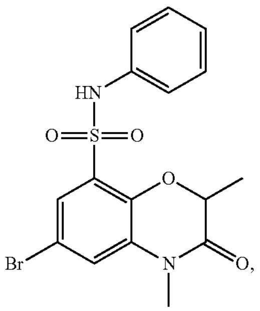
BC19791
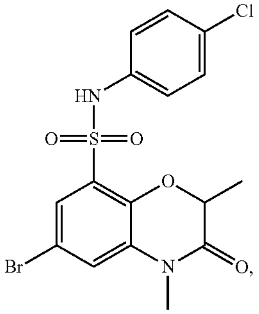
BC19793
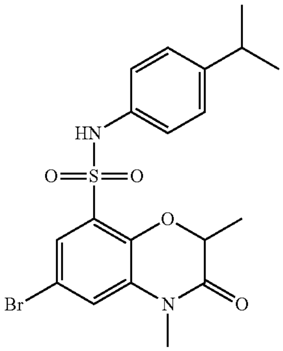
,
-continued
BC19796
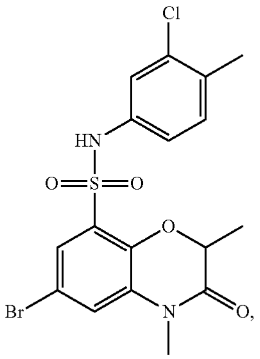
BC19798
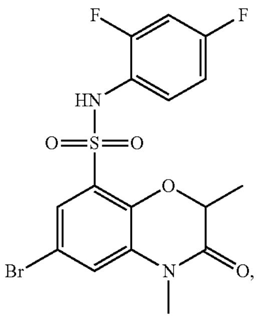
BC19900
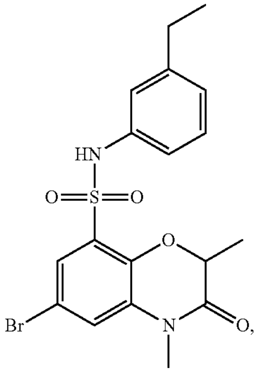
BC19902
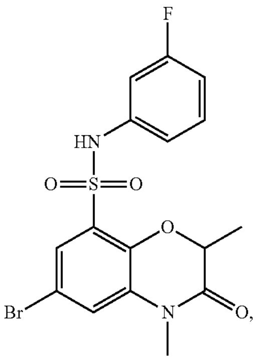

-continued
BC19904
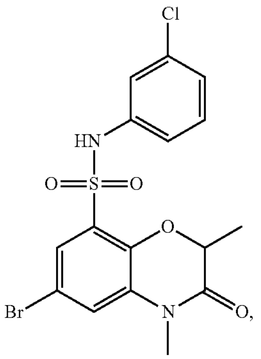
BC19906
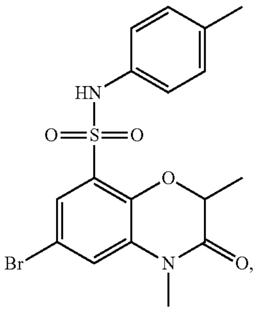
BC19908
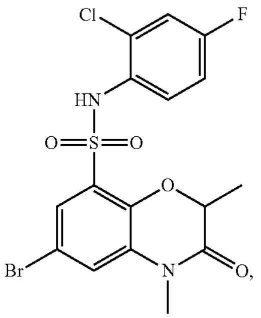
BC19909
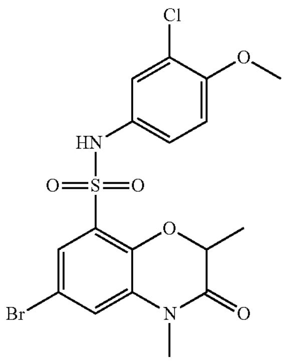
,
-continued
BC19911
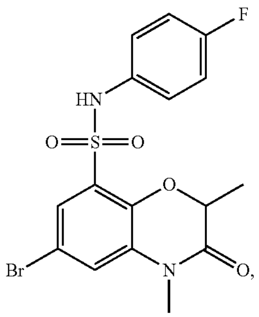
BC19913
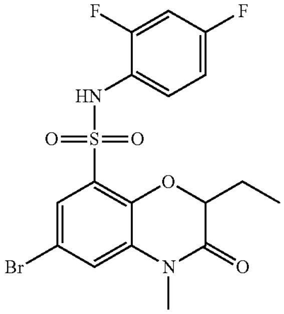
,
BC19915
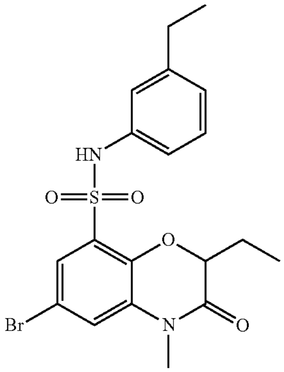
,
BC19921
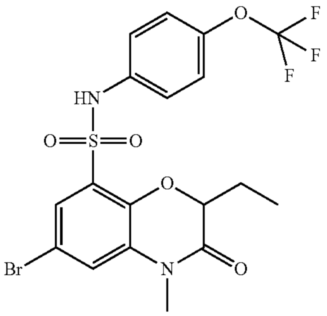
, -continued
BC19923
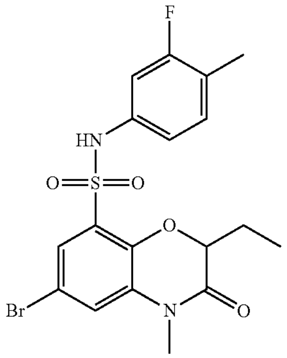
,
BC19925
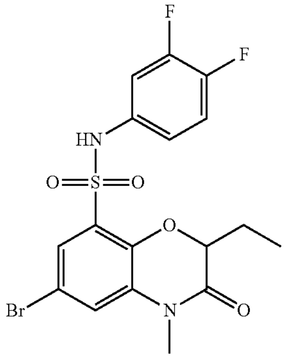
,
BC19927
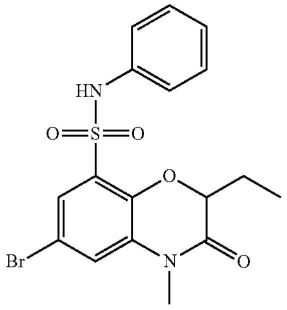
,
BC19929
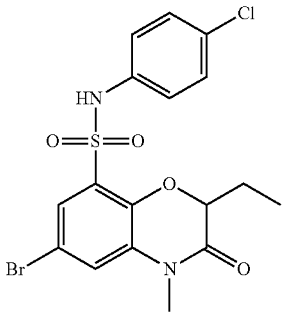
,
-continued
BC19931
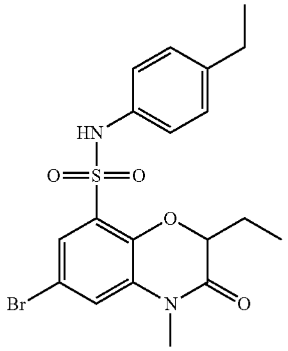
,
BC19933
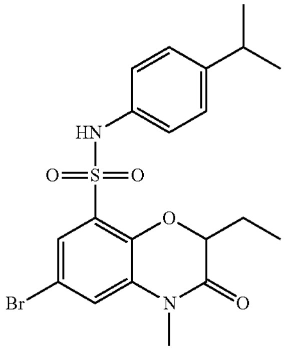
,
BC19935
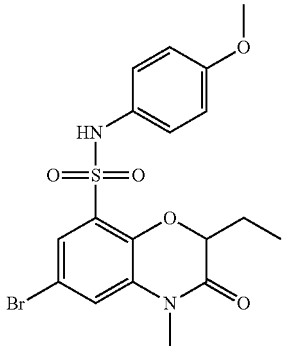
,
BC19937
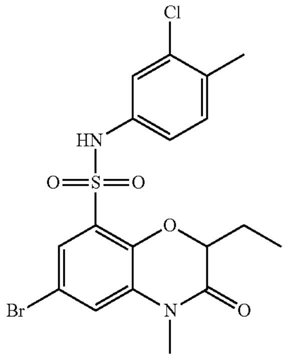
, -continued
BC19181
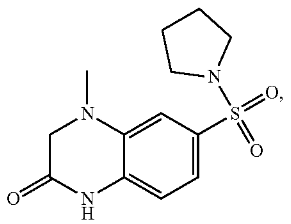
BC19182
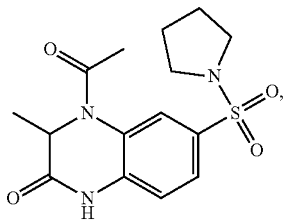
BC19183
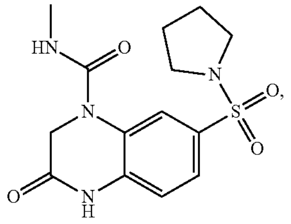
BC19184
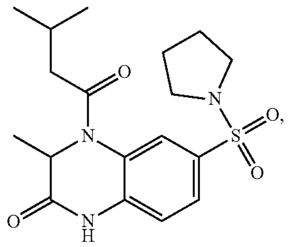
BC19235
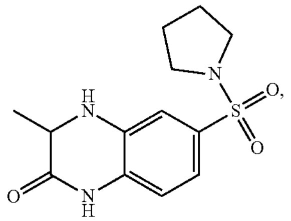
BC19236
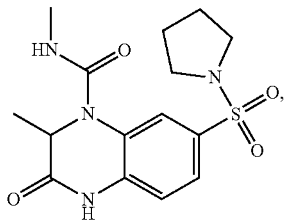
-continued
BC19295
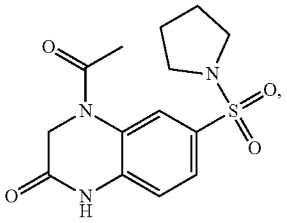
BC19296
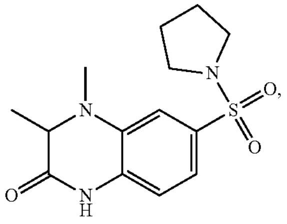
BC19297
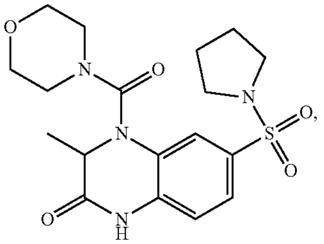
BC19298
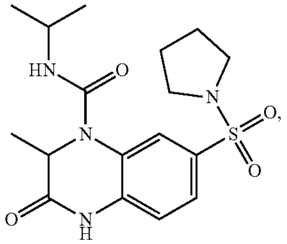
BC19299
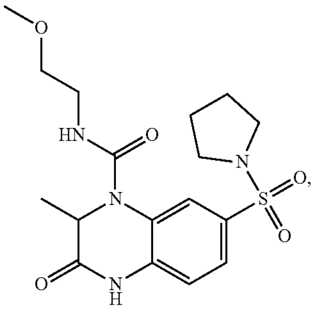
BC19300
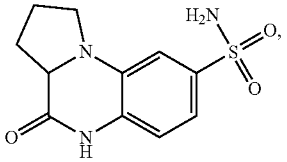

-continued
BC19917
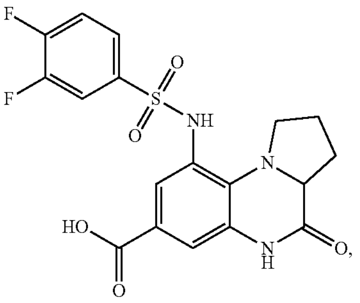
BC19549
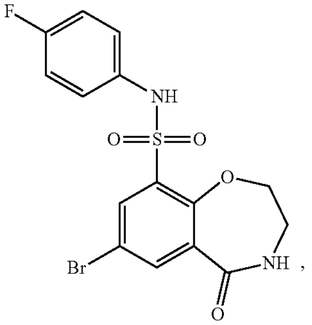
BC19550
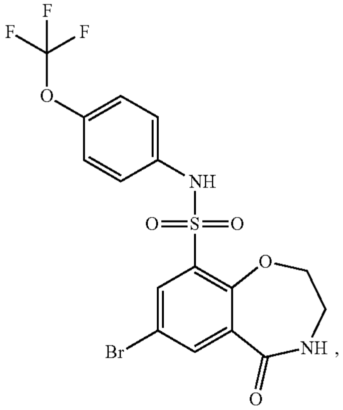
BC19551
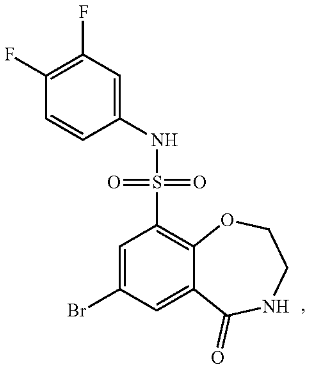
-continued
BC19552
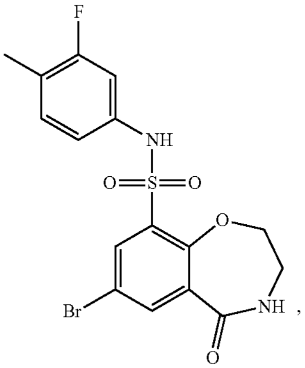
BC19553
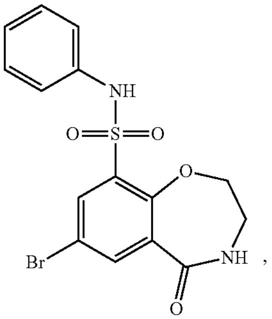
BC19603
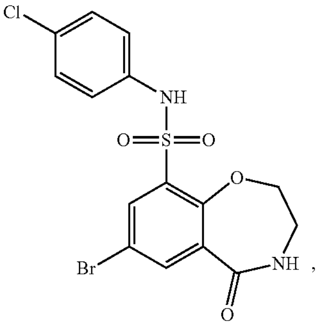
BC19604
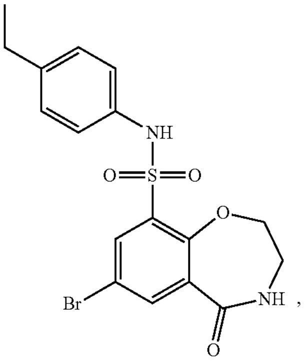

-continued
BC19605
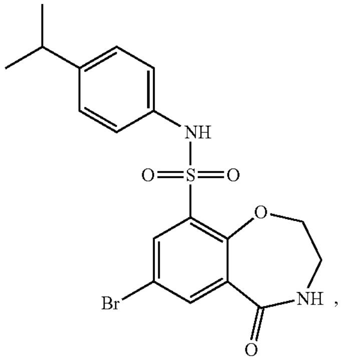
BC19606
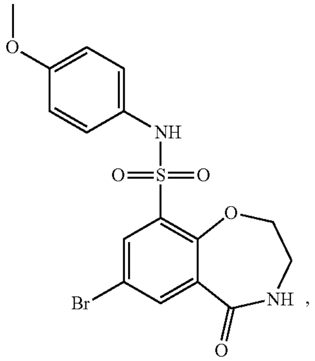
BC19607
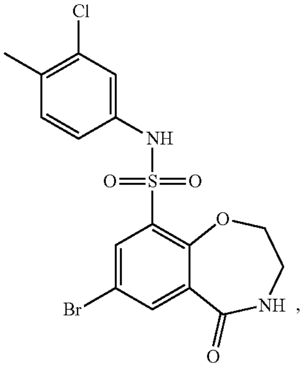
BC19608
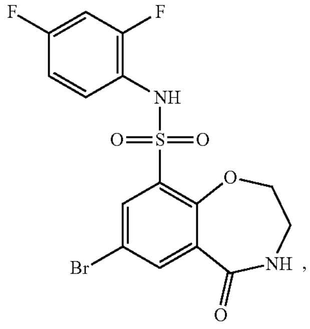
-continued
BC19609
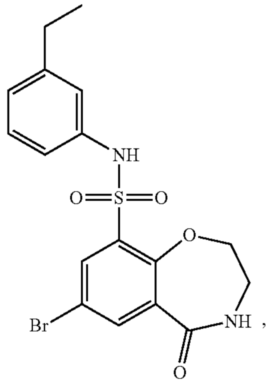
BC19610
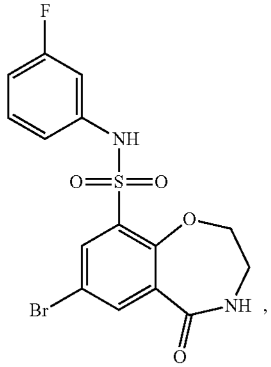
BC19611
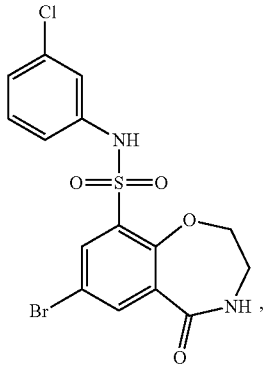
BC19612
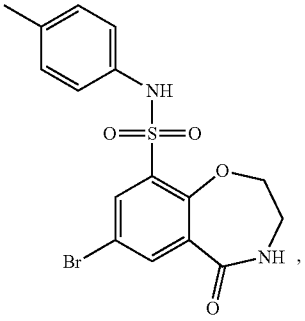

-continued
BC19613
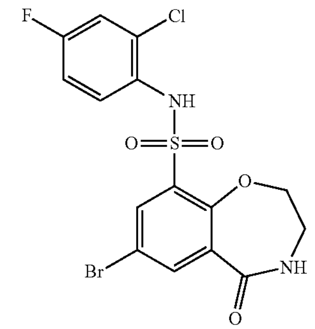
,
BC19614
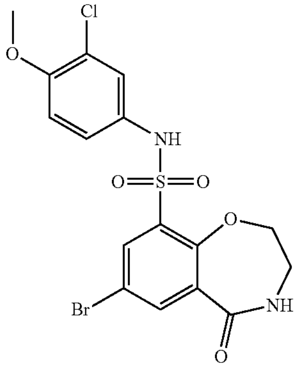
,
BC19615
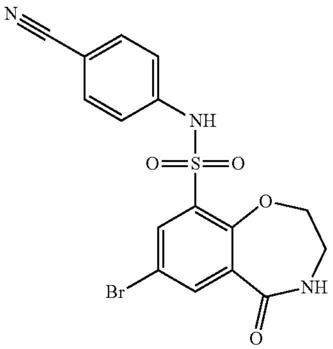
,
BC19652
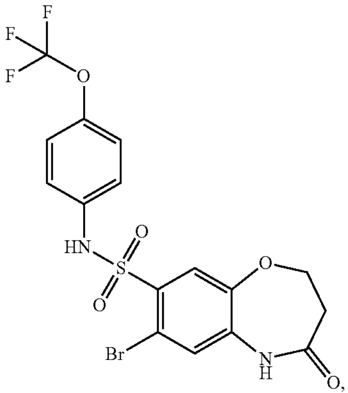
,
-continued
BC19653
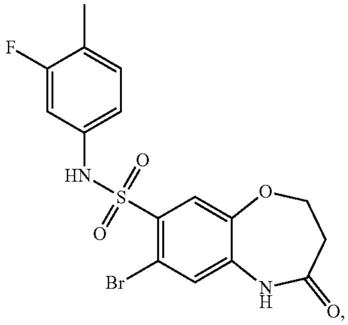
,
BC19654
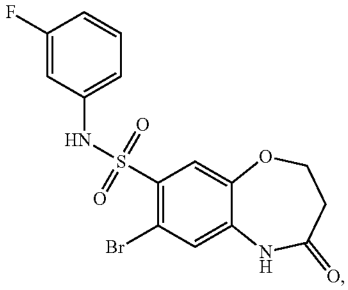
,
BC19655
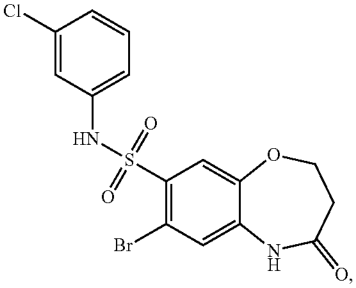
,
BC19656
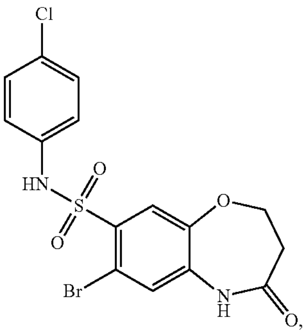
,
BC19657
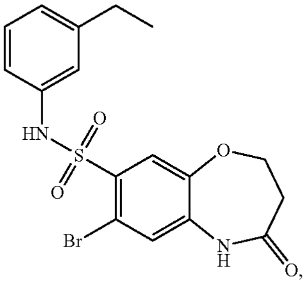
, -continued
BC19658
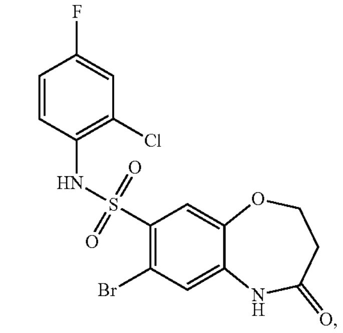
BC19659
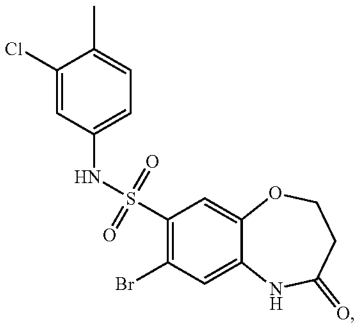
BC19660
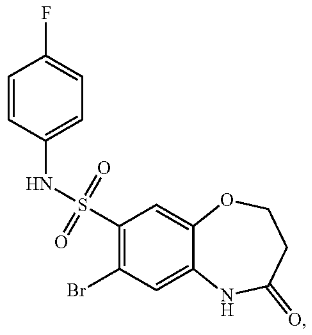
BC19661
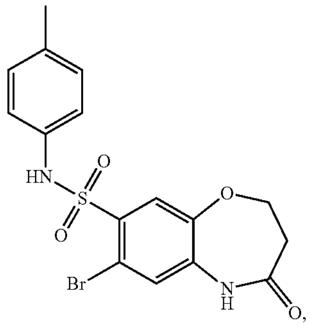
BC19689
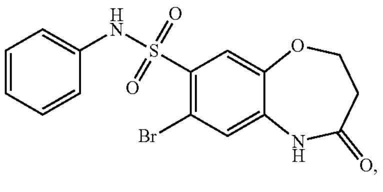
-continued
BC19690
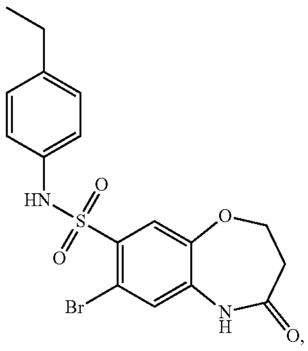
BC19691
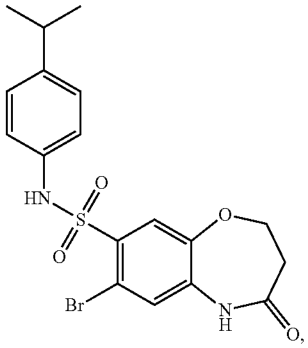
BC19692
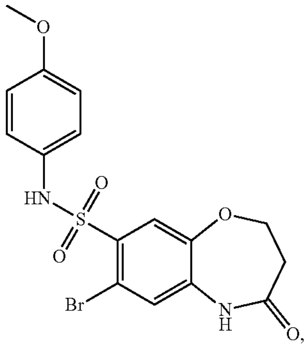
BC19693
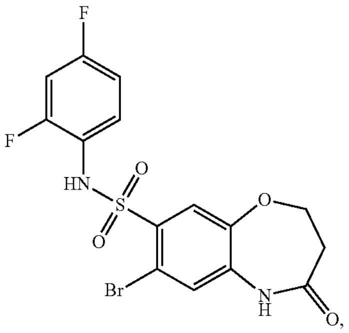

-continued
BC19694
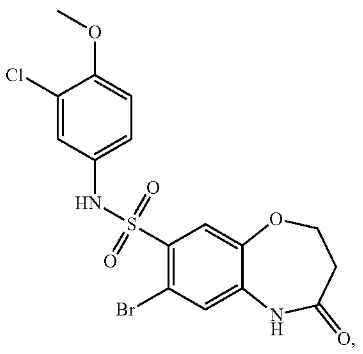
BC19695
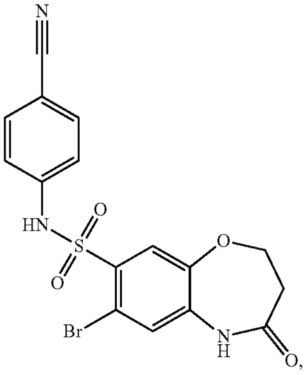
BC19648
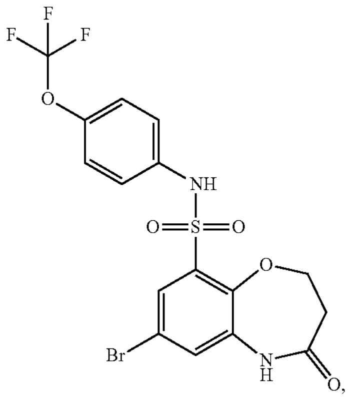
BC19649
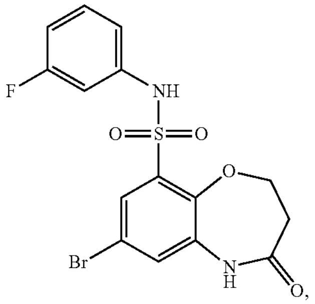
-continued
BC19650
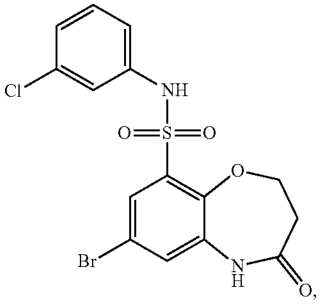
BC19651
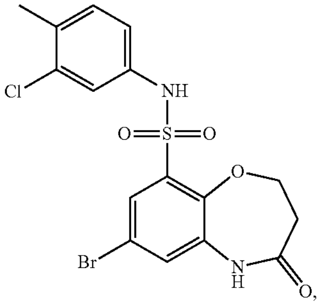
BC19685
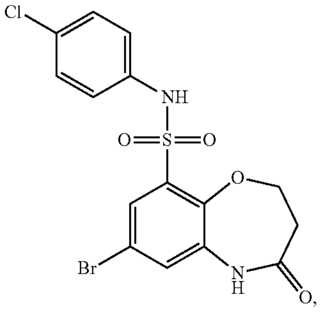
BC19686
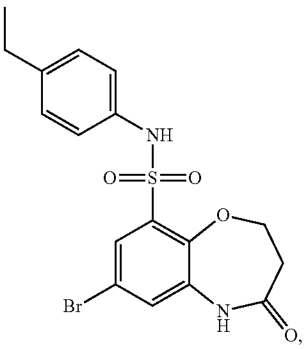

-continued
BC19687
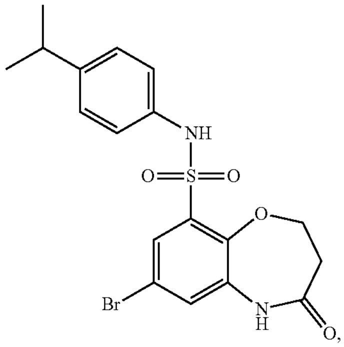
, and
BC19688
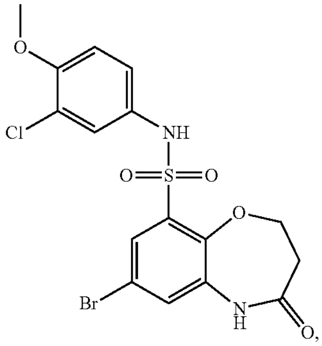
,
or a pharmaceutically acceptable salt thereof.
* * * * *